(12) United States Patent
Fernandez-Alcon et al.

(10) Patent No.: US 12,173,263 B2
(45) Date of Patent: Dec. 24, 2024

(54) ORGANOMIMETIC DEVICES AND METHODS OF USE AND MANUFACTURING THEREOF

(71) Applicants: President and Fellows of Harvard College, Cambridge, MA (US); Jose Fernandez-Alcon, Cambridge, MA (US); Norman Wen, Newton, MA (US); Richard Novak, Jamaica Plain, MA (US)

(72) Inventors: Jose Fernandez-Alcon, Cambridge, MA (US); Norman Wen, Newton, MA (US); Richard Novak, Jamaica Plain, MA (US); Donald E. Ingber, Boston, MA (US); Geraldine A. Hamilton, Cambridge, MA (US); Christopher Hinojosa, Cambridge, MA (US); Karel Domansky, Charlestown, MA (US); Daniel Levner, Cambridge, MA (US); Guy Thompson, II, Lexington, MA (US); Kambez Hajipouran Benam, Cambridge, MA (US); Remi Villenave, Boston, MA (US); Thomas Umundum, Salzburg (AT); Alfred Paris, Salzburg (AT); Georg Bauer, Salzburg (AT)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 0 days.

(21) Appl. No.: 15/105,388

(22) PCT Filed: Dec. 19, 2014

(86) PCT No.: PCT/US2014/071570
§ 371 (c)(1),
(2) Date: Jun. 16, 2016

(87) PCT Pub. No.: WO2015/138032
PCT Pub. Date: Sep. 17, 2015

(65) Prior Publication Data
US 2016/0326477 A1 Nov. 10, 2016

Related U.S. Application Data

(60) Provisional application No. 61/919,181, filed on Dec. 20, 2013.

(51) Int. Cl.
*C12M 3/06* (2006.01)
*B01D 61/18* (2006.01)
(Continued)

(52) U.S. Cl.
CPC ............. *C12M 23/16* (2013.01); *B01D 61/18* (2013.01); *B01D 63/081* (2013.01);
(Continued)

(58) Field of Classification Search
USPC ........... 422/68.1, 502–504, 48, 617; 436/180
See application file for complete search history.

(56) References Cited

U.S. PATENT DOCUMENTS

| 3,300,386 A | 1/1967 | Aron-Brunetiere |
| 3,313,290 A | 4/1967 | Chance |

(Continued)

FOREIGN PATENT DOCUMENTS

| EP | 1415788 A1 | 5/2004 |
| WO | WO 98/15614 A1 | 4/1998 |

(Continued)

OTHER PUBLICATIONS

US 6,465,252 B1, 10/2002, Toner (withdrawn)
(Continued)

*Primary Examiner* — Dean Kwak
(74) *Attorney, Agent, or Firm* — NIXON PEABODY LLP

(57) ABSTRACT

An organomimetic device includes a microfluidic device that can be used to culture cells in its microfluidic channels. The organomimetic device can be part of dynamic system that can apply mechanical forces to the cells by modulating the microfluidic device and the flow of fluid through the
(Continued)

microfluidic channels. The membrane in the organomimetic device can be modulated mechanically via pneumatic means and/or mechanical means. The organomimetic device can be manufactured by the fabrication of individual components separately, for example, as individual layers that can be subsequently laminated together.

8 Claims, 42 Drawing Sheets

(51) Int. Cl.
  *B01D 63/08*    (2006.01)
  *B01D 67/00*    (2006.01)
  *B01L 3/00*     (2006.01)
  *C12M 1/00*    (2006.01)
  *C12M 1/12*    (2006.01)
  *C12M 1/34*    (2006.01)
  *C12M 1/42*    (2006.01)
  *C12M 3/00*    (2006.01)

(52) U.S. Cl.
  CPC ........ *B01D 67/0023* (2013.01); *B01L 3/5027* (2013.01); *B01L 3/502753* (2013.01); *C12M 21/08* (2013.01); *C12M 23/26* (2013.01); *C12M 25/02* (2013.01); *C12M 35/04* (2013.01); *C12M 41/00* (2013.01); *C12M 41/46* (2013.01); *B01L 2200/0647* (2013.01); *B01L 2200/12* (2013.01); *B01L 2300/0645* (2013.01); *B01L 2300/0887* (2013.01); *B01L 2400/0487* (2013.01)

(56) References Cited

U.S. PATENT DOCUMENTS

| | | |
|---|---|---|
| 3,722,504 A | 3/1973 | Sawyer |
| 3,941,662 A | 3/1976 | Munder |
| 3,948,732 A | 4/1976 | Haddad |
| 4,197,369 A * | 4/1980 | Weaver ............... C12Q 1/00 435/12 |
| 4,225,671 A | 9/1980 | Puchinger |
| 4,436,824 A | 3/1984 | Bishop |
| 4,446,229 A | 5/1984 | Indech |
| 4,537,860 A | 8/1985 | Tolbert |
| 4,610,878 A | 9/1986 | Wilson |
| 4,629,686 A | 12/1986 | Gruenberg |
| 4,650,766 A | 3/1987 | Harm |
| 4,673,650 A | 6/1987 | Braden |
| 4,698,372 A | 10/1987 | Moss |
| 4,720,462 A | 1/1988 | Rosenson |
| 4,734,372 A | 3/1988 | Rotman |
| 4,737,455 A | 4/1988 | De Baetselier |
| 4,749,654 A | 6/1988 | Karrer |
| 4,835,102 A | 5/1989 | Bell |
| 4,839,280 A | 6/1989 | Banes |
| 4,851,354 A | 7/1989 | Winston |
| 4,929,542 A | 5/1990 | Risley |
| 4,940,853 A | 7/1990 | Vandenburgh |
| 5,002,890 A | 3/1991 | Morrison |
| 5,043,260 A | 4/1991 | Jauregui |
| 5,108,926 A | 4/1992 | Klebe |
| 5,160,490 A | 11/1992 | Naughton |
| 5,197,575 A | 3/1993 | Mangum et al. |
| 5,217,899 A | 6/1993 | Shapiro |
| 5,290,684 A | 3/1994 | Kelly |
| 5,316,905 A | 5/1994 | Mori |
| 5,348,879 A | 9/1994 | Shapiro |
| 5,486,335 A | 1/1996 | Wilding |
| 5,496,697 A | 3/1996 | Parce |
| 5,498,392 A | 3/1996 | Wilding |
| 5,587,128 A | 12/1996 | Wilding |
| 5,612,188 A | 3/1997 | Shuler |
| 5,637,469 A | 6/1997 | Wilding |
| 5,645,432 A | 7/1997 | Jessop |
| 5,726,026 A | 3/1998 | Wilding |
| 5,744,366 A | 4/1998 | Kricka |
| 5,750,329 A | 5/1998 | Quinn |
| 5,820,769 A | 10/1998 | Chou |
| 5,900,160 A | 5/1999 | Whitesides |
| 5,906,828 A | 5/1999 | Cima |
| 6,048,723 A | 4/2000 | Banes |
| 6,054,277 A | 4/2000 | Furcht |
| 6,133,030 A | 10/2000 | Bhatia |
| 6,197,575 B1 | 3/2001 | Griffith |
| 6,255,106 B1 | 7/2001 | Marx |
| 6,306,644 B1 | 10/2001 | Marx |
| 6,329,195 B1 | 12/2001 | Pfaller |
| 6,454,924 B2 | 9/2002 | Jedrzejewski |
| 6,472,202 B1 | 10/2002 | Banes |
| 6,530,370 B1 | 3/2003 | Heinonen |
| 6,562,616 B1 | 5/2003 | Toner |
| 6,586,235 B1 | 7/2003 | Banes |
| 6,630,801 B2 | 10/2003 | Schuurmans |
| 6,645,759 B2 | 11/2003 | Banes |
| 6,653,124 B1 | 11/2003 | Freeman |
| 6,730,516 B2 | 5/2004 | Jedrzejewski |
| 6,921,253 B2 | 7/2005 | Shuler |
| 6,998,265 B2 | 2/2006 | Banes |
| 7,049,057 B2 | 5/2006 | Atala |
| 7,288,405 B2 | 10/2007 | Shuler |
| 7,314,718 B1 | 1/2008 | Dasgupta |
| 7,438,856 B2 | 10/2008 | Jedrzejewski |
| 7,442,303 B2 | 10/2008 | Jacobson |
| 7,745,209 B2 | 6/2010 | Martin |
| 7,763,456 B2 | 7/2010 | Li |
| 7,790,028 B1 | 9/2010 | Weinberg |
| 7,960,166 B2 | 6/2011 | Vacanti |
| 7,964,078 B2 | 6/2011 | Lee |
| 7,976,795 B2 | 7/2011 | Zhou |
| 7,977,089 B2 | 7/2011 | Wikswo |
| 7,985,336 B2 | 7/2011 | Weinberg |
| 8,030,061 B2 | 10/2011 | Shuler |
| 8,147,562 B2 | 4/2012 | Vacanti |
| 8,187,863 B2 | 5/2012 | Sim |
| 8,268,152 B2 | 9/2012 | Stelzle |
| 8,273,572 B2 | 9/2012 | Martin |
| 8,318,479 B2 | 11/2012 | Domansky |
| 8,343,740 B2 | 1/2013 | Gonda |
| 8,357,528 B2 | 1/2013 | Vacanti |
| 8,460,546 B2 | 6/2013 | Weinberg |
| 8,470,589 B2 | 6/2013 | Martin |
| 8,647,861 B2 | 2/2014 | Ingber |
| 2002/0034634 A1 | 3/2002 | Denehy |
| 2002/0129813 A1 | 9/2002 | Litherland |
| 2002/0166585 A1 | 11/2002 | O'Connor |
| 2002/0173033 A1 | 11/2002 | Hammerick |
| 2003/0021792 A1 | 1/2003 | Roben |
| 2003/0082795 A1 | 5/2003 | Shuler |
| 2003/0096405 A1 | 5/2003 | Takayama |
| 2003/0175824 A1 | 9/2003 | Pishko |
| 2004/0034435 A1 | 2/2004 | Atala |
| 2004/0132166 A1 | 7/2004 | Miller |
| 2004/0197905 A1 | 10/2004 | Hafeman |
| 2005/0013732 A1* | 1/2005 | Battrell ............... B01F 5/0473 436/17 |
| 2005/0017354 A1* | 1/2005 | Paul ............... H01L 23/3128 257/738 |
| 2005/0032205 A1 | 2/2005 | Smith |
| 2005/0148084 A1 | 7/2005 | Parce et al. |
| 2005/0169962 A1 | 8/2005 | Bhatia |
| 2005/0206048 A1 | 9/2005 | Ryu |
| 2005/0266393 A1 | 12/2005 | Baxter |
| 2005/0273995 A1 | 12/2005 | Kanagasabapathi |
| 2006/0019326 A1 | 1/2006 | Vacanti |
| 2006/0099116 A1 | 5/2006 | Manger |
| 2006/0154361 A1 | 7/2006 | Wikswo |
| 2006/0263336 A1 | 11/2006 | Caplan |
| 2006/0270023 A1 | 11/2006 | LeDuc |
| 2007/0015273 A1 | 1/2007 | Shuler |
| 2007/0015274 A1 | 1/2007 | Shuler |
| 2007/0015275 A1 | 1/2007 | Shuler |

(56) References Cited

U.S. PATENT DOCUMENTS

| | | |
|---|---|---|
| 2007/0020693 A1 | 1/2007 | Shuler |
| 2007/0026519 A1 | 2/2007 | Shuler |
| 2007/0037273 A1 | 2/2007 | Shuler |
| 2007/0037275 A1 | 2/2007 | Shuler |
| 2007/0037277 A1 | 2/2007 | Shuler |
| 2007/0048727 A1 | 3/2007 | Shuler |
| 2007/0122794 A1 | 5/2007 | Shuler |
| 2007/0122896 A1 | 5/2007 | Shuler |
| 2007/0144514 A1 | 6/2007 | Yeates |
| 2007/0172943 A1 | 7/2007 | Freedman |
| 2007/0207194 A1 | 9/2007 | Grayburn |
| 2007/0224677 A1 | 9/2007 | Neumann |
| 2007/0243627 A1 | 10/2007 | Takayama |
| 2007/0275435 A1 | 11/2007 | Kim |
| 2007/0275455 A1 | 11/2007 | Hung |
| 2007/0275882 A1 | 11/2007 | Meijer |
| 2007/0281353 A1 | 12/2007 | Vacanti |
| 2008/0032380 A1 | 2/2008 | Kleis |
| 2008/0064088 A1 | 3/2008 | Shuler |
| 2008/0166794 A1 | 7/2008 | Shuler |
| 2008/0166795 A1 | 7/2008 | Shuler |
| 2008/0233607 A1 | 9/2008 | Yu |
| 2008/0318334 A1 | 12/2008 | Robotti |
| 2009/0028755 A1 | 1/2009 | Jedrzejewski |
| 2009/0074623 A1 | 3/2009 | Park |
| 2009/0078614 A1 | 3/2009 | Varghese |
| 2009/0131858 A1 | 5/2009 | Fissell |
| 2009/0134235 A1 | 5/2009 | Ivri |
| 2009/0220932 A1 | 9/2009 | Ingber |
| 2010/0041128 A1 | 2/2010 | Banes |
| 2010/0043494 A1 | 2/2010 | Gascon |
| 2010/0267136 A1 | 10/2010 | Vacanti |
| 2010/0294986 A1 | 11/2010 | Sultana |
| 2010/0304355 A1 | 12/2010 | Shuler |
| 2010/0323439 A1 | 12/2010 | Takayama |
| 2011/0000482 A1 | 1/2011 | Gumaste |
| 2011/0027804 A1 | 2/2011 | Yarmush |
| 2011/0053207 A1 | 3/2011 | Hoganson |
| 2011/0086382 A1 | 4/2011 | Marx |
| 2011/0183312 A1 | 7/2011 | Huang |
| 2011/0250585 A1* | 10/2011 | Ingber .................. C12N 5/0696 435/5 |
| 2011/0269226 A1 | 11/2011 | Van Noort |
| 2011/0287469 A1 | 11/2011 | Guenther |
| 2012/0003732 A1 | 1/2012 | Hung |
| 2012/0034695 A1* | 2/2012 | Sethu .................... C12M 29/18 435/401 |
| 2012/0058551 A1 | 3/2012 | Marzorati |
| 2012/0088693 A1 | 4/2012 | Lee |
| 2012/0135446 A1 | 5/2012 | Collins |
| 2012/0135452 A1 | 5/2012 | Shuler |
| 2012/0199487 A1 | 8/2012 | Stelzle |
| 2012/0214189 A1 | 8/2012 | Shuler |
| 2012/0318726 A1 | 12/2012 | Charest |
| 2012/0322097 A1 | 12/2012 | Charest |
| 2013/0059322 A1 | 3/2013 | Hung |
| 2013/0109594 A1 | 5/2013 | Gonda |
| 2014/0038279 A1 | 2/2014 | Ingber |
| 2014/0065660 A1* | 3/2014 | Kim .................... G01N 33/5058 435/297.2 |
| 2014/0158233 A1 | 6/2014 | Leslie |
| 2014/0186414 A1 | 7/2014 | Ingber |
| 2014/0199764 A1 | 7/2014 | Domansky |
| 2014/0342445 A1 | 11/2014 | Ingber |
| 2015/0004077 A1 | 1/2015 | Wikswo |
| 2015/0079670 A1 | 3/2015 | Domansky |
| 2015/0209783 A1 | 7/2015 | Ingber |
| 2015/0306596 A1 | 10/2015 | Thompson |
| 2016/0144362 A1* | 5/2016 | Lee .................... B01D 19/0031 436/175 |

FOREIGN PATENT DOCUMENTS

| | | |
|---|---|---|
| WO | WO 02/077202 A1 | 10/2002 |
| WO | WO 03/048313 A2 | 6/2003 |
| WO | WO 2004/074169 A1 | 9/2004 |
| WO | WO 2004/082588 | 9/2004 |
| WO | WO 2005/034624 A2 | 4/2005 |
| WO | WO 2005/065341 A2 | 7/2005 |
| WO | WO 2005/095582 A2 | 10/2005 |
| WO | WO 2006/004728 A2 | 1/2006 |
| WO | WO 2007/092253 A2 | 8/2007 |
| WO | WO 2007/106497 A2 | 9/2007 |
| WO | WO 2010/009307 A2 | 1/2010 |
| WO | WO 2010/096588 A2 | 8/2010 |
| WO | WO 2010/123594 A2 | 10/2010 |
| WO | WO 2012/118799 A2 | 9/2012 |
| WO | WO 2012/135834 A2 | 10/2012 |
| WO | WO 2012/154729 A1 | 11/2012 |
| WO | WO 2013/085909 A1 | 6/2013 |
| WO | WO 2013/086329 A1 | 6/2013 |
| WO | WO 2013/086486 A1 | 6/2013 |
| WO | WO 2013/086502 A2 | 6/2013 |
| WO | WO 2013/086512 A2 | 6/2013 |
| WO | WO 2013/155513 A1 | 10/2013 |
| WO | WO 2014/039514 A2 | 3/2014 |
| WO | WO 2014/210364 | 12/2014 |
| WO | WO 2015/006751 | 1/2015 |
| WO | WO 2015/013332 | 1/2015 |
| WO | WO 2015/138032 | 9/2015 |
| WO | WO 2015/138034 | 9/2015 |
| WO | WO 2017/003546 | 1/2017 |

OTHER PUBLICATIONS

Bhatia, S. et al.; "Microfluidic organs-on-chips"; Nature Biotechnology, vol. 32, No. 8; Aug. 5, 2014; pp. 760-772; XP002761628 (13 pages).
Huh, D. et al.; "From Three-Dimensional Cell Culture to Organs-on-Chips"; Trends Cell. Biol. vol. 21, No. 12; Dec. 2011; pp. 745-754; XP028120988 (19 pages).
Wyss Institute; "Wyss Institute Models a Human Disease in an Organ-on-a-Chip"; Wyss Institute of Harvard College News, Nov. 7, 2012; pp. 1-8; XP055312818; retrieved from http://wyss.harvard.edu/wyss-institute-models-a-human-disease-in-an-organ-on-a-chip/ (9 pages).
European Patent Office, Extended European Search Report for European Patent Application No. 14885808.7 mailed Feb. 3, 2017 (11 pages).
Extended European Search Report for Application No. EP 19184426.5, mailed Oct. 24, 2019 (14 pages).
Brigitte, M. et al.; "On chip porous polymer membranes for integration of gastrointestinal tract epithelium with microfluidic 'body-on-a-chip' devices"; Biomed. Microdevices (2012), 14:895-906 (12 pages).
Roy, E. et al.; "Prototyping of microfluidic systems using a commercial thermoplastic elastomer"; Microfluid Nanofluid (2011) 11:235-244 (11 pages).
Fisher, T. III; "Fix Thickness Variations in Extruded Sheet"; Aug. 1, 2005; retrieved from https://www.ptonline.com/articles/fix-thickness-variations-in-extruded-sheet (6 pages).
Abreu, F. O. M. et al.; "SBS and SEBS Block Copolymers as Impact Modifiers for Polypropylene Compounds"; J. Appl. Polym. Sci. vol. 95, pp. 254-263; 2005 (10 pages).
International Search Report, PCT/US2014/071570, date of mailing Oct. 7, 2015 (4 pages).
Written Opinion of the International Searching Authority, PCT/US2014/071570, date of mailing Oct. 7, 2015 (9 pages).
Thangawng et al., "An ultra-thin PDMS membrane as a bio/micro-nano interface: fabrication and characterization, Biomed Microdevices," (2007) 9:587-595 (Year: 2007).
Whitesides et al., "Soft Lithography in Biology and Biochemistry," Annu. Rev. Biomed. Eng. 2001. 3:335-73 (Year: 2001).
Tan et al., "A trap-and-release integrated microfluidic system for dynamic microarray applications," National Academy of Sciences Jan. 2007, 104 (4) 1146-1151 (Year: 2007).

(56) References Cited

OTHER PUBLICATIONS

Ahn et al., "High-Speed Roll-to-Roll Nanoimprint Lithography on Flexible Plastic Substrates," Adv. Mater. 2008, 20, 2044-2049 (Year: 2008).

Song et al., "Development of the Roll Type Incremental Micro Pattern Imprint System for Large Area Pattern Replication," IPAS 2010, IFIP AICT 315, pp. 97-104, 2010 (Year: 2010).

* cited by examiner

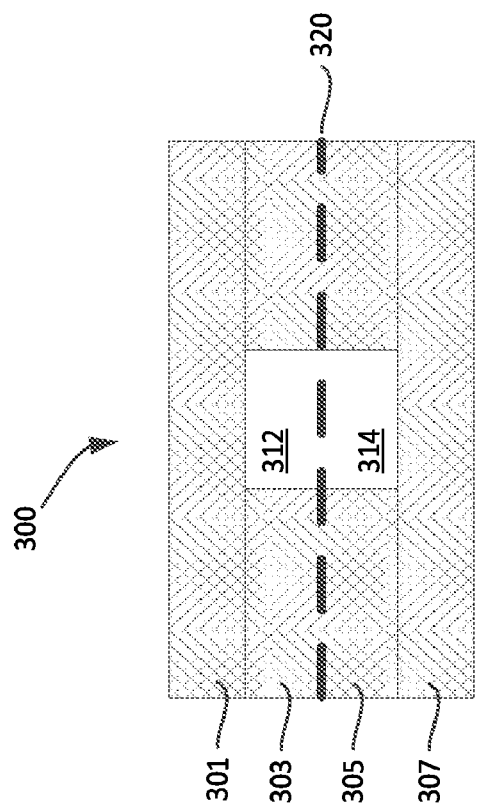
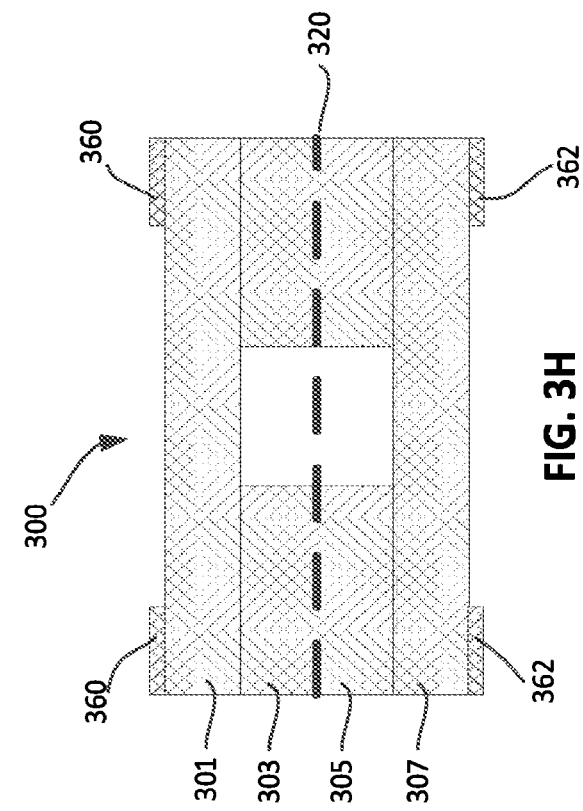

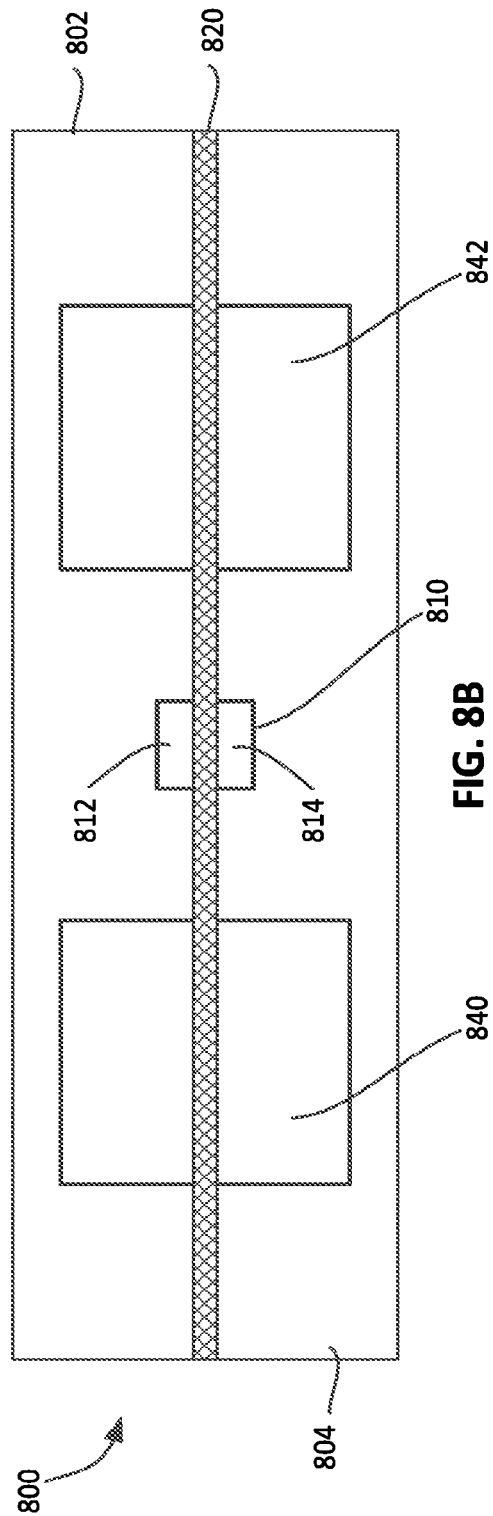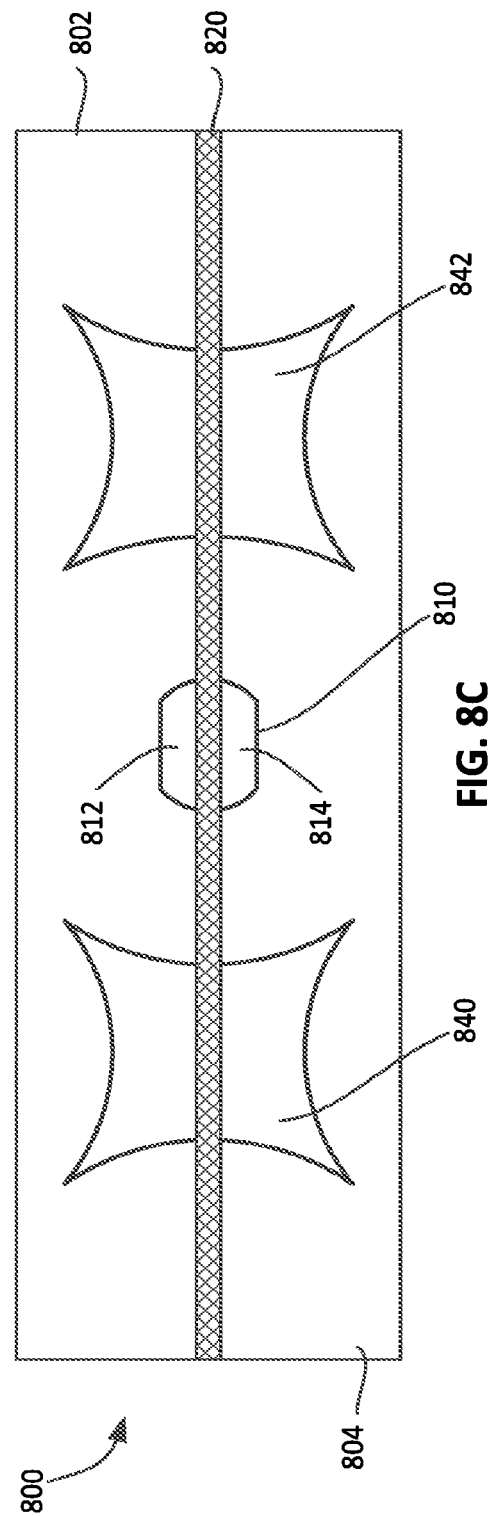

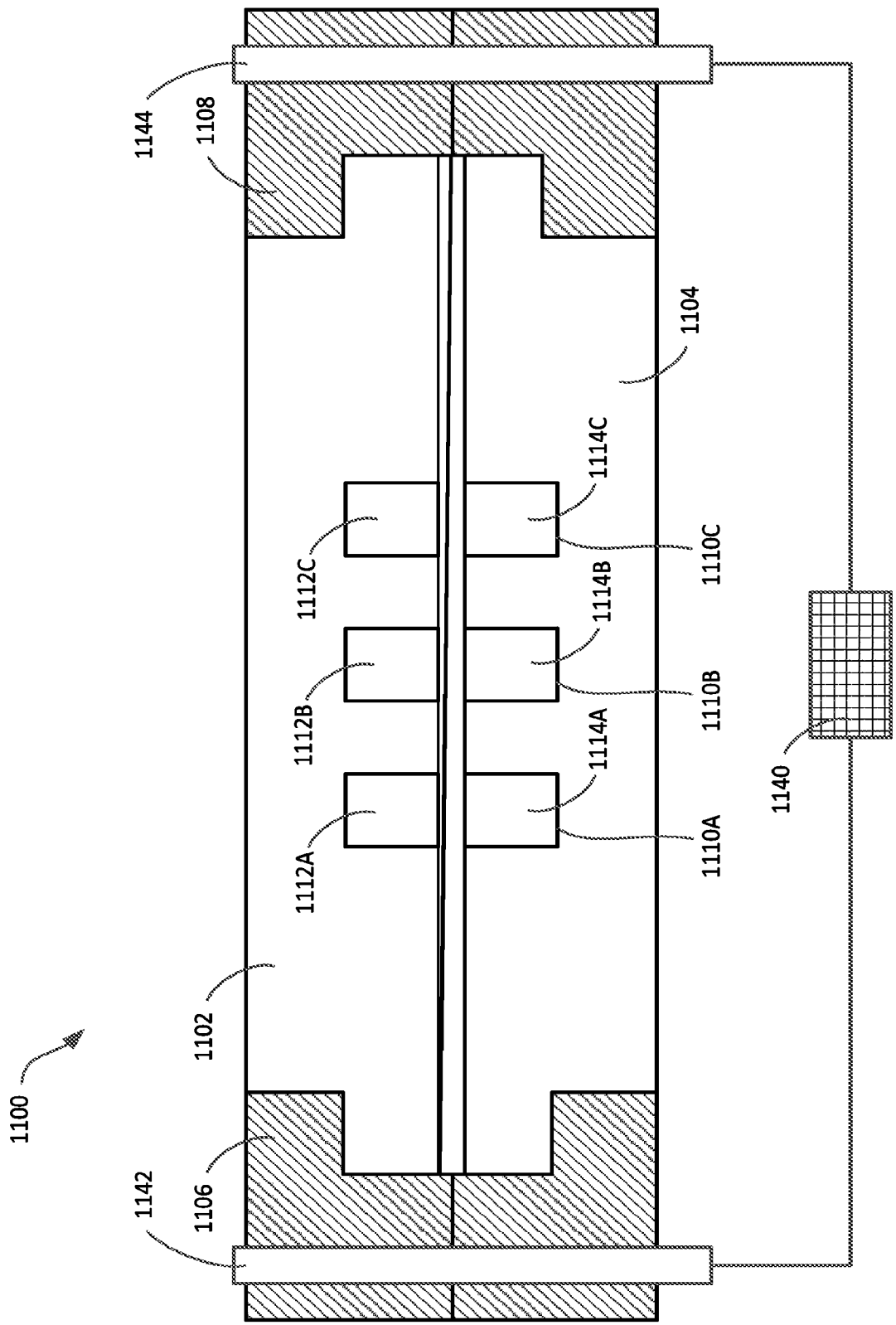

ORGANOMIMETIC DEVICES AND METHODS OF USE AND MANUFACTURING THEREOF

CROSS-REFERENCE TO RELATED APPLICATIONS

This application is a U.S. National Stage of International Application No. PCT/US2014/071570, filed Dec. 19, 2014, which claims priority to and the benefits of U.S. Patent Application No. 61/919,181, filed Dec. 20, 2013, each of which are hereby incorporated by reference herein in their entireties.

GOVERNMENT SUPPORT

This invention was made with government support under NS073474 awarded by National Institutes of Health (NIH) and under W911NF-12-2-0036 awarded by U.S. Department of Defense/Defense Advanced Research Projects Agency (DOD/DARPA). The government has certain rights in this invention.

TECHNICAL FIELD

The present disclosure relates generally to microfluidic devices and methods of use and manufacturing thereof, including in some aspects, microfluidic devices for culture and/or support of living cells such as mammalian cells, insect cells, plant cells, and microbial cells and stretch actuation of such microfluidic devices.

BACKGROUND

Currently, animal studies are an integral part of drug development and toxicology evaluation. Each year, hundreds of millions of animals are used for animal studies. It is expensive, cumbersome and ethically controversial. Furthermore, there are concerns for extrapolating the data from animal studies to be used in humans. Hence, there is a need in finding alternatives to animal studies that are cheaper, faster, more humane, and capable of achieving more accurate results.

One approach to replace or reduce reliance upon animal studies is to replicate tissue and organ-level functions in vitro. Living organs are three-dimensional vascularized structures composed of two or more closely apposed tissues that function collectively and transport materials, cells and information across tissue-tissue interfaces in the presence of dynamic mechanical forces, such as fluid shear and mechanical strain. These mechanical cues are generally known to have effects on organ formation and function, and they contribute to the etiology and/or therapeutic responsiveness of many diseases. However, certain aspects of existing approaches to replicate tissue and organ-level functionality in vitro have not been able to reproduce these dynamic mechanical forces in vitro.

SUMMARY

An organomimetic device (also called an organ-on-a-chip or organ-chip) is a microfluidic device (or in some aspects, a mesofluidic device) that can be used to culture and/or support living cells (e.g., but not limited to, mammalian cells such as human cells) under fluid or gas flow in its fluidic channels, wherein, for example, at least some cells can form functional tissues and tissue-tissue interfaces that can recapitulate those found in whole living organs. Mechanical forces can also be applied repetitively to the organ-on-a-chip in order to mimic the dynamic physical microenvironment of cells. A mechanically-actuated organomimetic device has the potential to replicate complex tissue and organ-level structures and functions, such as those exhibited by a breathing lung, beating heart, metabolic liver, flowing kidney, peristalsing gut, reactive airway, contracting skeletal muscle, stretching skin barrier, compressing bone with self-renewing marrow, pulsating blood-brain barrier, and reproductive/endocrine testis.

In addition, different organomimetic devices can be fluidically connected together to form microphysiological systems that mimic multi-organ interactions, for instance, lung coupled with heart, and liver coupled with intestine. Therefore, studies based on organ-on-chips can be performed in a more holistic manner that more closely mimics the function of living organs or organisms, including humans when human cells are used in the devices described herein. Organomimetic devices can potentially replace animal studies, and be used in a massively parallel manner for drug screening, disease models, and toxicology studies for drugs, nanomaterials and cosmetics.

In one aspect, the invention relates to a device for simulating a function of a tissue comprising (i) a first microchannel, (ii) a second microchannel, and (iii) a membrane located at an interface region between the first microchannel and the second microchannel. The membrane includes a first side facing toward the first microchannel and a second side facing toward the second microchannel. The first side typically has cells of a first type thereon. The membrane separates the first microchannel from the second microchannel, and permits the migration of cells, particulates, chemicals, molecules, fluids and/or gases between the first side to the second side. The device may further have a first wall portion coupled to the membrane. The device may also have a second wall portion with the membrane being fastened to the second wall portion such that the membrane is modulated by motion of at least one of the first wall portion and the second wall portion.

In some embodiments of this aspect and other aspects described herein, the second has cells of a second type thereon and the device includes a central microchannel with the membrane dividing the central microchannel into the first microchannel and the second microchannel.

In some embodiments of this aspect and other aspects described herein, the cells can be adhered to the first side and/or second side of the membrane.

In one aspect, provided herein is an organomimetic device comprising: (a) a body having a central channel therein; and wherein the central channel has a first wall portion; and (b) a membrane positioned within the central channel and extending along a plane, wherein the membrane is configured to separate the central channel to form a first central microchannel and a second central microchannel; wherein the membrane is fastened to the first wall portion whereby the membrane is modulated by motion of the first wall portion.

Another aspect provided herein is an organomimetic device comprising: (a) first microchannel; (b) a second microchannel; (c) a membrane located at an interface region between the first microchannel and the second microchannel, the membrane including a first side facing toward the first microchannel and a second side facing toward the second microchannel, the first side having cell of a first type thereon, the membrane separating the first microchannel from the second microchannel; and (d) a first engagement element coupled to the membrane whereby the membrane is modulated in at least a first direction along the plane by motion of the first engagement element.

Another aspect provided herein is an organomimetic device comprising: (a) a body having a central channel therein; and (b) a membrane positioned within the central channel and extending along a plane, wherein the membrane is configured to separate the central channel to form a first central microchannel and a second central microchannel, and wherein the membrane is coupled to a first engagement element, whereby the membrane is modulated in at least a first direction along the plane by motion of the first engagement element. The first direction can be perpendicular to or parallel to a fluid flow through the central channel.

In some embodiments, the first engagement element can be releasably engaged by an engagement element modulation device, the engagement element modulation device adapted to modulate the motion of the engagement element.

In some embodiments, the membrane can be coupled to at least a second engagement element, whereby the membrane can be modulated in at least a second direction along the plane by motion of the at least the second engagement element.

The devices described herein can be fabricated by any art-recognized methods. In some embodiments, the devices described herein can be fabricated as monolithic units. In other embodiments, the devices described herein can be fabricated by assembly of multiple parts or components. In some embodiments, the devices can be fabricated by injection molding, lamination, embossing, casting, or a combination thereof. Accordingly, some embodiments provided herein relate to an organomimetic device comprising: (a) a first microchannel height-defining layer having a bottom surface and a first microchannel disposed in the bottom surface; (b) a second microchannel height-defining layer having a top surface and a second microchannel disposed in the top surface; and (c) a membrane layer having a membrane portion, the membrane layer being laminated between the bottom surface of the first microchannel height-defining layer and the top surface of the second microchannel height-defining layer, wherein a first surface portion of the membrane portion provides a lower boundary of the first microchannel and a second surface portion of the membrane portion provides an upper boundary of the second microchannel; and wherein at least a portion of the first microchannel is aligned with at least a portion of the second microchannel on an opposite side of the membrane portion.

In some embodiments, at least one of the first microchannel height-defining layer and the second microchannel height-defining layer can produced by a process comprising molding.

In some embodiments, the first microchannel height-defining layer can comprise: (a) a first lamination layer having a first microchannel aperture therein, wherein thickness of the first lamination layer defines the height of the first microchannel; and (b) a first sealing layer disposed on top of the first lamination layer, wherein the first sealing layer is in contact with the first lamination layer and provides a top closure of the first microchannel aperture, thereby forming the first microchannel.

Similarly, in some embodiments, the second microchannel height-defining layer can comprise: (a) a second lamination layer having a second microchannel aperture therein, wherein thickness of the second lamination layer defines the height of the second microchannel; and (b) a second sealing layer disposed below the second lamination layer, wherein the second sealing layer is in contact with the second lamination layer and provides a bottom closure of the second microchannel aperture, thereby forming the second microchannel.

According to some aspects provided herein, an organomimetic device is produced by a process comprising: (a) providing at least one first body having a central channel therein along a first axis; and wherein the central channel has a first wall portion; and a membrane positioned within the central channel and extending along a plane, wherein the membrane is configured to separate the central channel to form a first central microchannel and a second central microchannel, wherein the membrane is fastened to the first wall portion whereby the membrane is modulated by motion of the first wall portion; and wherein the first wall portion comprises an elastomeric material; (b) providing a second body having a housing channel therein; wherein the housing channel has a height that is substantially the same as or greater than the height of the first body; and a width that is greater than the width of the first body; and wherein the second body comprises a rigid material; and (c) placing the at least one first body within the housing channel of the second body such that the at least one operating chamber forms adjacent to the first wall portion of the first body along the first axis, thereby forming at least one organomimetic device.

According to some aspects, a mechanical modulation system for stretch actuation of a microfluidic device comprises a mechanical actuation arrangement configured to impart an undulating motion along a single plane defined by a microfluidic device mounted within the mechanical modulation system. A plurality of opposing connection elements physically connect to the mechanical actuation system. The plurality of opposing connection elements are configured to fasten a first location and a second location of a microfluidic device to the opposing connection elements such that the first location and the second location of the microfluidic device are each fixed to one of the connection elements and such that straining of the microfluidic device during cyclical linear motions of a stretch actuation process is transferred to a portion of the microfluidic device between the first location and the opposing second location.

According to some aspects, a microfluidic system for monitoring a behavior of cells comprises a microfluidic device having at least one microchannel in which the cells are disposed. A mechanical actuation device for stretching the microfluidic device includes a plurality of opposing connection elements configured to be fastened to a first location and an opposing second location of a microfluidic device.

According to another aspect, a method of stretch actuation using a mechanical modulation system for a microfluidic device includes at least one microchannel in which cells are disposed. The method comprises mounting a first location and a second location of the microfluidic device to a first connection element and a second connection element of the mechanical modulation system. Stretching of the microfluidic device occurs in response to generally undulating motions imparted to the microfluidic device.

Additional aspects of the invention will be apparent to those of ordinary skill in the art in view of the detailed description of various embodiments, which is made with reference to the drawings, a brief description of which is provided below.

BRIEF DESCRIPTION OF THE DRAWINGS

The accompanying drawings, which are incorporated into and constitute a part of this specification, illustrate one or more examples of embodiments and, together with the description of example embodiments, serve to explain the principles and implementations of the embodiments. In the drawings:

FIG. 3G shows a transverse cross sectional view of a microfluidic device according to some embodiments of the invention.

FIG. 3H shows a transverse cross sectional view of a microfluidic device according to some embodiments of the invention.

FIGS. 8A-8C show transverse cross sectional views of a microfluidic device according to some embodiments of the invention.

FIG. 11C shows a diagrammatic transverse cross sectional view of the device of FIG. 11B.

DETAILED DESCRIPTION

Example embodiments of various aspects are described herein in the context of an organ simulating device and methods of use and manufacturing thereof.

Those of ordinary skill in the art will realize that the following description is illustrative only and is not intended to be in any way limiting. Other embodiments will readily suggest themselves to such skilled persons having the benefit of this disclosure. Reference will now be made in detail to implementations of the example embodiments as illustrated in the accompanying drawings. The same or similar reference indicators will be used throughout the drawings and the following description to refer to the same or like items. It is understood that the phrase "an embodiment" encompasses more than one embodiment and is thus not limited to only one embodiment.

As used herein, the term "rigid" refers to a material that is stiff and does not stretch easily, or maintains very close to its original form after a force or pressure has been applied to it. The term "elastomeric" as used herein refers to a material or a composite material that is not rigid as defined herein. An elastomeric material can be generally moldable, extrudable, cuttable, machinable, castable, and/or curable, and can have an elastic property that enables the material to deform (e.g., stretching, expanding, contracting, retracting, compressing, twisting, and/or bending) when subjected to a mechanical force or pressure and partially or completely resume its original form or position in the absence of the mechanical force or pressure. In some embodiments, the term "elastomeric" can also refer to a material that is flexible/stretchable but it does not resume its original form or position after pressure has been applied to it and removed thereafter. The terms "elastomeric" and "flexible" are used interchangeably herein.

Figure 1A:
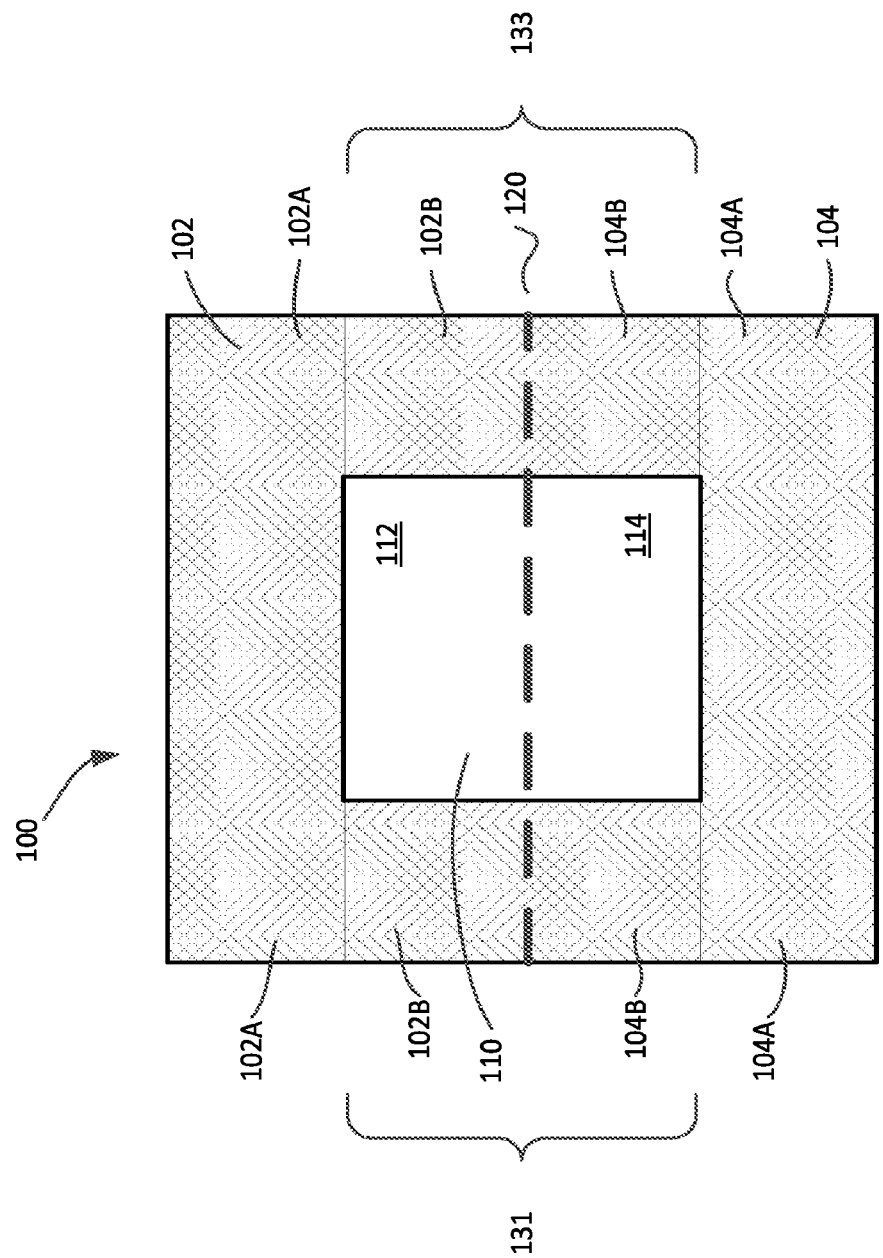
FIG. 1A shows a cross sectional view, transverse to the longitudinal axis of a microfluidic device according to some embodiments of the invention.

FIG. 1A shows a cross sectional view, transverse to the longitudinal axis of a microfluidic device 100 according to some embodiments of the invention. The body of device 100 can include, but not limited to, a first layer 102 and a second layer 104 that define a central channel 110. The central channel 110 can extend along the longitudinal axis of the microfluidic device 100. A membrane 120 can be configured to divide the central channel 110 into two closely apposed parallel central microchannels, first central microchannel 112 and second central microchannel 114. In some embodiments, the membrane 120 can be a porous membrane. While the membrane is shown as extending along a plane, the present invention contemplates, in this and all embodiments, membranes that extend in a non-planar fashion, e.g. curved membranes or multi-plane membranes). Furthermore, the membrane may include a series of uniform undulations.

In accordance with various embodiments, the central channel 110 of the microfluidic device 100 can include a first side wall portion 131 and a second side wall portion 133 and the membrane 120 can extend between the first side wall portion 131 and the second side wall portion 133. In accordance with some embodiments of the invention, portions 102A, 102B of the first layer 102 and portions 104A, 104B of the second layer 104 can form the first side wall portion 131 and the second side wall portion 133. In accordance with some embodiments of the invention, the first side wall portion 131 and/or the second side wall portion 133 can be constructed from added layers or elements 102A, 102B, 104A, 104B. While the drawings show the membrane 120 centrally located in the central channel 110, in accordance with some embodiments of the invention, the membrane 120 can be positioned vertically off-center within the central channel 110, such that the height of one of the first central microchannel 112 or the second central microchannel 114 can be greater than the other. While in some embodiments of the invention, the cross-sectional area of the first central microchannel can be the same as the cross-sectional area of the second central microchannel, in other embodiments of the invention, the cross-sectional area of the first central microchannel can be different (e.g., either larger or smaller) than the second central microchannel. In addition, the height or width (and/or the cross-sectional area) of the first central microchannel and the second central microchannel can change over at least a portion of the extent of the central channel along the longitudinal axis. While the channel shown in the figure is rectangular in cross section, the cross section of the channel can take on any form (e.g., circular, oval, etc.).

In summary, the device 100 includes the first microchannel 112, the second microchannel 114, and the membrane 120 located at an interface region between the first microchannel 112 and the second microchannel 114. The membrane 120 includes a first side facing toward the first microchannel 112 and a second side facing toward the second microchannel 114. As described in more detail below, the first side typically has cells of a first type thereon and the second side typically has cells of a second type thereon. The membrane 120 separates the first microchannel 112 from the second microchannel 114, and permits the migration of cells, particulates, chemicals, molecules, fluids and/or gases from the first side of cells to the second type of cells.

In some embodiments of this aspect and other aspects described herein, the cells of the first type can be adhered to the first side of the membrane. In some embodiments of this aspect and other aspects described herein, the cells of the second type can be adhered to the second side of the membrane.

In some embodiments, the width of the two channels can be configured to be different, with the centers of the channels aligned or not aligned. In some embodiments, the channel heights, widths and/or cross sections can vary along the longitudinal axis of the devices described herein.

In accordance with some embodiments of the invention, edge portions of the membrane 120 can be secured or fastened to at least one of the first side wall portion 131 and second side wall portion 133. In accordance with some embodiments of the invention, part of the first side wall 131 can extend from the first layer 102 and the membrane 120 can be bonded or adhered to the part of the first side wall 131 that extends from the first layer 102. In accordance with some embodiments of the invention, part of the first side wall 131 can extend from the second layer 104 and the membrane 120 can be bonded or adhered to the part of the first side wall 131 that extends from the second layer 104.

In accordance with some embodiments of the invention, the first side wall portion 131 and/or the second side wall portion 133 can include elastomeric materials.

Figure 1B:
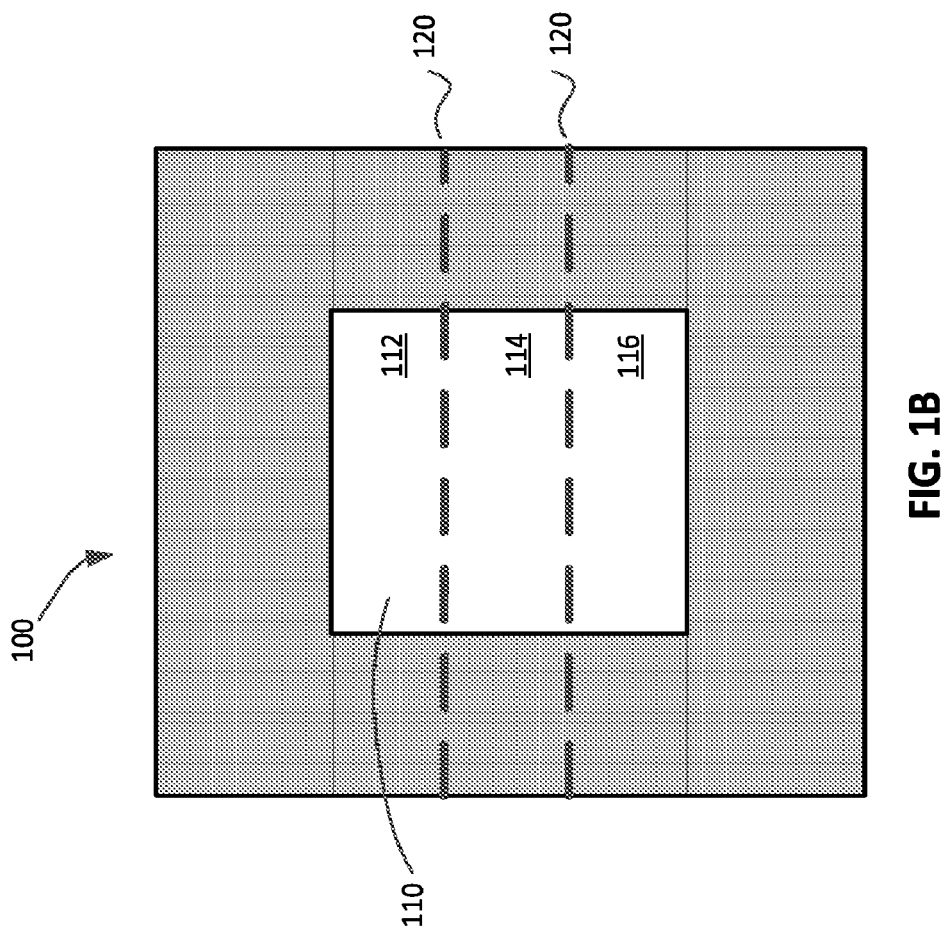
FIG. 1B shows a transverse cross sectional view of a microfluidic device wherein two or more membranes partition the central channel according to some embodiments of the invention.

In accordance with some embodiments as shown in FIG. 1B, the central channel 110 can be divided by two or more membranes 120 into three or more closely apposed parallel central microchannels, 112, 114, 116.

Figure 1C:
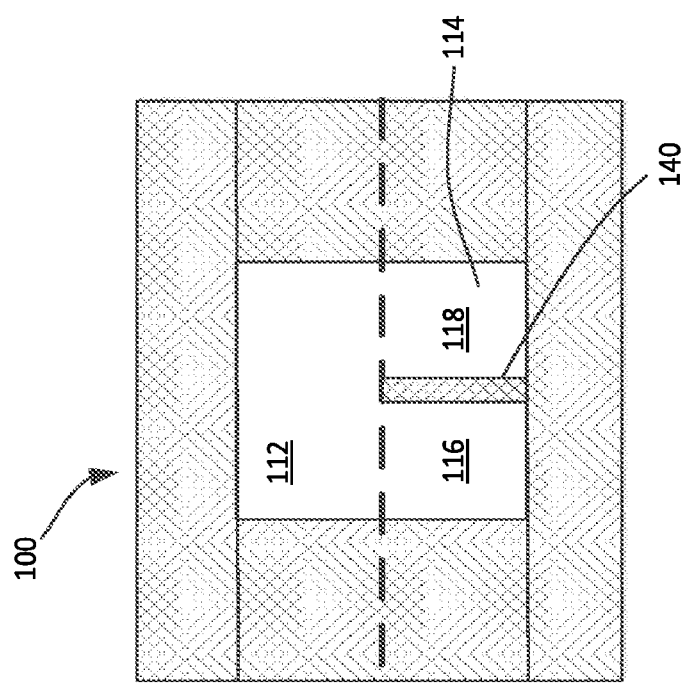
FIG. 1C shows a transverse cross sectional view of a microfluidic device according to some embodiments of the invention.

In accordance with some embodiments of the invention, as shown in FIG. 1C, at least one of the central microchannels 112, 114 can be further divided by one or more partitioning elements 140 to form sub-microchannels 116, 118. The partitioning element 140 can be made of rigid or elastomeric materials. In accordance with some embodiments of the invention, the partitioning element 140 can extend from the second layer 104 to the membrane 120. In accordance with some embodiments of the invention, the one or more of the partitioning elements 140 can be bonded or fastened to the membrane. In accordance with some embodiments of the invention, one or more partitioning elements can be provided in each of the first central microchannel 112 and the second central microchannel 114.

Figure 2A:
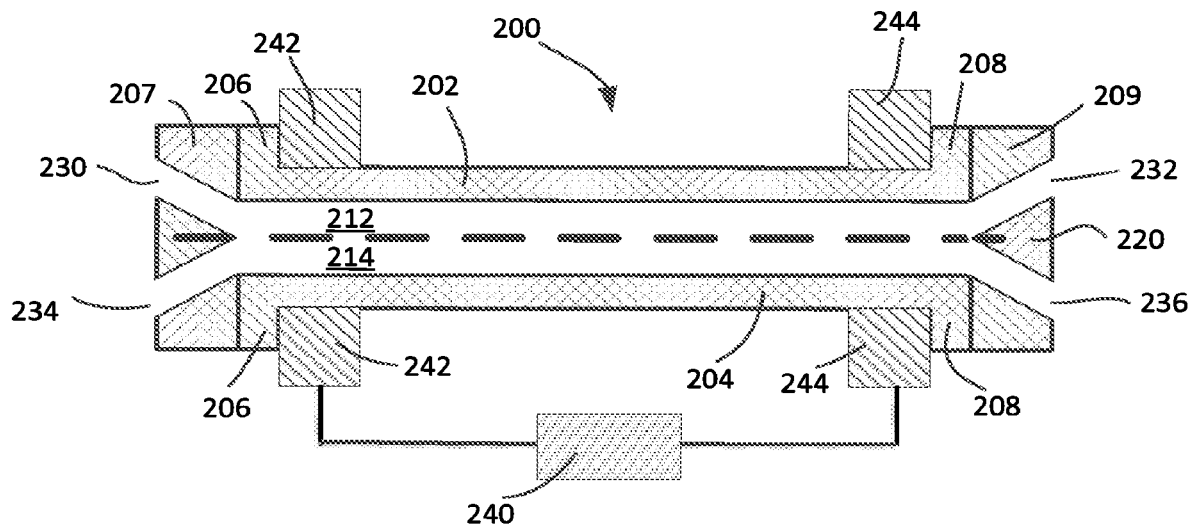
FIG. 2A shows a longitudinal cross sectional view of a microfluidic device according to some embodiments of the invention.
Figure 2B:
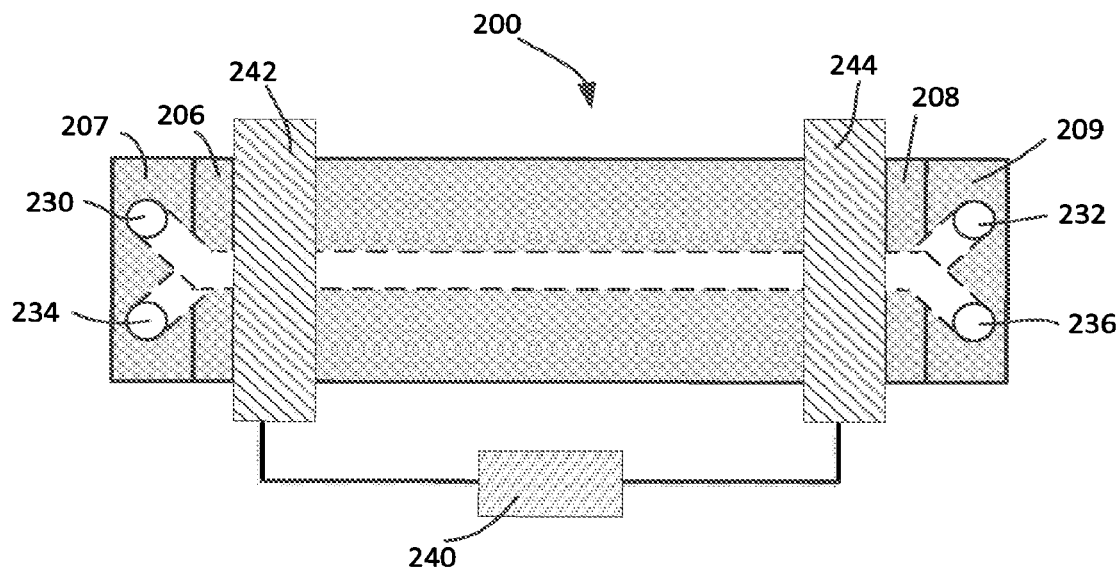
FIG. 2B shows a top view of the microfluidic device.

[Longitudinal stretching] FIG. 2A shows a longitudinal cross sectional view of a microfluidic device 200, similar to the device shown in FIG. 1A, according to some embodiments of the invention. FIG. 2B shows a top view of the microfluidic device 200. While the device 200 shown in FIG. 2B has a straight central channel 210, the central channel 210 can include at least a portion that is curved, S shaped, spiral shaped, or any other non-linear shape. The embodiment shown in FIGS. 2A and 2B can include substantially the same or similar features as in the device shown in FIG. 1A. The body of microfluidic device 200 can include a first elastomer layer 202 and a second elastomer layer 204. Additionally, device 200 can include a first end portion 207 and a second end portion 209 at each end of the central microchannels. The membrane 220 can extend along a plane and be mounted between the first end portion 207 and the second end portion 209. In accordance with some embodiments of the invention, the membrane 220 can be fastened to at least one of the first end portion 207 and the second end portion 209. Device 200 can be further coupled to a membrane modulation device 240 by a first modulation element 242 and optionally a second modulation element 244. The membrane modulation device 240 can be configured to modulate the movement of at least a portion of the membrane 220, causing the membrane 220 to move, stretch, compress or flex in a predefined way. As used herein, the term "engage" or "engagement" indicates any means to directly or indirectly couple an engagement element to a membrane modulation device in order to modulate (e.g., stretch, compress, and/or flex) the membrane 220. In accordance with some embodiments of the invention, the coupling between the engagement element and the membrane modulation device include a physical coupling (e.g., a pin, bead, ridge, flange, etc.). In other embodiments, the coupling between the engagement element and the membrane modulation device does not include a physical coupling (e.g., uses magnetic fields or fluid pressure, instead).

In some embodiments, one or more of the channels can be configured to change direction along the lengths of the channels, for example, using curved or sharp bends. This can provide a means to enable the direction of membrane modulation to vary along the length of the channel.

The first end portion 207 can include a first inlet 230, a second inlet 234 and a first engagement element 206. The second end portion 209 can include a first outlet 232, a second outlet 236 and optionally a second engagement element 208. For fluidic access, the first central microchannel 212 can be connected to the first inlet 230 and the first outlet 232, and the second central microchannel 214 can be connected to the second inlet 234 and the second outlet 236. In some embodiments, the height of the first engagement element 206 can be larger than the height of the first elastomer layer 202 and/or the second elastomer layer 204 such that the first modulation element 242 can apply a force, having at least a component that extends in a direction parallel to the longitudinal axis, on the first engagement element 206. In some embodiments, the first modulation element 242 can apply a force, having at least a component that extends in a direction perpendicular to the longitudinal axis, on the first engagement element 206. In accordance with some embodiments of the invention, optionally, the height of the second engagement element 208 can be larger than the height of the first elastomer layer 202 and/or the second elastomer layer 204 such that the second modulation element 244 can exert a force onto the second engagement element 208. In accordance with some embodiments of the invention, at least one of the engagement elements 206, 208 can include on or more holes, slots, flanges or notches that enables the engagement elements 206, 208 to be coupled to the membrane modulation device 240 by at least one of the modulation elements 242, 244 that can include one or more pins, flanges or tabs to mate with a corresponding hole, slot, flange or notch. In accordance with some embodiments of the invention, the first engagement element 206 and/or the second engagement element 208 can enable a membrane modulation device 240 to apply a force on at least one of the first elastomer layer 202, the second elastomer layer 204 and the membrane 220.

In operation, the membrane modulation device 240 can apply a force that moves the first modulation element 242 and the first engagement element 206, and causes the membrane 220 to modulate (e.g., stretch, compress, and/or flex) along the plane of the membrane 220 and/or transverse to the plane of the membrane. In accordance with some embodiments of the invention, the second modulation element 244 can remain stationary or optionally, the membrane modulation device 240 (or a second membrane modulation device) can apply a force that moves the second modulation element 244 and the second engagement element 208, and causes the membrane 220 to modulate along the plane of the membrane 220. In accordance with some embodiments of the invention, the modulation causes the membrane to expand and/or contract along the plane of the membrane. The membrane 220 can expand or contract in a direction parallel to the longitudinal axis and the direction of fluid flow in the central microchannels. In accordance with some embodiments of the invention, modulation can cause the membrane to move transverse to the plane of the membrane. In accordance with some embodiments of the invention, modulation can cause the membrane to move in more than one direction at the same time.

When a material (e.g., elastomers, flexible materials) is stretched, the material tends to contract in the directions transverse to the stretching direction. When the elastomer layers 202, 204 are stretched in the longitudinal direction, it can also result in strains/modulation in the transverse direction on the membrane.

Figure 2C:
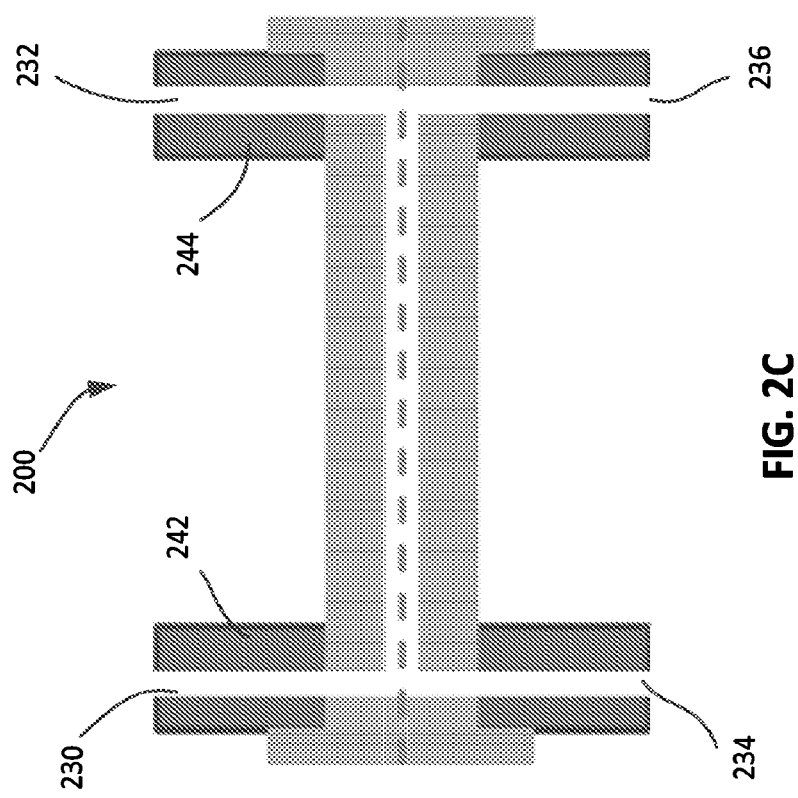
FIG. 2C shows a longitudinal cross sectional view of a microfluidic device according to some embodiments of the invention.

FIG. 2C shows a longitudinal cross sectional view of a microfluidic device 200 according to some embodiments of the invention. The embodiment shown in FIG. 2C is substantially the same as the device shown in FIGS. 2A and 2B, except that the inlets 230A, 234A and outlets 232A, 236A can be formed inside the modulation elements 242, 244 and be aligned with the inlets 230, 234 and the outlets 232, 236 in microfluidic device 200.

Device 200 can be constructed by assembling each component after they are fabricated. The choice of materials is discussed in detail in the section on manufacture. In accordance with some embodiments of the invention, each of the components can be fabricated using photolithography, casting (e.g., solvent casting), stamping, molding (e.g., injection molding, compression molding), machining (e.g., mechanical cutting, laser cutting, die cutting, ablation, and etching), extruding, embossing or solid free-form fabrication technologies such as three dimensional printing and stereolithography, or any combinations thereof. In accordance with some embodiments, the components can be fabricated using manufacturing technologies that provide the desired surface finish on the surfaces of the component. In accordance with some embodiments, a very smooth, biocompatible surface, for example, such as that produced by molding and casting processes can be used. In accordance with some embodiments of the invention, less smooth and more textured surfaces, for example, such as those produced by machining, laser cutting, casting, stamping and embossing can used. Methods to fabricate the membranes are disclosed in detail in the section on membranes.

The components of the microfluidic device 200 can be held together to form the device by thread forming screws, nuts and bolts, clips, clamps, pins, ultrasonic welding, solvent-assisted bonding, heat staking, laser welding, snap fits, glue (e.g., biocompatible, low absorption adhesives such as acrylates), surface treatment (e.g., oxygen plasma), or any combinations thereof. During the assembly, a microscope can be used to assist with the alignment of the components.

Figure 3B:
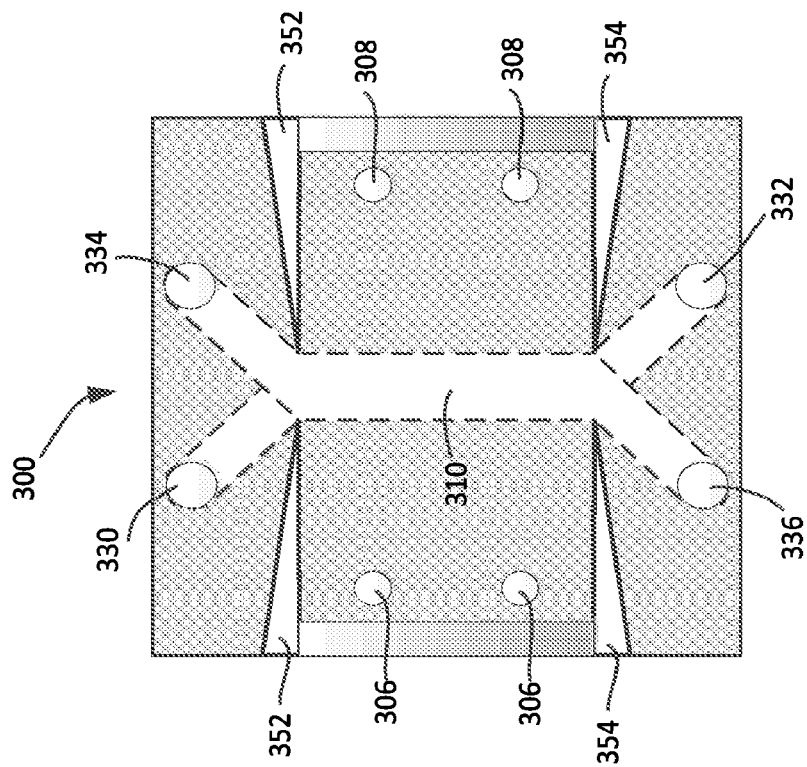
FIG. 3B shows a top-down view of the microfluidic device.
Figure 3A:
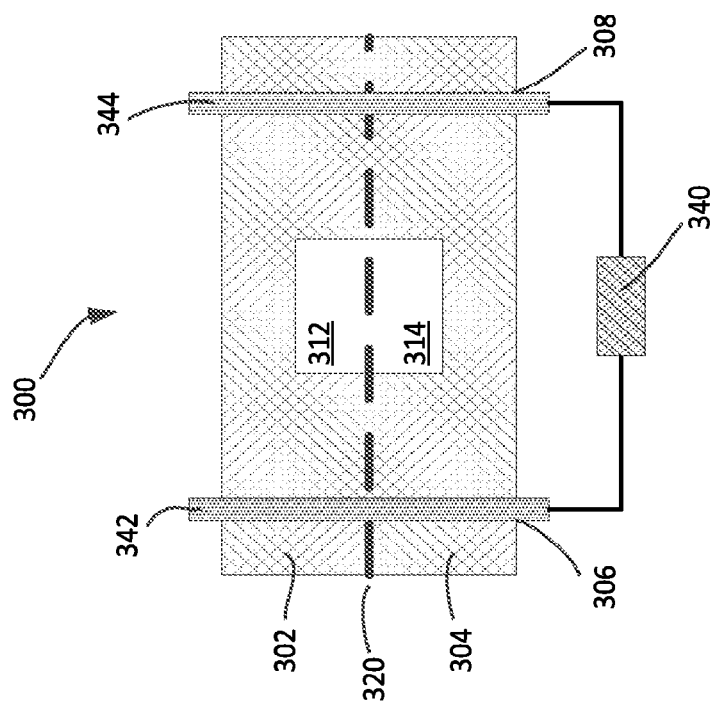
FIG. 3A shows a diagrammatic transverse cross sectional view of a microfluidic device according to some embodiments of the invention.

[Molded elastomer films for transverse stretching] FIG. 3A shows a transverse cross sectional view of a microfluidic device 300 according to some embodiments of the invention. FIG. 3B shows a top-down view of the device 300. The embodiment shown in FIGS. 3A and 3B can include substantially the same or similar features as in the device shown in FIG. 1A. The body of the microfluidic device 300 can include a first elastomer layer 302 and a second elastomer layer 304. Additionally, device 300 can include a membrane layer having a membrane portion 320, a first engagement element 306 and optionally a second engagement element 308 at each side of the central microchannels 312, 314. Device 300 can be further coupled to a membrane modulation device 340 by a first modulation element 342 and optionally a second modulation element 344.

The first elastomer layer 302 can include the first central microchannel 312 on a first side of the membrane 320. The second elastomer layer 304 can include the second central microchannel 314 on a second side of the membrane 320. The membrane layer 320 is sandwiched between the first elastomer layer 302 and the second elastomer layer 304. The engagement elements 306, 308 can include one or more holes, beads, ridges, flanges, clamps, slots or notches. The modulation elements 342, 344 can include one or more pins, posts, bars, flanges, jaws or clamps that can engage one or more holes, beads, ridges, flanges, clamps, slots or notches that form the engagement elements 306, 308. The modulation device 340 can be coupled to the first modulation element 342 and optionally the second modulation element 344. In order to minimize shape distortion of the inlets 330, 334 and outlets 332, 336 during mechanical modulation, the strains on the inlets 330, 334 and outlets 332, 336 can be minimized by isolating the inlets and outlets from the strain associated with modulation. Elastomer layers 302, 304 can include cut-outs 352 and 354 that enable the elastomer layers 302, 304 and the membrane 320 to stretch while minimizing the stress and/or strain applied to the inlets 330, 334 and outlets 332, 336. The size and shape of the cutouts 352 and 354 can be determined by strain simulations using software (e.g., Comsol, Abaqus). In accordance with some embodiments of the invention, the cut-outs 352, 354 can be slits that extend parallel to direction of the strain (e.g., transverse to longitudinal axis of the central channel 310). Some examples and aspects of systems and methods for mechanical stretch actuation and imparting strains to microfluidic devices, including microfluidic devices with microchannels and/or membranes with cells disposed thereon, are provided in the related discussions below in the context of FIGS. 16 through 29.

In accordance with some embodiments of the invention, the engagement elements 306, 308 can each include one or more holes 306, 308, and the modulation elements 342, 344 can include one or more pins, that extend through the holes 306, 308 in the layers of the device 300. The pin can engage the elastomer layers 302, 304 and the membrane 320, enabling the membrane modulation device 340 to modulate the membrane 320.

Figure 3D:
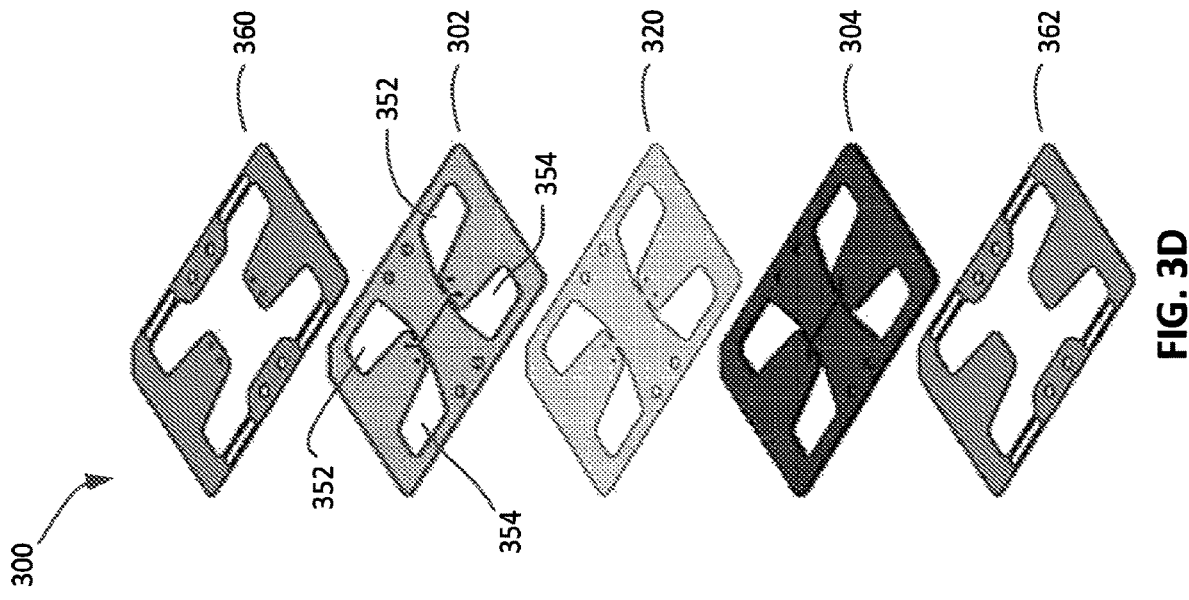
FIG. 3D shows an exploded, diagrammatic view of a microfluidic device 300, same as the device shown in FIG. 3C, according to some embodiments of the invention.
Figure 3C:
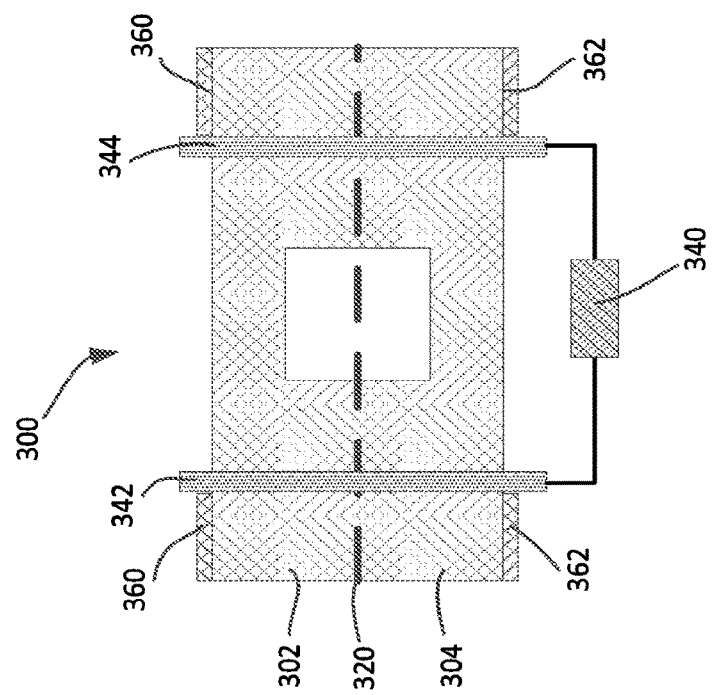
FIG. 3C shows a diagrammatic transverse cross sectional view of a microfluidic device according to some embodiments of the invention.

In accordance with some embodiments of the invention as shown in FIG. 3C, the device 300 can further include a first rigid layer 360 on top of the first elastomer layer 302, and a second rigid layer 362 below the second elastomer layer 304. These rigid layers 360, 362 can provide structural support. FIG. 3D shows an exploded, diagrammatic view of a microfluidic device 300 that is similar to the device shown in FIG. 3C. As shown in FIG. 3D, the cut-outs 352, 354 can be common to some or all layers 360, 302, 320, 304 and 362, in order to minimize shape distortion of the inlets and outlets during mechanical modulation.

In operation, the membrane modulation device 340 moves the first modulation element 342 and the first engagement element 306, causing modulation of the elastomer layers 302, 304 and the membrane 320. In accordance with some embodiments, the second engagement element 308 can be stationary or fixed to a non-moving object. In accordance with some embodiments of the invention, the membrane modulation device 340 (or a second membrane modulation device) can move the second modulation element 344 and the second engagement element 308, causing modulation of the elastomer layers 302, 304 and the membrane 320. The membrane 320 can be modulated (e.g., expanded, contracted, and/or flexed) in a direction transverse to the direction of fluid flow in the central microchannels.

Figure 3E:
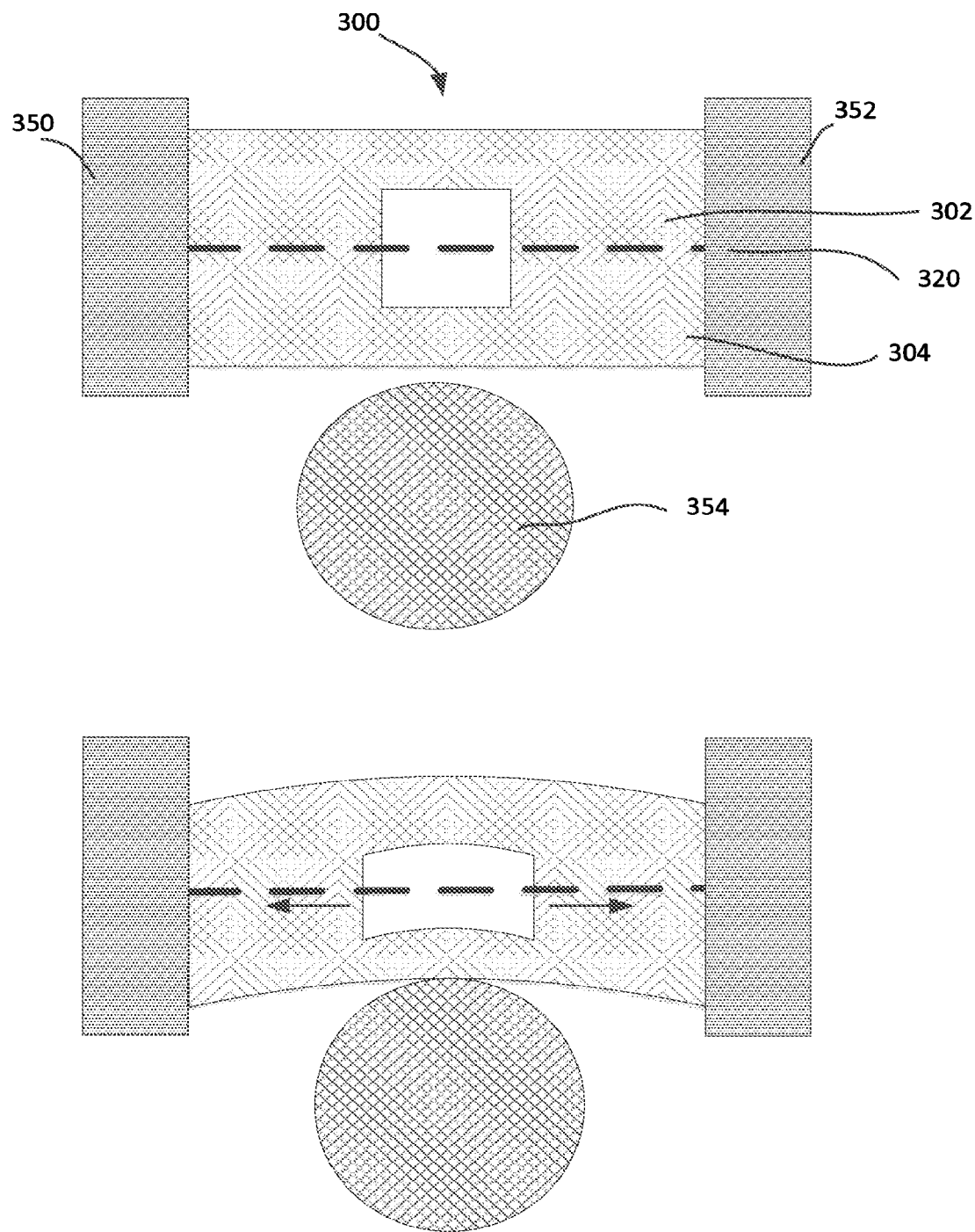
FIG. 3E shows a transverse cross sectional view of a microfluidic device during its operation according to some embodiments of the invention.
Figure 3F:
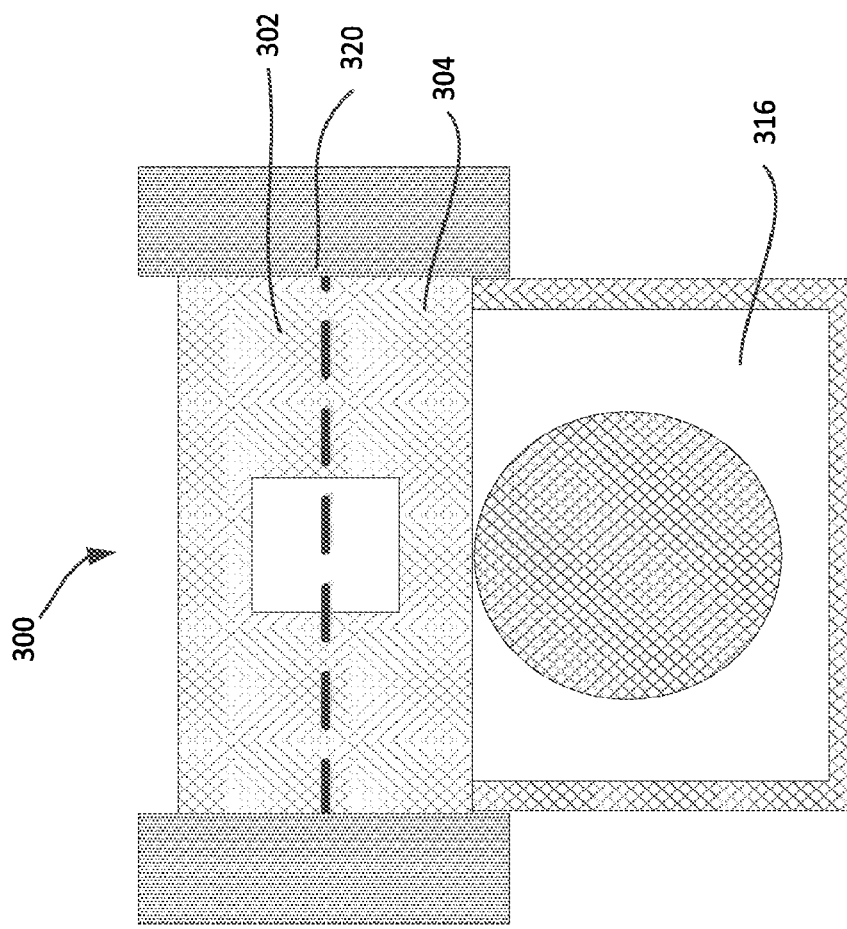
FIG. 3F shows a transverse cross sectional view of a microfluidic device according to some embodiments of the invention.

In accordance with some embodiments of the invention, as shown in FIG. 3E, the two opposing sides of the elastomer layers 302, 304 can be mounted or fastened to rigid, non-moving elements 350, 352. A load element 354 that can be positioned either above the elastomer layer 302 or below the elastomer layer 304 can be used as a modulation element. The load element 354 can be in the form of a ball, a block, a slab, a torus, a ring, or a shape designed to provide strain in one or more particular regions. When the load element 354 applies a force on the elastomer layer 302 or 304 in a direction transverse to the membrane 320, side walls of the elastomer layers 302, 304 deform, flexing outward, generating a strain on the membrane 320 in a direction transverse to fluid flow in the central microchannels. The load element 354 can also cause the membrane to move or become curved either due to the upward pressure applied to the lower microchannel in elastomer layer 304 or by causing elastomer layer 304 to apply a force on the membrane. The shape of the area where the load is applied can be defined based on the shape/size of the central microchannels and how the device is mounted. In accordance with some embodiments of the invention, as shown in FIG. 3F, the device 300 can include an operating channel 316 that is connected to a pressure generation device (not shown) that can generate a positive pressure, vacuum or suction. When a vacuum is applied to the operating channel 316, the elastomer layers 302, 304 deform, generating a strain on the membrane in a direction transverse to fluid flow in the central microchannels.

At least one of the elastomer layers 302, 304 can include a thin and transparent portion above or below the central microchannels 312, 314 to allow non-invasive external observation of cellular activities using a microscope and various microscopy techniques such as surface plasmon resonance spectroscopy.

The different layers of device 300 can be fabricated by machining the features into each layer. The machining methods can include, but not limited to, mechanical cutting, laser cutting, etching or any combinations thereof. Alternatively, general molding techniques including, but not limited to, photolithography, casting (e.g., solvent casting), stamping, injection molding, compression molding, extruding, embossing, or any combinations thereof, can be used to fabricate one or more of the layers. Solid free-form fabrication technologies such as three dimensional printing and stereolithography can also be used to fabricate one or more of the layers.

The layers can be held together to form the device by thread forming screws, nuts and bolts, clips, clamps, pins, ultrasonic welding, solvent-assisted bonding, heat staking, laser welding, snap fits, glue (e.g., biocompatible, low absorption adhesives such as acrylates) and/or surface treatment (e.g., oxygen plasma) or a combination thereof. During the assembly, a microscope can be used to assist with the alignment of the components.

[Laminated elastomer films for transverse stretching] FIG. 3G shows a transverse cross sectional view of a microfluidic device 300 according to some embodiments of the invention. The embodiment shown in FIG. 3G is substantially the same as the device shown in FIG. 3A, and the operation can be similar for both devices. The body of the microfluidic device 300 can include a first sealing layer 301, a first lamination layer 303 having a first microchannel aperture therein, one or more membranes 320, a second lamination layer 305 having a second microchannel aperture therein, and a second sealing layer 307.

The membrane layer 320 is sandwiched between the first lamination layer 303 and the second lamination layer 305. The first sealing layer 301 can be disposed on top of and in contact with the first lamination layer 303 to provide a top closure of the first microchannel aperture, forming a first central microchannel 312 on a first side of the membrane 320. The second sealing layer 307 can be disposed on the bottom of and in contact with the second lamination layer 305 to provide a bottom closure of the second microchannel aperture, forming a second central microchannel 314 on a second side of the membrane 320. In accordance with some embodiments of the invention, additional sealing layers and membrane layers can be provided to form additional central microchannels.

At least one of the sealing layers 301, 307 can include a thin and transparent portion above or below the central microchannels 312, 314 to allow non-invasive external observation of cellular activities using a microscope and various microscopy techniques such as surface plasmon resonance spectroscopy.

In accordance with some embodiments of the invention, at least one of the lamination layers 303, 305 can include an optically clear adhesive layer. One or more of the adhesive layers can be pressure sensitive adhesives (PSAs) based on materials such as acrylic, ethylene-vinyl acetate, nitriles, and vinyl ethers. In accordance with some embodiments of the invention, at least one of the sealing layers 301, 307 can include polyurethane. In some aspects, an adhesive layer can include at least one of a thermal adhesive, a light-sensitive adhesive, or an adhesive with solvent or solvent-based bonding.

Device 300 can further include one or more engagement elements, and the membrane 320 can be modulated in a similar manner as described for the embodiment shown in FIG. 3A.

Figure 3I:
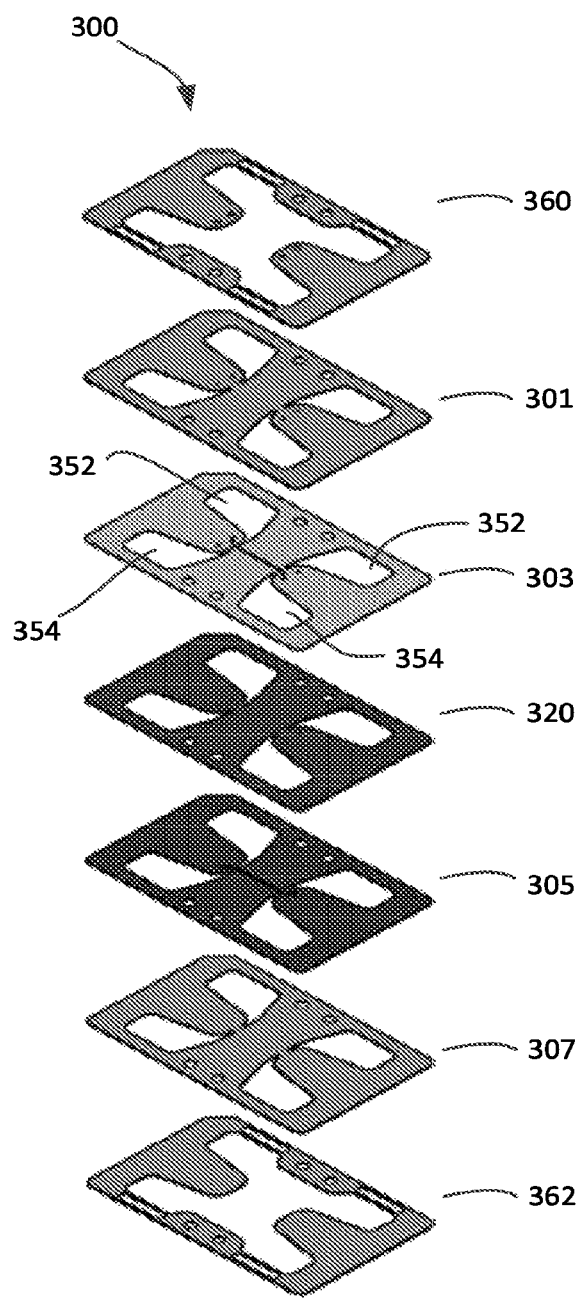
FIG. 3I shows an exploded, diagrammatic view of a microfluidic device 300, same as the device shown in FIG. 3H, according to some embodiments of the invention.

In accordance with some embodiments of the invention, as shown in FIG. 3H, the device 300 can further include a first rigid layer 360 on top of the first sealing layer 301, and a second rigid layer 362 below the second sealing layer 307. These rigid layers 360, 362 can provide structural support. In some embodiments, one or more of the rigid layers can also comprise one or more features that allow for precise alignment with other layers in the device 300 or with an external device or instrument with which the device 300 is adapted to engage. FIG. 3I shows an exploded, diagrammatic view of a microfluidic device 300 that is similar to the device shown in FIG. 3H. As shown in FIG. 3I, the cut-outs 352, 354 can be common to some or all layers 360, 301, 303, 320, 305, 307 and 362, in order to minimize shape distortion of the inlets and outlets during mechanical modulation.

The different layers of device 300 can be fabricated by first producing polymer layers through methods such as casting, spin-coating or extruding, and then machining the features into each layer. The machining methods can include, but not limited to, mechanical cutting, laser cutting, etching or any combinations thereof. In accordance with some embodiments of the invention, the microchannel aperture can be formed in the lamination layers 303, 305 by laser cutting.

The layers can then be laminated together with or without adhesives to form the device 300. Thin film-based polymeric laminate technology is well known in the art and is not discussed in detail herein (see e.g., Weigl, B, H., et al., Biomedical Microdevices 2001, 3: 267-274). The layers of device 300 can also be held together using thread forming screws, nuts and bolts, clips, clamps, pins, ultrasonic welding, solvent-assisted bonding, heat staking, laser welding, snap fits, glue (e.g., biocompatible, low absorption adhesives such as acrylates) and/or surface treatment (e.g., oxygen plasma). During the assembly, a microscope can be used to assist with the alignment of the components.

Figure 3J:
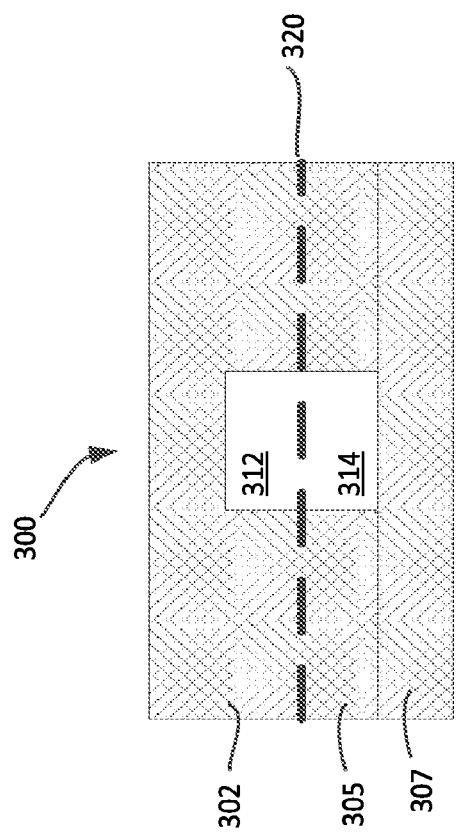
FIG. 3J shows a transverse cross sectional view of a microfluidic device according to some embodiments of the invention.

[Hybrid] FIG. 3J shows a transverse cross sectional view of a microfluidic device 300 according to some embodiments of the invention. Device 300 can include a membrane layer 320, an elastomer layer 302 having a first central microchannel 312 adjacent to a first side of the membrane 320, a lamination layer 305 having a microchannel aperture therein, and a sealing layer 307 forming a closure for a second central microchannel 314 on a second side of the membrane 320. The membrane layer 320 can be sandwiched between the first elastomer layer 302 and the lamination layer 305.

Device 300 can further include one or more engagement elements, and the membrane 320 can be modulated in a similar manner as described for the embodiment shown in FIGS. 2A, 2B, 2C, 3A, 3C, 3D, 3E, 3F, 3I and 4.

In accordance to some embodiments of the invention, the elastomer layer 302 can be fabricated by machining the features into the layer. The machining methods can include, but not limited to, mechanical cutting, laser cutting, die cutting, ablation, etching or any combinations thereof. Alternatively, general molding techniques including, but not limited to, photolithography, casting (e.g., solvent casting), stamping, injection molding, compression molding, extruding, embossing, or any combinations thereof, can be used to fabricate the elastomer layer 302. Solid free-form fabrication technologies such as three-dimensional printing and stereolithography can also be used to fabricate layer 302.

The lamination layer 305 can be fabricated by first producing polymer layer through methods such as casting, spin-coating or extruding, and then machining the features into the layer. The machining methods can include, but not limited to, mechanical cutting, laser cutting, etching or any combinations thereof.

The layers can then be bonded together to form the device by lamination, thread forming screws, nuts and bolts, clips, clamps, pins, ultrasonic welding, solvent-assisted bonding, heat staking, laser welding, snap fits, glue (e.g., biocompatible, low absorption adhesives such as acrylates), surface treatment (e.g., oxygen plasma), or any combinations thereof. During the assembly, a microscope can be used to assist with the alignment of the components.

Figure 4:
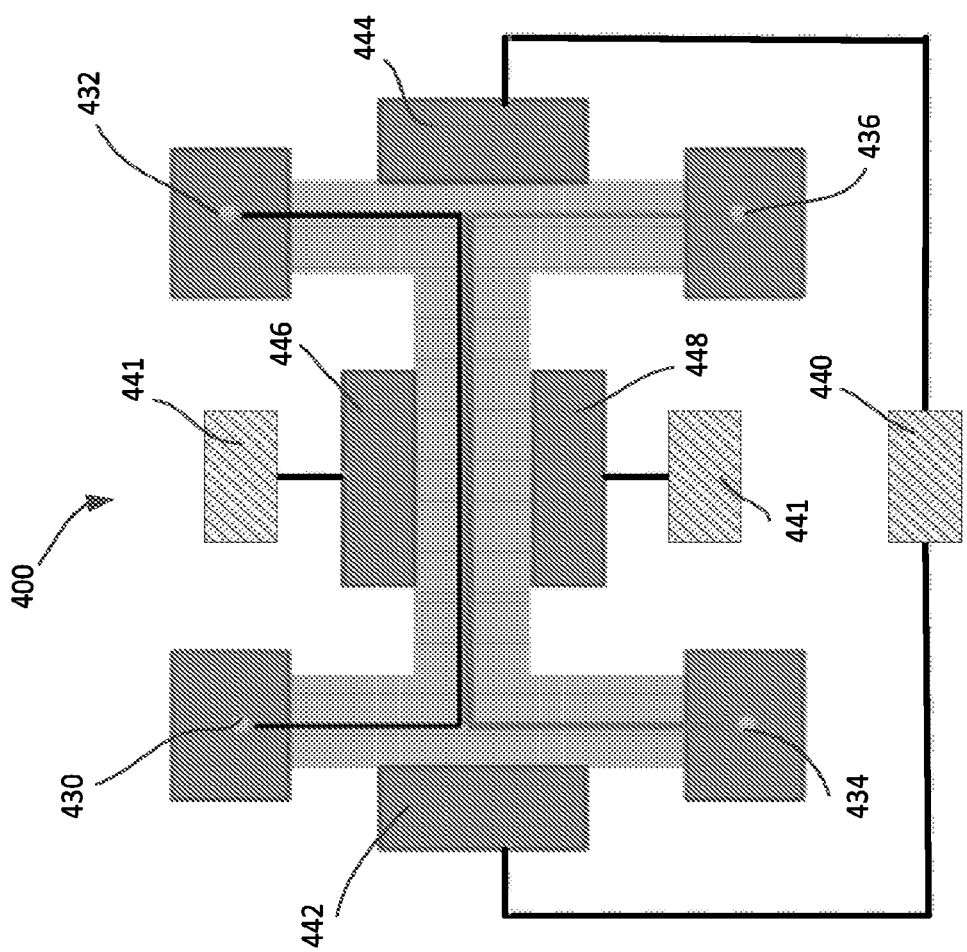
FIG. 4 shows a cross sectional view of a microfluidic device according to some embodiments of the invention.

[Multidirectional stretching] FIG. 4 shows a top-down view of a microfluidic device 400 according to some embodiments of the invention. The body of microfluidic device 400 can include a first layer 402 and a second layer 404 that form a fluidic channel 410. Device 400 can include a first longitudinal modulation element 442 and optionally a second longitudinal modulation element 444 positioned at substantially the ends of the central microchannels (not shown), and a first transverse modulation element 446 and optionally a second transverse modulation element 448 on each side of the central microchannel. The longitudinal modulation elements 442, 444 can be coupled to a first modulation device 440, while optionally, the modulation elements 446, 448 can be coupled to the first modulation device 440 or a second modulation device 441. Device 400 can further include a first inlet 430, a first outlet 432, a second inlet 434 and a second outlet 436.

In a manner similar to that shown in FIG. 2A, the first membrane modulation device 440 can engage the microfluidic device 400 and modulate the membrane in a direction parallel to the longitudinal axis and the direction of fluid flow in the central microchannels. In a manner similar to that shown in FIGS. 3A, 3B, 3C, and 3D, the second membrane modulation device 441 can engage the microfluidic device 400 and modulate the membrane in a direction transverse to the longitudinal axis and the direction of fluid flow in the central microchannel. In accordance with some embodiments of the invention, the membrane can be modulated simultaneously in both directions parallel and transverse to the longitudinal axis and the direction of fluid flow in the central microchannels.

Device 400 can be constructed by assembling each component after they are fabricated. In accordance with some embodiments of the invention, each of the components can be fabricated by photolithography, casting such as solvent casting, stamping, molding (e.g., injection molding, compression molding), machining (e.g., mechanical cutting), laser cutting, etching, extruding, embossing or solid free-form fabrication technologies such as three dimensional printing and stereolithography, or any combinations thereof. The fabrication of membranes is disclosed in details in the section on membranes.

The components of the microfluidic device 400 can be held together to form the device by thread forming screws, nuts and bolts, clips, clamps, pins, ultrasonic welding, solvent-assisted bonding, heat staking, laser welding, snap fits, glue (e.g., biocompatible, low absorption adhesives such as acrylates), surface treatment (e.g., oxygen plasma), or any combinations thereof. During the assembly, a microscope can be used to assist with the alignment of the components.

Figure 5:
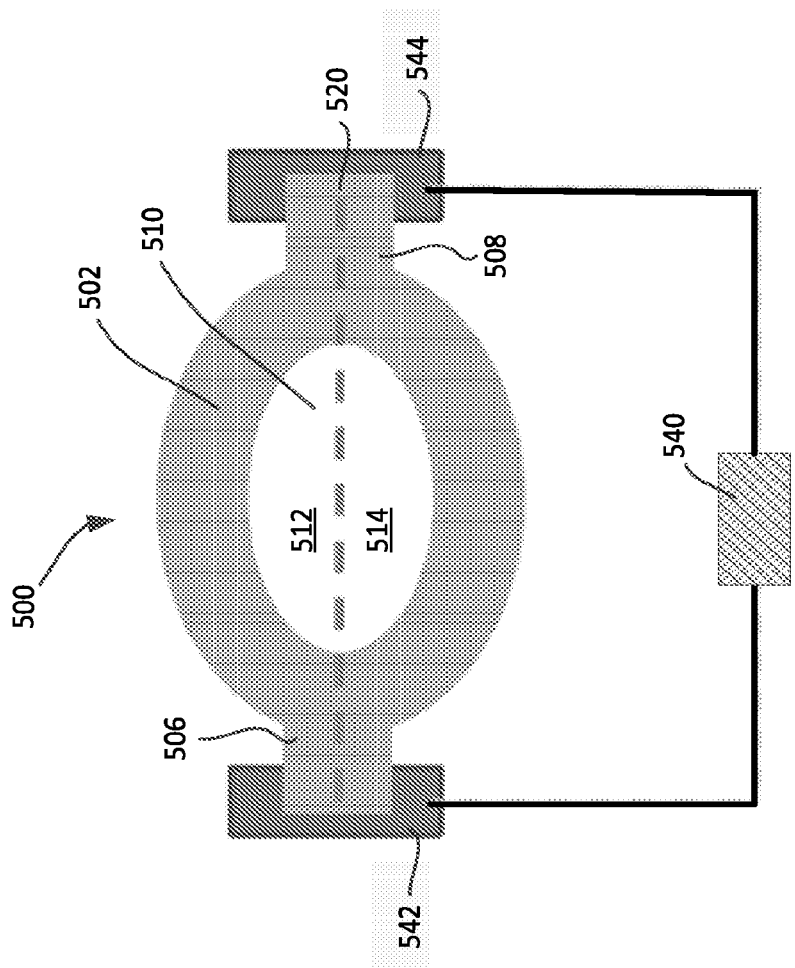
FIG. 5 shows a transverse cross sectional view of a microfluidic device according to some embodiments of the invention.

[Half pipe] FIG. 5 shows a transverse cross sectional view of a microfluidic device 500 according to some embodiments of the invention. The body of the microfluidic device 500 can include a curved wall 502 that forms a completely or partially circular, oval, or elliptical central channel 510. The microfluidic device 500 can further include one or more membranes 520 that extend across the central microchannel 510 dividing the central channel 510 into two or more microchannels 512, 514.

In accordance with some embodiments of the invention, edge portions of the membrane 520 can be bonded or fastened to diametrically opposed portions of the curved wall 502. In accordance with some embodiments of the invention, a first curved wall portion can be bonded or secured to a first side of the membrane and a second curved wall portion can be bonded or secured to a second side of the membrane. In accordance with some embodiments of the invention, the membrane 520 and/or the curved wall 502 can include one or more engagement elements 506, 508 that can be engaged by one or more modulation elements 542, 544 to enable a membrane modulation device 540 to modulate the membrane 520. In accordance with some embodiments of the invention, the curved wall 502 can include a first engagement element 506 and a second engagement element 508. At least one of engagement elements 506, 508 can be coupled to the membrane 520 such that modulation of at least one of the engagement elements 506, 508 causes the membrane 520 to expand, contract and/or flex in a predefined way. In a manner similar to the other embodiments, the engagement elements can include one or more holes, beads, ridges, flanges, notches, slots, clamps or couplings that enable one or more modulation elements to be coupled to the membrane and/or the curved wall 502.

In accordance with some embodiments of the invention, the curved wall portion 502 can include an elastomeric material. The curved wall 502 and the membrane 520 can be extruded together. Two or more laser beams can then be focused onto the membrane 520 to ablate materials precisely from designated locations, and generate pores of predefined spacing and dimensions. Because the curved wall 502 is out of the focal point of the lasers, it can remain intact. In accordance with some embodiments of the invention, the lasers can be excimer lasers.

Figure 6:
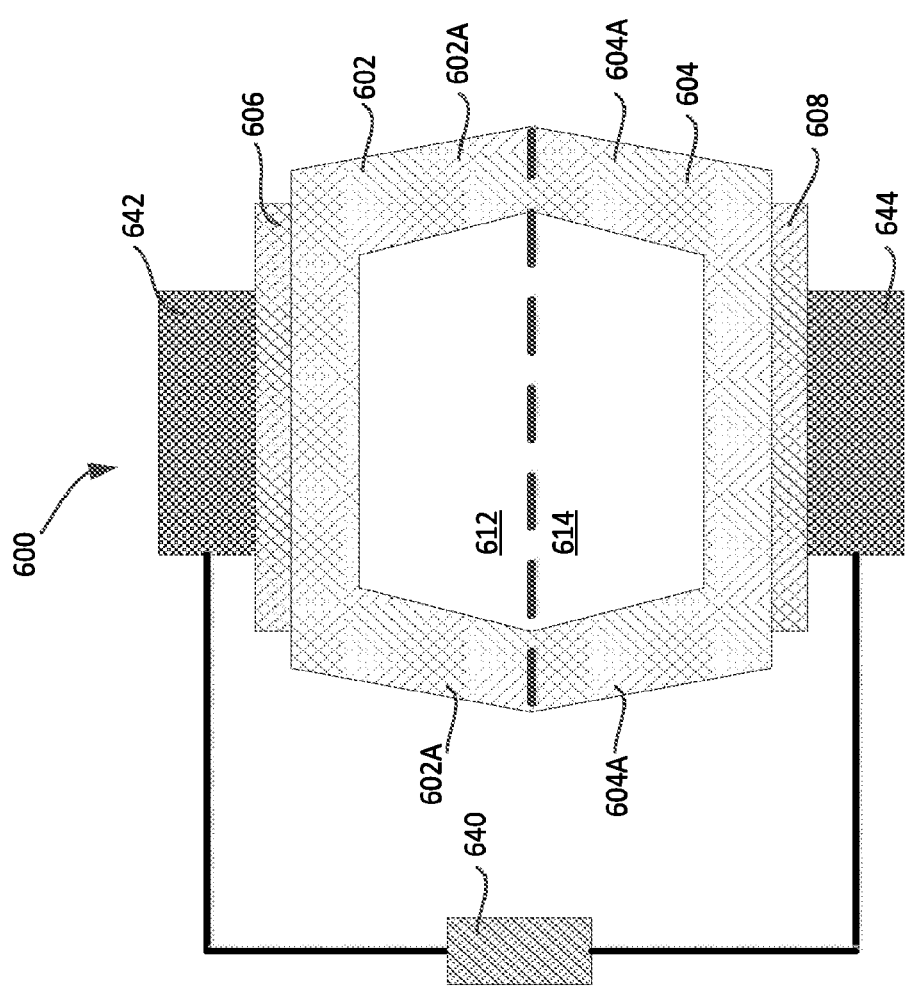
FIG. 6 shows a transverse cross sectional view of a microfluidic device according to some embodiments of the invention.

[Compression] FIG. 6 shows a transverse cross sectional view of a microfluidic device 600, according to some embodiments of the invention. Device 600 can include a first elastomer layer 602, a second elastomer layer 604 and a membrane layer 620. The membrane layer 620 and the first elastomer layer 602 define the first central microchannel 612. The membrane layer 620 and the second elastomer layer 604 define the second central microchannel 614. Device 600 can include a first engagement element 606 and optionally a second engagement element 608. Device 600 can be further coupled to a membrane modulation device 640 by a first modulation element 642 and optionally a second modulation element 644.

The first elastomer layer 602 can include a first side portion 602A, and the second elastomer layer 604 can include a second side portion 604A. The first side portion 602A and the second side portion 604A can be connected together at an angle. The angle can be between 0° to 180°. The membrane layer 620 can be connected to or sandwiched between the side portions 602A, 604A. The first engagement element 606 can be above and in contact with the first elastomer layer 602. Optionally, the second engagement element 608 can be below and in contact with the second elastomer layer 604.

In operation, the membrane modulation device 640 engages device 600 by applying a force onto the first engagement element 606 through the first modulation element 642, while device 600 is positioned against a non-moving rigid surface. When the modulation device 640 is compressing the elastomer body portion 602, the membrane 620 expands. The compression force causes layers 602, 604 to become closer together, causing the side portions 602A, 604A (which can be at an angle greater than 90 degrees to the layers 602, 604) to be pushed outward, and the membrane 620 to stretch. In an alternative embodiment, both modulation elements 642, 644 can operate simultaneously. The direction of membrane modulation can be transverse to and/or along the longitudinal axis and the direction of fluid flow in the central microchannels.

The engagement elements 606, 608 can be made of rigid materials including stiff elastomeric materials, acrylic, polystyrene, polypropylene, polycarbonate, glass, epoxy fiberglass, ceramic and metal. They can be in a form selected from a group consisting of a plate, a slide, a block, a slab, a disc or any combinations thereof. Without wishing to be bound by theory, the engagement elements 606, 608 enable uniform distribution of pressure on the elastomer layers 602, 604 exerted by the membrane modulation device 640.

In accordance with some embodiments of the invention, the elastomer layers 602, 604 and the membrane layer 620 can be extruded together. Two or more laser beams can then be focused onto the membrane 620 to ablate materials precisely from designated locations, and thus generating pores of desirable density and dimensions. In accordance with some embodiments of the invention, the lasers can be excimer lasers. Because elastomer layers 602, 604 are out of the focal point of the lasers, they can remain intact. In accordance with some embodiments of the invention, the layers 602, 604 can be fabricated by photolithography, casting (e.g., solvent casting), stamping, molding (e.g., injection molding, compression molding), machining including (e.g., mechanical cutting, laser cutting, etching), extrusion, embossing or solid free-form fabrication technologies such as three dimensional printing and stereolithography, or any combinations thereof.

The components of the microfluidic device 600 can then be bonded together to form the device by thread forming screws, nuts and bolts, clips, clamps, pins, ultrasonic welding, solvent-assisted bonding, heat staking, laser welding, snap fits, glue (e.g., biocompatible, low absorption adhesives such as acrylates) and/or surface treatment (e.g., oxygen plasma). During the assembly, a microscope can be used to assist with the alignment of the components.

Figure 7A:
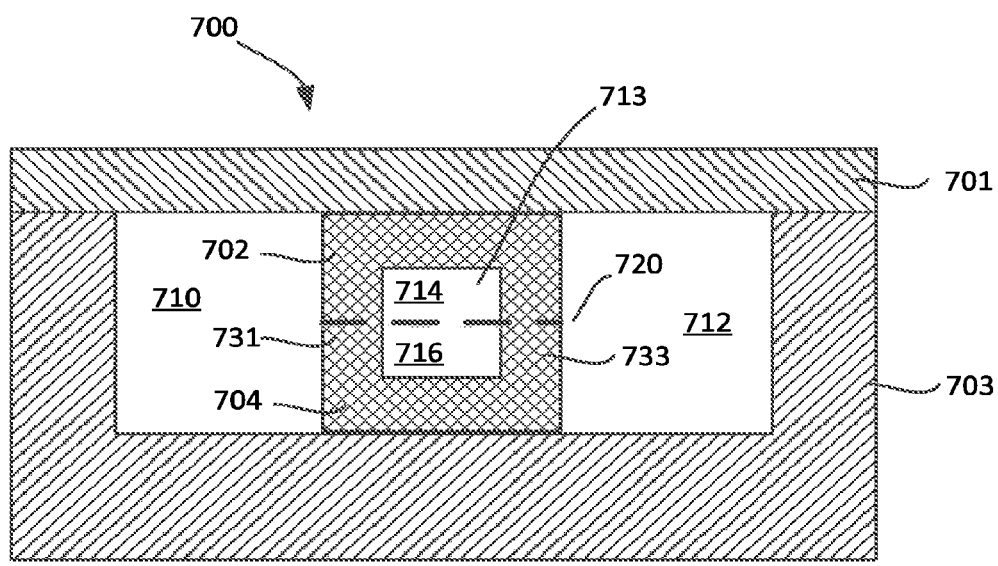
FIG. 7A shows a transverse cross sectional view of a microfluidic device according to some embodiments of the invention.
Figure 7B:
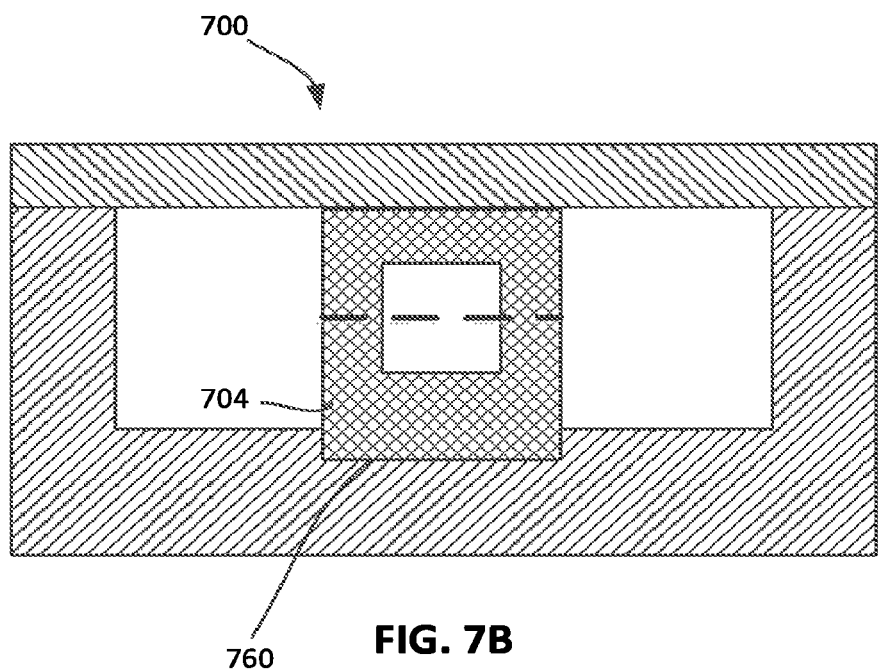
FIG. 7B shows a transverse cross sectional view of a microfluidic device according to some embodiments of the invention.

[Tube (pneumatic)] FIG. 7A shows a cross sectional view of a microfluidic device 700 according to some embodiments of the invention. The embodiment shown in FIGS. 7A, 7B, 7C can include substantially the same or similar features as in the device shown in FIG. 1A. Device 700 can include a substantially rigid body, for example, formed by a rigid layer 701 bonded to a rigid body portion 703. The rigid layer 701 and the rigid body portion 703 can form an inner chamber that encloses a flexible microfluidic device 700A formed from an elastomeric material. The flexible microfluidic device 700A can include a first elastomer layer 702, a second elastomer layer 704, and a membrane layer 720. The first elastomer layer 702 and the second elastomer layer 704 define a central channel 713. The membrane layer 720 can be mounted or fastened to the side walls 731, 733 of the flexible microfluidic device 700A and partition the central channel 713 into a first central microchannel 714 and a second central microchannel 716. When the flexible microfluidic device 700A is positioned in the inner chamber of the rigid body, at least one of a first operating microchannel 710, and a second operating microchannel 712 can be defined by the space between the walls of the inner chamber and the outer walls of the flexible microfluidic device 700A. In accordance with some embodiments of the invention, only one operating channel, for example, the first operating microchannel 710 can be created. In accordance with some embodiments of the invention, as shown in FIGS. 7A and 7B, the flexible microfluidic device 700A can be centrally located with the inner chamber such that a first operating microchannel 710, and a second operating microchannel 712 can be created. The operating microchannels 710, 712 can each be connected to a vacuum port and a vent port (not shown). In accordance with some embodiments of the invention, a single operating channel can be defined by space adjacent to three or more sides of the flexible microfluidic device 700A (e.g., the microfluidic device 700A can be supported above the bottom of the inner chamber). The inner chamber can be connected to a vacuum source (or a positive pressure source) and the side walls 731 and 733 can be configured to be more flexible than the top and bottom walls of the first elastomer layer 702 and the second elastomer layer 704 such that when either positive or negative fluid pressure is applied to inner chamber, the side walls 731, 733 flex inwardly or outwardly, respectively, causing the membrane to compress or stretch.

The first operating microchannel 710 can be separated from the central microchannels by a first elastomer wall 731. The second operating microchannel 712 can be separated from the central microchannels by a second elastomer wall 733. In accordance with some embodiments of the invention, as shown in FIG. 7B, the rigid body portion can include a notch 760 in which the second elastomer layer 704 is mounted to restrain the flexible microfluidic device 700A from moving.

In operation, the operating microchannel 710 and/or 712 can each include a port that can be connected to a pressure generation device (not shown) that can generate a positive pressure or negative pressure (e.g., vacuum or suction) in one or both of the operating microchannels 710, 712. In accordance with some embodiments of the invention, the pressure differential between the operating microchannels 710, 712 and the central channel 713 can be generated by creating a vacuum in the operating microchannels 710, 712. The pressure differential causes the walls 731, 733 to bend or bulge outward and applies a strain on the membrane 720 causing it to stretch along the plane of the membrane.

When the negative pressure is no longer applied (and/or positive pressure is applied to the operating microchannels), the pressure differential between the operating microchannels 710, 712 and the central microchannels decreases and the walls 731, 733 retract elastically toward their neutral position. During operation, the negative pressure can be alternately applied in predefined time intervals to cause continuous modulation of the membrane along its plane.

The pressure differential can be created in a number of ways to achieve the goal of modulating the membrane. As stated above, a negative pressure can be applied to one or more of the operating microchannels 710, 712. Alternatively, the membrane can be pre-loaded or pre-stressed to be in a stretched state prior to fluid pressure being applied (and optionally, the walls 731, 733 can be in the bent or bulged configuration). In this embodiment, positive pressure can be applied to one or both of the operating microchannels 710, 712 to create a pressure differential that causes the walls 731, 733 to move inward causing the membrane 720 to contract along the plane of the membrane 720.

In accordance with some embodiments of the invention, a combination of positive and negative pressure can be applied to one or more operating microchannels 710, 712 to cause movement and or stretching of the membrane 720 along its plane in the central channel.

Figure 7C:
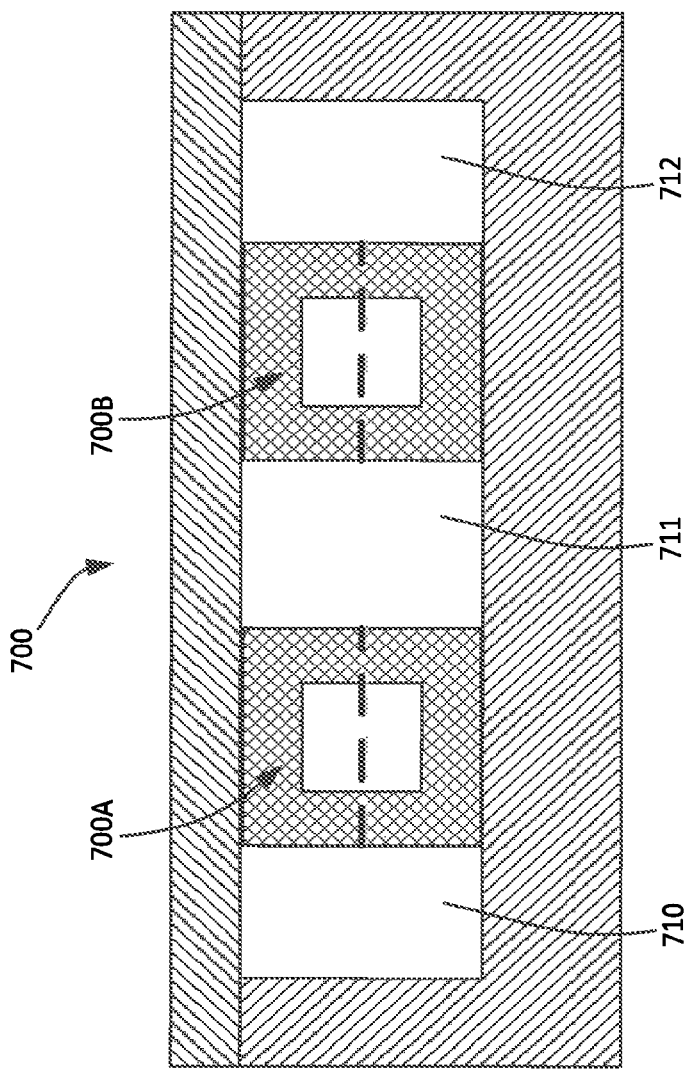
FIG. 7C shows a transverse cross sectional view of a microfluidic device according to some embodiments of the invention.

In accordance with some embodiments of the invention, as shown in FIG. 7C, device 700 can include two or more flexible microfluidic devices 700A, 700B, each of which is separated by an operating microchannel 711 and optionally surround by an operating microchannel 710, 712. In operation, and depending on how each of the flexible microfluidic devices 700A, 700B is configured (e.g., to stretch or compress the membrane), the application of a negative or positive pressure to one or more of the operating microchannels 710, 711, 712 can cause one or more walls 731, 733 of one or more of the flexible microfluidic devices 700A, 700B to bend or bulge inwardly or outwardly causing the membrane 720 to expand or contract.

Device 700 can be constructed by assembling each component after they are fabricated. The elastomeric components (elastomer layers 702, 704 and the membrane 720) can be fabricated using the methods described for device 300. The rigid layer 701 and rigid body portion 703 can be fabricated from rigid materials including, but not limited to, polytetrafluroethylene, polypropylene, polyethylene terephthalate and polyvinyl chloride, stiff elastomeric materials, acrylic, polystyrene, polycarbonate, glass, epoxy fiberglass, ceramic and metal.

The rigid layer 701 and rigid body portion 703 can be fabricated by photolithography, casting (e.g., solvent casting), stamping, molding (e.g., injection molding, compression molding), machining (e.g., mechanical cutting, laser cutting, etching), extruding, embossing or solid free-form fabrication technologies such as three dimensional printing and stereolithography, or any combinations thereof.

The components of the microfluidic device 700 can then be bonded together to form the device by thread forming screws, nuts and bolts, clips, clamps, pins, ultrasonic welding, solvent-assisted bonding, heat staking, laser welding, snap fits, glue (e.g., biocompatible, low absorption adhesives such as acrylates) and/or surface treatment (e.g., oxygen plasma) or any combinations thereof. During the assembly, a microscope can be used to assist with the alignment of the components.

Figure 7D:
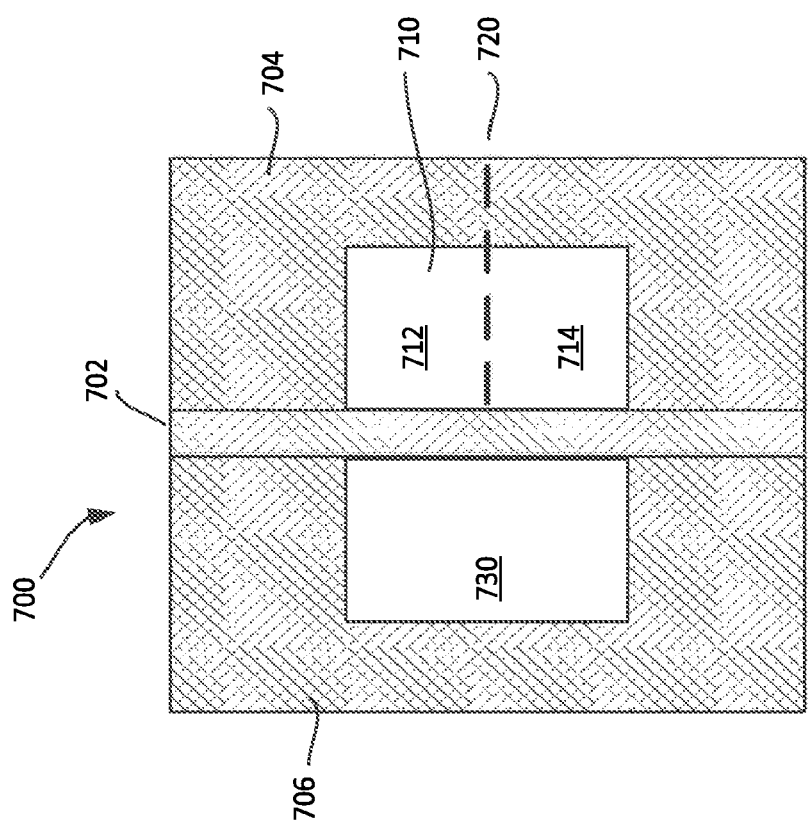
FIG. 7D shows a transverse cross sectional view of a microfluidic device according to some embodiments of the invention.

[Film & vacuum] FIG. 7D shows a transverse cross sectional view of a microfluidic device 700 according to some embodiments of the invention. Device 700 can include an elastomer layer or wall 702, a first rigid body portion 704, a second rigid body portion 706, a first central microchannel 712, a second central microchannel 714, a membrane 720 and an operating microchannel 730. The operating microchannel 730 can be connected to a vacuum port 732 and a vent port 734 (not shown).

The elastomer layer 702 separates the operating microchannel 730 from the central microchannels 712 and 714. The membrane 720 can be mounted between the first rigid body portion 704 and the elastomer layer 702, separating the central channel 710 into the first central microchannel 712 and the second central microchannel 714. In accordance with some embodiments of the invention, the membrane 720 can be fastened to at least one of the first rigid body 704 and the elastomer layer 702. The elastomer layer 702 and the second rigid body portion 706 define the operating microchannel 730.

In operation, the operating microchannel 730 can include a port that can be connected to a pressure generation device that can generate a positive pressure or negative pressure (e.g., vacuum or suction). A negative pressure can be generated in the operating microchannel 730 by pumping air out. Due to the pressure differential generated between the operating microchannel 730 and the central channel 710, the elastomer layer 702 flexes outward away from the central channel 710, which then causes the membrane 720 to stretch along the plane of the membrane 720. The amount of flexing/modulation can be controlled by the magnitude of the pressure differential applied. The pressure differential can be created by removing or adding a fluid (e.g., a gas such as air or a liquid such as water) from/to the operating channel 730 through a port in the operating channel 730, causing the membrane 720 to stretch or compress. During operation, the pressure differential can be alternately applied in predefined time intervals to cause continuous expansion and contraction of the membrane 720 along its plane. In an alternative embodiment, a positive pressure can be applied to the operating microchannel 730 in order to modulate the membrane 720.

Device 700 can be constructed by assembling each component after they are fabricated. In accordance with some embodiments of the invention, each of the components can be fabricated using photolithography, casting (e.g., solvent casting), stamping, molding (e.g., injection molding, compression molding), machining (e.g., mechanical cutting, laser cutting, etching), extruding, embossing or solid free-form fabrication technologies such as three dimensional printing and stereolithography, or any combinations thereof.

The components of the microfluidic device 700 can be held together to form the device by thread forming screws, nuts and bolts, clips, clamps, pins, ultrasonic welding, solvent-assisted bonding, heat staking, laser welding, snap fits, glue (e.g., biocompatible, low absorption adhesives such as acrylates), surface treatment (e.g., oxygen plasma) or any combinations thereof. During the assembly, a microscope can be used to assist with the alignment of the components.

Figure 8A:
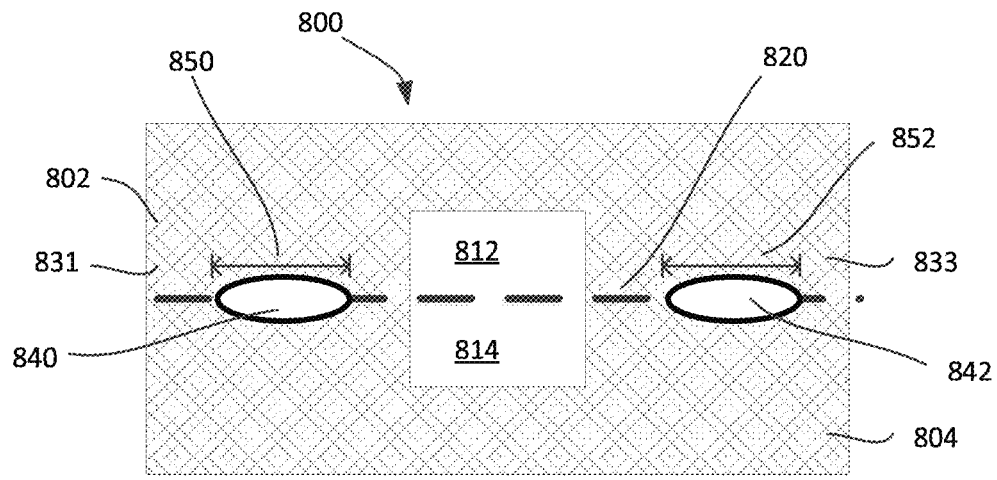

[Elastomer body (pneumatic)] FIG. 8A shows a transverse cross sectional view of a microfluidic device 800 according to some embodiments of the invention. The embodiment shown in FIG. 8A can include similar features as the device shown in FIGS. 3A, 7A and 7B. Device 800 can include a first elastomer layer 802 and a second elastomer layer 804 configured to define a central channel 810 that can extend into one of the elastomer layers. The central channel 810 can be partitioned by a membrane layer 820 into a first central microchannel 812 and a second central microchannel 814. The membrane layer 820 is sandwiched between the first elastomer layer 802 and the second elastomer layer 804. The first elastomer layer 802 and the second elastomer layer 804 can be configured define a first operating microchannel 840 adjacent the central channel 810 and optionally, a second operating microchannel 842 adjacent the central channel

810. Each of the operating microchannels 840, 842 can be connected to one or more pressure generating devices, for example via a port (not shown).

In accordance with some embodiments of the invention, the operating microchannels 840, 842 can have flat, rectangular, elliptical or oval cross sections whose major axes 850, 852 are on the same plane or a parallel plane as the membrane 820. In operation, when a positive pressure is applied to at least one of the operating microchannels 840, 842, at least one of the cross sections of the operating microchannels 840, 842 become more circular, and at least one of the major axes 850, 852 become shorter, applying a strain force on the membrane 820 causing the membrane to stretch. When the positive pressure is removed, the cross sections relax back to their original elliptical shapes, and the membrane 820 reverts to its neutral state. To prevent the membrane 820 from over-stretching, at least one of the elastomer walls 831, 833 can include a hard stop. The hard stop can be made of a rigid material. In some aspects, it is also contemplated that to better promote the shortening of the major axis, such as axes 850, 852, any of the top and/or bottom walls of the operating microchannels 840, 820 can include one or more layers that are bendable but not substantially stretchable and/or one or more layers made of a rigid material.

In accordance with some embodiments of the invention, the cross sections of the operating microchannels 840, 842 can be of any elongated shape having an axis 850, 852 on the same plane or a parallel plane as the membrane 820 such that the membrane can be modulated by applying a positive pressure to one or both of the operating microchannels 840, 842.

FIGS. 8B and 8C shows diagrammatic transverse cross sectional views of a microfluidic device 800 according to some embodiments of the invention. The embodiment shown in FIG. 8A can include similar features as the device shown in FIGS. 3A, 7A, 7B, and 8A. Device 800 can include a first elastomer layer 802 and a second elastomer layer 804 configured to define a central channel 810 that can extend into one of the elastomer layers. The central channel 810 can be partitioned by a membrane layer 820 into a first central microchannel 812 and a second central microchannel 814. The membrane layer 820 is sandwiched between the first elastomer layer 802 and the second elastomer layer 804. The first elastomer layer 802 and the second elastomer layer 804 can be configured define a first operating microchannel 840 adjacent the central channel 810 and optionally, a second operating microchannel 842 adjacent the central channel 810. Each of the operating microchannels 840, 842 can be connected to one or more vacuum generating devices, for example via a port (not shown).

In accordance with some embodiments of the invention, the operating microchannels 840, 842 can have square, rectangular, circular, oval or other cross sections, including asymmetric cross sections and cross-sections that vary along the length of the operating microchannels, 840, 842. In operation, when a vacuum (e.g., negative) pressure is applied to at least one of the operating microchannels 840, 842, the wall between the operating channel and the central channel 810 bows outwardly, applying a strain force on the membrane 820 inside central channel 810 causing the membrane to stretch as shown in FIG. 8C. When the vacuum pressure is removed, the operating microchannels 840, 842 relax back to their original shape, and the membrane 820 reverts to its neutral state.

In accordance with some embodiments of the invention, the cross sections of the operating microchannels 840, 842 can be of any shape enabling the wall between the operating microchannel and the central channel 810 to bow outwardly, such that the membrane 820 can be modulated by applying a vacuum pressure to one or both of the operating microchannels 840, 842.

Device 800 can be fabricated using the same or similar methods and materials described for the devices 300, 700 shown in FIGS. 3A, 7A and 7B.

Figure 9:
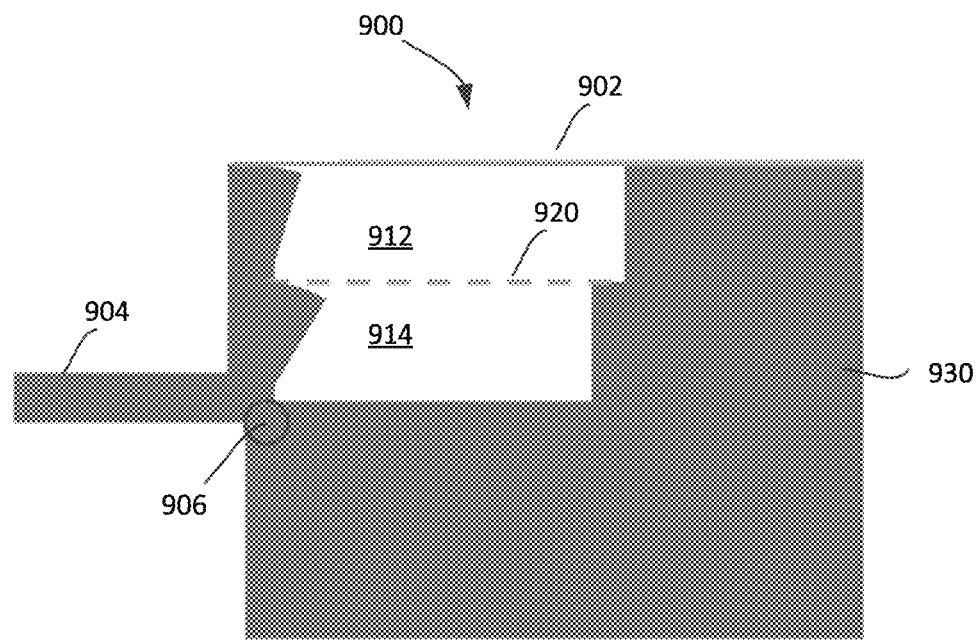
FIG. 9 shows a transverse cross sectional view of a microfluidic device according to some embodiments of the invention.

[Lever design] FIG. 9 shows a transverse cross sectional view of a microfluidic device 900 according to some embodiments of the invention. Device 900 can include an elastomer layer 902, a lever 904, a hinge 906, a first central microchannel 912, a second central microchannel 914, a membrane 920, and a rigid body portion 930.

The elastomer layer 902 and the membrane 920 define the first central microchannel 912. The membrane 920 and the rigid body portion 930 define the second central microchannel 814. The elastomer layer 902 and membrane 920 can extend between the wall portion 904A of the lever 904 and the rigid body portion 930.

The elastomer layer 902 can include a thin and transparent portion above the central microchannels 912, 914 to allow non-invasive external observation of cellular activities using a microscope and various microscopy techniques such as surface plasmon resonance spectroscopy.

In operation, the rigid L-shaped lever 904 can be pivoted at the hinge 906 such that when a force/pressure is exerted on the handle portion 904B of the lever 904, the wall portion 904A of the lever 904 moves and modulates (e.g., stretches, compresses, and/or flexes) the elastomer layer 902 and the membrane 920. The membrane 920 can be modulated in a direction transverse to fluid flow in the central microchannels 912, 914.

Device 900 can be constructed by assembling each component after they are fabricated. The components can be fabricated by photolithography, casting (e.g., solvent casting), stamping, molding (injection molding, compression molding), machining (e.g., mechanical cutting, laser cutting, etching), extruding, embossing or solid free-form fabrication technologies such as three dimensional printing and stereolithography, or any combinations thereof.

The components of the microfluidic device 900 can then be bonded together to form the device by thread forming screws, nuts and bolts, clips, clamps, pins, ultrasonic welding, solvent-assisted bonding, heat staking, laser welding, snap fits, glue (e.g., biocompatible, low absorption adhesives such as acrylates), surface treatment (e.g., oxygen plasma), or any combinations thereof. During the assembly, a microscope can be used to assist with the alignment of the components.

In summary, the microfluidic devices in FIGS. 1-9 generally include at least a first microchannel, a second microchannel, and a membrane located at an interface region between the first microchannel and the second microchannel. The membrane may deform (e.g., stretch) and relax so as to controllably apply forces to cells adhered to one or both sides of the membrane. The membrane separates the first microchannel from the second microchannel, but permits the migration of cells, particulates, chemicals, molecules, fluids and/or gases therethrough.

It should be noted that all microfluidic embodiments according to the invention can include inlet and outlet ports for at least one fluid source to access the first and second central microchannels. The fluid source can include air, culture medium, blood, water, cells, compounds, particulates, and/or any other media. Any known fluid inlet and outlet devices for microfluidic devices can be used.

Examples include Luer connections as well as threaded connections. At least one of the central microchannels can be adapted to fluidically connect to at least one fluid flow-modulation device via the inlets and outlets. The fluid flow-modulation device can be controlled by a central processing unit to modulate flow of a liquid or a gas through at least one of the central microchannels. The fluid flow-modulation device can include a pump. For example, a peristaltic fluid pump can be used. In accordance with some embodiments of the invention, the fluid flow-modulation device can be incorporated into the body of the microfluidic device. In alternative embodiments, the fluid flow-modulation device can be separately connected to the microfluidic device. In accordance with some embodiments of the invention, at least one of the first and second central microchannels is adapted to fluidically connect to at least one bubble trap for removing gas bubbles from a liquid flowing through the first or second central microchannel.

In accordance with some embodiments of the invention, the fluid passing through the first central microchannel can be different from and controlled independently from the fluid passing through the second central microchannel and vice versa. In accordance with some embodiments of the invention, the fluid passing between the inlets and outlets can be shared between the first and second central microchannels. In either embodiment, characteristics of the fluid flow, such as flow rate, pressure, fluid type and/or composition, and the like, passing through the first central microchannel can be controllable independently of fluid flow characteristics through the second central microchannel and vice versa.

The microfluidic device can be equipped with a variety of sensors to monitor cellular activities, measure mechanical strains, measure analyte concentration as well as to perform other functions. These sensors can be incorporated into the body of the organomimetic device or separately connected to the device. These sensors can include, but not limited to, optical sensors, electrical sensors or mechanical sensors.

The microfluidic devices according to the invention can have one or more central channels, each of which can be separated into at least two or more central microchannels (e.g., a first central microchannel and a second central microchannel) by at least one membrane. In accordance with some embodiments of the invention, the microfluidic device can have one central channel. In other embodiments, the microfluidic device can have two or more central channels, including, e.g., 2, 3, 4, 5, 6, 7, 8, 9, 10 or more central channels (termed "a multiple-channel device" herein). The two or more central channels can be arranged on a single device in series, in parallel, in a pre-defined way, or any combinations thereof.

In a multiple-channel device, each individual central channel can have the same or different dimensions and/or shapes. Each central channel can be adapted to mimic the same or different tissue. In accordance with some embodiments of the invention where each central channel is adapted to mimic the same tissue, same or different tissue-specific condition (e.g., normal vs. diseased condition) can be modeled in each central channel within the same device. For example, in accordance with some embodiments of the invention, each substantially identical central channel can be used as replicates and model the same tissue-specific condition. In alternative embodiments, one or more central channels can be used to model a normal condition of a specific tissue, while the remaining central channels can be used to model a specific disease associated with the same tissue.

In other embodiments, each central channel on the device can be adapted to mimic a different tissue and form an in vitro microphysiological system within the same device instead of connecting different devices to form such microphysiological system as described in detail below. In these embodiments, the central channels on the device can be fluidically connected to each other.

Figure 10:
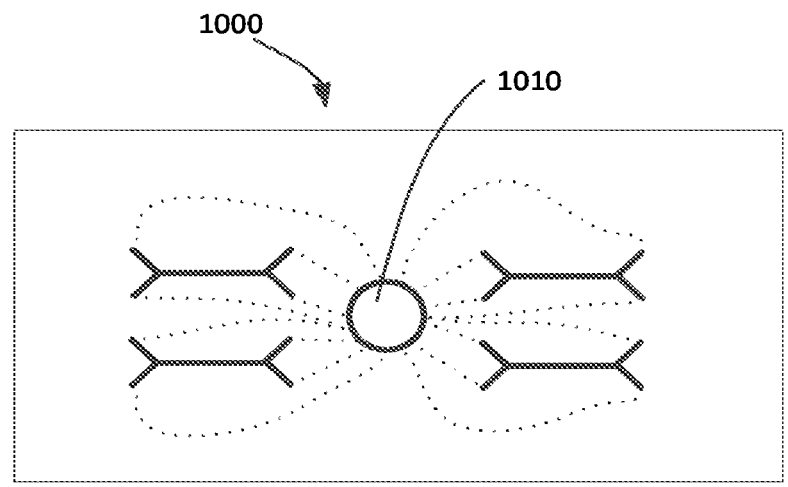
FIG. 10 shows a schematic diagram of fluidic connections for a microfluidic device including two or more central channels.

In some embodiments of a multiple-channel device, each of the first central microchannels and/or the second central microchannels in the device can have its individual fluid inlet and/or fluid outlet. In accordance with some embodiments of the invention, as shown in FIG. 10, the microfluidic device 1000 can include multiple central channels and each can have separate inlets and/or outlets. The inlets and/or outlets can be selectively connected to a single pump and fluid reservoir 1010. In these embodiments, the same fluid can be introduced into the inlets of each central channel, and/or a fluid can be withdrawn from different outlets at the same time or different times. As one of skill in the art will appreciate, where a different fluid is desired to be delivered to at least some of the first central microchannels present on the device, the inlets of those microchannels can also be each connected to a different pump and fluid reservoir accordingly. One or more pumps and one or more fluid reservoirs can be disposed on or integrated into the microfluidic device, or can be separate from and connected to the microfluidic device 1000.

Figure 11A:
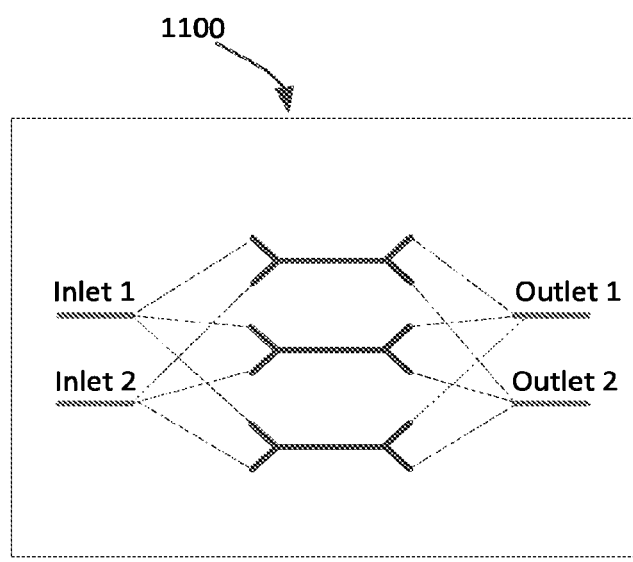
FIG. 11A shows a schematic diagram of fluidic connections for a microfluidic device including two or more central channels.

In alternative embodiments as shown in FIG. 11A, at least two or more (including all) of the first central microchannels within the same microfluidic device 1100 can share the same fluid inlet and/or fluid outlet. Alternatively or additionally, at least two or more (including all) of the second central microchannels within the same device can share the same fluid inlet and/or fluid outlet. The inlets and/or outlets can be selectively connected to one or more pumps and fluid reservoirs as described above.

Figure 11B:
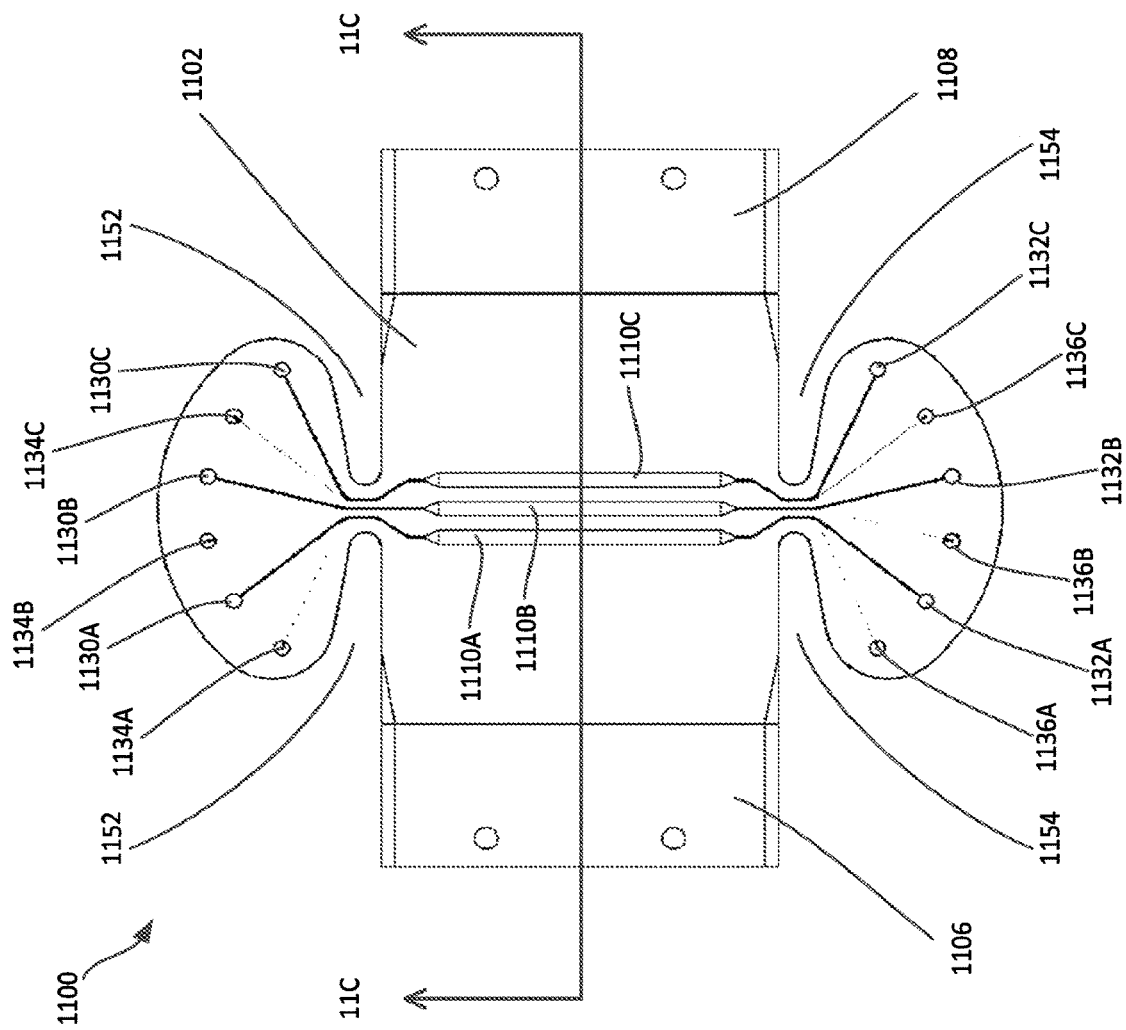
FIG. 11B shows a top view of a microfluidic device according to some embodiments of the invention.

FIG. 11B shows a top view of a microfluidic device 1100 according to some embodiments of the invention. FIG. 11C shows a diagrammatic transverse cross sectional view of the device 1100. The embodiment shown in FIGS. 11B and 11C can include substantially the same or similar features as in the device shown in FIGS. 1A, 3A and 3B. The body of the microfluidic device 1100 can include a first elastomer layer 1102 and a second elastomer layer 1104. As shown in FIG. 11B, the device 1100 can include three central channels 1110A, 1110B, 1110C that can be formed in the first elastomer layer 1102 and/or the second elastomer layer 1104. In accordance with some embodiments of the invention, two or more central channels can be provided. Additionally, as shown in FIG. 11C, device 1100 can include a membrane layer having a membrane portion 1120 that divides each of three central channels 1110A, 1110B, 1110C into a first central microchannel 1112A, 1112B, 1112C and a second central microchannel 1114A, 1114B, 1114C. Device 1100 can also include a first engagement element 1106 and optionally a second engagement element 1108 adjacent the outer sides of the central channels 1110A, 1110C. Device 1100 can be further coupled to a membrane modulation device 1140 by a first modulation element 1142 and optionally a second modulation element 1144.

The engagement elements 1106, 1108 can be over-molded onto the body formed by the first elastomer layer 1102 and the second elastomer layer 1104. It is also contemplated that in some aspects the over-molding can occur in reverse where the body formed by the elastomer layers are over-molded onto the engagement elements. The engagement elements 1106, 1108 can include one or more holes (or other engagement features such as, beads, ridges, flanges, clamps, slots or notches) that enable a modulation element to apply a force to the body of the microfluidic device 1100. The modulation elements 1142, 1144 can include one or more pins, posts, or bars (or other modulation features such as, flanges, jaws or clamps) that can engage one or more holes, beads, ridges, flanges, clamps, slots or notches that form the engagement features in the engagement elements 1106, 1108. The modulation device 1140 can be coupled to the first modulation element 1142 and optionally the second modulation element 1144. In order to minimize shape distortion of the inlets 1130A, 1130B, 1130C, 1134A, 1134B, 1134C and outlets 1132A, 1132B, 1132C, 1136B, 1136B, 1136C during mechanical modulation, the strains on the inlets 1130A, 1130B, 1130C, 1134A, 1134B, 1134C and outlets 1132A, 1132B, 1132C, 1136B, 1136B, 1136C can be minimized by isolating the inlets and outlets from the strain associated with modulation. Elastomer layers 1102, 1104 can include cut-outs 1152 and 1154 that enable the elastomer layers 1102, 1104 and the membrane 1120 to stretch while minimizing the stress and/or strain applied to the inlets 1130A, 1130B, 1130C, 1134A, 1134B, 1134C and outlets 1132A, 1132B, 1132C, 1136B, 1136B, 1136C. The size and shape of the cutouts 1152 and 1154 can be determined by strain simulations using software (e.g., Comsol, Abaqus). In accordance with some embodiments of the invention, the cut-outs 1152, 1154 can be slots that extend parallel to direction of the strain (e.g., transverse to longitudinal axis of the three central channels 1110A, 1110B, 1110C).

[Mechanical stretch actuation] As discussed above, microfluidic devices (e.g., 200, 300, 400, 500, 600, 1100) can be further coupled to a membrane modulation device (e.g., 240, 340, 440, 441, 540, 640, 1140) by one or more modulation elements (e.g., 242, 244, 342, 344, 442, 444, 446, 448, 542, 544, 642, 644, 1142, 1144). FIGS. 16-29 illustrate some exemplary aspects of systems and methods for mechanical stretch actuation of microfluidic devices, such as the organomimetric and other devices described in this disclosure.

Mechanical stretch actuation of organomimetric devices can provide desirable outcomes and advantages in recapitulating in vivo physiology. For example, mechanical stretch actuation can be used to mimic the mechanical forces experienced by a tissue-tissue interface in a living organism, such as in the lungs as part of a breathing motion. It is also contemplated that mechanical stretch actuation can be applied to mimic peristalsis, such as in the gut. In the context of the exemplary aspects of a lung-on-a-chip or a gut-on-a-chip type organomimetric device, cell layers are stretched by applying tension to the flexible membrane of the organomimetric device on which the cell layers reside.

Stretch actuation of the membrane of an organomimetric device has been accomplished using vacuum channels on either side of a main channel. In practice, the use of vacuum channels for stretch actuation typically includes vacuum walls, which separate vacuum channels from the main channel, which are thin and have a high aspect-ratio. In turn, the use of vacuum channels can increase the complexity of manufacturing an organomimetric device, such as where an organomimetric device is made using injection molding, which is a desirable process for high-volume production.

The present disclosures include descriptions of several of different mechanisms and methods for attaching and mechanically actuating a microfluidic device, such as an organomimetric device organ-chip. The described systems use external, lateral forces. Some of the different mechanisms are illustrated in the context of FIGS. 16 to 29. It would also be understood that the different mechanisms and methods can apply more broadly to different types of microfluidic devices (e.g., other than organomimetric devices) that can take advantage of external mechanical stretch or force application. Desirable aspects of a mechanical stretch actuation system can include configurations that allow the microfluidic device to be mechanically "plugged in" or otherwise mechanically fastened into the stretch apparatus to allow for easy insertion and removal of the microfluidic device. The stretch actuation device can be part of a larger instrument (e.g. to perfuse the organomimetric devices) or the device can be a stand alone device.

Different methods and system are contemplated for connecting a microfluidic device (e.g., an organomimetric device) to a mechanical stretch actuation system. Microfluidic devices may or may not be part of a microfluidic cartridge or chip carrier. Some examples of connections can include those that apply tension, compression, or no net load on the microfluidic device when it is installed into the stretch actuation system. Different non-limiting exemplary aspects of connections, described in more detail below, can include male with mating female features, magnets, grippers, bolted connections, camming latches, conducting polymers, artificial muscles, or piezoelectric actuators, along with combinations or variations thereof that would be known to one skilled in the field of microfluidic devices and stretch actuation systems. It is contemplated that the connection systems are configured to be a part of one or both of the microfluidic device (e.g., elements 200, 300, 400, 500, 600, 1100, 1600, 1700, 1800, 1900, 2000, 2100, 2200, 2300, 2400, 2500, 2600, 2700, 2800, 2900) and the connection element(s) (e.g., elements 1652, 1654, 1752, 1754, 1852, 1854, 1952, 1954, 2052, 2054, 2152, 2154, 2252, 2254, 2352, 2354, 2452, 2454, 2552, 2554, 2652, 2654, 2752, 2754, 2852, 2854, 2952, 2954 in FIGS. 16-29) or connection element(s) that are part of a modulation element (e.g., elements 242, 244, 342, 344, 442, 444, 542, 544, 642, 644, 1142, 1144 in FIGS. 2-6 and 11) for the stretch actuation system.

In some aspects, a connection includes male features (e.g. pins) with mating female features (e.g. holes, slots). Male pins in of a connection element on a mechanical stretch actuation system align to a hole and a slot integral to the microfluidic device. In some aspects, the pins can be made from stainless steel or other metals and the female features can be made from plastic materials, such as polypropylene, acetals, Rulon®, polytetrafluoroethylene, and finished plastics with similar properties. It is also contemplated that in some aspects male pins in a microfluidic device align to a hole and a slot integral to the mechanical stretch actuation system, or that a connection includes a combination of male and female features on both the mechanical stretch actuation system and the microfluidic device.

It is also contemplated that a connection can include dovetail joints or other shaped mating joints. The male and female features of the joints can both be made from plastic, or one of the features (e.g., the male feature) can be made from metal and the other (e.g., the female feature) can be made from plastic. For a dovetail component, as the fluidic device is engaged, the dovetail joint makes the connection. The dovetail joint may be a passive element, engaging as the microfluidic device is installed. In some aspects, an actuator be used to cause the engagement.

The direction of mating of male and female connection elements can be in a direction perpendicular to the surface of the microfluidic device where the device or cartridge is placed onto the mating feature (e.g., analogous to a DVD being placed onto the tray of a DVD player). The direction of mating can also be parallel to the surface of the microfluidic device, where the mating features in the mechanical stretch actuation system and the microfluidic device mate as a track (e.g., analogous to an audio cassette or a VHS tape being slid into their players. It is also contemplated that the position of the corresponding male and female features, on the microfluidic device and on the connection elements of the stretch actuation system, determines the orientation of how the microfluidic device is to be inserted in the stretch actuation system, such that the male and female counterparts properly align and fasten the microfluidic device to the connection elements on the stretch actuation system.

In some aspects, connection of the microfluidic device to the stretch actuation system can be accomplished using magnets. For example, opposing pole magnets may be positioned on both a microfluidic device and a connection element for the mechanical stretch actuation system where the magnetic attraction between the opposing pole magnets is of such strength to extend through the microfluidic device and the connection element and hold the microfluidic device to the stretch actuation system. It is also contemplated that a magnet on or within the mechanical stretch actuation system (e.g., on a microfluidic device connection element of the system) is attracted to a ferritic material on or within the microfluidic device to fasten the microfluidic device to the stretch actuation system. In other embodiments, the magnet may be on or within the microfluidic device and attracted to a ferritic material on or within the mechanical stretch actuation system.

In some aspects, connection of the microfluidic device to the stretch actuation system can be accomplished with a bolted connection. For example, threaded studs on the microfluidic device can be fed through holes or slots at a connection element on the mechanical stretch actuation system. The threaded studs can then be fastened using nuts. It is also contemplate that the microfluidic device can have threaded holes and the connection elements on the mechanical stretch actuation system can have through-holes. Bolts can then be fed through the through-holes of the mechanical stretch actuation system that engage the threads of the microfluidic device causing the microfluidic device to fasten to the stretch actuation system.

In some aspects, connection of the microfluidic device to the stretch actuation system can be accomplished with a camming latch. For example, the microfluidic device can be engaged with the mechanical stretch actuation system where a retaining latch is configured to be moved to a position that locks the microfluidic device to the connection element(s) of the mechanical stretch actuation system. The movement of the retaining latch may be performed by the user of the stretch system, by a motor or other type of automated actuation, or by a passive action caused by the movement of the microfluidic device itself.

In some aspects, connection of the microfluidic device to the stretch actuation system can also be accomplished with a gripper. For example, a gripper can be actuated to grab a feature, such as a handle, that is integral with, or otherwise secured to, the microfluidic device. The feature (e.g., handle) much like the features of the other described connections is configured to allow the transmission of motion from the mechanical stretch actuation system into the microfluidic device.

It is contemplated that the described attachment configurations for connecting the microfluidic device to connection element(s) of the stretch actuation system can be adapted or configured such that the microfluidic device is inserted in a given orientation and/or to register of fix its location with respect to other components of the mechanical stretch actuation system (e.g. with respect to a microscopy system).

The systems and methods of connecting the microfluidic device to the connection elements of the stretch actuation system that are described above are desirable and beneficial in the context of microfluidic devices subject to dynamic aspect such as stretch actuation. The connections between the microfluidic device and the stretch actuation system are desirably configured to induce strain in certain parts of the microfluidic device, while keep other parts fixed or static (see, for example, FIG. 11B). Such arrangements can be desirable because it minimizes, or does not allow, strains to be applied to, or to affect, the entry and exit ports that allow the entry and exit of fluids for the microfluidic device.

In some aspects, a connection to a stretch actuation system is positioned at one location of a microfluidic device and an opposing end can be kept fixed or static (for example, one-sided mechanical stretch actuation). In other aspects, connections to a stretch actuation system can be positioned at opposing locations of the microfluidic device. Such aspects allow stretch from opposing directions, which can be configured to keep at least one designated location on the microfluidic device nominally stationary during stretch. In some aspects, multiple connections to the stretch actuation system or multiple stretch actuation systems are present at several locations of the microfluidic device to allow simultaneous or independent actuation involving two or more axes or modes of stretch.

Referring now to FIGS. 16-29, a plurality of exemplary aspects for mechanical stretch actuation of a microfluidic device are illustrated.

Figure 16:
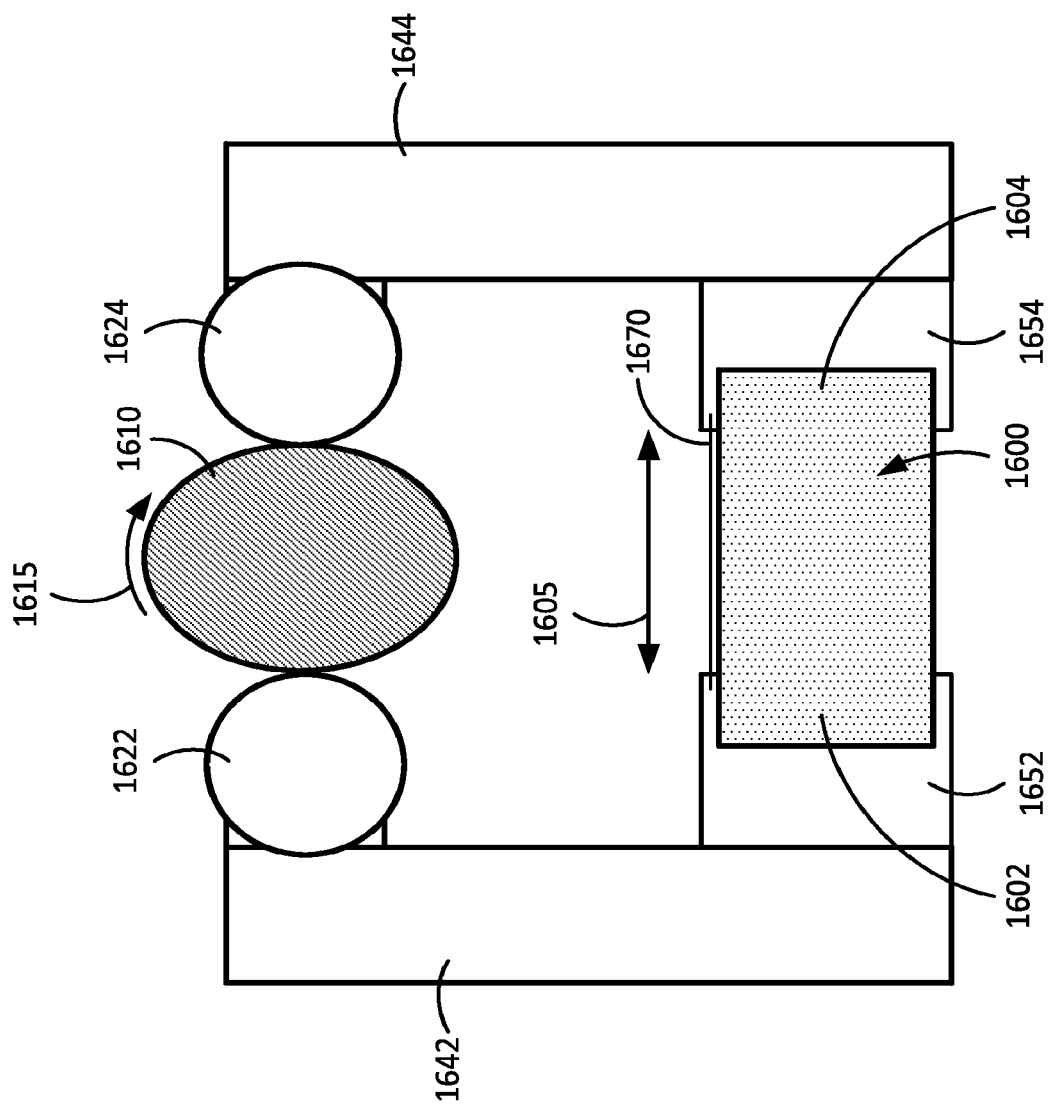
FIG. 16 illustrates an exemplary aspect of a cam-based mechanical system for stretch actuation of microfluidic devices.

FIG. 16 illustrates an example of cam actuation. A cam 1610, which is coupled to a motor (not shown), rotates in a cam rotation direction as illustrated by arrow 1615 (or in the opposite direction). As the cam 1610 rotates from its narrowest point, the rotation causes the cam follower(s) 1622, 1624 and drive arm(s) 1642, 1644 on each side of the cam 1610 to move apart. This motion is translated to the microfluidic device 1600 via the drive arm's 1642, 1644 connection to the microfluidic device. For example, each drive arm 1642, 1644 may have an extension, such as connection elements 1652, 1654, that provide the connection elements from a drive arm to one of a first end 1602 and a second opposing end 1604 of the microfluidic device 1600. The actual connection of fastening of the microfluidic device to the connection element on the stretch actuation system can be accomplished using any of the connection methods or systems described above or variations thereof. As the cam 1610 rotates between its narrow and long diameter, a fastened microfluidic device experiences as part of the stretch actuation process alternating stretch states and relaxation states along its long axis as illustrated by arrow 1605.

In some aspects, a cam follower 1622, 1624 can include a radial bearing on a stationary shaft fixed to the drive arm 1642, 1644. As the cam 1610 rotates, the cam follower also rotates, reducing the friction and wear between the two components. Reduction of the friction and wear between the cam, cam follower, and drive arm components is desirable as it assists with maintaining the shape of the cam 1610 and it keeps the strain that is applied to the microfluidic device the same over time.

Figure 17:
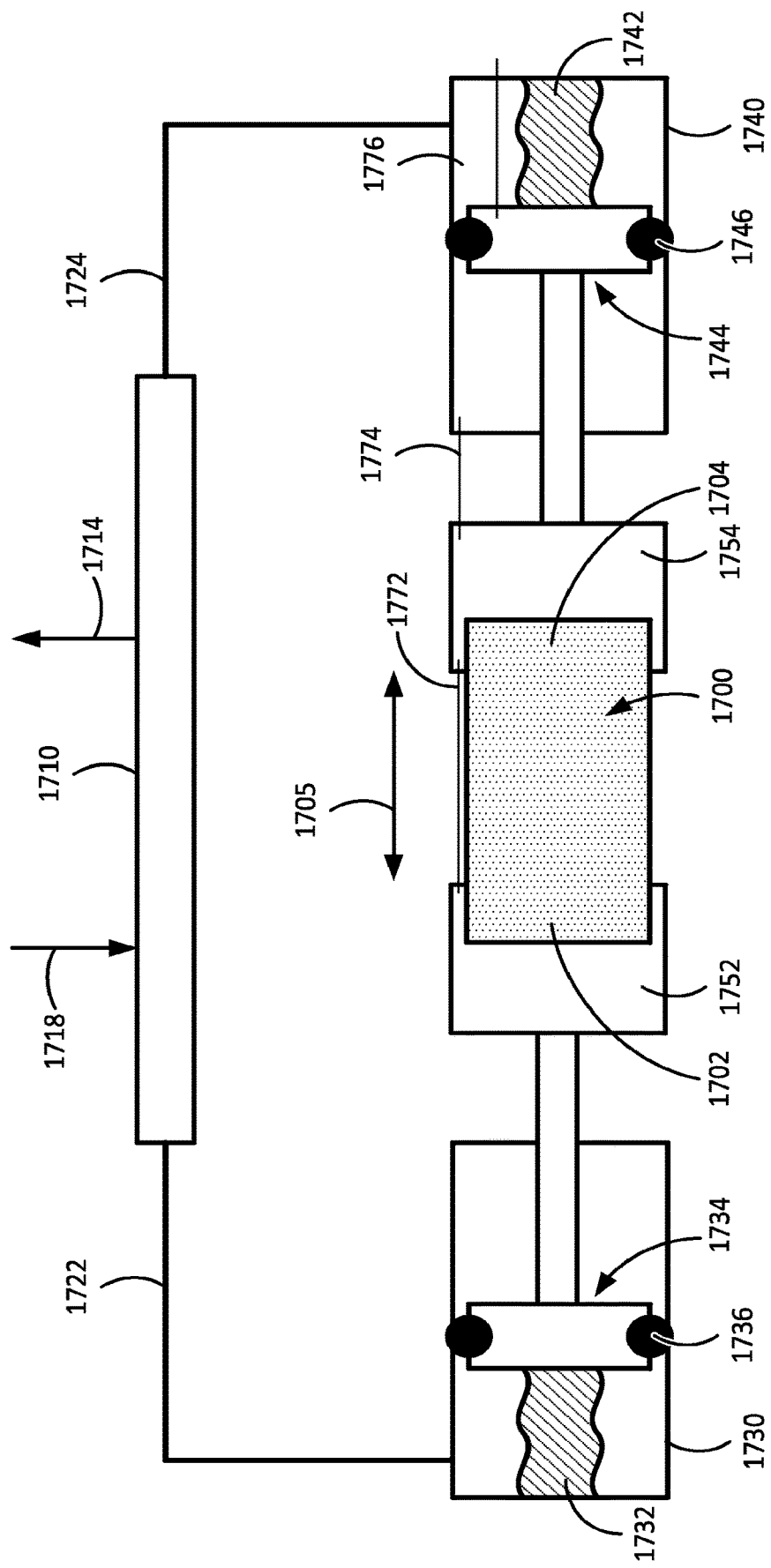
FIGS. 17-20 illustrate exemplary aspects of pneumatic-based mechanical systems for stretch actuation of microfluidic devices.

FIG. 17 illustrates an example of a pneumatic mechanical stretch actuation system including a vacuum regulator 1710. It is contemplated that one or both ends 1702, 1704 of a microfluidic device 1700 are connected to a pressure chamber 1730, 1740 that includes a piston 1734, 1744. The shaft(s) of piston(s) 1734, 1744 are each connected to a connection element, such as connection elements 1752, 1754, where the ends 1702, 1704 of the microfluidic device 1700 are fastened to the connection elements. Through use of the piston(s), motion is translated to the microfluidic device 1700.

The pressure chamber 1730, 1740 defines an interior volume. Pneumatic connecting line(s) 1722, 1724 connect the pressure chamber(s) 1730, 1740 to the vacuum regulator 1710. Piston seal(s) 1736, 1746 (e.g., O-ring) on the piston head(s) create a working volume within the portion of the pressure chamber 1730, 1740 that is located above the piston head. The working volume (e.g., a portion of the interior volume) above the piston head can be driven by the vacuum regulator via the pneumatic connecting lines 1722, 1724. It is contemplated that the vacuum system may independently or simultaneously affect the working volume in each pressure chamber 1730, 1740.

As a vacuum is applied by removing air via an air extraction point 1714 of the vacuum regulator 1710, a vacuum is also created as air is removed from the working volume. The vacuum created in the working volume draws the piston(s) 1734, 1744 toward the pneumatic line(s) 1722, 1724. When the vacuum regulator vents to atmosphere at a venting point 1718, air is then allowed to enter the system which vents the working volume to push the piston(s) 1734, 1744 toward their starting point. In some aspects, an optional spring 1732, 1742 may also be used to push the piston 1734, 1744 to its starting location. It is also contemplated that the microfluidic device itself can act as a spring, as well, to cause the return of the microfluidic device to its initial starting position. Similar to the device in FIG. 16, the microfluidic device also experiences as part of the stretch actuation process an alternating stretch and relaxation along its long axis as illustrated by arrow 1705. In some aspects, a hard stop (e.g. a pin in the path of the piston) can be placed in the pressure chamber to provide a fixed and consistent starting location for the piston(s) 1734, 1744.

Figure 18:
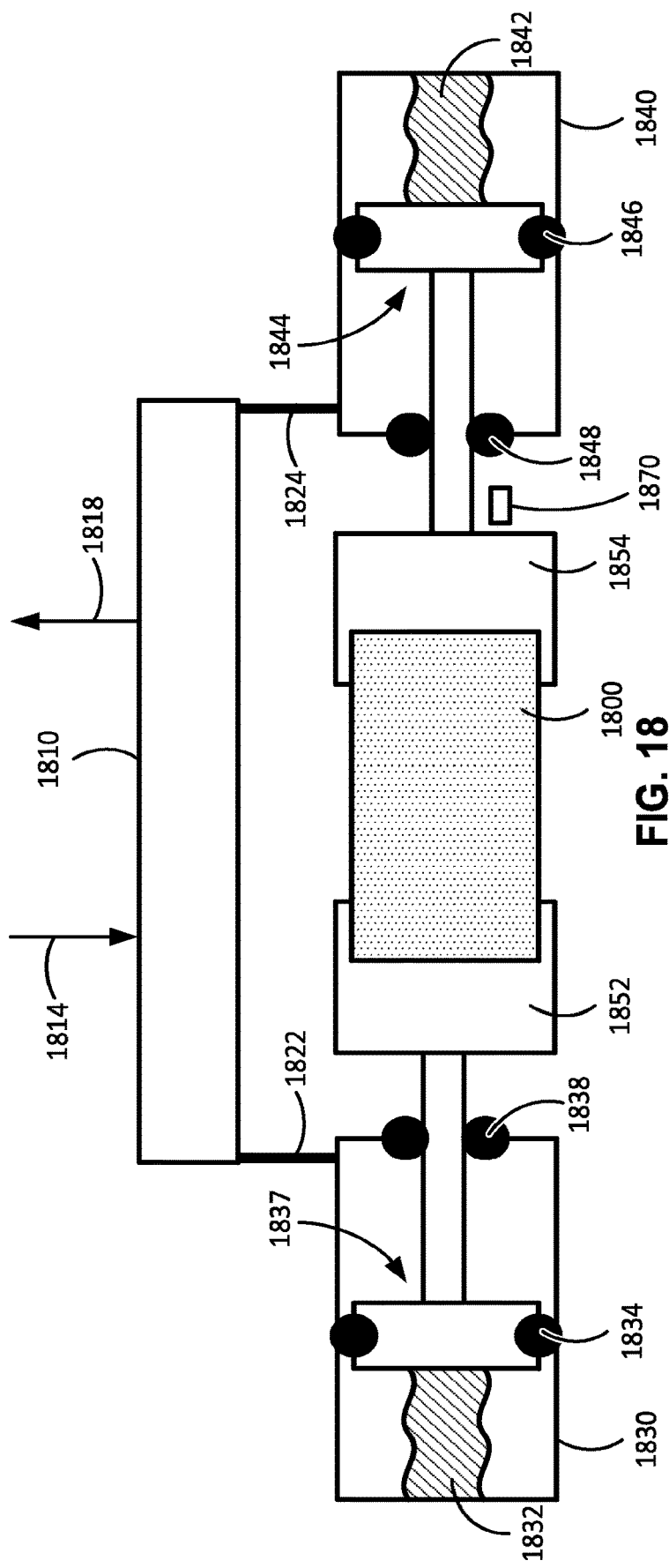

FIG. 18 illustrates another example of a pneumatic mechanical stretch actuation system that is different from FIG. 17 in that the pneumatic lines enter different locations of the pressure chamber. The system includes a pressure regulator 1810 providing positive pressure via pressurized gas that enters the pressure regulator 1810 through via a pressurized gas entrance point 1814 and a vent for venting gas to atmosphere via a venting gas exit point 1818. It is contemplated that one or both ends of a microfluidic device 1800 are connected to a pressure chamber 1830, 1840 that includes a piston 1837, 1844. The shaft(s) of piston(s) 1837, 1844 are each connected to a connection element, such as connection elements 1852, 1854, where the ends of the microfluidic device 1800 are fastened to the connection elements. Through use of the piston(s), motion is translated to the microfluidic device 1800.

Each pressure chamber 1830, 1840 includes an interior volume. Pneumatic connecting line(s) 1822, 1824 connect the pressure chamber(s) 1830, 1840 to the pressure regulator 1810. Piston seal(s) 1834, 1846 (e.g., O-ring) on the piston head(s) and piston seal(s) 1838, 1848 on the piston shaft(s) create a working volume (e.g., a portion of the interior volume) within the portion of the pressure chamber 1830, 1840 that is located below the piston head(s). The working volume below the piston head can be driven by the pressure regulator 1810 via the pneumatic connecting lines 1822, 1824. It is contemplated that the vacuum system may independently or simultaneously affect the working volume in each pressure chamber 1830, 1840.

As a pressure is applied through pressurized gas entering the working volume (via point 1814, the pressure regulator 1810, and the pneumatic connecting line(s) 1822, 1824), the piston 1837, 1844 is pushed away from the point of entry of the pressurized gas into the working volume (e.g., away from where the pneumatic line enters the pressure chamber). When the pressure regulator vents to atmosphere at venting point 1818, the pressurized gas exits the working volume and pushes piston(s) 1837, 1844 back toward their starting point. In some aspects, an optional spring 1832, 1842 may also be used to push the piston 1837, 1844 to its starting location. It is also contemplated that the microfluidic device itself can act as a spring, as well, to cause the return of the microfluidic device to its initial starting position. Similar to the system in FIGS. 16 and 17, microfluidic device 1800 also experiences alternating stretch and return along its long axis. In some aspects, a hard stop (e.g. a pin in the path of the piston) can be placed in the pressure chamber to provide a fixed and consistent starting location for the piston(s) 1837, 1844.

Figure 19:
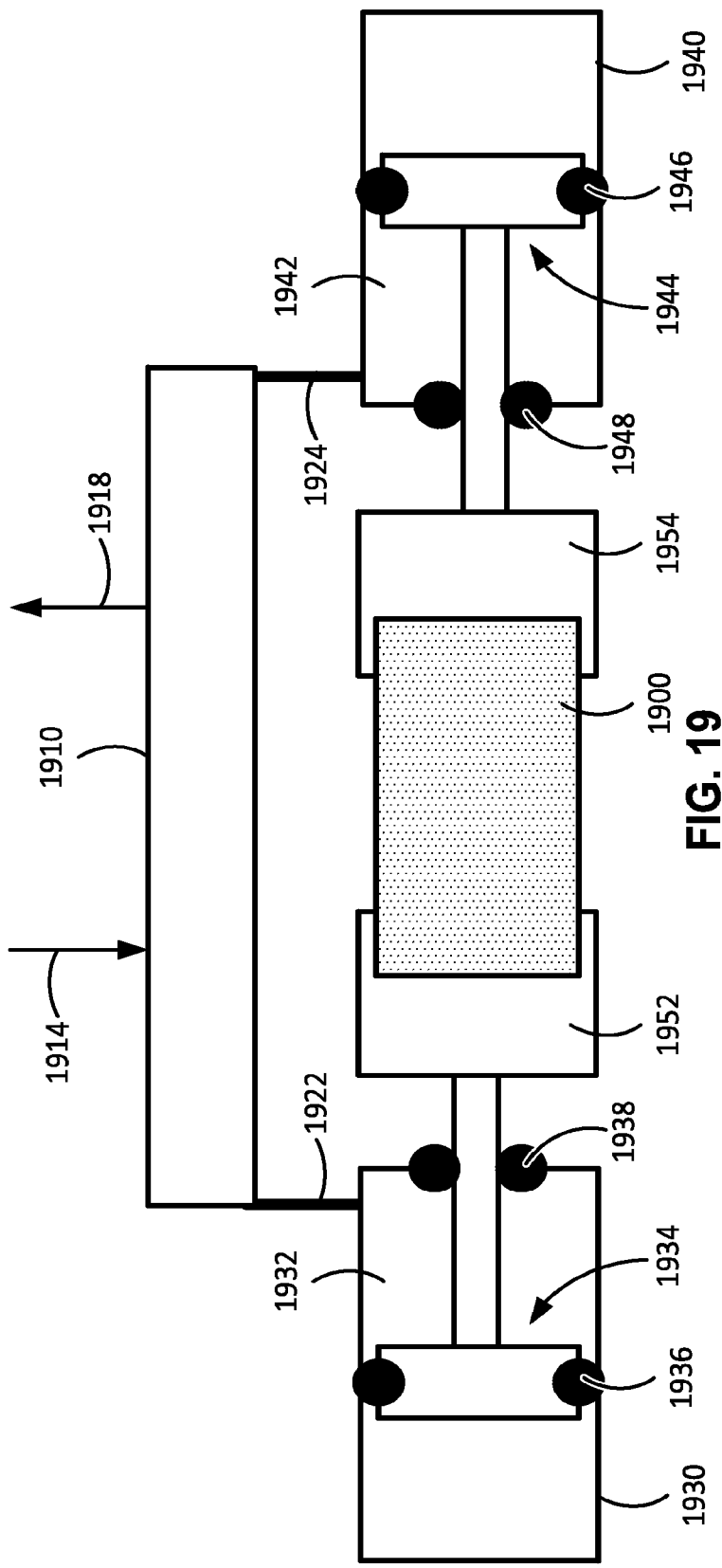

FIG. 19 illustrates another example of a pneumatic mechanical stretch actuation system that includes a pressure and vacuum regulator 1910 providing positive pressure via pressurized gas that enters the pressure and vacuum regulator 1910 through via a pressurized gas entrance point 1914 and a vacuum for removing gas to atmosphere via a vacuum exit point 1918. It is contemplated that one or both ends of a microfluidic device 1900 are connected to a pressure chamber 1930, 1940 that includes a piston 1934, 1944. The shaft(s) of piston(s) 1937, 1944 are each connected to a connection element (e.g., elements 1952, 1954) where the ends of the microfluidic device 1900 are fastened to the connection elements. Through use of the piston(s) 1934, 1944, motion is translated to the microfluidic device 1900.

Each pressure chamber 1930, 1940 includes an interior volume. Pneumatic connecting line(s) 1922, 1924 connect the pressure chamber(s) 1930, 1940 to the pressure and vacuum regulator 1910. Piston seal(s) 1936, 1946 (e.g., O-ring) on the piston head(s) and piston seal(s) 1938, 1948 on the piston shaft(s) create a working volume 1932, 1942 within the portion of the pressure chamber 1930, 1940 that is located below the piston head(s), similar to the system illustrated in FIG. 18. The working volume 1932, 1942 (e.g., a portion of the interior volume) below the piston head can be driven by the pressure and vacuum regulator 1910 via the pneumatic connecting lines 1922, 1924. It is contemplated that the vacuum system may independently or simultaneously affect the working volume (e.g., a portion of the interior volume) in each pressure chamber 1930, 1940.

As a pressure is applied through pressurized gas entering the working volume 1932, 1942 (via point 1914, the pressure and vacuum regulator 1910, and the pneumatic connecting line(s) 1922, 1924), the piston(s) 1934, 1944 are pushed away from the point of entry of the pressurized gas into the working volume 1932, 1942 (e.g., away from where the pneumatic line enters the pressure chamber). When the pressure and vacuum regulator 1910 applies a vacuum to the working volume 1932, 1942, gas is removed to atmosphere at vacuum exit point 1918. The pressurized gas exits the working volume 1932, 1942 and pushes piston(s) 1934, 1944 back toward their starting point. Similar to the systems in FIGS. 16-18, microfluidic device 1900 also experiences alternating stretch and return along its long axis. In some aspects, a hard stop (e.g. a pin in the path of the piston) can be placed in the pressure chamber 1930, 1940 to provide a fixed and consistent starting location for the piston(s) 1934, 1944. It is also contemplated that in some aspects it is desirable to exclude a hard stop to allow the range of motion of the piston(s) to generate a buckling or compression on the microfluidic device 1900.

Figure 20:
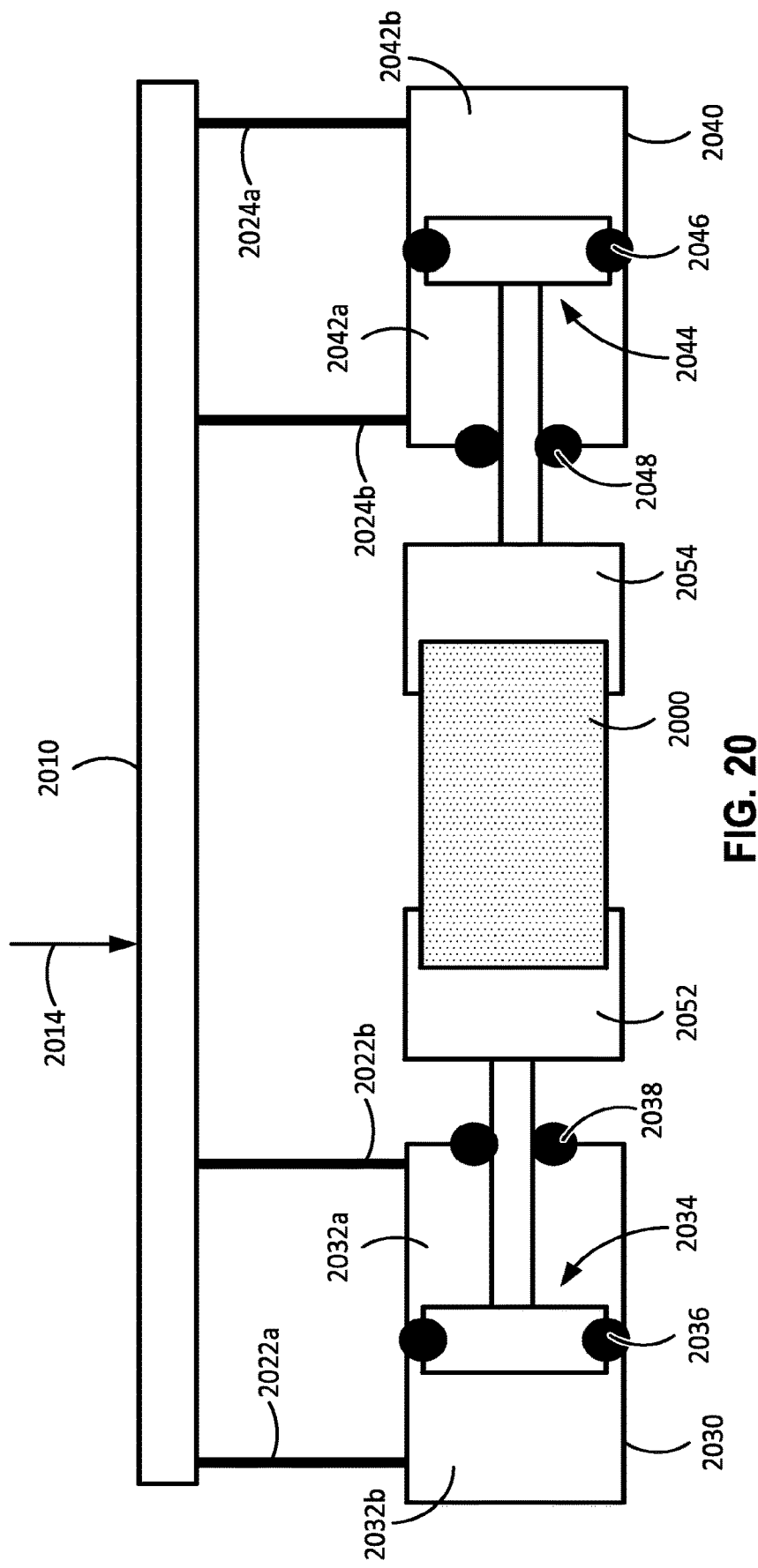

FIG. 20 illustrates another example of a pneumatic mechanical stretch actuation system that is different from FIGS. 17 through 19 by including a pressure regulator 2010 that provides a dual positive pressure. Pressurized gas enters the pressure regulator 2010 through a pressurized gas entrance point 2014. It is contemplated that one or both ends of a microfluidic device 2000 are connected to a pressure chamber 2030, 2040 that includes a piston 2034, 2044. The shaft(s) of piston(s) 2034, 2044 are each connected to a connection element, such as connection elements 2052, 2054, where the ends of the microfluidic device 2000 are fastened to the connection elements. Through use of the piston(s) 2034, 2044, motion is translated to the microfluidic device 2000.

Each pressure chamber 2030, 2040 includes an interior. Upper pneumatic connecting line(s) 2022*a*, 2024*a* connect a respective upper working volume 2032*b*, 2042*b* of the pressure chamber(s) 2030, 2040 to the pressure regulator 2010. Lower pneumatic connecting line(s) 2022*b*, 2024*b* connect a respective lower working volume 2032*a*, 2042*a* of the pressure chamber(s) 2030, 2040 to the pressure regulator 2010. Piston seal(s) 2036, 2046 (e.g., O-ring) on the piston head(s) and piston seal(s) 2038, 2048 on the piston shaft(s) create a seal between the upper working volume 2032*b*, 2042*b* and the lower working volume 2032*a*, 2042*a* within the pressure chamber 2030, 2040. The pressure in each of the working volumes, such as volumes 2032*a*, 2032*b*, 2042*a*, 2042*b*, in each pressure chamber 2030, 2040 can be increased and/or decreased by the pressure regulator 2010. For example, as pressure is applied by the pressure regulator 2010 to one or both of the lower working volumes 2032*a*, 2042*a*, the piston 2034, 2044 is pushed away from, and creates strain in, the microfluidic device 2000. As pressure is applied by the pressure regulator 2010 to one or both of the upper working volumes 2032*b*, 2042*b*, the piston 2034, 2044 is pushed toward the microfluidic device 2000, relieving the strain. Thus, similar to the systems in FIGS. 16-19, microfluidic device 2000 also experiences alternating stretch (e.g., strain) and return (e.g., relief) along its long axis. It is contemplated that the vacuum system may independently or simultaneously affect the upper and lower working volumes in each pressure chamber 2030, 2040.

In some aspects, a hard stop (e.g. a pin in the path of the piston) can be placed in the pressure chamber 2030, 2040 to provide a fixed and consistent starting location for the piston(s) 2034, 2044. It is also contemplated that in some aspects it is desirable to exclude a hard stop to allow the range of motion of the piston(s) to generate a buckling or compression on the microfluidic device 2000.

Figure 21:
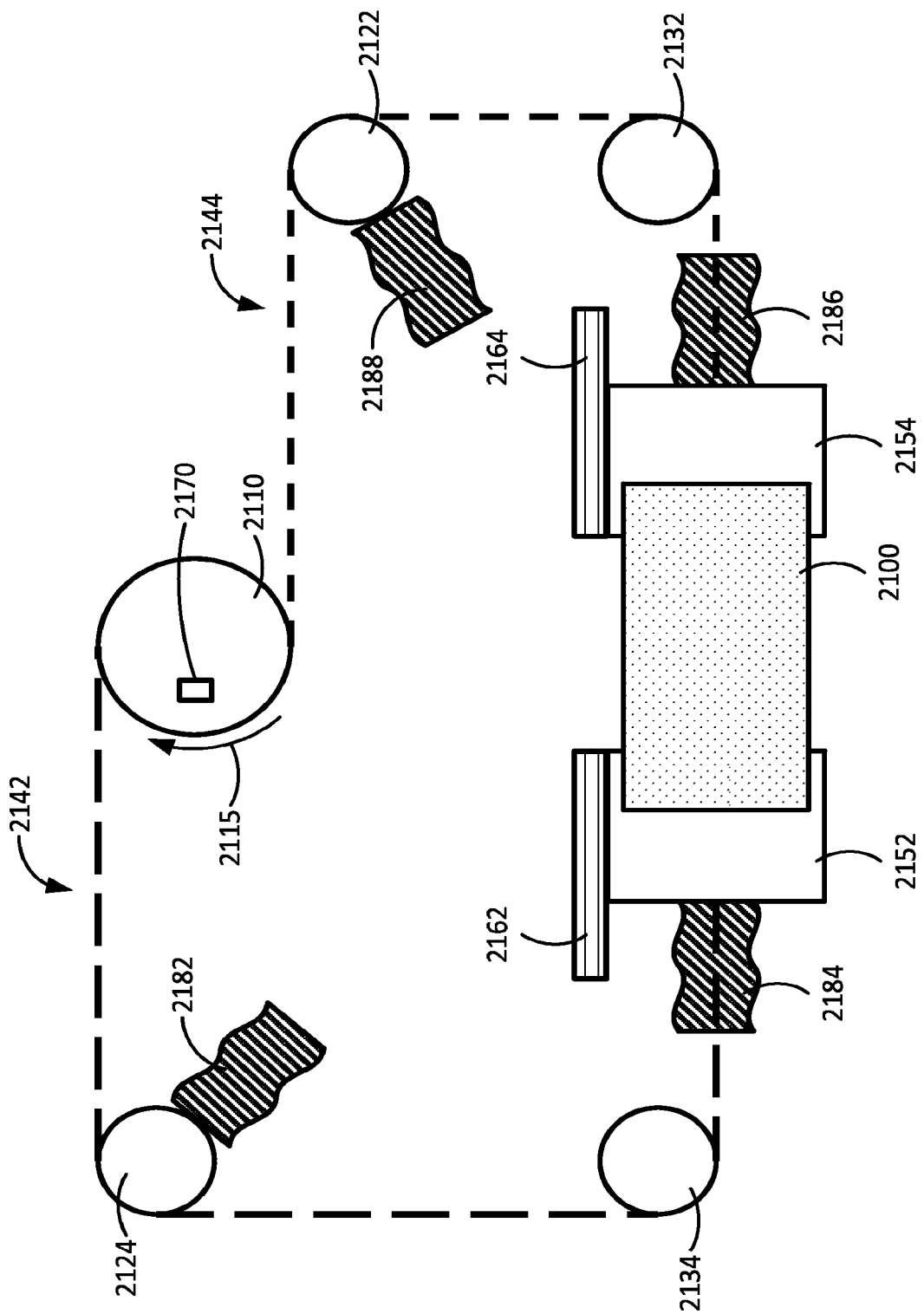
FIG. 21 illustrates an exemplary aspect of a tension element based mechanical system for stretch actuation of microfluidic devices.

FIG. 21 illustrates another example of a mechanical stretch actuation system using a tension element, such as a belt, wire, or chain. For example, a system can include a first tension element 2142 and a second tension element 2144 that are both connected to a tension element connector 2110 that is coupled to a motor (not shown). The first and second tension elements 2142, 2144 can be connected to the tension element connector through a series of pulleys and/or sprockets. One or more pre-tensioning pulleys 2122, 2124 can be used to remove any slack from tension element(s) 2142, 2144 based on desired manufacturing or assembly tolerances. Once pre-tensioned, the pre-tensioning pulleys 2122, 2124 are often fastened in place so that they do not provide varying loads during operation of the stretch actuation system. The tension elements 2142, 2144 can be rigidly attached to the tension element connector 2110. In some aspects, the tension element connector can be a cylinder with the tension elements 2142, 2144 fastened to the cylindrical surface.

It is contemplated that one or both opposing ends of the microfluidic device 2100 are each connected to a connection element, such as elements 2152, 2154. Each connection element 2152, 2154 is positioned between a tension element 2142, 2144 and the respective ends of the microfluidic device. The connection elements can be located on a guide rail, such as rails 2162, 2164, that allows pure line motion (e.g. a linear bearing rail), such that the microfluidic device effectively experiences strain along a single axis parallel to the direction of motion along the guide rail. It is also contemplated that guide rails or guiding tracks having an arc shape can be used to provide for non-planar stretch actuation of a microfluidic device.

As the tension element connector 2110 rotates in a winding direction, as exemplified by arrow 2115 (and in the opposite direction for unwinding), the tension elements 2142, 2144 wind themselves onto the surface of the tension element connector 2110 which translates a force to the connection element(s) 2152, 2154 and effectively to the microfluidic device 2100, which causes the microfluidic device 2100 to stretch or experience strain. The guide rails 2162, 2164 provide for the movement to be linear, and thereby minimizing any twisting movements that might otherwise be experienced due to the tension elements.

As the tension element connector 2110 rotates opposite to the winding direction (e.g., opposite the direction of arrow 2115), the tension elements 2152, 2154 unwind from the tension element connector 2110. Springs 2184, 2186 in contact with the connection element 2152, 2154 or springs 2182, 2188 in contact with the pre-tensioning pulleys 2122, 2124 can assist with maintaining tension in tension elements 2142, 2144 and can facilitate the connection elements 2152, 2154 returning to their starting position. It is also contemplated that the springs may be integral to the microfluidic device 2100 (e.g. the microfluidic device is composed of elastomeric materials). In some aspects, combinations of springs in the stretch actuation system and integral with the microfluidic device may be used.

Figure 22:
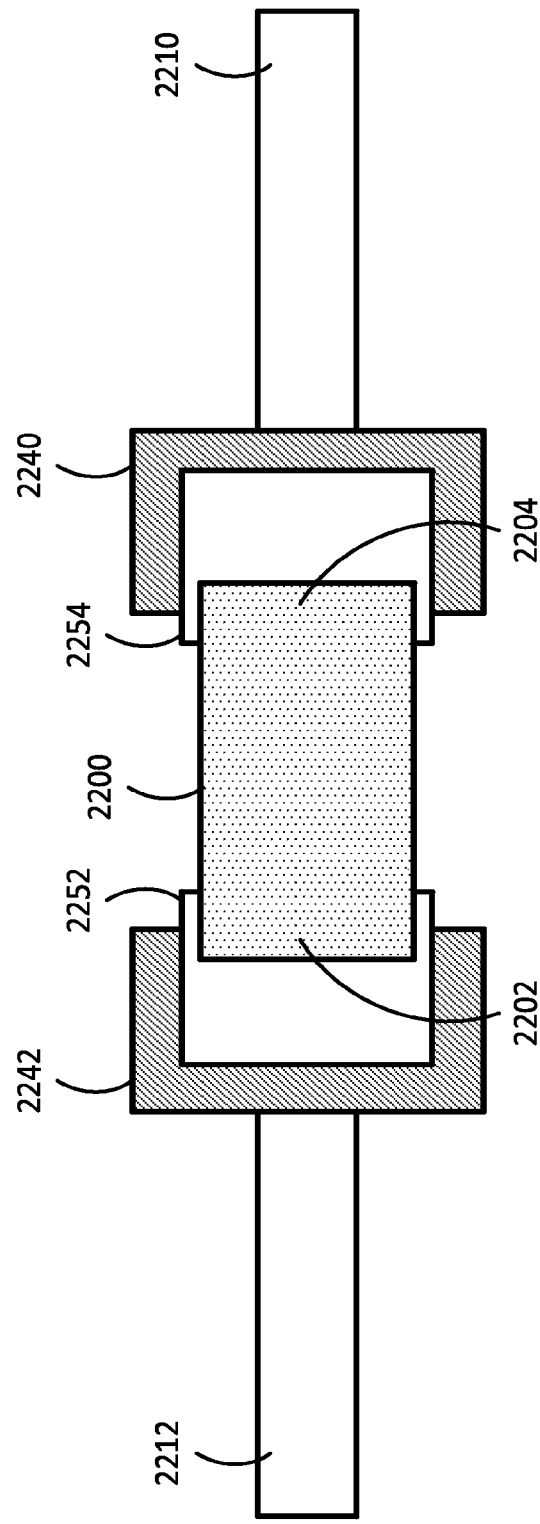
FIG. 22 illustrates an exemplary aspect of a linear motor based mechanical system for stretch actuation of microfluidic devices.

FIG. 22 illustrates another example of a mechanical stretch actuation system using a linear motor. One or both opposing ends 2202, 2204 of a microfluidic device 2200 are connected to a connection element 2252, 2254. Each connection element 2252, 2254 is positioned between a linear motor carriage 2240, 2244 and the respective ends 2202, 2204 of the microfluidic device. In some aspects, the linear motor carriage 2240, 2242 is integral with the connection element 2252, 2254. Each linear motor carriage is coupled to a linear motor 2210 2212 which drives the respective carriage(s) to positions that induce the desired strain and relief in the microfluidic device 2200 by pulling or inducing tension in the microfluidic device or pushing or inducing compression in the microfluidic device. After inducing the desired strain, the linear motor(s) 2210, 2212 then return the linear motor carriage(s) 2240, 2242 to the starting position before strain was introduced into the microfluidic device by the stretch actuation system.

Figure 23:
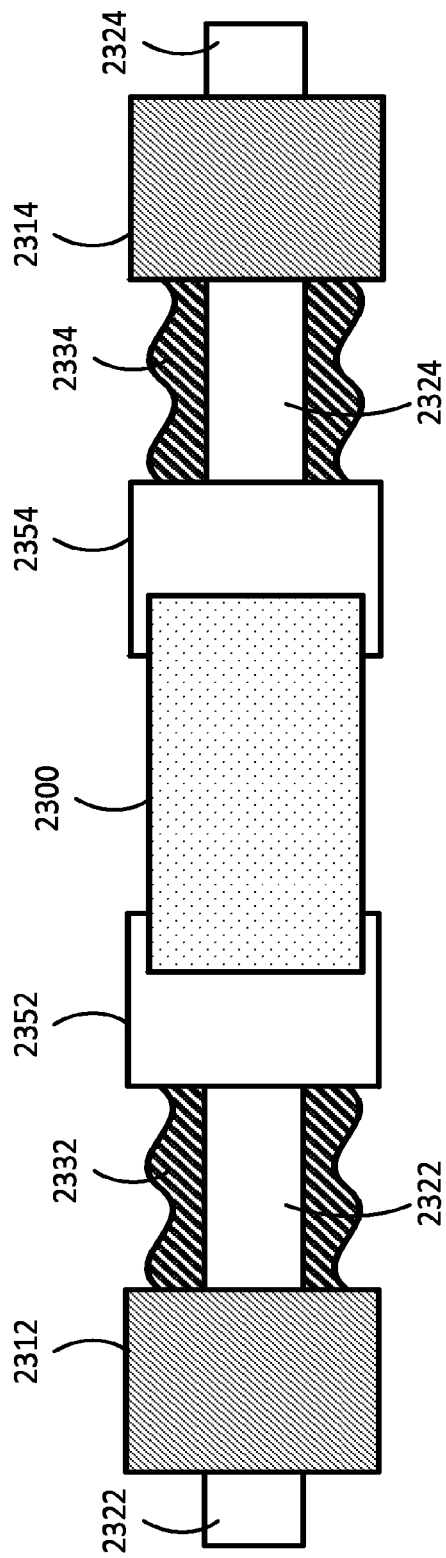
FIG. 23 illustrates an exemplary aspect of a coil-based mechanical system for stretch actuation of microfluidic devices.

FIG. 23 illustrates another example of a mechanical stretch actuation system using a solenoid coil. One or both opposing ends of a microfluidic device 2300 are connected to a connection element, such as connection elements 2352, 2354. Each connection element 2352, 2354 is positioned between a solenoid 2312, 2314 or a voice coil and the respective ends of the microfluidic device 2300. Each solenoid 2312, 2314 includes a solenoid shaft 2324, 2322 that may pass through the center of the solenoid 2312, 2314. Energizing the solenoid causes the solenoid shaft to move away from the fastened microfluidic device 2300, and thus, induce strain into the microfluidic device 2300. Similarly, for voice coil aspects, energizing a voice coil that is positioned similarly as the solenoid(s) 2312, 2314 pulls a respective moving element (e.g., an element analogous to the solenoid shaft) that is attached to the microfluidic device. It is contemplated that the moving element for a voice coil embodiment may be a permanent or induced magnet.

Next, as the solenoid(s) 2312, 2314 or the voice coil(s) are de-energized, spring(s) 2332, 2334 positioned to be in contact with the connection element(s) 2352, 2354 push the microfluidic device 2300 back to its starting position. Alternatively, the springs may be integral to the microfluidic device 2300 (e.g. the microfluidic device 2300 may be composed of elastomeric materials), or a combination of both springs and elastomeric materials may be used in the system.

Figure 24:
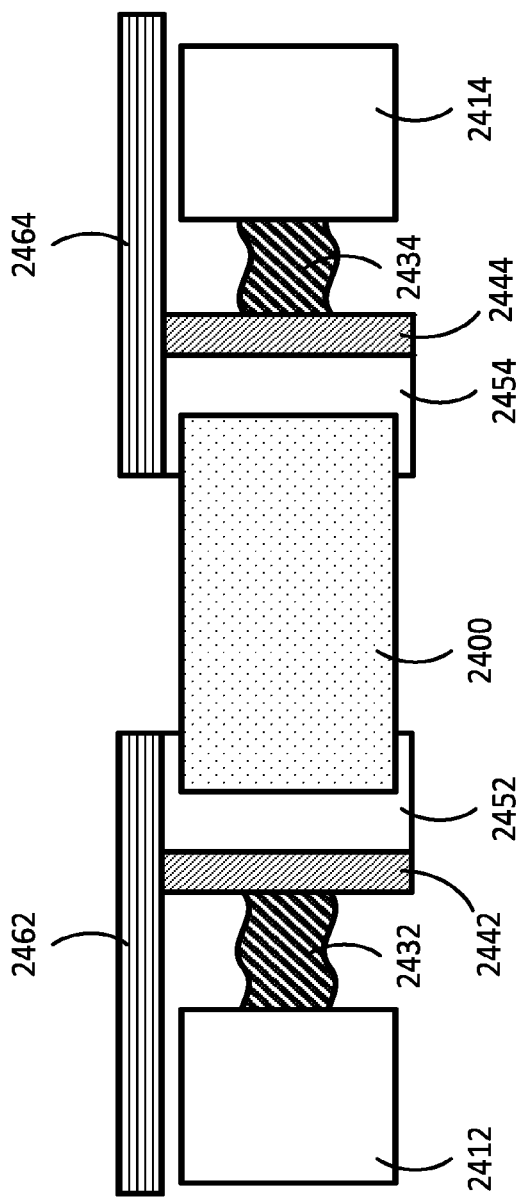
FIG. 24 illustrates an exemplary aspect of a magnetic-based mechanical system for stretch actuation of microfluidic devices.

FIG. 24 illustrates another example of a mechanical stretch actuation system using an electromagnet. One or both opposing ends of a microfluidic device 2400 are connected to a connection element, such as connection elements 2452, 2454. Each connection element 2452, 2454 may be positioned between a permanent or induced magnetic element(s) 2442, 2444 and the respective ends of the microfluidic device 2300 or the connection element may be integral with the magnetic element(s) 2442, 2444. The connection element(s) and/or the magnetic element can further be connected to guide rail(s) 2464 that maintain a linear motion parallel to the guide rails during stretch actuation of the microfluidic device 2400. In some aspects, it is also contemplated that guide rails or guiding tracks having an arc shape can be used to provide for non-planar stretch actuation of a microfluidic device.

In some aspects, a rigidly fixed electromagnet 2412, 2414 is positioned opposite a respective magnetic element 2442, 2444 on either side of the microfluidic device 2400. When the electromagnet(s) 2412, 2414 are energized, the respective opposing magnetic element(s) 2442, 2444 are drawn toward the electromagnet, and thus, induces strain in the microfluidic device 2400. Then, as the electromagnets are de-energized, springs (e.g., 2432, 2434) positioned to be in contact (or in operative connection, such as through the magnetic element) with the connection element 2452, 2454 push the microfluidic device 2400 back to its starting position. Alternatively, the springs may be integral to the microfluidic device 2400 (e.g. the microfluidic device 2400 may be composed of elastomeric materials), or a combination of both springs and elastomeric materials may be used in the system.

Figure 25:
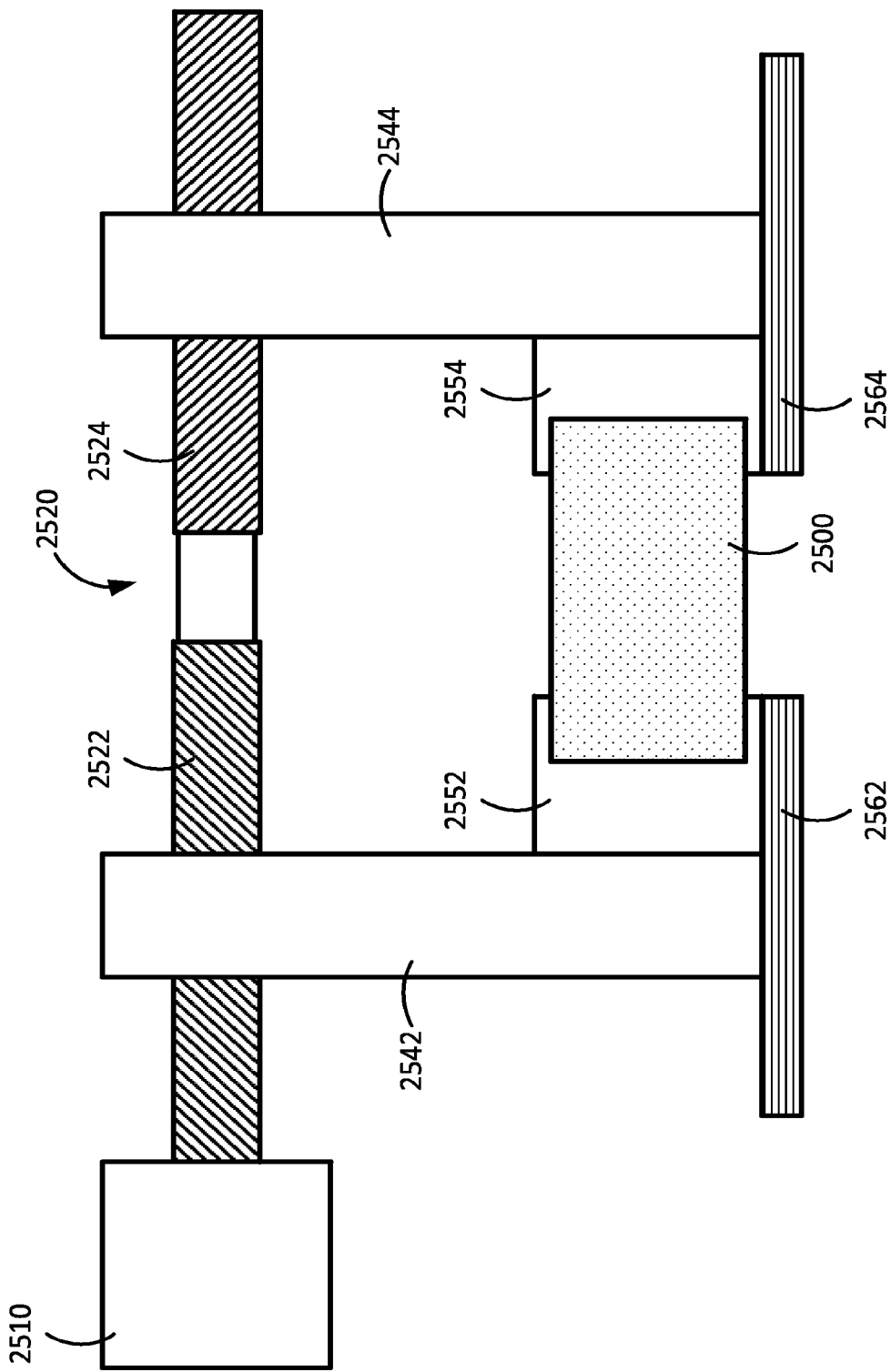
FIGS. 25 and 26 illustrate exemplary aspects of a drive-arm based mechanical system for stretch actuation of microfluidic devices.

FIG. 25 illustrates another example of a mechanical stretch actuation system using a threaded drive shaft that moves a drive arm. It is contemplated that one or both ends of a microfluidic device 2500 are connected to a drive arm 2542, 2544 and optional guide rail(s) 2562, 2564 via connection element(s) 2552, 2554. The optional guide rail serves a similar purpose as described in the other embodiments, such as those illustrated in FIGS. 21 and 24—to assist with providing linear motion in the microfluidic device 2500 as the device is subject to stretch actuation. In some aspects, the drive arms(s) 2542, 2544 are each connected to a connection element 2552, 2554 where the opposing ends of the microfluidic device 2500 are fastened to the connection elements.

Each drive arm 2542, 2544 can include an integral internal threaded surface extended therethrough that has either a left-hand thread or a right-hand thread of a particular size (e.g., ¼-20 or other standard or non-standard sizes). A drive shaft 2520 with a left-hand threaded portion 2522 and right-hand threaded portion 2524 is threaded or otherwise placed into the nuts of both drive arms 2542, 2544. A motor 2510 is coupled with the drive shaft 2520. As the motor 2510 turns the drive shaft 2520, the drive arms 2542, 2544 move either away from (e.g., inducing strain in the microfluidic device 2500) or toward (relieving the strain in the microfluidic device 2500) each other depending on the drive shaft 2520 rotation direction and the thread type for the drive arm 2542, 2544 (e.g., a left-hand or right-hand thread).

In some aspects, of the system described in FIG. 25, each drive arm may be driven by a separate motor and by two drive shafts extending from or otherwise coupled to the motor. In this type of a modified configuration, a double-threaded rod or drive shaft 2520 is replaced by the drive shafts or rods coupled to each of the individual motors.

The actual connections of fastening of the microfluidic device 2500 to the connection element 2552, 2554 on the stretch actuation system can be accomplished using any of the connection methods or systems described above or variations thereof.

Figure 26:
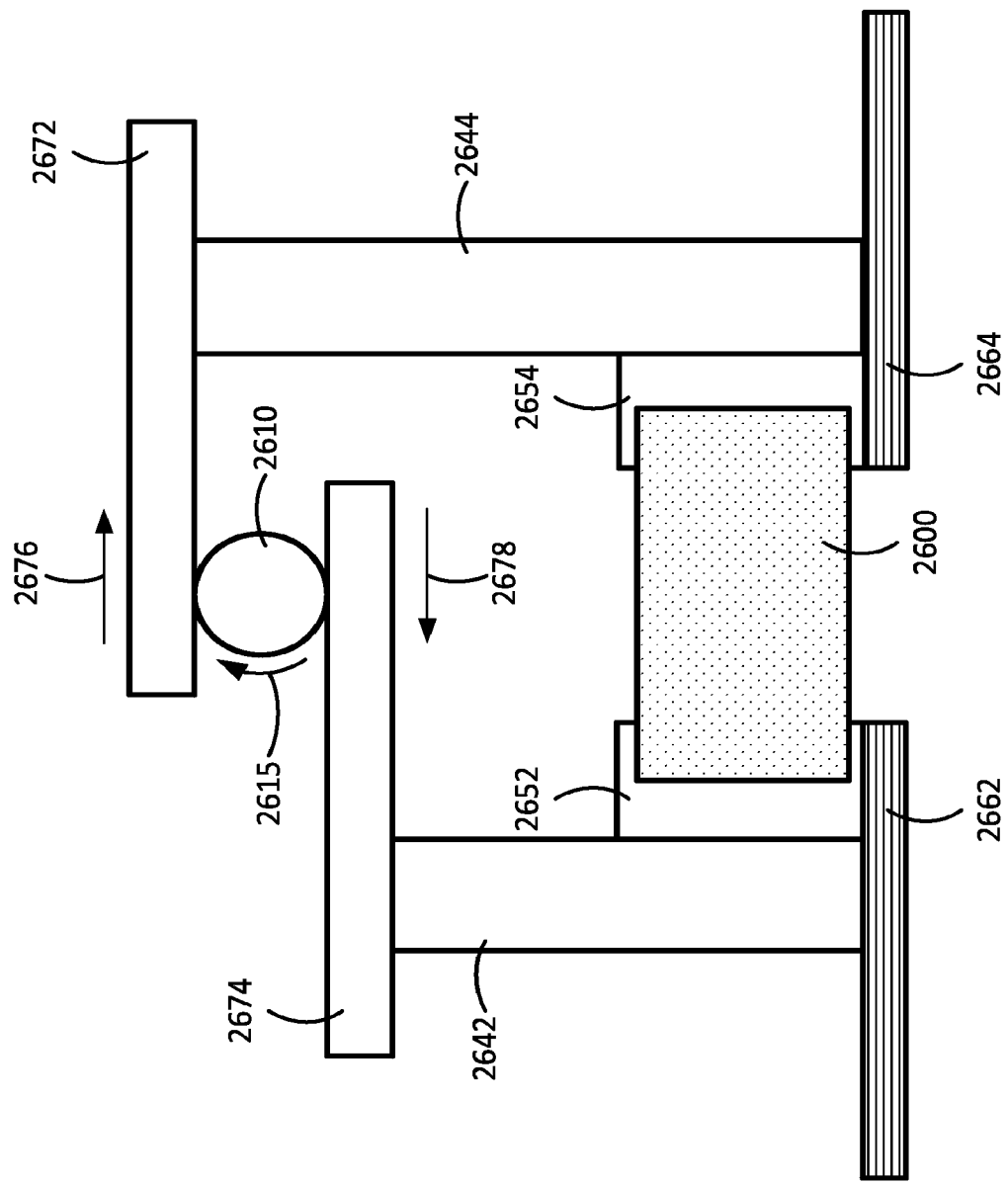

FIG. 26 illustrates another example of a mechanical stretch actuation system using a gear rack system. It is contemplated that one or both ends of a microfluidic device 2600 are connected to a drive arm 2642, 2544 and optional guide rail(s) 2662, 2664 via connection element(s) 2652, 2654. The optional guide rail serves a similar purpose as described in the other embodiments, such as those illustrated in FIGS. 21, 24, and 25—to assist with providing linear motion in the microfluidic device 2600 as the device is subject to stretch actuation. In some aspects, the drive arms(s) 2642, 2644 are each connected to a connection element 2652, 2654 where the opposing ends of the microfluidic device 2600 are fastened to the connection elements. It is also contemplated that guide rails or guiding tracks having an arc shape can be used to provide for non-planar stretch actuation of a microfluidic device.

Each drive arm 2642, 2644 can include a gear rack 2672, 2674 that may or may not be integral with the drive arm. In some aspects, the gear rack teeth associate with each drive arm face each other. For example, the teeth for the gear rack 2674 face upward and the teeth for the gear rack 2672 face downward. A drive gear 2610 that is coupled to a motor meshes with the gear rack 2672, 2674. In the exemplary aspect of FIG. 26, as the drive gear 2610 rotates clockwise as illustrated by rotational arrow 2615, gear racks 2672, 2674 move away from each other as shown by arrows 2676 and 2678. As the drive gear 2610 rotates the opposite direction, the gear racks move toward each other. As shown, a clockwise rotation pushes the drive arms 2642, 2644 away from each other, inducing strain in the microfluidic device 2600. In some aspects, it is contemplated that each drive arm and gear rack assembly can be driven by its own drive gear.

Figure 27:
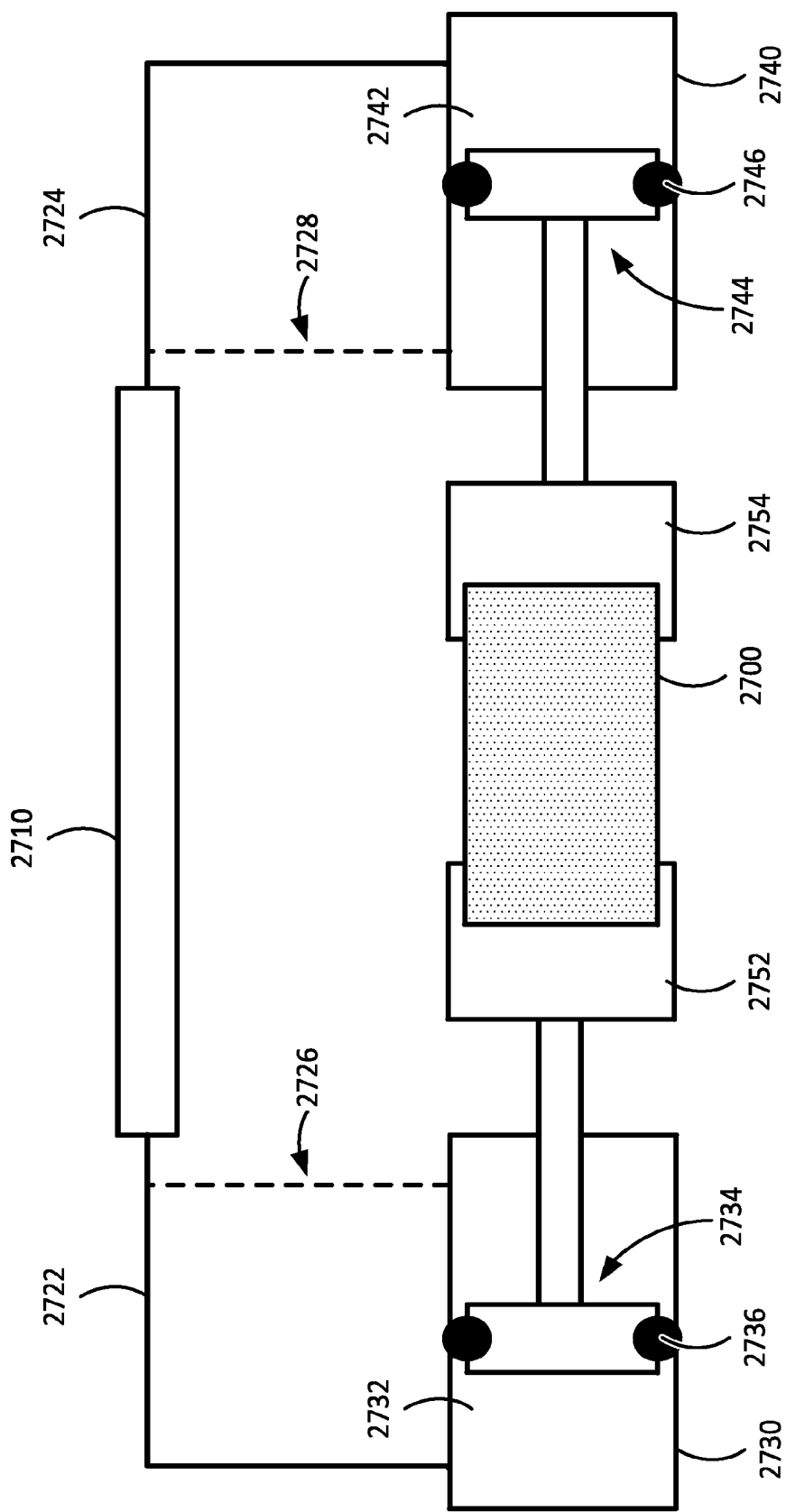
FIG. 27 illustrates an exemplary aspect of a fluid-based mechanical system for stretch actuation of microfluidic devices.

FIG. 27 illustrates another example of a mechanical stretch actuation system using a hydraulic or combination hydraulic and pneumatic system. Similar to the pneumatic systems shown in FIGS. 17-20, a mechanical stretch actuation system can also use a liquid, multiple liquids, or a combination of liquids and gasses to drive the stretch actuation of a microfluidic device 2700. The use of one or more liquids can be desirable over a purely pneumatic design for a plurality of reasons including that liquids can transmit volumetric control. For example, an actuation by a particular volume at the liquid-control mechanism (e.g., liquid pump 2710) can correspond to a similar volumetric actuation on a piston (e.g., pistons 2737, 2744). In turn, the volumetric actuation of the piston can correspond to a designated length of translation and stretch on a microfluidic device 2700. This can allow for simple control of the extent the microfluidic device 2700 is stretched. It is also contemplate that the liquid pump 2710 may be more than one pump and can include a volumetric pump such as a syringe pump or peristaltic pump, which can be driven to dispense or remove specified volumes. Use of volumetric pumps can be desirable as they can simplify system calibration and control. The types of liquids contemplated for the system shown in FIG. 27 can include water, oil, or similar liquids.

Analogous to one or more of the system(s) of FIGS. 17-20, it is contemplated that one or both ends of microfluidic device 2700 are connected to a pressure chamber 2730, 2740 that includes a piston 2734, 2744. The shaft(s) of piston(s) 2734, 2744 are each connected to a connection element 2752, 2754 where the opposing ends of the microfluidic device 2700 are fastened to the connection elements. Through use of the piston(s) 2734, 2744, motion is translated to the microfluidic device 2000.

Each pressure chamber 2730, 2740 includes an interior. Fluid connecting line(s) 2722, 2724 can connect to a working volume 2732, 2742 of the pressure chamber(s) 2730, 2740 to a fluid pump (e.g., liquid pump 2710). Alternate fluid connecting line(s) 2726, 2728 can alternatively connect to a lower working volume of the pressure chamber(s) 2730, 2740 to the fluid pump. Piston seal(s) 2736, 2746 (e.g., O-ring) on the piston head(s) create a seal to form the different working volumes within the pressure chamber. The pressure in each of the working volumes in each pressure chamber 2030, 2040 can be increased and/or decreased by the fluid pump (e.g., liquid pump 2710). For example, as liquid is removed by the liquid pump 2710 from one or both of working volumes 2732, 2742, the pistons 2734, 2744 are pushed away from, and a strain is created in the microfluidic device 2700. As liquid is moved into to one or both of working volumes 2732, 2742, the piston 2734, 2744 is pushed toward the microfluidic device 2700, relieving the strain. Thus, similar to the systems previously described, microfluidic device 2700 also experiences alternating stretch (e.g., strain) and return (e.g., relief) along its long axis.

Figure 28:
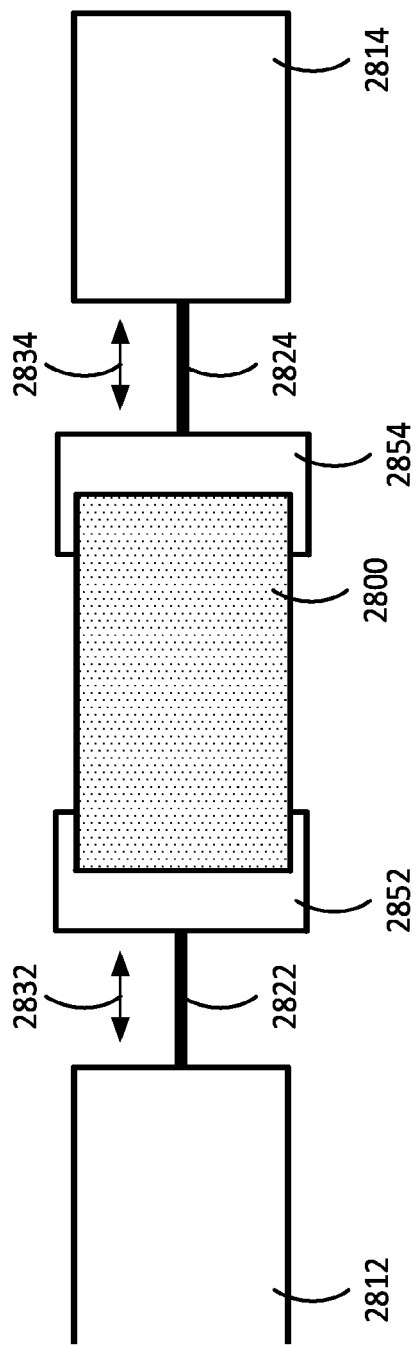
FIG. 28 illustrates an exemplary aspect of a motion converter based mechanical system for stretch actuation of microfluidic devices.

FIG. 28 illustrates another example of a mechanical stretch actuation system using a motion converter. One or both of the opposing ends of a microfluidic device 2800 are connected to a connection element 2852, 2854. Each connection element is positioned between a motion converter 2812, 2814 and the respective ends of the microfluidic device 2800. Each motion converter 2812, 2814 is connected or coupled to a linkage 2822, 2824 that transmits linear motion generated by the motion converter 2812, 2814 to the connection element(s) 2852, 2854, which are fastened to the microfluidic device 2800. The linear motion causes the linkage(s) 2822, 2824 to move away from the fastened microfluidic device 2800, and thus, induce strain into the microfluidic device 2800 and to push the microfluidic device 2800 back to its starting position. Similar to the guide rails shown in FIGS. 24 through 26, option guide rail(s) may be used in the exemplary system shown in FIG. 28. For example, certain motion converter may impart movements to the microfluidic device that are not entirely or effectively a linear motion, where the guide rails can provide for that linear motion.

Motion converters can translate linear motion to linear motion (in different directions) or rotational motion to linear motion as such converters are known in the art. An example of a rotational to linear motion converter includes a lead screw with nuts or ball screws with ball nuts. Examples of motion converters can be found in *Mechanisms and Mechanical Devices Sourcebook*, $3^{rd}$ Ed., by Neil Sclater and Nicholas Chironis, as published by McGraw-Hill (2001). In addition to translating linear and rotational motion into linear motion, motion converters can also translate heat and electricity into linear motion. Examples of such motion converters include solenoids, linear motors, piezoelectric actuators, or shape memory alloy (SMA) actuators (e.g., a lightweight, solid-state alloy alternative to conventional actuators that when deformed returns to its pre-deformed shape when heated).

Figure 29:
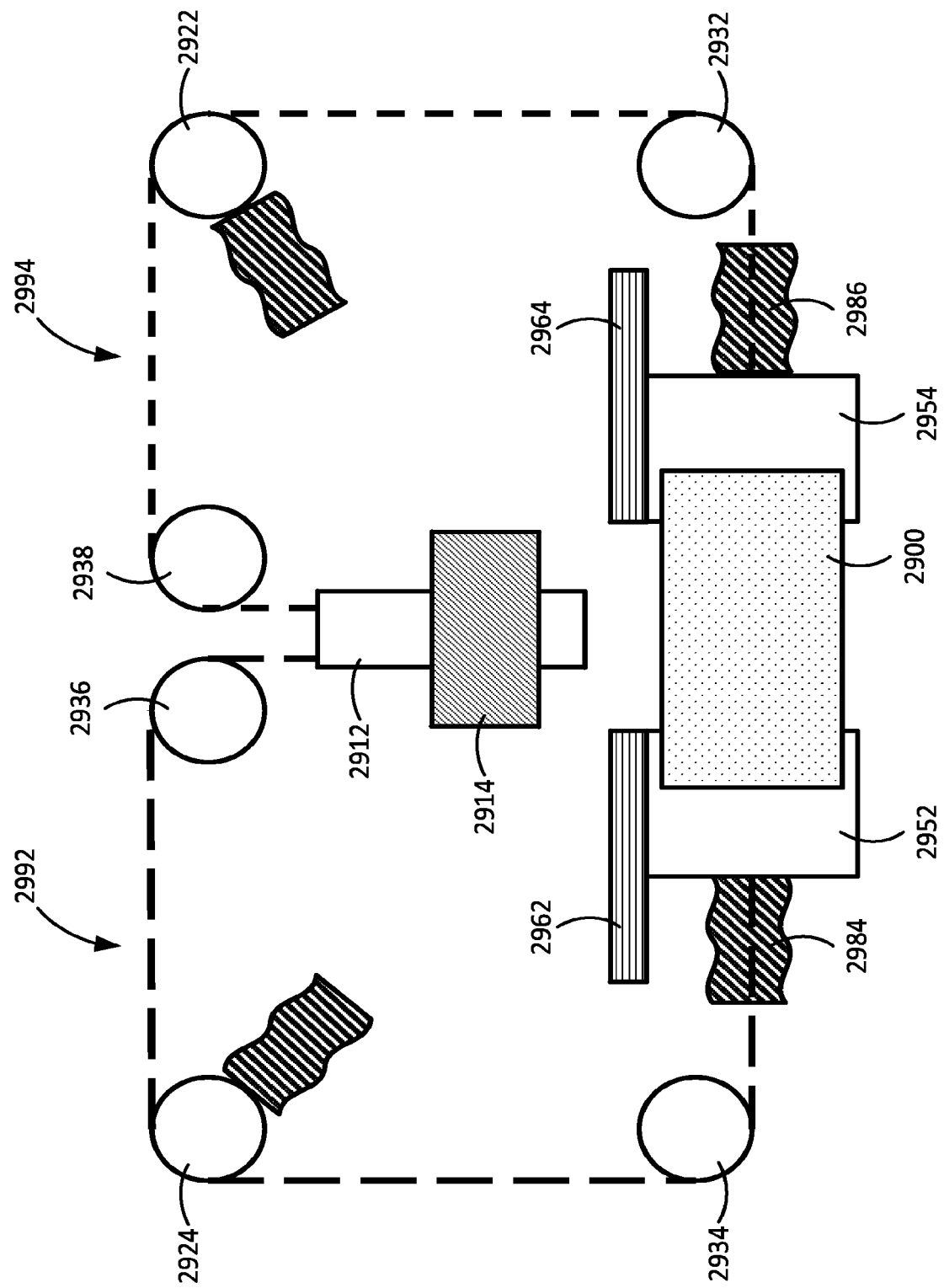
FIG. 29 illustrates an exemplary aspect of a combination solenoid and tension element based mechanical system for stretch actuation of microfluidic devices.

FIG. 29 illustrates another example of a mechanical stretch actuation system using a combination of the systems and processes described above. For example, a solenoid 2914 with tension elements 2992, 2994 can be applied to drive the stretch actuation of a microfluidic device 2900. In this exemplary aspect, the tension elements 2914, 2992 are connected to the solenoid 2914 via the solenoid shaft 2912 in place of a motor and tension element connector (e.g., see FIG. 21). Similar to the system of FIG. 21, the combination system can include pre-tensioning pulleys 2922, 2924 and idler pulleys 2932, 2934. As the solenoid 2914 is energized, the solenoid shaft 2912 pulls on the tension elements 2914, 2992 translating a force to the microfluidic device 2900 and inducing strain. As the solenoid 2914 is de-energized, springs 2984, 2986 in contact with respective connection element(s) 2954, 2984 maintain tension in tension elements 2914, 2992 and facilitate the connection elements returning to their starting position. Alternatively, the springs 2984, 2986 can be integral to the microfluidic device 2900, such as where a microfluidic device is composed of elastomeric materials. A combination of springs in contact with connection elements and the use of elastomeric materials in the microfluidic device are also contemplated.

While the embodiments illustrated in FIGS. 16 through 29 show strain being induced by stretching a microfluidic device in a direction parallel to the devices long dimension, it is also contemplated that strain can be induced in a direction parallel to the microfluidic device's narrow dimension. Stretch actuation can further be applied along any desired axis or line of a microfluidic device where the microfluidic device can be fastened to the stretch actuation system using the described connection systems and methods in this disclosure.

In some aspects, it is contemplated that each of the described stretch actuation systems can have one-sided variations for microfluidic devices where it is allowable for the microfluidic device's centerline to move during stretch actuation. For example, the opposing end of the microfluidic device can fastened to a fixed connection element rather than one that moves. A benefit of a one-sided stretch actuation system is that the complexity of the mechanical stretch actuation system is decreased. For microfluidic devices where an increased movement in fluidic ports is of minimal consequence, the breaking of symmetry about the centerline of the microfluidic device can be acceptable and the one sided variation can be a desirable configuration.

In some aspects, it is also contemplated that actuation on one side or at one end of a microfluidic device can be mirrored or translated to the opposing end of a microfluidic device using a variety of mechanical configurations, such as the use of pulleys or mechanical linkages.

Exemplary aspects of strain sensors are illustrated in FIGS. 16, 17, 21 that may be applied to any of the mechanical stretch actuation systems described above. Exemplary aspects of sensor locations across which strain can be measured using any of the below described strain monitoring techniques, include sensor locations 1670, 1772, 1774, 1776, 1870, and 2170.

The biological effect experienced in an experiment using a microfluidic device, such as a organomimetric device, depends on the magnitude of the applied strain during stretch actuation. Thus, method of targeting and/or monitoring the strain in the microfluidic device is desirable. Typical strain rates for organomimetric devices (e.g., organ-chips) are about 5 percent to about 30 percent at stretch actuation frequencies of about 0.3 Hz to about 1 Hz.

Exemplary systems and methods are now described below for monitoring the stretch actuation induced strains in the microfluidic devices for the mechanical stretch actuation systems described above, for example in FIG. 16 through 29.

Strains experienced by a microfluidic device subject to stretch actuation can be measured by incorporating or mounting one or more strain gauges into the microfluidic device itself (e.g., the organ-chip) or across the mounts (e.g., sensor locations 1670, 1772) for the microfluidic device (e.g., a string or wire stretched across or between two connection elements). It is also contemplated that strains can be measured by incorporating or mounting one or more strain gauges along or across any section (e.g., sensor locations 1670, 1772, 1774, 1776) of the stretch mechanism that moves in correspondence with the microfluidic device stretch. While different strain gauge types and technologies are contemplated, one exemplary aspect of a strain gauge includes resistive sensors. In one exemplary aspect, a strain gauge can include a string across the connection elements that includes a flag on it so the user can visually observe the straining during stretch actuation of the microfluidic device.

In some aspects, linear encoders, such as exemplary linear encoder 1870 in FIG. 18, can be incorporated in one or more locations in a mechanical stretch actuation system, such as across the chip or microfluidic device mount (e.g., see 1670 or 1772 in FIGS. 16 and 17), along a piston (e.g., see pistons 1734, 1744, 1837, or 1844 in FIGS. 17 and 18), along a tension element (e.g., see tension elements 2142 or 2144 in FIG. 21), along a rack (e.g., see racks 2672 or 2674 in FIG. 26), along a linear motor (e.g., see 2210 or 2212 in FIG. 22), along a guide rail (e.g., see guide rails 2162, 2164, 2462, 2464, 2562, or 2564 in FIGS. 21, 24, and 25), or along or on any system components that translates linearly as the microfluidic device is actuated. It is contemplated that any of the various linear encoding devices and methods known in the art can be applied for measuring strains in a mechanical stretch actuation system, including optical, resistive, and magnetic methods and systems.

In some aspects, rotary encoders can be incorporated in one or more stretch actuation system locations including, such as on cams (e.g., see 1610 in FIG. 16), pulleys (e.g., see 2122, 2124, 2132, 2134, 2922, 2924, 2932, 2934, 2936, or 2938 in FIGS. 21 and 29), motors (e.g., see the motor for tension element connector 2110, 2510, or the motor for drive gear 2610 in FIGS. 21, 25, and 26), shafts (e.g., see 2520 in FIG. 25), gears (e.g., see drive gear 2610 in FIG. 26), or any system components that translates rotationally as the microfluidic device is actuated. It is contemplated that any of the various rotary encoding devices and methods known in the art can be applied for measuring strains in a mechanical stretch actuation system, including optical, resistive, and magnetic methods and systems.

In some aspects, microfluidic device strain can be controlled in stretch actuation systems that include pneumatics by applying a controlled positive or negative pressure via a pressure or vacuum regulator connected to a pressure chamber. The relationship between applied pressures and the corresponding strain can be established beforehand or calibrated using other strain feedback mechanisms or through observational techniques. Such pressure control techniques can be used, for example, in the systems shown in FIGS. 17 through 20 and 27.

In some aspects, microfluidic device strain can be controlled in stretch actuation systems that include motors, voice coils, solenoids, or piezo drivers by applying a controlled force, current, or voltage. The relationship between applied force, current, or voltage and the corresponding strain can be established beforehand or calibrated using other strain feedback mechanisms or through observational techniques. Such force, current, or voltage techniques can be used, for example, in the systems shown in FIGS. 16, 21 through 26, 28, and 29.

In some aspects, imaging techniques can be applied to determine the strain or extent of stretch in a microfluidic device. Imaging can be done of the microfluidic device itself, or alternatively, of any moving portion of the stretch actuation system. It is contemplated that imaging also can be used to provide feedback to the stretch actuation system. Imaging can also be used intermittently for purposes of calibration of the actuation-to-stretch relationship. For example, images might be taken on a periodic basis, once for each microfluidic device, or once per experiment. In one exemplary aspect, a microscope can be used to evaluate how much the microfluidic device stretches at a particular pneumatic pressure and to construct a pressure-to-stretch relationship. Thereafter, the determined relationship could be used as part of the pressure control embodiment described above for pneumatic systems without further microscopic imaging.

In some aspects, photogate monitoring of the extent of a microfluidic device or a suitable part of the stretch actuation system can be applied to determine at what actuation setting the microfluidic device has reached a certain stretch. The determination of the actuation setting to preselected stretch can then be used to define an actuation-to-stretch relationship, which in turn, can be applied to drive the microfluidic device to a desired stretch. Alternatively, one or more photogates can be used to specify predetermined stretch setpoints that can be used to provide feedback to the stretch actuation mechanism.

In some aspects, limit switch monitoring of the extent of a microfluidic device or a suitable part of the stretch actuation system can be applied to determine at what actuation setting the microfluidic device has reached a certain stretch. Similar to photogate monitoring, the determination of the actuation setting to preselected stretch can then be used to define an actuation-to-stretch relationship, which in turn, can be applied to drive the microfluidic device to a desired stretch. Alternatively, one or more limit switches can be used to specify predetermined stretch setpoints that can be used to provide feedback to the stretch actuation mechanism.

In some aspects, optical sensors, such as quadrant detectors, lateral effect position sensors, or their one-dimensional counterparts, or proximity sensors can be used to determine the stretch of the microfluidic device or the position(s) of moving portions of the stretch actuation system that directly correlate to strain.

It is contemplated that the above described systems and methods (and the sensor arrangement(s) associated with each system and method) for strain targeting and monitoring in a mechanical stretch actuation system can be combined for a particular stretch actuation mechanism for a microfluidic device. For example, strain in a microfluidic device during stretch actuation can be controlled by monitoring the linear position of one of the connection elements on a guide rail (e.g., see FIGS. 21 and 24 through 26) using, for example, a linear encoder, such as the linear encoder 1870 in FIG. 18. One exemplary aspect of a linear encoder is the RG2 linear encoder available from Renishaw plc of Gloucestershire, United Kingdom or Hoffman Estates, Illinois in the USA. In some aspects, instead of the position sensor on the guide rail, the strain in the microfluidic device could be targeted by monitoring the rotational position of the tension element connector 2110 (e.g., using a rotary encoder 2170 in FIG. 21). One exemplary aspect of a rotary encoder is the GHM3 incremental rotary encoder available from BEI Sensors of Strasbourg, France or Goleta, California in the USA. The amount of rotation of the tension element connector 2110 can be correlated to the displacement of the connection elements which corresponds to the strain in the microfluidic device. In some aspects, the strain in the microfluidic device could also be targeted by monitoring the linear position of the solenoid shaft (e.g., 2324, 2912) relative to its starting position (e.g., using a linear encoder). Similarly, the strain in the microfluidic device could also be targeted by monitoring the position of the connection element with a position sensor (e.g., using a linear encoder). In further aspects, the strain in the microfluidic device could be targeted through a known correlation between solenoid power and microfluidic device strain allowing for a determination to be made of the amount of energy to deliver to the solenoid (e.g., see solenoids 2312, 2314, 2914 in FIGS. 23 and 29) based on desired microfluidic device strain. It is also contemplated that active monitoring of a target feature can be performed optically. For example, features on the surface of a membrane could be tracked using software and the strain could be calculated based on their deformation or change in relative position.

It is contemplated that some of the stretch targeting or measurement methods can also be used for calibration purposes, such as to derive relationship between actuation and the extent of stretch. For example, imaging can be applied to determine a pressure-to-stretch relationship, or a proximity switch can be applied to define a current-to-stretch relationship, such as for a voice coil. Calibration determinations can be completed according to different plans, including one calibration per microfluidic device, once per stretch actuation session, or repeated on some periodic basis.

According to an alternative embodiment A, a mechanical modulation system for stretch actuation of a microfluidic device includes a mechanical actuation arrangement configured to impart a generally cyclical linear motion along a single plane defined by a microfluidic device mounted within the mechanical modulation system. A plurality of opposing connection elements are physically connected to the mechanical actuation system. The plurality of opposing connection elements are configured to fasten a first end and an opposing second end of a microfluidic device to the opposing connection elements such that the first end and the second end of a microfluidic device are each fixed to one of the connection elements and such that straining of the microfluidic device during cyclical linear motions of a stretch actuation process is transferred to the portion of the microfluidic device between the first end and the opposing second end. A sensor arrangement identifies strain in the microfluidic device.

According to an alternative embodiment B, the system of alternative A further comprises the microfluidic device including a membrane with cells adhered thereto.

According to an alternative embodiment C, the system of one of alternatives A or B comprises the straining causing a deformation to both the membrane and the microfluidic device.

According to an alternative embodiment D, the system of any one of alternatives A to C further comprises that the fastening of the opposing first end and second end of the microfluidic device to the opposing connection elements includes a plurality of male pin and female slot mating elements.

According to an alternative embodiment E, the system of any one of alternatives A to D further comprises that the cyclical linear motion during stretch actuation is generally parallel to a long dimension of the microfluidic device. The linear motion is controlled by at least one of one or more guide rails operatively connected to one of more of the plurality of opposing connection elements.

According to an alternative embodiment F, the system of any one of alternatives A to E further comprises that one of the plurality of opposing connection elements is a fixed connection that is non-movable and the other connection element is a non-fixed connection that is movable.

According to an alternative embodiment G, the system of any one of alternatives A to E further comprises that at least two of the plurality of opposing connection elements are movable.

According to an alternative embodiment H, the system of any one of alternatives A to G further comprises that the mechanical actuation system include at least one arm integral with at least one of the plurality of opposing connection elements.

According to an alternative embodiment I, the system of any one of alternatives A to H further comprises that the mechanical actuation arrangement includes a motor coupled to a rotating cam configured to impart movement to at least one drive arm that is operatively connected to at least one of the plurality of connection elements.

According to an alternative embodiment J, the system of any one of alternatives A to I further comprises that the mechanical actuation arrangement is a fluid-based system including one or more piston shafts connected to at least one of the plurality of opposing connection elements.

According to an alternative embodiment K, the system of alternative J further comprises that the sensor arrangement is a pressure control system including one or more pressure sensors such that straining of the microfluidic device is controlled based on applied pressures to a piston connected to at least one of the plurality of opposing connection elements. The applied pressures correlate to predetermined strain values.

According to an alternative embodiment L, the system of any one of alternatives A to K further comprises that the sensor arrangement includes one or more strain gauges mounted between the plurality of opposing connection elements.

According to an alternative embodiment M, the system of any one of alternatives A to L further comprises that the sensor arrangement includes one or more strain gauges mounted along a piston shaft.

According to an alternative embodiment N, the system of any one of alternatives A to M further comprises that at least one of the strain gauges includes a marking element to allow for visual observation of straining due to stretch actuation of the microfluidic device.

According to an alternative embodiment O, the system of any one of alternatives A to N further comprises that the sensor arrangement includes a linear encoder, a rotary encoder, an optical positioning detector, and/or any combinations thereof.

According to an alternative embodiment P, the system of any one of alternatives A to O further comprises that the sensor arrangement includes imaging for calibrating the strain associated with the linear motions imparted to the microfluidic device by the mechanical actuation arrangement.

According to an alternative embodiment Q, the system of any one of alternatives A to P further comprises that the sensor arrangement indirectly identifies strain in the microfluidic device through monitoring of a moving portion of the mechanical actuation arrangement. Movement of the moving portion is directly correlated to the stretch of the microfluidic device.

According to an alternative embodiment R, the system of any one of alternatives A to Q further comprises that the first end and the second end of the microfluidic device are each fixed to one of the connection elements such that entry and exit ports positioned at the first end and second end are not exposed to additional strains during stretch actuation of the microfluidic device.

According to an alternative embodiment S, the system of any one of alternatives A to R further comprises that the sensor arrangement includes an imaging device, a limit switch, a proximity switch, and/or any combinations thereof.

According to an alternative embodiment T, the system of any one of alternatives A to S further comprises that the mechanical actuation arrangement includes an electric motor, a voice coil, a solenoid, a piezo driver, and/or any combinations thereof.

According to an alternative embodiment U, the system of any one of alternatives A to T further comprises that the sensor arrangement includes one or more sensors for determining a current, a voltage, an applied force, and/or any combinations, in the electric motor, voice coil, solenoid, and/or piezo driver.

According to an alternative embodiment V, the system of any one of alternatives A to U further comprises that the microfluidic device includes a plurality of microfluidic devices each having a first end and an opposing second end. Each of the first ends of the microfluidic devices is fastened to the one of the plurality of opposing connection elements and each of the opposing second ends of the microfluidic devices is fastened to another one of the plurality of opposing connection elements.

According to an alternative embodiment W, a microfluidic system for monitoring a behavior of cells includes a microfluidic device having at least one microchannel in which the cells are disposed. A mechanical actuation device for stretching the microfluidic device along a single plane is defined by the microfluidic device. The mechanical actuation system includes a plurality of opposing connection elements configured to be fastened to a first end and an opposing second end of a microfluidic device. A strain monitoring system identifies a strain in the microfluidic device in response to the stretching.

According to an alternative embodiment X, the system of alternatives W further comprises that the microfluidic device includes a membrane on which the cells are attached.

According to an alternative embodiment Y, the system of one of alternatives W or X further comprise that the mechanical actuation device imparts cyclic linear motion along the single plane. The fastening of the first end and the opposing second end of the microfluidic device provides a fixed connection such that the strain of the microfluidic device during the cyclic linear motions of the stretching is transferred to the portion of the microfluidic device between the first end and the opposing second end.

According to an alternative embodiment Z, the system of any one of alternatives W to Y further comprises that entry and exit ports to the at least one microchannel are positioned at the first end and opposing second end of the microfluidic device. The first end and the opposing second end are each fixed to one of the connection elements such that the entry and exit ports are not exposed to additional strains during the stretching of the microfluidic device.

According to an alternative embodiment AA, the system of any one of alternatives W to Z further comprises that one of the plurality of opposing connection elements is a fixed connection that is non-movable and another of the opposing connection elements is a non-fixed connection that is movable.

According to an alternative embodiment AB, the system of any one of alternatives W to AA further comprises that at least two of the plurality of opposing connection elements are movable.

According to an alternative embodiment AC, the system of any one of alternatives W to AB further comprises that the microfluidic device includes a plurality of microfluidic devices each having a first end and an opposing second end. Each of the first ends of the microfluidic devices is fastened to the one of the plurality of opposing connection elements and each of the opposing second ends of the microfluidic devices is fastened to another one of the plurality of opposing connection elements.

According to an alternative embodiment AD, a method of stretch actuation using a mechanical modulation system for a microfluidic device including at least one microchannel in which cells are disposed includes mounting a first end and an opposing second end of the microfluidic device to a first connection element and an opposing second connection element of the mechanical modulation system. The microfluidic device is stretched along a single plane defined by the microfluidic device. The stretching occurs in response to generally cyclical linear motions imparted to the microfluidic device along the single plane. Strains are identified in the microfluidic device in response to the stretching. The strains are identified by one or more sensor arrangements.

According to an alternative embodiment AE, the method of alternative AD further comprises that the microfluidic device includes a membrane on which the cells are disposed.

According to an alternative embodiment AF, the method of one of alternatives AD or AE further comprises that the mounting of the first end and the opposing second end of the microfluidic device provides a fixed connection such that strains in the microfluidic device in response to the stretching are transferred to the portion of the microfluidic device between the first end and the opposing second end.

Exemplary Materials for Construction: The devices and/or membranes described herein can be generally produced from any naturally-occurring and/or synthetic materials known in the art, provided that surfaces of the devices and membranes that are in contact with a fluid and/or cells introduced into the central microchannels (i) are chemically and biologically inert (or non-reactive); (ii) do not leach molecules into the fluid that can affect cell response; (iii) do not significantly absorb molecules from the fluid that can result in an adverse effect to the application, e.g., a reduction in the effective molecule concentration available to the cells, inaccurate dose-response interpretation, cross-contamination, and/or lower detection sensitivity; or (iv) any combinations of (i)-(iii).

In some embodiments, the devices and/or membranes described herein can be made from one or a mixture of biocompatible materials. In some embodiments, the devices and/or membranes described herein can comprise a core material surrounded by a biocompatible surface coating. By the term "biocompatible material" meant is a naturally-occurring or synthetic material which when in contact with a biological cell does not provoke an adverse response in the cell.

In some embodiments, the biocompatible materials used for fabricating the devices and/or membranes described herein can comprise a biocompatible synthetic polymer. Examples of biocompatible polymers include, but are not limited to, silicone and silicone-based polymers (e.g., polydimethylsiloxane (PDMS)); liquid silicon rubber; polymethylmethacrylate (PMMA), polyurethane, styrenic block copolymers, polytetrafluoroethylene (PTFE); a natural or synthetic hydrogel; polysulfone; polyethylene; polycarbonate, polypropylene; polyamide; polyester; polymethylmethacrylate, polylactic acid (PLA), polylactide, polyglycolic acid (PGA), poly(lactic-co-glycolic acid) (PLGA), polyvinyl alcohol, any art-recognized biocompatible polymers, and any combinations thereof. Examples of polyurethane include, but are not limited to, thermoplastic polyurethane elastomers (e.g., but not limited to Texin® and Desmopan® by Bayer, Bionatc® by the Polymer Technology Group), as well as ether-based, aliphatic polyurethane disclosed in the International Pat. App. No. PCT/US12/36920, filed May 8, 2012, now published as International Publication No. WO 2012/154729, the contents of the forgoing application and publication being incorporated herein by reference in their entireties.

In some embodiments, the biocompatible materials used for fabricating the devices and/or membranes described herein can comprise an extracellular matrix-based, carbohydrate-based, and/or protein-based polymer, gel, and/or scaffold. Examples of such biocompatible materials include, but are not limited to, glycoproteins, collagen, alginate, gelatin, fibronectin, laminin, vitronectin, elastins, fibrin, protcoglycans, heparin sulfate, chondroitin sulfate, keratan sulfate, hyaluronic acid, silk, chitosan, nucleic acids, lipids, carbohydrates, or any combinations thereof.

In some embodiments, the selected core material and/or the biocompatible material can be optically clear. As used herein, the term "optically clear" refers to a material having an optical transmission value of at least 50% or more for a visible spectrum, e.g., having a light wavelength of about 400 nm to about 800 nm. In some embodiments, an optically clear material can have an optical transmission value of at least about 60%, at least about 70%, at least about 80%, at least about 90% or more for a visible spectrum, e.g., having a light wavelength of about 400 nm to about 800 nm.

In some embodiments, the selected core material and/or the biocompatible material can be rigid or flexible. In some embodiments, the selected core material and/or biocompatible material can be flexible as characterized by a Young's modulus value of less than 0.2 GPa or less than 0.1 GPa. In some embodiments, the selected core material and/or biocompatible material can be rigid as characterized by a Young's modulus value of at least about 0.5 GPa. For example, rigid materials such as unreinforced plastics generally have a Young's modulus value of about 0.8 GPa to about 10 GPa. Metals usually have a Young's modulus value of at least 30 GPa or greater. For example, aluminum can have a Young's modulus value up to about 69 GPa.

In some embodiments, the rigidity or flexibility of the selected core material and/or the biocompatible material can be determined by the material hardness. For example, hardness of a material can be typically measured by its resistance to indentation under a static load. The most commonly used measures are the Shore hardness and Rockwell hardness. Both are empirical relative measures. The Shore hardness is a measure often used as a proxy for flexural modulus of elastomers. The Shore A scale is typically used for softer elastomers while Shore scale D is used for harder elastomers or softer rigid thermoplastic materials. By way of example only, rigid but softer thermoplastic materials such as polypropylenes can have typical values between 75 and 85 on the Shore D scale. Harder rigid thermoplastic materials such as acrylic can be usually characterized on Rockwell M scale. For example, Rockwell M value of acrylic can be 85-105, polycarbonate 72, polystyrene 68-70, and polysulfone 70.

In some embodiments, the selected core material and/or the biocompatible material can be adaptable for large scale manufacturing techniques, e.g., but not limited to, injection molding, extrusion, embossing, and any combinations thereof. For example, the selected core material and/or the biocompatible material can have a durometer value high enough to be processed by injection molding, and/or extrusion. Durometer is an art-recognized term and is generally a measure of the hardness of a material by measuring the depth of an indentation in the material created by a given force on a standardized presser foot. In one embodiment, the selected core material and/or the biocompatible material have a Shore A hardness of about 20 to about 90.

In some embodiments, the selected core material and/or the biocompatible material can be adaptable for solid free-form fabrication techniques, e.g., but not limited to, casting.

In some embodiments, the selected core material and/or the biocompatible material can decrease or inhibit absorption of molecules thereon. Examples of such molecules include, but are not limited to drugs, biologics, contrast agents, fluorescent dyes, proteins, peptides, antibodies, nucleic acids, and any combinations thereof. In some embodiments, the core material and/or the biocompatible material can decrease or inhibit absorption of hydrophobic molecules. The term "hydrophobic", as used herein, refers to a characteristic of a molecule or part of a molecule which is non-polar and/or is immiscible with charged and polar molecules, and/or has a substantially higher dissolvability in nonpolar solvents as compared with their dissolvability in water and other polar solvents. The term "dissolvability" refers to either a complete or partial dissolution of molecules in a substance, e.g., a solvent. Exemplary hydrophobic molecules include, without limitations, molecules comprising one or more alkyl groups, such as oils and fats, one or more aromatic groups, such as polyaromatic compounds, and/or one or more non-polar groups.

In some embodiments, the selected core material and/or the biocompatible material can decrease absorption of molecules or hydrophobic molecules by at least about 30% or more, including, e.g., at least about 40%, at least about 50%, at least about 60%, at least about 70%, at least about 80%, at least about 90%, at least about 95% or more, as compared to a silicon-based material (e.g., PDMS). In some embodiments, the core material and/or the biocompatible material can absorb no more than 50% or less (including, e.g., no more than 40%, no more than 30%, no more than 20%, no more than 10% or less) of the original amount of molecules or hydrophobic molecules present in a fluid. The term "absorption" as used herein generally refers to a process in which atoms, molecules or ions dispersed in a first material transferring, separating and/or diffusing therefrom into a second material. In some embodiments, absorption can encompass molecules depositing or binding onto a surface of the second material. In some embodiments, separation of molecules from one material into another is based on the intermolecular interaction of molecules between two different materials. In some embodiments, separation of molecules from one material into another can occur due to random and/or non-specific binding.

In accordance with some embodiments of various aspects described herein, the selected core material and/or the biocompatible material can be a styrenic block copolymer-comprising composition. The styrenic block copolymer-comprising composition comprises (a) at least 50 wt % of a styrenic block copolymer; wherein the styrenic block copolymer comprises a polymer block of predominantly styrene monomers and a random polymer block of predominantly alkene monomers, and (b) from about 0.5 wt % to about 30 wt % of a polyolefin. In some embodiments, the styrenic block copolymer-comprising composition can comprise more than 50 wt % of a styrenic block copolymer, including, e.g., at least about 60 wt %, at least about 70 wt %, at least about 80 wt %, at least about 90 wt % or more (but less than 100%), of the styrenic block copolymer. In some embodiments, the styrenic block copolymer-comprising composition can comprise about 50 wt % to about 99.5 wt % of the styrenic block copolymer. In some embodiments, the styrenic block copolymer-comprising composition can comprise about 85 wt % to about 95 wt %, or about 90 wt % to about 95 wt % of the styrenic block copolymer.

As used herein, the term "alkene monomers" refer to monomers of branched or unbranched hydrocarbon molecules having one or more carbon-carbon double bonds, including, one, two, three or more carbon-carbon double bonds. In some embodiments, the alkene monomers can have a structural formula of $(C_nH_{2n})$. Examples of alkene monomers having a structural formula of $(C_nH_{2n})$ include, but are not limited to, ethylene, propylene or isomers thereof, butylene or isomers thereof, and any combinations thereof. In other embodiments, the alkene monomers can have a structural formula of $(C_nH_{2n-2})$. Examples of alkene monomers having a structural formula of $(C_nH_{2n-2})$ include, but are not limited to, isoprene, butadiene, or isomers of these, and any combinations thereof.

As used herein, the term "random polymer block of predominantly alkene monomers" refers to a random arrangement of predominantly alkene monomers in the polymer block. As used herein, the term "predominantly alkene monomers" refers to substantially pure alkene monomers or a mixture comprising at least about 95 wt % or more (including, e.g., at least about 96%, about 97%, at least about 98%, at least about 99% or more) of the alkene monomers and minor amounts (e.g., no more than 5% or less of the alkene monomers) of other co-monomers. Examples of other co-monomers present in a minor amount in the poly (alkene monomer) block include, but are not limited to, styrene, and/or structurally-related alkene monomers.

In some embodiments, the alkene monomers included in the styrenic block can completely exclude isoprene or butadiene, or both. In some embodiments, the alkene monomers included in the styrenic block can comprise isoprene and/or butadiene in no more than 5% or less, including, e.g., no more than 3%, no more than 1%, of the alkene monomers. Accordingly, in some embodiments, the styrene block copolymer can comprise a polymer block of predominantly styrene monomers and a random polymer block of predominantly alkene monomers, provided that (a) the alkene monomers completely exclude isoprene or butadiene; or (b) isoprene and/or butadiene is present in no more than 5% of the alkene monomers.

In some embodiments, the alkene monomers included in the styrenic block can be predominantly alkene monomers having a structural formula of $(C_nH_{2n})$. In these embodiments, the alkene monomers included in the styrenic block can be selected from the group consisting of ethylene, propylene, butylene, isomers thereof, and any combinations hereof. In some embodiments, the alkene monomers included in the styrenic block copolymer can be predominantly ethylene and butylene. In some embodiments, the random polymer block of predominantly alkene monomers can be a random polymer block of ethylene and butylene.

In some embodiments, the alkene monomers in the styrenic block copolymer can be hydrogenated.

As used herein, the term "predominantly styrene monomers" refers to a substantially pure styrene or a mixture comprising at least about 95 wt % or more (including, e.g., at least about 96%, about 97%, at least about 98%, at least about 99% or more) of styrene and minor amounts (e.g., no more than 5% or less of the styrene monomers) of other co-monomers. Examples of other co-monomers in the poly (styrene) block include, but are not limited to, alpha-methyl styrene, p-methyl styrene, o-methyl styrene, p-tert-butyl styrene, dimethyl styrene and vinyl naphtalene, alkene monomers and any combinations thereof.

In some embodiments, the styrenic block copolymer can be branched or linear. In some embodiments, the styrenic block copolymer can be a diblock, a triblock, a tetrablock, or multiblock.

In some embodiments, the styrenic block copolymer contains polymer blocks of substantially pure styrene monomers and mixtures of substantially pure ethylene and butylene.

In some embodiments, the styrenic block copolymer can comprise a styrene content of about 10% to about 60 wt %, or about 10 wt % to about 30 wt %. In one embodiment, the styrenic block copolymer can comprise a styrene content of about 15 wt % to about 25 wt %.

In some embodiments, the styrenic block copolymer can be selected from the group consisting of styrene-ethylene-butylene-styrene (SEBS), styrene-ethylene-propylene-styrene (SEPS), or a combination thereof. In one embodiment, the styrenic block copolymer can be SEBS. In some embodiments, the SEBS can include any SEBS formulations available in the art, e.g., from Kraton Performance Polymers, Inc.

In addition to the styrenic block copolymer described herein, the styrenic block copolymer-comprising composition described herein further comprises about 0.5 wt % to about 30 wt % of a polyolefin. In some embodiments, the styrenic block copolymer-comprising composition described herein can comprise about 1 wt % to about 20 wt % of a polyolefin, or about 3 wt % to about 15 wt % of a polyolefin, or about 5 wt % to about 10 wt % of a polyolefin.

As used herein, the term "polyolefin" refers to a polymer derived from olefins, both mono-olefinically unsaturated and polyunsaturated, and includes, but is not limited to, polyethylene, polypropylene, polybutenes, polyisoprene, as well as homopolymers and copolymers thereof. In some embodiments, polyolefin can include chlorinated polyolefins. In one embodiment, the polyolefin included in the styrenic block copolymer-comprising composition described herein can comprise polypropylene. In one embodiment, the polyolefin included in the styrenic block copolymer-comprising composition described herein is polypropylene. In one embodiment, the styrenic block copolymer-comprising composition described herein can comprise about 5 wt % to about 10 wt % of polypropylene.

Blends of polypropylene and SEBS, where SEBS is used as an additive with an amount of no more than 30 wt %, have been previously discussed to be used in extrusion and injection molding processes; however, in accordance with some embodiments of the invention, SEBS is not present as an additive but as a primary material with a small amount of polypropylene blended therein.

In some embodiments, the styrenic block copolymer-comprising composition described herein can further comprise an additive. The additive can be present in an amount of no more than 45.5 wt %, no more than 40 wt %, no more than 30 wt %, no more than 20 wt %, no more than 10 wt %, no more than 5 wt %, no more than 1 wt %, no more than 0.5 wt %, no more than 0.1 wt % or less. Additives well known in the art include, but are not limited to, inert additives such as filler, as well as or may be used to affect one or more properties of the styrenic block copolymer-comprising composition. For example, one or more additives can be added to improve optical properties, thermal properties, adhesiveness (e.g. tackifiers), and/or flexibility (e.g., plasticizers)), and/or to facilitate curing or processing of the material. In some embodiments, an additive can comprise oil, silica, and/or an antioxidant (e.g., phenolic antioxidant).

In some embodiments, the styrenic block copolymer-comprising composition described herein can be oil-free.

In some embodiments, the styrenic block copolymer-comprising composition can comprise about 85-95 wt % of SEBS and about 5-15 wt % of polypropylene. In some embodiments, the styrenic block copolymer-comprising composition can comprise about 90-95 wt % of SEBS and about 5-10 wt % of polypropylene. In one embodiment, the styrenic block copolymer-comprising composition comprises about 90 wt % of SEBS and about 10 wt % of polypropylene.

In some embodiments, the styrenic block copolymer-comprising composition described herein can form at least one fluidic-contact surface of the central channel of the device described herein. For example, the fluidic-contact surface of the central channel of the device described herein can be coated with the styrenic block copolymer-comprising composition described herein, while the rest of the device described herein can be made from any other biocompatible material(s) described earlier. In some embodiments, the styrenic block copolymer-comprising composition described herein can be used to form the entire device described herein. In some embodiments, the styrenic block copolymer-comprising composition described herein can be used to form the membrane described herein.

Without wishing to be limiting, the styrenic block copolymer-comprising composition described herein can also be used to form any microfluidic device comprising a body and a fluidic element. Examples of a fluidic element include, but are not limited to, a microchannel, and/or a microwell.

In some embodiments, the styrenic block copolymer-comprising composition described herein can be adapted for use in injection molding and/or extrusion to form any solid article. For example, in some embodiments, the styrenic block copolymer-comprising composition can be formulated to have a Shore A hardness of at least about 30 or higher, including, at least about 40, at least about 50, at least about 60, at least about 70 or higher. Accordingly, in some embodiments, the devices and/or membranes described herein can be produced by injection molding and/or extrusion, using one or more embodiments of the styrenic block copolymer-comprising composition described herein. In some embodiments, the styrenic block copolymer-based composition can have a Shore A hardness of about 30 to about 60. In some embodiments, the styrenic block copolymer-based composition can have a Shore A hardness of about 50 to about 55.

Without wishing to be bound by theory, in some embodiments, the styrenic block copolymer-based composition can yield a reduced material shrinkage during fabrication and/or subsequent processing such as annealing, as compared to a composition without the polyolefin. In some embodiments, shrinkage can also be reduced by optimizing manufacturing process (e.g., conditions for injection molding and/or extrusion). Alternatively or additionally, shrinkage can be reduced by using rigid thermoplastic frames, overmolding (e.g., by injection) the material, and/or performing bonding with the material constrained.

In some embodiments, the solid structures formed by the styrenic block copolymer-based composition can have a reduced tackiness, as compared to a composition without the polyolefin. The reduced tackiness of the solid structures can facilitate handling the parts and/or assembling some embodiments of the devices described herein from multiple parts.

In some embodiments, the styrenic block copolymer-based composition can have an increased draw ratio allowed for an extrusion production process, as compared to a composition without the polyolefin. The increased ductility of the solid structures can facilitate production of a thin structure, e.g., a thin membrane for use in the device described herein.

In some embodiments, the solid structures formed by the styrenic block copolymer-based composition can display an increased stress relaxation, as compared to one formed by a composition without the polyolefin, when the solid structure is subjected to a cyclic strain.

Figure 12A:
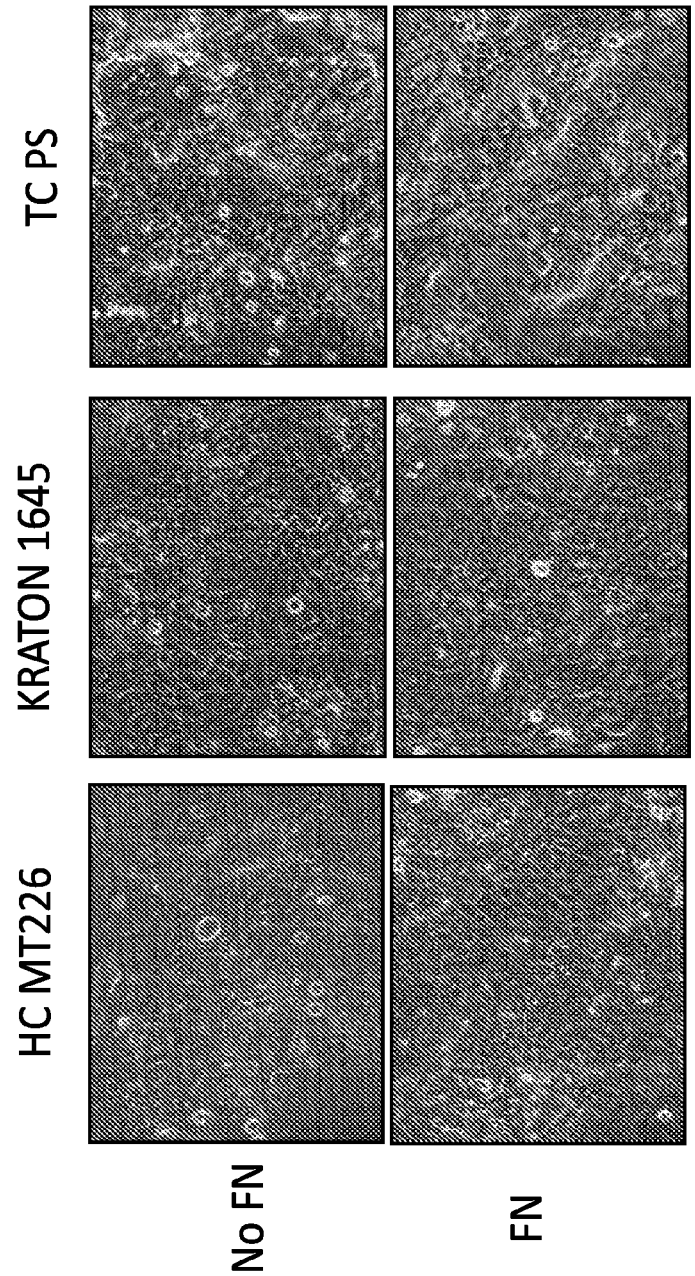
FIG. 12A shows human lung epithelial cells NCI-H441 cultured on oil-free styrene-ethylene-butylene-styrene (SEBS) formulations injection molded Versaflex HC MT226 (a hemocompatible grade) and Kraton® G1645 (melted pellets). The samples were activated in oxygen plasma for 30 seconds. Control substrate was tissue culture treated polystyrene (TC PS). Lower row of samples was coated with fibronectin (FN). Phase contrast imaging, 20× magnification, cell culture day 7.
Figure 12B:
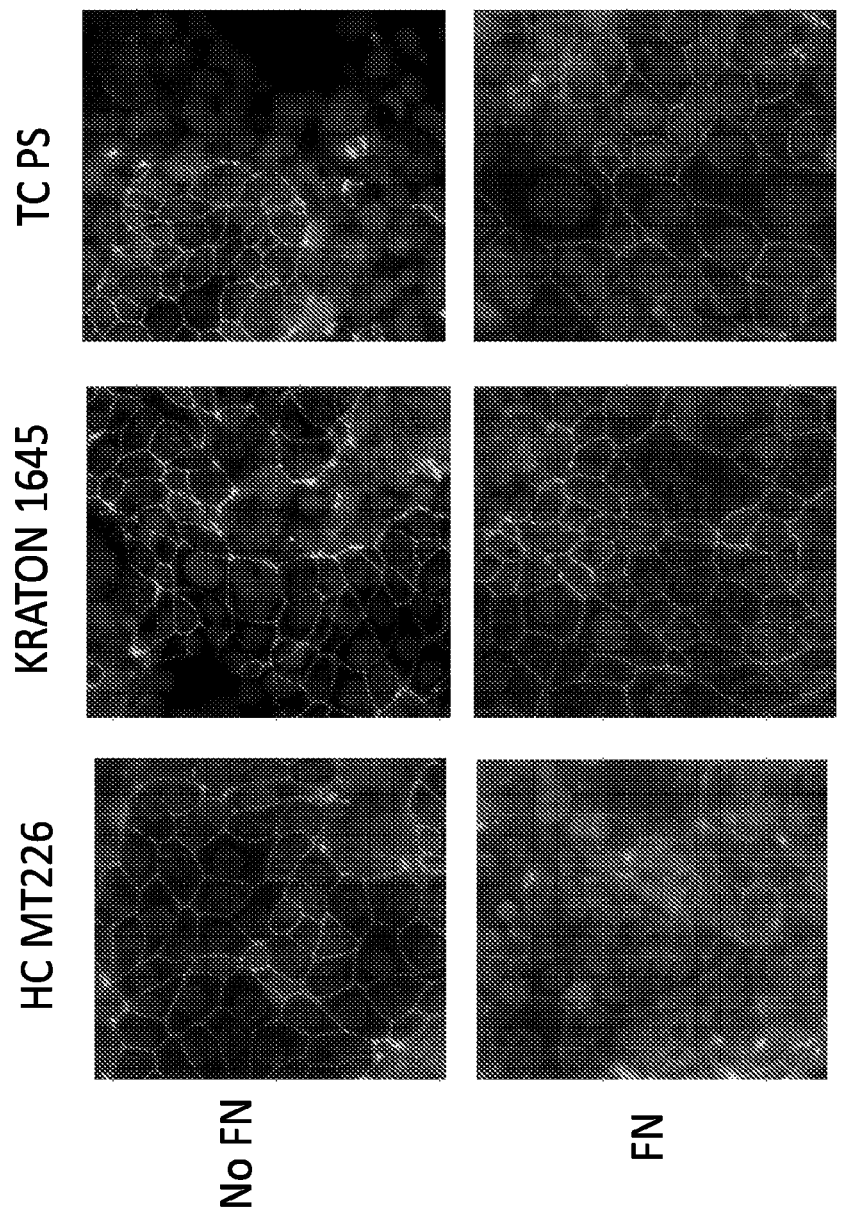
FIG. 12B shows that human lung epithelial cells NCI-H441 cultured on hemocompatible Versaflex HC MT 226, Kraton® 1645, and TC PS was stained for tight junctions.
Figure 13:
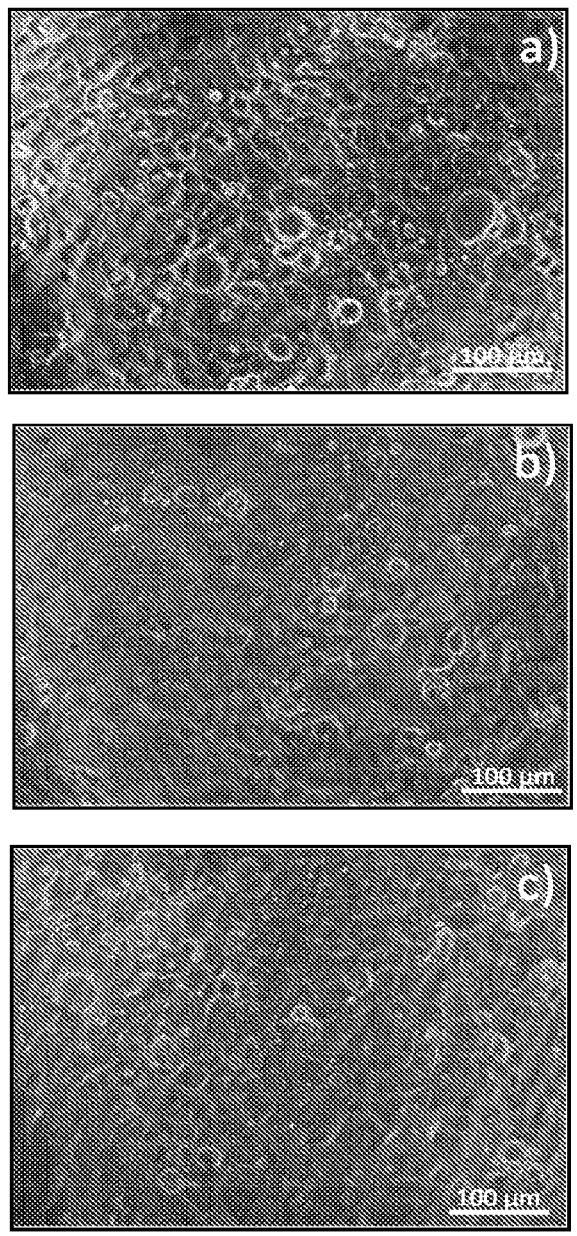
FIG. 13 shows Caco-2 cells cultured on samples injection molded from Kraton® G1643 with 0% (a), 5% (b), and 10% (c) of blended polypropylene (PP). Samples were treated with oxygen plasma for 30 seconds and coated in a solution of collagen I and matrigel. Phase contrast imaging, cell culture day 7.
Figure 14:
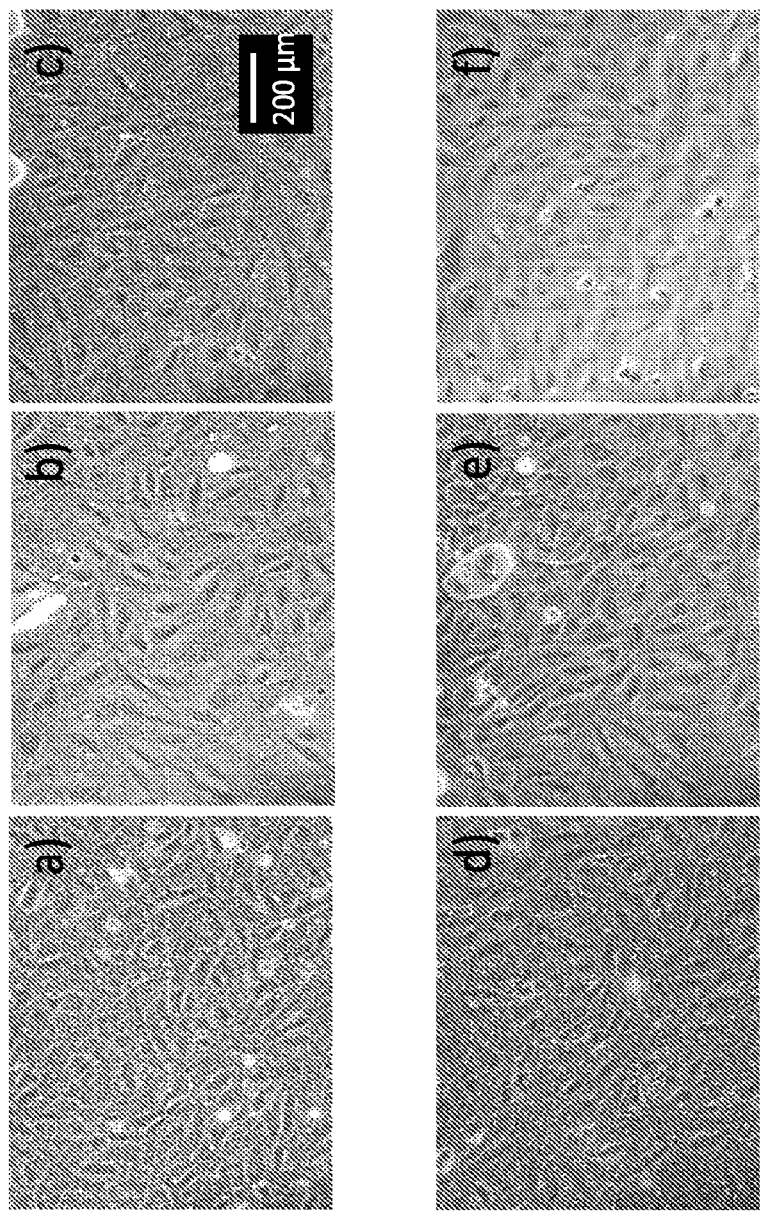
FIG. 14 human umbilical vein endothelial cells (HUVECs) cultured on membrane (~23 μm thick) extruded from Kraton G1645 with 10-30% of blended PP. Samples were subjected to different surface treatments. a) 30 s oxygen plasma, no fibronectin, b) 30 s oxygen plasma, fibronectin, c) no oxygen plasma, EtO, fibronectin, d) UV ozone, fibronectin, e) UV ozone, no fibronectin, f) tissue culture treated polystyrene, no fibronectin. Phase contrast imaging, 10× magnification, cell culture day 2.
Figure 15:
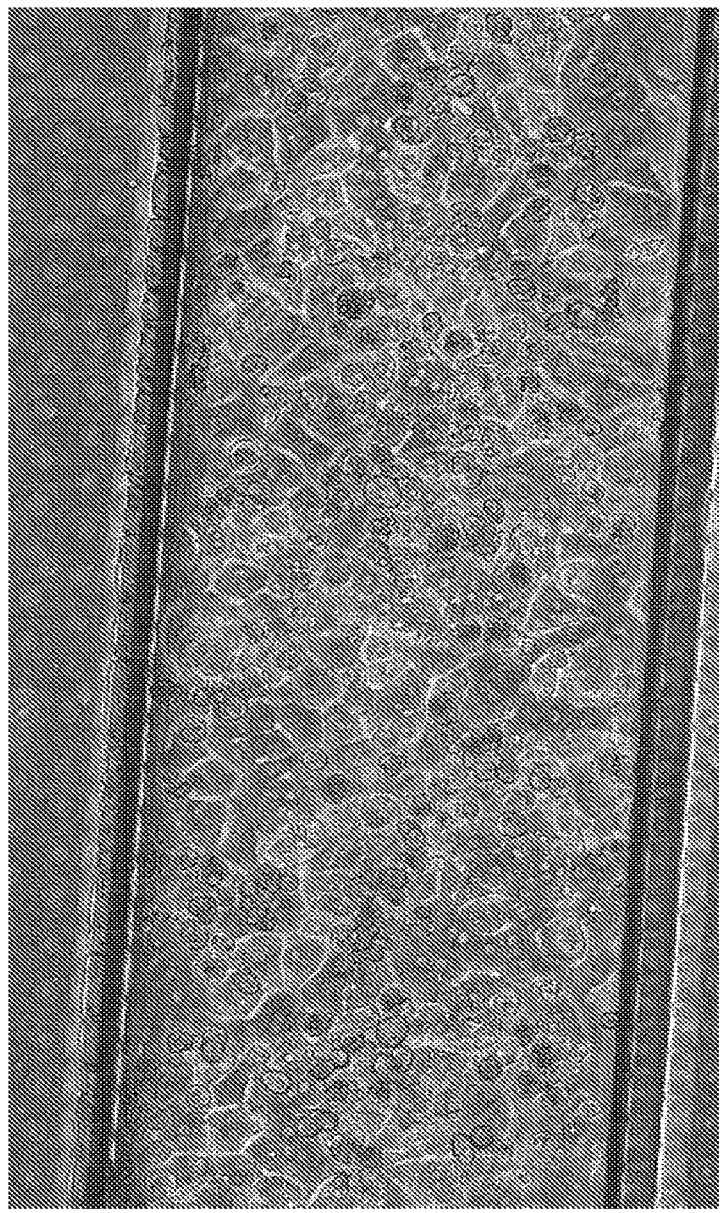
FIG. 15 shows primary human hepatocytes cultured on extruded & laser machined SEBS/PP porous membrane in an injection molded SEBS lung chip.

In some embodiments, the styrenic block copolymer-comprising composition described herein can be optically clear as defined earlier. In these embodiments, the resulting solid structure is optically clear. High optical clarity of the styrenic block copolymer-comprising composition described herein permits optical examination of cells present on the membrane within the device, when the membrane and/or the device in accordance with one embodiment described herein are formed from such composition. By way of example only, FIG. 15 shows an example phase contrast cell imaging of cells cultured on a SEBS/polypropylene membrane in an injection molded SEBS organomimetic device. In some embodiments, the styrenic block copolymer-based composition can provide low fluorescence background. See, e.g., FIGS. 12A-12B for fluorescent image of cells on one embodiment of the styrenic block copolymer-based membrane where cells were stained with ZO-1 for tight junctions and DAPI for nuclei.

In some embodiments, a decreased absorption of molecules onto fluid-contact surfaces of the devices and/or membrane described herein can be desirable. For example, certain class of polymers (e.g., PDMS) can absorb molecules, e.g., small hydrophobic molecules, and thus these materials can be less desirable for use in fabrication of the devices described herein for applications where small hydrophobic molecules (e.g., drug molecules) are to be used in the device, e.g., for research, clinical and/or drug development applications. In accordance with some embodiments of the invention, the fluid-contact surfaces of the device and/or membrane described herein comprising one or more embodiments of the styrenic block copolymer-based composition described herein can have reduced absorption of molecules thereon. In some embodiments, the styrenic block copolymer-based composition can reduce absorption of molecules by at least about 10% or more, including, e.g., at least about 20%, at least about 30%, at least about 40%, at least about 50%, at least about 60%, at least about 70%, at least about 80%, at least about 90% or more, as compared to the extent of molecule absorption onto PDMS. In some embodiments, the molecules, of which absorption onto a fluid-contact surface comprising the styrenic block copolymer-based composition is reduced, can be hydrophobic molecules as defined earlier. Examples of such molecules or hydrophobic molecules include, but are not limited to drugs, biologics, contrast agents, fluorescent dyes, proteins, peptides, antibodies, nucleic acids, and any combinations thereof. In some embodiments, the styrenic block copolymer-based composition for decreased molecule absorption does not contain oil.

Membrane: As used herein, a membrane portion means the portion of a layer that is made of the membrane material and functions as a substrate for cell growth and differentiation. In accordance with some embodiments of the invention, a membrane layer can include a membrane portion. In other embodiments, a membrane layer can include a membrane portion and other features such as a carrier layer adapted to provide structural support for the membrane portion.

The membrane can be porous (e.g., permeable or selectively permeable), non-porous (e.g., non-permeable), rigid, flexible, elastic or any combinations thereof. Accordingly, the membrane can have a porosity of about 0% to about 99%. As used herein, the term "porosity" is a measure of total void space (e.g., through-holes, openings, interstitial spaces, and/or hollow conduits) in a material, and is a fraction of volume of total voids over the total volume, as a percentage between 0 and 100% (or between 0 and 1). A membrane with substantially zero porosity is non-porous or non-permeable.

As used interchangeably herein, the terms "non-porous" and "non-permeable" refer to a material that does not allow any molecule or substance to pass through.

In accordance with some embodiments of the invention, the membrane can be porous and thus allow molecules, cells, particulates, chemicals and/or media to migrate or transfer between the central microchannels via the membrane from the first central microchannel to the second central microchannel or vice versa.

As used herein, the term "porous" generally refers to a material that is permeable or selectively permeable. The term "permeable" as used herein means a material that permits passage of a fluid (e.g., liquid or gas), a molecule, and/or a whole living cell. The term "selectively permeable" as used herein refers to a material that permits passage of one or more target group or species, but acts as a barrier to non-target groups or species. For example, a selectively-permeable membrane can allow passage of a fluid (e.g., liquid and/or gas), nutrients, wastes, cytokines, and/or chemokines from one side of the membrane to another side of the membrane, but does not allow whole living cells to pass therethrough. In accordance with some embodiments of the invention, a selectively-permeable membrane can allow certain cell types to pass therethrough but not other cell types.

The permeability of the membrane to individual matter/species can be determined based on a number of factors, including, e.g., material property of the membrane (e.g., pore size, and/or porosity), interaction and/or affinity between the membrane material and individual species/matter, individual species size, concentration gradient of individual species between both sides of the membrane, elasticity of individual species, and/or any combinations thereof.

A porous membrane can have through-holes or pore apertures extending vertically and/or laterally between two surfaces of the membrane, and/or a connected network of pores or void spaces (which can, for example, be openings, interstitial spaces or hollow conduits) throughout its volume. The porous nature of the membrane can be contributed by an inherent physical property of the selected membrane material, and/or introduction of conduits, apertures and/or holes into the membrane material.

In accordance with some embodiments of the invention, a membrane can be a porous scaffold or a mesh. In accordance with some embodiments of the invention, the porous scaffold or mesh can be made from at least one extracellular matrix polymer (e.g., but not limited to collagen, alginate, gelatin, fibrin, laminin, hydroxyapatite, hyaluronic acid, silk, and/or chitosan), and/or a biopolymer or biocompatible material (e.g., but not limited to, polydimethylsiloxane (PDMS), polyurethane, styrene-ethylene-butylene-styrene (SEBS), poly(hydroxyethylmethacrylate) (pHEMA), polyethylene glycol, polyester (e.g., thermoplastic aliphatic polyester or polylactide), polyethylene, polypropylene, polyvinyl alcohol, and/or any biocompatible material described herein for fabrication of the device body) by any methods known in the art, including, e.g., but not limited to, electrospinning, cryogelation, evaporative casting, and/or 3D printing. See, e.g., Sun et al. (2012) "Direct-Write Assembly of 3D Silk/Hydroxyapatite Scaffolds for Bone Co-Cultures." Advanced Healthcare Materials, no. 1: 729-735; Shepherd et al. (2011) "3D Microperiodic Hydrogel Scaffolds for Robust Neuronal Cultures." Advanced Functional Materials 21: 47-54; and Barry III et al. (2009) "Direct-Write Assembly of 3D Hydrogel Scaffolds for Guided Cell Growth." Advanced Materials 21: 1-4, for examples of a 3D biopolymer scaffold or mesh that can be used as a membrane in the device described herein.

In accordance with some embodiments of the invention, a membrane can be a hydrogel or a gel comprising an extracellular matrix polymer, and/or a biopolymer or biocompatible material. In accordance with some embodiments of the invention, the hydrogel or gel can be embedded with a conduit network, e.g., to promote fluid and/or molecule transport. See, e.g., Wu et al. (2011) "Omnidirectional Printing of 3D Microvascular Networks." Advanced Materials 23: H178-H183; and Wu et al. (2010) "Direct-write assembly of biomimetic microvascular networks for efficient fluid transport." Soft Matter 6: 739-742, for example methods of introducing a conduit network into a gel material.

In accordance with some embodiments of the invention, a porous membrane can be a solid biocompatible material or polymer that is inherently permeable to at least one matter/species (e.g., gas molecules). In accordance with some embodiments of the invention, through-holes or apertures can be introduced into the solid biocompatible material or polymer, e.g., to enhance fluid/molecule transport and/or cell migration. In one embodiment, through-holes or apertures can be cut or etched through the solid biocompatible material such that the through-holes or apertures extend vertically and/or laterally between the two surfaces of the membrane. It should also be noted that the pores can additionally or alternatively incorporate slits or other shaped apertures along at least a portion of the membrane which allow cells, particulates, chemicals and/or fluids to pass through the membrane from one section of the central channel to the other.

The pores of the membrane (including pore apertures extending through the membrane from the top to bottom surfaces thereof and/or a connected network of void space within the membrane) can have a cross-section of any size and/or shape. For example, the pores can have a pentagonal, circular, hexagonal, square, elliptical, oval, diamond, and/or triangular shape.

The cross-section of the pores can have any width dimension provided that they permit desired molecules and/or cells to pass through the membrane. In accordance with some embodiments of the invention, the pore size can be selected to permit passage of cells (e.g., immune cells and/or cancer cells) from one side of the membrane to the other. In accordance with some embodiments of the invention, the pore size can be selected to permit passage of nutrient molecules. When cells are cultured on the membrane at an air-liquid interface, the pore size of the membrane should be big enough to provide the cells sufficient access to nutrients present in the "liquid" channel (or the microchannel). In accordance with some embodiments of the invention, the width dimension of the pores can be selected to permit molecules, particulates and/or fluids to pass through the membrane but prevent cells from passing through the membrane. In accordance with some embodiments of the invention, the width dimension of the pores can be selected to permit cells, molecules, particulates and/or fluids to pass through the membrane. Thus, the width dimension of the pores can be selected, in part, based on the sizes of the cells, molecules, and/or particulates of interest. In accordance with some embodiments of the invention, the width dimension of the pores (e.g., diameter of circular pores) can be in the range of 0.01 microns and 20 microns, or in one embodiment, approximately 0.1-10 microns, or approximately 7-10 microns. However, in accordance with some embodiments of the invention, the width dimension can be outside of the range provided above. In accordance with some embodiments of the invention, the membrane has pores or apertures larger than traditional molecular/chemical filtration devices, which allow cells as well as molecules to migrate across the membrane from one channel section to the other channel section or vice versa. In one embodiment, the width dimension of the pores can be selected such that a selected type of cells, but not all different types of the cells present on the membrane, can migrate through the pores.

In accordance with some embodiments of the invention where the porous membrane comprise through-holes or pore apertures, the pore apertures can be randomly or uniformly distributed (e.g., in an array or in a specific pattern, or in a gradient of pore sizes) on the membrane. In one embodiment, the pore apertures are hexagonally arranged on the membrane. In one embodiment, at least some or all of the pore apertures are equidistant to each neighboring pore aperture. In this embodiment, at least some or all of the pore apertures can have a center-to-center pore spacing of about 1 µm to about 1000 µm, or about 10 µm to about 500 µm, or about 20 µm to about 100 µm. In one embodiment, at least some or all of the pore apertures can have a center-to-center pore spacing of about 20 µm to about 50 µm. The spacing between pores can vary, e.g., with cell sizes. Without wishing to be bound by theory, larger pore spacing can be used for bigger cells, e.g., epithelial cells, and similarly, smaller pore spacing can be used for smaller cells.

In an embodiment, the porous membrane can be designed or surface patterned to include micro and/or nanoscopic patterns therein such as grooves and ridges, whereby any parameter or characteristic of the patterns can be designed to desired sizes, shapes, thicknesses, filling materials, and the like.

The surface area of the membrane exposed to the central microchannels can vary, e.g., depending on the physiological ratio(s) of the surface area to the volume of an organ or a tissue to be modeled, volume of the microchannels, cell analysis and/or detection methods, and any combinations thereof. A proper ratio(s) of the surface area of the membrane exposed to the central microchannels to the volume of the central microchannels can ensure that the device can function more like an in vivo organ or tissue, which can in turn allow for in vitro results to be extrapolated to an in vivo system. In accordance with some embodiments of the invention, the surface area of the membrane exposed to the central microchannels can be configured to satisfy the physiological ratio(s) of the surface area to the volume of an organ or tissue to be modeled. In accordance with some embodiments of the invention, the surface area of the membrane can be configured to provide a sufficient space for cell culture, e.g., such that a sufficient amount of cellular materials (e.g., protein, RNA, secreted cytokines and/or chemokines) can be collected for analysis, e.g., using quantitative PCR, ELISA, sequencing and/or mass spectroscopy. In accordance with some embodiments of the invention, the surface area of the membrane can be configured to provide a sufficient space for examination and/or monitoring of cell behavior, e.g., but not limited to, immune cell recruitment and/or extravasation.

The membrane can have any thickness provided that the selected thickness does not significantly affect cell behavior and/or response. For example, in accordance with some embodiments of the invention, the thickness of the membrane can be selected such that it does not significantly slow down or inhibit transmigration of cells (e.g., immune cells and/or cancer cells) from one side of the membrane to the other. In accordance with some embodiments of the invention, the thickness of the membrane can range between 70 nanometers and 100 microns, or between 1 micron and 100 microns, or between 10 and 100 microns. In one embodiment, the thickness of the membrane can range between 10 microns and 50 microns. In some embodiments, the thickness of the membrane can range between 100 nm to about 10 µm. While the membrane generally has a uniform thickness across the entire length or width, in accordance with some embodiments of the invention, the membrane can be designed to include regions which have lesser or greater thicknesses than other regions in the membrane. The decreased thickness area(s) can run along the entire length or width of the membrane or can alternatively be located at only certain locations of the membrane. The decreased thickness area can be present along the bottom surface of the membrane, or additionally/alternatively be on the opposing surface of the membrane. It should also be noted that at least portions of the membrane can have one or more larger thickness areas relative to the rest of the membrane, and capable of having the same alternatives as the decreased thickness areas described above.

The membrane can be rigid or flexible. Some of the material requirements for the membrane are that it should enable the fabrication of well-defined microscale or nanoscale features, and that it can facilitate cell adhesion. In accordance with some embodiments of the invention, the membrane can be made of a rigid material, e.g., but not limited to polycarbonate. In accordance with some embodiments of the invention, the membrane can be made of flexible material, e.g., a polydimenthylsiloxane (PDMS) or any other polymeric compound or material. For instance, the membrane can be made of polyimide, polyester, polycarbonate, cyclicolefin copolymer, polymethylmethacrylate, nylon, polyisoprene, polybutadiene, polychlorophene, polyisobutylene, poly(styrene-butadiene-styrene), nitriles, polyurethanes and polysilicones. GE RTV 615, a vinyl-silane crosslinked (type) silicone elastomer (family) can be used. PDMS membranes are available, for example, HT-6135 and HT-6240 membranes from Bisco Silicons (Elk Grove, Ill.), and are useful in selected applications. In accordance with some embodiments of the invention, the membrane is made of styrene-ethylene-butylene-styrene (SEBS) (e.g., Kraton® G1645 or G1643) mixed with polypropylene. The weight percentage of polypropylene mixed in SEBS can be 0 to 100%, 0 to 90%, 0 to 75%, 0 to 50%, 0 to 30%, 5 to 40%, 5 to 30% and 10 to 30%. The choice of materials typically depends upon the particular material properties (e.g., solvent resistance, stiffness, fluid permeability, and/or temperature stability) required for the application being conducted. Additional elastomeric materials that can be used in the manufacture of the components of the microfluidic devices described in Unger et al. (2000 Science 288:113-116). Some elastomers of the present devices are used as diaphragms and in addition to their stretch and relax properties, are also selected for their porosity, permeability, chemical resistance, and their wetting and passivating characteristics. Other elastomers are selected for their thermal conductivity. Micronics Parker Chomerics Thermagap material 61-02-0404-F574 (0.020" thick) is a soft elastomer (<5 Shore A) needing only a pressure of 5 to 10 psi to provide a thermal conductivity of 1.6 W/m-° K. Deformable films, lacking elasticity, can also be used in the microfluidic device.

The membrane can be fabricated by photolithography, molding and/or machining (e.g., including mechanical cutting, laser cutting and etching), solid free-form fabrication technologies (e.g., three dimensional printing and stereolithography), extruding, machining, casting, stamping (e.g., hot embossing), track etching, using photocurable materials, or any combinations thereof. In accordance with some embodiments of the invention, pores are formed in the membrane prior to the membrane being incorporated into the device. In alternative embodiments, pores are formed after the membrane is incorporated into the device. This can be achieved by focusing two or more laser beams onto the membrane layer to ablate materials precisely from designated locations, and thus generating pores of desirable density and dimensions. Because other components are out of the focal point of the lasers, they remain intact. In accordance with some embodiments of the invention, the lasers can be excimer lasers.

Without limitations, in accordance with some embodiments of the invention, the membrane can be formed by first extruding a thin polymer film with uniform thickness. The material used for extruding can be SEBS (e.g., Kraton® G1645) mixed with about 10-30% polypropylene. A liner can be used to provide structural support and ease of handling for the membrane layer during subsequent pore fabrication. The liner can be made of rigid polymers such as polyethylene terephthalate. The membrane is then covered by a mask containing holes of desired dimension and spacing. An excimer laser can be used to raster scan the surface and ablate materials that are exposed to the laser. Laser focus and power can be tuned to achieve optimal pore qualities such as roundness and diameter uniformity. The membrane can then be subjected to further processing.

To seed cells onto the membrane, a portion of the membrane can be treated by coating at least one surface of the membrane with one or more cell adhesion agents (e.g., extracellular matrix molecules comprising glycoproteins, collagen, fibronectin, laminin, vitronectin, elastins, fibrin, proteoglycans, heparin sulfate, chondroitin sulfate, keratan sulfate, hyaluronic acid, or any combinations thereof). In accordance with some embodiments of the invention, no treatment is needed. A first fluid containing a first desired cell population can flow into the first inlet, travel through the first central microchannel and exit through the first outlet. Optionally and independently, the second fluid containing a second desired cell population can flow into the second inlet, travel through the second central microchannel and exit through the second outlet. In an alternative embodiment, the inlets and outlets can be switched. In accordance with embodiments of the invention, a first cell population can be seeded on the top surface of the membrane, while optionally a second cell population can be seeded on the bottom surface of the membrane.

Once cells are seeded onto the membrane surfaces, fluids containing the necessary nutrients (e.g., oxygen) and growth factors can flow through the central microchannels to sustain cell growth and differentiation. In accordance with some embodiments of the invention, the fluid flows through the central microchannels while the membrane is modulated simultaneously. In accordance with some embodiments of the invention, the membrane comprises a plurality of pores or apertures therethrough, whereby molecules, cells, fluid or any media is capable of passing through the membrane via one or more pores in the membrane. Exogenous agents (e.g., drugs) can be introduced to the central microchannels to evaluate cellular responses. Examples of means to introduce exogenous agents are disclosed in PCT Patent Application Serial No. PCT/US2012/037096 filed on May 9, 2012, now published as International Publication No. WO 2012/154834, the contents of the application and publication being incorporated herein by reference in their entireties.

The modulation of the membrane can be achieved through pressure differentials or mechanical means, or any means that can cause the movement of an object, including use of one or more magnetic forces. The modulation of the membrane can mimic the mechanical forces experienced by a tissue-tissue interface in a living organism, for example, in the lung alveolus during breathing. It should be noted that the modulation magnitude and frequency should depend on the specific desired experimental outcomes. In addition, the pores mimic the microenvironment where cells communicate with each other by exchanging molecules and/or forming cell-cell contacts.

In accordance with some embodiments of the invention, to modulate the membrane through mechanical means, at least one membrane modulation device can be used to modulate the movement of the engagement element. The membrane modulation device can include a motor, an actuator, a piezo-material based actuator, a shape memory alloy based actuator (e.g., nitinol wire), a pneumatic cylinder, a gas or vacuum pump, a voice-coil device, or a magnetic-field modulating device (e.g., solenoid). In accordance with some embodiments of the invention, the engagement element can include ferromagnetic materials such as cobalt, iron or $Fe_2O_3$, and a membrane modulating device capable of modulating the magnetic field can vary the amount of magnetic force between the membrane modulating device and the engagement element, thereby modulating the movements of the engagement element/membrane.

In some embodiments, at least one magnet can be employed to drive or actuate the modulation of the membrane. For example, at least one magnetic material can be incorporated into a flexible or elastic membrane layer, and/or into one or more rigid components that attach to the membrane. By applying an external cyclic or static magnetic field gradient, a mechanical force can be magnetically generated to modulate the membrane, in addition or alternative to modulation of the membrane by direct physical movements and pneumatic means such as vacuum and/or pressure as described herein.

The central microchannels should have a cross section at least large enough to accommodate cells and sufficient fluid flow to maintain cell growth. The central microchannels can be at least about 20 µm in height, at least 50 µm in height, at least 200 µm in height, at least 300 µm in height, at least 500 µm in height, at least 750 µm in height, at least 1000 µm in height, or at least 2000 µm in height. The width of the central microchannels can be at least about 20 µm, at least 50 µm, at least 200 µm, at least 300 µm, at least 500 µm, at least 750 µm, at least 1000 µm, at least 2000 µm, or at least 5000 µm. The length of the central microchannels can be at least 0.5 cm, at least 1 cm, at least 2 cm, at least 5 cm, or at least 20 cm.

The central microchannel wall thickness can vary, for example, depending on the selected means to modulate the membrane. Without wishing to be bound by theory, linear mechanical stretching of the membrane can be less sensitive to the central microchannel wall thickness than when the membrane is modulated, e.g., by vacuum. For example, in some embodiments of the devices with pneumatically-actuated membranes, the central microchannel walls should be thick enough to have structural integrity, but they should also be thin enough that the walls can deform during modulation of the membrane. In these embodiments, the central microchannel walls can have a thickness range between about 5 µm to 400 µm, although other width dimensions are contemplated depending on the material used for the walls, application in which the device is used and the like.

The central microchannel wall thickness can be virtually of any dimension for devices with mechanically-actuated membranes. In some embodiments, the central microchannel wall thickness can be larger for devices with mechanically-actuated membranes, as compared to the central microchannel wall thickness of devices with pneumatically-actuated membrane.

Manufacture: All embodiments (discussed above) of the microfluidic device or any conceivable variations can include elastomeric portions and/or rigid portions. The device can be constructed by fabricating different components separately and assembling them subsequently. The components can be in the form of blocks, layers or any other shapes.

The rigid portions can be fabricated from rigid materials including, but not limited to, polytetrafluroethylene, polypropylene, polyethylene terephthalate and polyvinyl chloride, stiff elastomeric materials, acrylic, polystyrene, polycarbonate, glass, epoxy fiberglass, ceramic and metal.

The elastomeric portions can be fabricated from elastomeric materials such as Versaflex CL30, Mediprene 500422M, SEBS, silicone, polyurethane, and PDMS. Some of the material requirements for the elastomers are that it should enable the fabrication of well-defined microscale or nanoscale features, and that the structures made of such material should resist the absorption of small hydrophobic molecules. In accordance with some embodiments of the invention, the elastomeric portions can be made of styrene-ethylene-butylene-styrene (SEBS) (e.g., Kraton® G1645 or G1643) mixed with polypropylene. The weight percentage of polypropylene mixed in SEBS can be 0 to 100%, 0 to 90%, 0 to 75%, 0 to 50%, 0 to 30%, 5 to 40%, 5 to 30% and 10 to 30%. In accordance with some embodiments of the invention, one layer can be formed by combining two or more different materials, for example, where one portion of a layer can be fabricated from SEBS and the remainder of the layer can be formed from acrylic or one portion of a layer can be fabricated from an elastomeric formulation of SEBS and the remainder from a rigid formulation of SEBS.

In accordance with some embodiments of the invention, each of the components can be fabricated by molding (e.g. injection molding) and/or machining (e.g., including mechanical cutting, laser cutting and etching) the various features into each component. The components can also be fabricated using extruding, embossing or solid free-form fabrication technologies (e.g., three dimensional printing and stereolithography). In accordance with some embodiments, photolithography can be used to fabricate the mold forms that can be used to produce each of layers. Other well-known mold fabrication methods, such as machining, casting and stamping can also be used.

In accordance with some embodiments of the invention, the central microchannels can be formed in one or more layers using photolithography, etching, molding, embossing, casting, extrusion, machining, stamping, or any combinations thereof. In alternative embodiments, the central microchannels can be formed by laminating two or more layers together. In these embodiments, a microchannel aperture can be formed in one layer by photolithography, etching, molding, embossing, casting, machining, stamping, or any combinations thereof. The thickness of the layer can be used to define the height of the microchannel. Another layer can be placed in contact with the layer having the microchannel aperture to provide a closure and form the microchannel. Thickness of the top and bottom layers of the central channel can be determined, for example, by the readout method used. If the readout is optical and high resolution is necessary, lower or upper wall thickness (depending if optical interrogation is performed from the top of from the bottom) can be configured to be as low as possible. In some embodiments, the upper and/or lower wall thickness of the device can be less than 0.2 millimeters. Thinner walls used to provide a closure for the top or bottom central microchannel can facilitate examination or visualization of cells using an optical method. In addition, one of the advantages of providing a closure using a laminated layer is that it may permit a thin aperture that allows optical observation into one or more regions of the central channel. In accordance with some embodiments of the invention, all the central microchannels can be formed using the same or similar method. In alternative embodiments, one of the two central microchannels can be formed by a molded elastomer layer, while the other central microchannel can be formed by laminating two elastomer layers together.

In some embodiments, a combination of one or more of the aforementioned methods can be used to form the central channel and/or other portion of the devices described herein. For example, multiple parts of the central channel can be formed using molding and some of the molded parts can be laminated with one or more other layers.

In accordance with some embodiments of the invention, within a single layer, different portions of the layer can have different physical and/or chemical properties, such as thickness, elasticity, hardness, affinity to attract or repel components of the fluid and porosity. This can be accomplished by separately treating the desired portions to have the desired properties or molding together different materials into a single layer.

The components can be held together to form a device by thread forming screws, nuts and bolts, clips, clamps, gaskets, pins, ultrasonic welding, solvent-assisted bonding, heat staking, laser welding, snap fits, glue (e.g., biocompatible, low absorption adhesives such as acrylates), surface treatment (e.g., oxygen plasma), or any combinations thereof. During the assembly, alignment of the components can be facilitated by using a microscope.

After the device is fabricated, the device can be sterilized by a number of means including, but not limited to, heat, radiation, chemical sterilization (e.g., ethylene oxide gas), plasma treatment, or any combinations thereof.

In accordance with this disclosure, the microfluidic device (also referred to as "present device") is preferably utilized in an overall system incorporating sensors, computers, displays and other computing equipment utilizing software, data components, process steps and/or data structures. The components, process steps, and/or data structures described herein with respect to the computer system with which the organ mimic device is employed can be implemented using various types of operating systems (e.g., Windows™, LINUX, UNIX, etc.) computing platforms (e.g., Intel, AMD, ARM, etc.), computer programs, and/or general purpose machines. In addition, those of ordinary skill in the art will recognize that devices of a less general purpose nature, such as hardwired devices, field programmable gate arrays (FPGAs), digital signal processors (DSPs), or application specific integrated circuits (ASICs), can also be used without departing from the scope and spirit of the inventive concepts disclosed herein.

Where a method comprising a series of process steps is implemented by a computer or a machine with use with the microfluidic device described below and those process steps can be stored as a series of instructions readable by the machine, they can be stored on a tangible medium such as a computer memory device (e.g., ROM (Read Only Memory), PROM (Programmable Read Only Memory), EEPROM (Electrically Erasable Programmable Read Only Memory), FLASH Memory, Jump Drive, and the like), magnetic storage medium (e.g., tape, magnetic disk drive, and the like), optical storage medium (e.g., CD-ROM, DVD-ROM, paper card, paper tape and the like) and other types of program memory.

In accordance with some embodiments of the invention, the device can be placed in or secured to a cartridge. In accordance with some embodiments of the invention, the device can be integrated into a cartridge and form a monolithic part. Some examples of a cartridge are described in U.S. Application No. 61/856,876, filed Jul. 22, 2013; U.S. Provisional Application No. 61/696,997, filed on Sep. 5, 2012 (subsequently published in International Publication No. WO 2014/039514); and No. 61/735,215, filed on Dec. 10, 2012 (subsequently published in International Publication No. WO 2014/039514), the contents of each of the foregoing applications and publications being incorporated herein by reference in their entireties. The cartridge can be placed into and removed from a cartridge holder that can establish fluidic connections upon or after placement and optionally seal the fluidic connections upon removal. In accordance with some embodiments of the invention, the cartridge can be incorporated or integrated with at least one sensor, which can be placed in direct or indirect contact with a fluid flowing through a specific portion of the cartridge during operation. In accordance with some embodiments of the invention, the cartridge can be incorporated or integrated with at least one electric or electronic circuit, for example, in the form of a printed circuit board or flexible circuit. In accordance with some embodiments of the invention, the cartridge can comprise a gasketing embossment to provide fluidic routing.

In accordance with some embodiments of the invention, the cartridge and/or the device described herein can comprise a barcode. The barcode can be unique to types and/or status of the cells present on the membrane. Thus, the barcode can be used as an identifier of each device adapted to mimic function of at least a portion of a specific tissue and/or a specific tissue-specific condition. Prior to operation, the barcode of the cartridge can be read by an instrument so that the cartridge can be placed and/or aligned in a cartridge holder for proper fluidic connections and/or proper association of the data obtained during operation of each device. In accordance with some embodiments of the invention, data obtained from each device include, but are not limited to, cell response, immune cell recruitment, intracellular protein expression, gene expression, cytokine/chemokine expression, cell morphology, functional data such as effectiveness of an endothelium as a barrier, concentration change of an agent that is introduced into the device, or any combinations thereof.

In accordance with some embodiments of the invention, the device can be connected to the cartridge by an interconnect adapter that connects some or all of the inlet and outlet ports of the device to microfluidic channels or ports on the cartridge. Some examples interconnect adapters are disclosed in U.S. Provisional Application No. 61/839,702, filed on Jun. 26, 2013, which is hereby incorporated by reference in its entirety. The interconnect adapter can include one or more nozzles having fluidic channels that can be received by ports of the device described herein. The interconnect adapter can also include nozzles having fluidic channels that can be received by ports of the cartridge.

In accordance with some embodiments of the invention, the interconnect adaptor can comprise a septum interconnector that can permit the ports of the device to establish transient fluidic connection during operation, and provide a sealing of the fluidic connections when not in use, thus minimizing contamination of the cells and the device. Some examples of a septum interconnector are described in U.S. Provisional Application No. 61/810,944 filed Apr. 11, 2013, the content of which is incorporated herein by reference in its entirety.

Kits: Kits comprising at least one device described herein are also provided. In accordance with some embodiments of the invention, the kit can comprise two or more (e.g., 2, 3, 4, 5, 6, 7, 8, 9, 10, 20, 30 or more) devices described herein. The devices provided in the kit can have the same or different dimensions and/or shapes.

In accordance with some embodiments of the invention, the device(s) provided in the kit can comprise no cells on either surface of the membrane. However, in accordance with some embodiments of the invention, the cells can be provided as frozen cells or a cell suspension in a separate vial within the kit. Users can introduce the cells from the vial into the devices on their own.

In accordance with some embodiments of the invention, the device(s) provided in the kit can comprise cells on at least one surface of the membrane. The cells on the membrane can display at least one characteristic corresponding to a pre-determined physiological endpoint as described herein, e.g., depending on the target applications. By way of example only, in accordance with some embodiments of the invention, the cells on the membrane can be differentiated cells (e.g., differentiated airway epithelial cells, skin epithelial cells, or intestinal epithelial cells) arranged in a stratified structure or a three-dimensional structure. In accordance with some embodiments of the invention, the cells on the membrane can be disease-specific, for example, having a disease-specific phenotype or genotype. In accordance with some embodiments of the invention, the cells on the membrane can be normal healthy cells. In these embodiments, the cells on the membrane can be maintained and/or cultured at an air-liquid interface or a liquid-liquid interface during storage and/or transportation.

In accordance with some embodiments of the invention, the device(s) provided in the kit can have fluid inlets, fluid outlets and/or any ports fluidically connected to the central microchannels adaptably connected to a self-healing septum. The self-healing septum can permit the ports of the devices to establish transient fluidic connection during operation, and provide a sealing of the fluidic connections during storage and/or transportation, thus maintaining sterility of the devices. In one embodiment, the self-healing septum is a septum interconnector described in U.S. Provisional Application No. 61/810,944 filed Apr. 11, 2013, the content of which is incorporated herein by reference.

In accordance with some embodiments of the invention, at least one or more devices provided in the kit can be placed or secured in a single cartridge as described earlier. In accordance with some embodiments of the invention, each device can be placed or secured in its individual cartridge. Some examples of a cartridge are described in U.S. Application No. 61/856,876 filed Jul. 22, 2013; U.S. Provisional Application No. 61/696,997, filed on Sep. 5, 2012 (subsequently published in International Publication No. WO 2014/039514), and No. 61/735,215, filed on Dec. 10, 2012 (subsequently published in International Publication No. WO 2014/039514), the contents of each of the forgoing applications and publications being incorporated herein by reference in their entireties. The cartridge can be placed into and removed from a cartridge holder that can establish fluidic connections upon or after placement and optionally seal the fluidic connections upon removal.

In accordance with some embodiments of the invention, the kit can comprise an appropriate quantity of liquid culture medium for use during operation. The liquid culture medium can be specifically formulated for cells with different predetermined physiological endpoints. The liquid culture medium can be packaged in any format. For example, the liquid culture medium can be packaged as powder, which requires reconstitution prior to use, or as a ready-to-use liquid in a container (e.g., a bottle or a bag).

In accordance with some embodiments of the invention, the kit can include instructions on how to operate device(s) optionally in conjunction with at least one instrument. In accordance with some embodiments of the invention, the kit can include instructions on how to introduce, grow, differentiate, culture and/or support or sustain the cells in the device(s).

Embodiments of the present device can be applied in numerous fields including basic biological science, life science research, drug discovery and development, drug pharmacodynamic and/or pharmacokinetic testing, drug safety and/or toxicology testing, chemical and biological assays, as well as tissue and organ engineering. In an embodiment, the organ mimic device can be used as microvascular network structures for basic research in cardiovascular, cancer, and organ-specific disease biology. Furthermore, one or more embodiments of the device find application in organ assist devices for liver, kidney, lung, intestine, bone marrow, and other organs and tissues, as well as in organ replacement structures. These devices can be lined by cells from humans, other mammals, plants, or insects, in the presence or absence of normal or pathological microbes.

The cellular responses to the various environmental cues can be monitored using various systems that can be combined with the present device. One can monitor changes in pH using well known sensors. One can integrate force sensors into the membrane to measure changes in the mechanical properties of the cells. One can also sample cells, continuously or periodically for measurement of changes in gene transcription or changes in cellular biochemistry or structural organization. For example, one can measure reactive oxygen species (ROSs) that are a sign of cellular stress. One can also subject the "tissue" grown on the membrane to microscopic analysis, immunohistochemical analysis, in situ hybridization analysis, or typical pathological analysis using staining, such as hematoxylin and eosin staining. Samples for these analyses can be carried out in real-time, or taken after an experiment or by taking small biopsies at different stages during a study or an experiment.

One can directly or indirectly expose the cells grown on the membrane to at least one agent (e.g., at least 2 agents or more) or toxic exposure (e.g., radiation). For example, the agent can be introduced into the same central microchannel in which the cells are grown; and/or the agent can be introduced into a central microchannel that is separated from the cells-comprising central microchannel by the membrane. The agent can be any living or non-living matter that can produce an effect on the cells grown on the membrane, be affected by or respond to the cells on the membrane, and/or is desired to assess its effect on the cells grown on the membrane. Examples of an agent that can be exposed to the cells grown on the membrane include, but are not limited to, a cell, a microorganism, a molecule, a particle, a cytokine, a therapeutic agent, an antibody, a protein, a peptide, a nucleic acid molecule, an oligonucleotide, an aptamer, a contrast agent, a dye, a cell-labeling agent, gamma irradiation, or any combinations thereof. In accordance with some embodiments of the invention, the cells grown on the membrane can be exposed to at least one another cell. For example, immune cells, tumor cells, epithelial cells, and/or microbial cells (e.g., bacteria, fungus, parasites, and/or viruses). In one embodiment, the cells grown on the membrane can be exposed to an antibody and/or antibody-directed cell, for example to target specific cellular receptors. In another embodiment, one can expose the cells to viruses or other particles. To assist in detection of movement of externally supplied substances, such as cells, viruses, particles or proteins, one can label them using typical means such as radioactive or fluorescent labels.

Cells can be grown, differentiated, cultured, supported or sustained, and/or analyzed using the present device for at least about 1 week, at least about 2 weeks, at least about 3 weeks, at least about 4 weeks, at least about 5 weeks, at least about 6 weeks, at least about 7 weeks, at least about 8 weeks or longer. For example, as discussed below, it has been shown that the cells can be maintained viable and differentiated on a membrane in an embodiment of the described device for at least about 1 month or longer. In some embodiments, cells can be cultured in the device to induce cell growth. In some embodiments, cells (e.g., some primary cells) can be sustained, rather than continue proliferating, in the device.

The organomimetic device described herein can be adapted to many different applications including, but not limited to, cell differentiation, formation of a stratified and/or three-dimensional tissue structure, development of a disease model in a tissue of interest, development of a mucosal immunity platform; studies on ciliary clearance of a particle; studies on airborne or body fluid-borne transmissibility of pathogens; studies on immune cell response (e.g., trans-epithelial migration, maturation, activation, cell killing, and/or drainage); studies on various tissue-specific diseases such as respiratory, intestinal, digestive, skin, cardiac, and/or ocular diseases; studies of mechanism of action of drugs, target identification and/or validation, identification of markers of disease; assessing pharmacokinetics and/or pharmacodynamics of various chemical or biological agents; assessing efficacy of therapeutics and/or vaccines; testing gene therapy vectors; drug and/or vaccine development; molecule or drug screening or drug discovery; determination of an appropriate treatment or drug for a specific patient population or individual patient; identification of a risk population to a disease or disorder; identification of a new drug target for a patient population that is non-responsive to a previously-administered treatment; studies of cell behavior in a physiologically-relevant model (including, e.g., stem cells and bone marrow cells); studies on biotransformation, absorption, clearance, metabolism, and activation of xenobiotics; studies on bioavailability and transport of chemical or biological agents across epithelial or endothelial layers; studies on transport of biological or chemical agents across the blood-brain barrier; studies on transport of biological or chemical agents across the intestinal epithelial barrier; studies on acute basal toxicity of chemical agents; studies on acute local or acute organ-specific toxicity of chemical agents; studies on chronic basal toxicity of chemical agents; studies on chronic local or chronic organ-specific toxicity of chemical agents; studies on teratogenicity of chemical agents; studies on genotoxicity, carcinogenicity, and/or mutagenicity of chemical agents; detection of infectious biological agents and/or biological weapons; detection of harmful chemical agents and chemical weapons; studies on infectious diseases (e.g., bacterial, viral and/or fungal infections); assessing infectivity and/or virulence of a new strain; studies on the optimal dose range of a chemical and/or biological agent to treat a disease; prediction of the response of an organ in vivo exposed to a biological and/or chemical agent; studies concerning the impact of genetic content on response to agents; studies on gene transcription in response to chemical or biological agents; studies on protein expression in response to chemical or biological agents; studies on changes in metabolism in response to chemical or biological agents; as well as example uses described below. The organ mimic device can also be used to screen on the cells, for an effect of the cells on the materials (for example, in a manner equivalent to tissue metabolism of a drug).

In accordance with some embodiments of the invention, the devices described herein can be used to simulate the mechanical load environment of walking, running, breathing, peristalsis, flow of a bodily fluid (e.g., blood or urine), or the beat of a heart, to cells cultured from mechanically active tissues, such as heart, lung, skeletal muscle, bone, ligament, tendon, cartilage, smooth muscle cells, intestine, kidney, endothelial cells and cells from other tissues. Rather than testing the biological or biochemical responses of a cell in a static environment, a range of frequencies, amplitudes and duration of mechanical stresses and/or strains, including tension, compression and shear, can be applied to cultured cells grown on one surface or both surfaces of the membrane. For example, one can mechanically modulate the membrane within the device to simulate the mechanical load environment of walking, running, breathing/respiration, or peristalsis.

A skilled artisan can place various types of cells on one or both surfaces of the membrane. Cells include any cell type from a multicellular structure, including nematodes, amoebas, plants, insects, up to animals and mammals such as humans. Cell types grown on the device can depend on the type of tissue/organ or organ function one intends to mimic. More details of the various types of cells that can be grown on the membrane of the devices described herein are discussed below.

Examples of Tissue/Organ-Mimic Devices (Also Termed "Organ Chips" Herein)

The devices described herein can be adapted to mimic function of any portion of a tissue or organ in any living organisms, e.g., vertebrates (e.g., but not limited to, human subjects or animals such as fish, birds, reptiles, and amphibians), invertebrates (e.g., but not limited to, protozoa, annelids, mollusks, crustaceans, arachnids, echinoderms and insects), plants, fungi (e.g., but not limited to mushrooms, mold, and yeast), and microorganisms (e.g., but not limited to bacteria and viruses). In accordance with some embodiments of the invention, the devices described herein can be adapted to mimic cell behavior or function of at least a portion of a tissue or organ of a mammalian subject, including, e.g., but not limited to, an eye, a lung, an airway, a bronchus, a trachea, an esophagus, an intestine, a pancreas, a stomach, a heart, a liver, a spleen, a blood-brain-barrier, a skin, bone marrow, a reproductive organ (e.g., an ovary or a testis), or any combinations thereof. For examples, the devices described herein can be adapted to form an organ-on-a-chip or organ-chip device as described, for example, in U.S. Provisional Application No. 61/470,987, filed Apr. 1, 2011 (subsequently published in International Publication No. WO 2012/135834); U.S. Provisional Application No. 61/492,609, filed Jun. 2, 2011 (subsequently published in International Publication No. WO 2012/166903); U.S. Provisional Application No. 61/447,540, filed Feb. 28, 2011; U.S. Provisional Application No. 61/449,925, filed Mar. 7, 2011; U.S. Provisional Application No. 61/569,029, filed on Dec. 9, 2011; U.S. patent application Ser. No. 13/054,095, filed Jul. 16, 2008, now published as U.S. Patent Application Publication No. 2011/0250585; International Application No. PCT/US2009/050830, filed Jul. 16, 2009, now published as International Publication No. WO 2010/009307; and PCT/US2010/021195, filed Jan. 15, 2010, now published as International Publication No. WO 2010/123594, the contents of each of the forgoing applications and publications being incorporated herein by reference in their entireties.

In some embodiments, devices with a taller first central microchannel can be used to mimic a portion of a tissue or an organ. The taller first central microchannel can provide low shear stress to the cells present therein as in a native physiological microenvironment. The taller first central microchannel can alternatively or additionally provide more space for cell layers and/or structures as they mature or differentiate. For example, liver cells and associated cellular structures are generally larger than cells from another tissue; or skin cells can form multiple cell layers. The devices described in the International Patent Application entitled "LOW SHEAR MICROFLUIDIC DEVICES AND METHODS OF USE AND MANUFACTURING THEREOF" filed concurrently with the current application on Dec. 19, 2014, as PCT Application No. PCT/US2014/071611, now published as International Publication No. WO 2015/138034, can be modified to adopt different methods of membrane modulation as described herein.

In accordance with some embodiments of the invention, the devices described herein can be used to mimic function of an alveolar-capillary unit of a lung tissue, for example, as described in PCT Application No. PCT/US2009/050830, now published as International Publication No. WO 2010/009307; PCT Application No. PCT/US2012/068766, now published as International Publication No. WO 2013/086502; and U.S. application Ser. No. 13/054,095, now published as U.S. Application Publication No. 2011/0250585, the contents of each of the forgoing applications and publications being incorporated herein by reference in their entireties.

In accordance with some embodiments of the invention, the devices described herein can be used to mimic function of at least a portion of a kidney tissue, for example, as described in U.S. Provisional App. No. 61/449,925, and International App. No. PCT/US2012/068766, now published as International Publication No. WO 2013/086502, the contents of each of the forgoing applications and publication being incorporated herein by reference in their entireties.

In accordance with some embodiments of the invention, the devices described herein can be used to mimic function of at least a portion of a muscle tissue, for example, as described in U.S. Provisional Patent Application Ser. No. 61/569,028, filed on Dec. 9, 2011 and U.S. Provisional Patent Application Ser. No. 61/697,121, filed on Sep. 5, 2012 (both subsequently published in WO 2013/086512), the contents of each of the foregoing application and publications being incorporated herein by reference in their entireties.

In accordance with some embodiments of the invention, the devices described herein can be used to mimic function of at least a portion of a gut or an intestinal tissue as described in International App. No. PCT/US2012/026934, now published as International Publication No. WO 2012/118799; and International App. No. PCT/US2012/068766, now published as International Publication No. WO 2013/086502, the contents of each of the forgoing applications and publications being incorporated herein by reference in their entireties. In accordance with some embodiments of the invention, the devices can be adapted to model a three-dimensional (3D) intestinal villi, e.g., by having the first central microchannel sufficiently high to accommodate the height of the 3D structure. For example, human intestinal epithelial cells (e.g., epithelial cells associated with an intestine such as duodenum, jejunum, ileum, cecum, colon and an appendix) can be cultured on the surface of the membrane facing the first central microchannel, with or without endothelial cells lining another surface of the membrane facing the second central microchannel. By exposing the cultured cells to a physiological peristalsis-motion produced by stretching and retracting the membrane and flowing a liquid at low shear stress in the first central microchannel, the intestinal cells can grow into folds and form tubular projections (villi) projecting into the first central microchannel (which is modeled as "intestinal lumen") to recapitulate the 3D structure.

In accordance with some embodiments of the invention, the liquid can be flowed through the first central microchannel at a rate that results in a shear stress appropriate for inducing formation of a three-dimensional intestinal villi. In accordance with some embodiments of the invention, the shear stress level can range from about 0.001 dyne cm$^{-2}$ to about 1 dyne cm$^{-2}$ or about 0.005 dyne cm$^{-2}$ to about 0.5 dyne cm$^{-2}$, or about 0.01 dyne cm$^{-2}$ to about 0.1 dyne cm$^{-2}$. In one embodiment, the shear stress can be about 0.02 dyne cm$^{-2}$. Upon formation of the intestinal villi, the cells can be subjected to the same or a normal fluid shear stress as in a normal physiological native microenvironment. In other embodiments, the cells can be subjected to a higher or lower shear stress, for example, to mimic an intestine-related disease or disorder model.

In accordance with some embodiments of the invention, the peristalsis motion can be mimicked by stretching and/or retracting the membrane that results in a strain appropriate for inducing formation of three-dimensional intestinal villi. In accordance with some embodiments of the invention, the membrane can be stretched or retracted to a strain of about 0.1% to about 40%, or about 1% to about 30% or about 5% to about 20%. Upon formation of the intestinal villi, the cells can be subjected to the same or normal strain as in a normal physiological native microenvironment. In other embodiments, the membrane can be stretched and/or retracted to strain of about 0.1% to about 70%, or about 1% to about 50%, depending on the physiological microenvironment to be simulated (e.g., a normal intestine vs. a disease or disorder that can affect peristalsis). In accordance with some embodiments of the invention, the membrane can be stretched or retracted with a strain of about 20% to about 70% or about 30% to about 60%, or about 40% to about 50%. Some examples and aspects of systems and methods for mechanical stretch actuation and imparting strains to microfluidic devices, including microfluidic devices with microchannels and/or membranes with cells disposed thereon, are provided in the related discussions above in the context of FIGS. 16 through 29.

In accordance with some embodiments of the invention, the peristalsis motion can be mimicked by stretching and/or retracting the membrane at a frequency appropriate for inducing formation of three-dimensional intestinal villi. In accordance with some embodiments of the invention, the membrane can be stretched and/or retracted at a frequency of about 0.01 Hz to about 0.5 Hz or about 0.05 Hz to about 0.3 Hz. In one embodiment, the membrane can be stretched and/or retracted at a frequency of about 0.15 Hz. Upon formation of the intestinal villi, the cells can be subjected to the same or normal frequency of the mechanical strain as in a normal native physiological microenvironment. In other embodiments, the cells can be subjected to a lower or higher frequency of mechanical strain depending on the physiological microenvironment to be simulated (e.g., a normal intestine vs. a disease or disorder that can affect peristalsis). In accordance with some embodiments of the invention, the physiologically-relevant frequency can range from about 0.01 Hz to about 5 Hz, or about 0.05 Hz to about 1 Hz, or about 0.05 Hz to about 0.3 Hz.

In addition to modeling a portion of an intestine (e.g., a small or large intestine) as described earlier, in accordance with some embodiments of the invention, the devices described herein can be used to model at least a portion of an organ associated with a gastrointestinal tract or a digestive system, including, e.g., but not limited to, oropharynx, stomach, esophagus, pancreas, rectum and anus. In accordance with some embodiments of the invention, the devices described herein can be used to model at least a portion of a pancreatic tissue, which can be in turn used to study or mimic a pancreas-related physiologically-relevant condition (e.g., a normal and/or pathological condition) for various applications described herein. The taller first central microchannel can provide low shear stress to pancreas-associated cells, such as endocrine islet beta cells or exocrine acinar cells, as in a native physiological environment, optionally along with vascular endothelial cells lining the opposite side of the porous membrane under normal hemodynamic flow conditions.

In accordance with some embodiments of the invention, the devices described herein can be used to mimic function of a blood-brain barrier. For example, brain cells (e.g., neurons and/or astrocytes) can be cultured on one surface of the membrane and blood vessel-associated cells (e.g., endothelial cells, fibroblasts, smooth muscle cells, pericytes, and/or any combinations thereof) on another surface of the membrane. It is commonly believed that the native brain cells are usually exposed to a high shear stress. Thus, in accordance with some embodiments of the invention, a liquid fluid can be flowed over the brain epithelial cells with a high shear stress. In other embodiments, application of a mechanical strain/stress to the brain cells can be used instead in place of a high-shear flow.

In accordance with some embodiments of the invention, the devices described herein can be used to mimic operation of an airway or a bronchus. See, e.g., the devices and methods of use described in the U.S. Provisional Application No. 61/919,193, entitled "LOW SHEAR MICROFLUIDIC DEVICES AND METHODS OF USE AND MANUFACTURING THEREOF" filed concurrently with related U.S. Patent Application No. 61/919,181 on Dec. 20, 2013, as U.S. Patent Application No. 61/919,193 (and International Patent Application entitled "LOW SHEAR MICROFLUIDIC DEVICES AND METHODS OF USE AND MANUFACTURING THEREOF" filed concurrently with the current application on Dec. 19, 2014, as PCT Application No. PCT/US2014/071611, now published as International Publication No. WO 2015/138034).

In accordance with some embodiments of the invention, the devices described herein can be used to model at least a portion of a skin tissue or organ, which can be in turn used to study or mimic a skin-related physiologically-relevant condition (e.g., a normal and/or pathological condition) for various applications described herein.

A mammalian skin is generally composed of two primary layers: the epidermis, which provides a protective barrier; and the dermis, which is the layer of skin beneath the epidermis. The epidermis is a stratified squamous epithelium comprising multiple cell layers, namely (beginning with the outermost layer), stratum corneum, stratum lucidum (primarily in palms and soles), stratum *granulosum*, stratum *spinosum*, stratum germinativum (also known as stratum basale). Keratinocytes constitute a majority of the epidermis, while Merkel cells, melanocytes, and Langerhans cells are also present.

The dermis layer is primarily composed of connective tissue and extracellular matrix (e.g., collagen fibrils, microfibrils, and elastic fibers) which provide tensile strength and elasticity to the skin. The dermis layer also harbors many mechanoreceptors (e.g., nerve endings) that provide sense of touch and heat. It also contains hair follicles, sweat glands, sebaceous glands, apocrine glands, lymphatic vessels and blood vessels. The blood vessels in the dermis can provide nourishment and/or waste removal from its own cells as well as for the epidermis.

In accordance with some embodiments of the invention, the devices described herein can be used to model at least a portion of a heart. In accordance with some embodiments of the invention, the heart-mimic device can be used to study or mimic a heart-related physiologically-relevant condition (e.g., a normal and/or pathological condition) for various applications described herein. In accordance with some embodiments of the invention, contractile heart muscle cells (e.g., cardiomyocytes) can be grown on a surface of a flexible and porous membrane facing the first central microchannel, while the other surface facing the second central microchannel can be coated with or without blood vessel-associated cells as described herein. As the heart muscle cells contract, the pore apertures on the membrane can deform due to cell contraction. By way of example only, the pore apertures can remain as a circle when the heart muscle cells are in a relaxed state, but the circular pore apertures become deformed, e.g., becoming an oval, or an ellipse, due to muscle cell contraction. See, e.g., International Patent Application: PCT/US12/68766, filed Dec. 10, 2012, now published as International Publication No. WO 2013/086502, the content of the foregoing application and publication being incorporated herein by reference in their entireties. In this embodiment, a taller first central microchannel can provide low shear stress to heart muscle cells as in a native physiological microenvironment.

In accordance with some embodiments of the invention, myoblasts can be grown on the membrane facing the first central microchannel (with or without mechanical modulation of the membrane) to induce differentiation of the myoblasts to form myocytes or cardiomyocytes.

In accordance with some embodiments of the invention, the devices described herein can be used to model at least a portion of an eye, which can be in turn used to study or mimic an ocular condition (e.g., a normal and/or pathological condition) for various applications described herein. In some embodiments, the devices described herein can be used to model at least a front portion of an eye. In some embodiments, the devices described herein can be used to model at least a back portion of an eye, e.g., a portion of a retina.

In accordance with some embodiments of the invention, the devices described herein can be used to model bone with a functional marrow. In accordance with some embodiments of the invention, stromal cells of the bone marrow can be placed on one surface of the membrane, while the other surface of the membrane can be placed with or without endothelial cells. Exemplary stromal cells of the bone marrow include, but are not limited to, fibroblasts (e.g., reticular connective tissue cells); macrophages, adipocytes, osteoblasts, osteoclasts, endothelial cells, or any combinations thereof.

In accordance with various embodiments of the devices described herein, while tissue-specific cells can be seeded or placed on the membrane to model function of at least a portion of a specific tissue, precursor cells or stem cells that can be differentiated to become tissue-specific cells can also be used in place of or in combination with the tissue-specific cells. In these embodiments, the precursor cells and/or stem cells can be cultured under a differentiation-inducing microenvironment in the device described herein to generate differentiated tissue-specific cells. For example, the precursor cells and/or stem cells can be cultured in the device at a gas-liquid interface, or liquid-liquid interface, optionally in combination with a cell differentiation agent.

Use of the devices described herein to model various specific tissues are provided herein as illustrative examples and are not intended to be in any way limiting. Those of skill in the art will realize that the devices described herein can be adapted to model any tissues or organs of a human, an animal, a plant or an insect in view of the specification and examples provided herein. The devices described herein can have a first central microchannel with a height dimension sufficient to accommodate formation of one or more cell layers to mimic the native tissue microenvironment. In accordance with some embodiments of the invention, the devices described herein can have a first central microchannel with a height dimension sufficient for formation of a stratified, pseudostratified or three-dimensional structure, and/or provide sufficient overhead space to permit low shear stress produced by air and/or liquid flow over the cells in order to simulate a native physiological environment.

In Vitro Microphysiological Systems

In one aspect, provided herein are integrated networks or functional in vitro microphysiological systems comprising two or more devices described herein. Each of the devices can mimic at least one physiological function and/or response of one or more systems in vivo, e.g., of a mammal (e.g., a human), other animal, insect and/or plant. In accordance with some embodiments of the invention, the in vitro microphysiological systems described herein can mimic at least one physiological function and/or response of one or more systems in vivo, e.g., of a mammal (e.g., a human), including, e.g., but not limited to, a circulatory system, a respiratory system, an excretory system, a nervous system, a gastrointestinal system, or any combinations thereof. The in vitro microphysiological systems described herein are generally formed by connecting (e.g., fluidically connecting) together at least two organ chips representing different organs described herein. Different combinations of organ chips can be used in the system for different applications. In accordance with some embodiments of the invention, a plurality of organ chips (e.g., at least 1, at least 2, at least 3, at least 4, at least 5 or more organ chips) can be fluidically connected, e.g., via a tubing, to each other to form a microphysiological system, e.g., a circulatory system (comprising a heart chip with vascular endothelium and a bone marrow chip), a respiratory system (comprising a lung chip, and an airway smooth muscle chip), an immune system (comprising a bone marrow chip with other immune cells, e.g., macrophages); a musculoskeletal system (comprising a skeletal muscle chip), an excretory system (comprising a lung chip, a gut chip, and a kidney chip), an urinary system (comprising a bladder chip and a kidney chip), a nervous system (comprising a brain chip with astrocytes and neuronal networks), a reproductive system (comprising testis chip), an endocrine system (comprising a testis chip), a gastrointestinal system (comprising a liver chip, and a gut chip), an integumentary system (comprising a skin chip), and a urinary system (comprising a kidney chip).

Depending on target applications, e.g., but not limited to, for use as a disease model or for pharmacokinetics study of a drug, different combinations of organ chips can be selected. For example, in one embodiment, Lung Chips, Heart Chips and Liver Chips can be selected to form an in vitro microphysiological system, e.g., for determination of clinically relevant pharmacokinetics (PK)/pharmacodynamics (PD) as well as efficacy and toxicity (e.g., cardiotoxicity, which is the cause of more than 30% of all drug failures).

In accordance with some embodiments of the invention, the in vitro microphysiological system can be used to evaluate a therapeutic agent that is effective in treating a disease or disorder in a specific organ, but might be toxic to other organ systems. For example, a drug, e.g., Ventolin, known to treat or prevent bronchospasm in subjects with reversible obstructive airway disease can be toxic to or adversely affect heart function. Thus, integration of two or more organ chips to form an in vitro microphysiological system can allow for testing or screening of drugs that are effective in treatment of a certain disease or disorder with minimal side effects or undesirable effects on other organs.

In accordance with some embodiments of the invention, the in vitro microphysiological system can comprise a bone marrow chip fluidically connected to the at least two different organ chips. In one embodiment, the bone marrow chip described in the International Appl. No. PCT/US 12/40188, now published as International Publication No. WO 2012/166903, the content of the forgoing application and publication being incorporated herein by reference in their entireties, can be utilized in the in vitro microphysiological system described herein.

In accordance with some embodiments of the invention, the in vitro microphysiological system can comprise a spleen chip fluidically connected to the at least two different organ chips.

In accordance with some embodiments of the invention, the in vitro microphysiological system comprising a combination (e.g., at least 2 or more) of different organ chips can be disposed in a housing and/or a cartridge unit or assembly that can hold one or more organ chips, for example, as described in U.S. Provisional App. No. 61/856,876, filed Jul. 22, 2013; U.S. Provisional Application No. 61/810,931, filed Apr. 11, 2013; PCT Application No. PCT/US2012/068725, filed Dec. 10, 2012, now published as International Publication No. WO 2013/086486; U.S. Provisional Appl. No. 61/569,004, filed Dec. 9, 2011 (subsequently published in International Publication No. WO 2013/086486); U.S. Provisional Application No. 61/696,997, filed on Sep. 5, 2012 (subsequently published in International Publication No. WO 2014/039514); and U.S. Provisional Application No. 61/735,215, filed on Dec. 10, 2012 (subsequently published in International Publication No. WO 2014/039514), the contents of each of the forgoing applications and publications being incorporated herein by reference in their entireties. For example, a housing to enclose various combinations of organ chips therein can provide functionalities, e.g., but not limited to temperature control, nutrient replenishment, pressure adjustment, imaging, sample analysis, and/or any combinations thereof.

In accordance with some embodiments of the invention, the in vitro microphysiological system can comprise an analytical system that can be used to monitor, detect, and/or measure a response and/or morphology of the cells grown in the devices described herein. The sensing or detection module of the analytical system and the device to be examined can be brought proximal to each other when needed. Accordingly, in accordance with some embodiments of the invention, an analytical system can comprise a platform where at least one or more devices can be disposed thereon, and a movable sensing or detection module that can be transiently moved to the desirable location of the device disposed on the platform. An exemplary analytical system can include an optical imaging system and/or an electron-based sensing system. In one embodiment, a microscope with a camera capable of recording images or a time-lapse movie of cell behavior and/or morphology can be included in the in vitro microphysiological system. In one embodiment, a microscopic blade system as described in U.S. Provisional Application No. 61/839,637 filed Jun. 26, 2013 can be used as an analytical system in the in vitro microphysiological system described herein. In another embodiment, a surface plasmon resonance system can be included in the in vitro microphysiological system.

The devices described herein can be fluidically connected by any methods recognized in the art. As used herein, the term "fluidically connected" refers to two or more devices connected in an appropriate manner such that a fluid or a least a portion of a fluid (e.g., any flowable material or medium, e.g., but not limited to, liquid, gas, suspension, aerosols, cell culture medium, and/or biological fluid) can directly or indirectly pass, flow or be transferred from one device to another device. In accordance with some embodiments of the invention, two or more devices can be fluidically connected together, for example, using one or more fluid-transfer connecting means (e.g., adaptors, tubing, splitters, valves, pumps, and/or channels) between the two or more devices. For example, two or more devices can be fluidically connected by connecting an outlet of one device to an inlet of another device using tubing, a conduit, a channel, piping or any combinations thereof. In accordance with some embodiments of the invention, two or more devices can be fluidically connected by, e.g., at least one pumping device and/or at least one valve device. In accordance with some embodiments of the invention, the pumping device and/or valve device can be configured for microfluidic applications, e.g., the membrane-based fluid-flow control devices as described in U.S. Provisional Application No. 61/735,206, filed Dec. 10, 2012 (subsequently published in International Publication No. WO 2014/133624), the contents of the forgoing application and publication being incorporated herein by reference in their entireties. In accordance with some embodiments of the invention, one or more interconnect elements, devices and/or adaptors, e.g., a septum interconnect as described in U.S. Provisional Application No. 61/810,944, filed Apr. 11, 2013 and/or an interconnect adaptor as described in U.S. Provisional Application No. 61/839,702, filed Jun. 26, 2013, the contents of which are incorporated herein by reference in their entireties, can be used to fluidically connected at least two devices together.

In accordance with some embodiments of the invention, methods and systems for interconnecting microfluidic devices as described in U.S. Provisional Application No. 61/845,666, filed Jul. 12, 2013, the content of which is incorporated herein by reference in its entirety, can be used to fluidically connect two or more devices together. As disclosed in U.S. Provisional Application No. 61/845,666, two or more devices can be fluidically connected using a pipette or a similar fluid collection device to transfer discrete volumes of fluid between two devices. For example the pipette or the fluid collection device can be used to collect a volume of fluid from the output of a first microfluidic device and deposit the collected fluid into the input of a second device, thereby fluidically connecting the two devices together.

In other embodiments, two or more devices can be fluidically connected together when one or more other connecting means (e.g., devices, systems, and/or modules that can perform an additional function other than fluid transfer, e.g., but not limited to, filtration, signal detection, and/or imaging) are present between the two or more devices. In these embodiments, by way of example only, two or more devices can be fluidically connected, when the two or more devices are indirectly connected, e.g., through a biosensor, a filter, and/or an analytical instrument (e.g., via tubing), such that a fluid exiting the previous device can be detoured to first flow through the biosensor, filter and/or analytical instrument, e.g., for detection, analysis and/or filtration of the fluid, before it enters the next device. In these embodiments, at least a portion of the fluid can pass or flow from one device to another device. In accordance with some embodiments of the invention, two or more organ chips can be fluidically connected by, e.g., at least one bubble trap, e.g., the bubble trap can be a membrane-based bubble trap as described in U.S. Provisional Application No. 61/696, 997, filed Sep. 5, 2012 (subsequently published in International Publication No. WO 2014/039514); and U.S. Provisional Application No. 61/735,215, entitled "Cartridge Manifold and Membrane Based-Microfluidic Bubble Trap," filed on Dec. 10, 2012 (subsequently published in International Publication No. WO 2014/039514, the contents of each of the forgoing applications and publications being incorporated herein by reference in their entireties. Alternatively, two or more devices can be connected such that a fluid can pass or flow directly from one device to another device without any intervening components. In such an embodiment, the two or more devices can be designed and/or integrated into one single unit such that the outlet of one device and the inlet of another device share the same port.

In accordance with some embodiments of the invention, at least two of the devices with the in vitro microphysiological system can be fluidically connected in a transient manner. For example, a robotic transfer device, such as the one described in U.S. Provisional Application No. 61/845,666 filed Jul. 12, 2013, can be used to transfer at least a portion of a fluid from one device to another device. This embodiment can not only eliminate the use of a tubing to connect two devices, but it can also permit a fluid flowing in the two devices at a different rate.

In accordance with some embodiments of the invention, the in vitro microphysiological system can be used in combination with a mathematical model. For example, in accordance with some embodiments of the invention, the mathematical model can be used to mathematically model an organ or tissue within the in vitro microphysiological system that was not simulated using the device. In accordance with some embodiments of the invention, data obtained from each device of the in vitro microphysiological system can be analyzed and facilitate development of a mathematical model for an in vitro microphysiological system. Data obtained from each device include, but are not limited to, cell response, immune cell recruitment, intracellular protein expression, gene expression, cytokine/chemokine expression, cell morphology, functional data such as effectiveness of an endothelium as a barrier, concentration change of an agent that is introduced into the device, or any combinations thereof.

Exemplary Methods of Uses and Applications Thereof

Methods for using one or more embodiments of the devices are also provided herein. In one aspect, the method comprises (i) providing at least one device described herein; (ii) introducing a first fluid (e.g., gas or liquid) into the first central microchannel; (iii) introducing a second fluid (e.g., gas or liquid) into the second central microchannel. The first fluid and/or the second fluid can be a static fluid or a flowing fluid within their respective microchannel.

The device provided in the method can comprise cells or no cells. In accordance with some embodiments of the invention, the device provided herein in the method can comprise no cells. In these embodiments, the method can further comprise seeding or placing cells on a first surface of the membrane facing the first central microchannel and/or a second surface of the membrane facing the second central microchannel. The cells can be fully-differentiated, partially-differentiated or non-differentiated cells. In accordance with some embodiments of the invention, the cells can be tissue-specific cells and/or precursor cells that can be differentiated in the devices to form tissue-specific cells. In accordance with some embodiments of the invention, the cells can be stem cells (e.g., embryonic stem cells, induced pluripotent stem cells, bone marrow-derived stem cells, adipocyte-derived stem cells, and adult stem cells) that can be differentiated to form tissue-specific cells. In accordance with some embodiments of the invention, the method can further comprise culturing the cells until they reach a specific physiological endpoint, which is further described in detail below, prior to use for an intended application. In other embodiments, the device provided in the method can have cells pre-seeded on at least one side of the membrane, wherein the cells have reached a specific physiological endpoint.

In accordance with some embodiments of the invention, the cells on the membrane can be mechanically stimulated by mechanically modulating the membrane. Methods for mechanically modulating the membrane include, but are not limited to, pneumatic means, mechanical means, and any combinations thereof. Without wishing to be bound by theory, mechanical modulation of the membrane (e.g., stretching, retraction, compression, bending, vibration, twisting of the membrane) in turn can apply mechanical forces to the cells on the membrane and extracellular matrix molecules (ECM) that mimic physiological mechanical cues that can influence transport of chemicals, molecules particulates, and/or fluids or gas across the tissue-tissue interface, and alter cell physiology. Accordingly, in accordance with some embodiments of the invention, the membrane can be subjected to physiological mechanical strain generated by cyclic stretching and retracting of the membrane and/or the flow of biological fluids (e.g. air, mucus, blood, culture medium) in either one or both of the first central microchannel and second central microchannel to recapitulate the native microenvironment of a tissue or an organ to be mimicked. In accordance with some embodiments of the invention, the culture conditions of cells upon the membrane can be optimized under extracellular matrix (ECM) coating, media perfusion, and/or mechanical strain to maintain morphological and functional characteristics of the cultured cells and to permit their direct cellular interaction across the membrane. The device described herein can thus permit long-term cell culture and optional dynamic mechanical stimulation of adjacent monolayers or multi-layers of cells grown on the membrane at the same time. Some examples and aspects of systems and methods for mechanical stretch actuation and imparting strains to microfluidic devices, including microfluidic devices with microchannels and/or membranes with cells disposed thereon, are provided in the related discussions above in the context of FIGS. 16 through 29.

In accordance with some embodiments of the invention, the cells present on one or both sides of the membrane can be exposed to a gas flow. For example, alveolar cells, airway cells, nasal cells, and/or skin cells can be exposed to a gaseous fluid as in their native physiological microenvironment. In one embodiment, the gaseous fluid is air. In these embodiments, one end of the first and/or second central microchannel can be adapted to engage to a gas-flow modulation device, which can be used to control the flow of a gas through the respective microchannel. The gas-flow modulation device can be adapted to provide a directional flow of gas or an alternating flow of gas that can reverse its direction periodically. The gas-flow modulation device can be in a form of any reversibly inflatable or reversibly expandable chamber, which can expand and contract to receive and expel a gaseous fluid, respectively. The gas-flow modulation device can also allow introduction of a particular sample such as polluted air, cigarette smoke or air-borne viruses. By way of example only, the gas-flow modulation device can be in a form of a balloon, a drum, or a thin-walled tube. As an example, the drum can comprise a flexible diaphragm, which can move outward (inflates—away from the inflow direction) and inward (deflates—toward the inflow direction) to accumulate and expel a gaseous fluid, respectively. To visualize and measure the direction/rate of the gas flow, art-recognized techniques such as particle image velocimetry or micron-resolution particle image velocimetry can be employed. For example, fluorescence beads or particles can be added into the central microchannel filled with the gaseous volume, i.e., over the cells on the membrane, and the movement of the fluorescent beads or particles by the gas flow can be captured with a microscope.

In accordance with some embodiments of the invention, the gas-flow modulation device can be configured to create an alternating inspiratory and expiratory air flow with an average tidal volume ranging from about 10 µL to about 5000 µL, or from about 50 µL to about 2500 µL, or from about 75 µL to about 1000 µL, or from about 100 µL to about 500 µL. The term "tidal volume" as used herein refers to a volume of air displaced between inspiration and expiration when no external pressure is not applied (e.g., to mimic breathing during a resting state). The tidal volume can vary depending on the size of the lung to be mimicked, e.g., a newborn vs. an adult; or a human being vs. a large animal such as an elephant. In accordance with some embodiments of the invention, the gas-flow modulation device can be configured to create an alternating inspiratory and expiratory air flow where a volume of air displaced between inspiration and expiration is greater or smaller than the tidal volume as defined herein, for example, to mimic breathing during exercise or illness.

In accordance with some embodiments of the invention, the gas-flow modulation device can be configured to create an alternating inspiratory and expiratory air flow with a respiratory frequency or rate of about 5 breaths/min to about 100 breaths/min, or about 10 breaths/min to about 50 breaths/min.

Accordingly, in accordance with some embodiments of the invention, the devices described herein can be used to mimic alternating inspiratory and expiratory airflow during respiration and thus mimic a breathing pattern and/or rhythm. For example, in accordance with some embodiments of the invention, the devices described herein can be used to mimic a breathing pattern and/or rhythm during a resting state, exercise, stress, or illness, e.g., suffering from a respiratory disease or distress.

The cells on the membrane can be cultured or provided in the devices to display at least one characteristic corresponding to a pre-determined physiological endpoint. As used herein, the term "physiological endpoint" refers to a pre-determined state of cells desired to be reach at a certain time point. The cells can be maintained at the same physiological endpoint in the devices over time, or they can reach a different physiological endpoint in the devices at a later time point. Examples of the pre-determined physiological endpoint can include, but are not limited to, a mature state, a differentiated state, a precursor state, a stratified state, a pseudo-stratified state, a confluency state, an inflamed state, an infected state, a stimulated state, an activated state, an inhibitory state, a normal healthy state, a disease-specific state, a pre-disease state, a distressed state, a growth state, a migratory state, a three-dimensional state, a metamorphosing state, or any combinations thereof.

As used herein, the term "precursor state" refers to a cell having a capability to differentiate into a mature cell. Thus, a precursor state refers to a cell which is partially or fully undifferentiated. In accordance with some embodiments of the invention, a cell at a precursor state can include a partially-undifferentiated cell that is capable of de-differentiating to a more primitive state. In accordance with some embodiments of the invention, the term "precursor state" can refer to a progenitor cell or a stem cell. Examples of stem cells can include, but are not limited to, embryonic stem cells, fetal stem cells, adult stem cells, induced pluripotent stem cells, bone marrow-derived stem cells, cord blood-derived stem cells, amniotic fluid-derived stem cells, adipocyte-derived stem cells, and patient-specific stem cells.

As used herein, the term "mature state" refers to a fully differentiated cell of a specific tissue. A mature cell is neither a fetal cell nor an embryonic cell, and is not of the gamete lineage.

As used herein, the term "differentiated state" refers to a cell that is partially or fully differentiated to a tissue-specific cell. A fully-differentiated cell can be considered as a cell in a mature state as defined herein. In accordance with some embodiments of the invention, the differentiated cells can form a stratified structure. In accordance with some embodiments of the invention, the differentiated cells can form a 3-D structure.

As used herein, the term "stratified state" refers to cells substantially arranged in more than one layer, e.g., 2 layers, 3 layers, 4 layers, or more.

As used herein, the term "pseudo-stratified state" refers to cells present in a single layer, but when they are visualized by immunostaining they appear as if they form multiple layers. For example, a pseudostratified epithelium is a type of epithelium that, though comprising only a single layer of cells, has its cell nuclei positioned at different levels, thus creating an illusion of cellular stratification.

As used herein, the term "confluency state" refers to a state where complete or almost complete (at least approximately 50-60% coverage) coverage of a surface area by the cells (e.g., available membrane surface area allowed for cell proliferation).

As used herein, the term "inflamed state" refers to cells showing at least one phenotype associated with inflammation. Exemplary phenotypes associated with inflammation include, but are not limited to, attachment and recruitment of immune cells, presence or increased expression of inflammation-associated secreted cytokines/chemokines and/or intracellular molecules, decreased number of ciliated cells, abnormal cilia morphology, increased proportion of goblet cells, increased mucus secretion, abnormal cilia beating frequency, and any combinations thereof. Examples of immune cells include, but are not limited to neutrophils, monocytes, lymphocytes, dendritic cells, immature macrophages, resting macrophages, activated macrophages, resident macrophages, and any combinations thereof.

As used herein, the term "infected state" refers to cells showing at least one phenotype associated with microbial infection, e.g., but not limited to, viral infection, bacterial infection, fungus infection, parasitic infection, and/or any combinations thereof. Exemplary phenotypes associated with microbial infection, include, but are not limited to, presence of microbial proteins (e.g., viral/bacterial/fungal proteins) in an infected cell, damage to an infected cell's epithelium, elevated levels of cytokines/chemokines such as CXCL10 or IL8 secreted by an infected cell, presence of a cellular antimicrobial protein (e.g., antiviral protein such as MX proteins), microbial replication in effluents from the first central microchannel/second central microchannel, and any combinations thereof.

As used herein, the term "activated state" refers to cells having at least one cellular process (e.g., but not limited to, migration potential, cell proliferation, protein synthesis and/or cytokine secretion) in an active state. The cellular process can be effected, for example, by a change in at least one gene expression and/or phosphorylation/dephosphorylation of at least one protein.

As used herein, the term "inhibitory state" refers to cells having at least one cellular process (e.g., but not limited to, migration potential, cell proliferation, protein synthesis and/or cytokine secretion) in an inhibitory state. The cellular process can be effected, for example, by a change in at least one gene expression and/or phosphorylation/dephosphorylation of at least one protein.

As used herein, the term "stimulated state" refers to a state of cells that are responsive to a condition-inducing agent exposed to them. As used herein, the term "condition-inducing agent" refers to any agent that can cause a cell to display a phenotype that is deviated from a basal state (without exposure to the condition-inducing agent). The condition-inducing agent can provoke a beneficial or adverse effect such as cytotoxic effect on the cells. In accordance with some embodiments of the invention Examples of a condition-inducing agent can include, but are not limited to, environmental agents such as radiation and mechanical stress (e.g., fluid shear stress); proteins, peptides, nucleic acids, antigens, cytokines, growth factors, toxins, cells (including prokaryotic and eukaryotic cells such as virus, bacteria, fungus, parasites, and mammalian cells), particulates (e.g., smoke particles or asbestos), particles (e.g., nanoparticles or microparticles, magnetic particles), small molecules, biologics, and any combinations thereof. Thus, a stimulated state can encompass a mature state, a differentiated state, a precursor state, a stratified state, a pseudo-stratified state, an inflamed state, an infected state, an activated state, a disease-specific state, and any combinations thereof.

As used herein, the term "normal healthy state" refers to a state without any symptoms of any diseases or disorders, or not identified with any diseases or disorders, or not on any physical, chemical and/or biological treatment, or a state that is identified as healthy by skilled practitioners based on microscopic examinations.

As used herein, the term "disease-specific state" refers to a state of cells that recapitulates at least one characteristic associated with a disease, disorder or an injury, or different stages thereof. In accordance with some embodiments of the invention, the term "disease-specific state" can refer to a specific stage or grade of a disease, disorder or an injury. Examples of diseases, disorders, or injuries can be related to any organ or tissue, e.g., but not limited to, lung, brain, nerve network, blood-brain-barrier, vascular, kidney, liver, heart, spleen, pancreas, ovary, testis, prostate, skin, eye, car, skeletal muscle, colon, intestine, and esophagus.

In accordance with some embodiments of the invention, the disease-specific state can be associated with a lung disease, e.g., but not limited to, asthma, chronic obstructive pulmonary disease (COPD), pulmonary hypertension, radiation induced injury, cystic fibrosis, or any combinations thereof.

In accordance with some embodiments of the invention, the disease-specific state can be associated with an intestinal disease as described earlier.

In accordance with some embodiments of the invention, the disease-specific state can be associated with an ocular disease as described earlier.

In accordance with some embodiments of the invention, the disease-specific state can be associated with a skin disease as described earlier.

In accordance with some embodiments of the invention, the disease-specific state can be associated with a heart disease as described earlier.

In accordance with some embodiments of the invention, the disease-specific state can be associated with a pancreatic disease as described earlier.

In accordance with some embodiments of the invention, the disease-specific state can be associated with a liver disease, including, e.g., but not limited to, fibrosis, cirrhosis, acute liver failure, fulminant hepatic failure (FHF), hepatitis (e.g., inflammation of the liver caused by various viruses (e.g., viral hepatitis), liver toxins (e.g. alcoholic hepatitis), autoimmunity (autoimmune hepatitis) or any combinations thereof), alcoholic liver disease (e.g., fatty liver disease, alcoholic hepatitis, and cirrhosis), liver cancer, biliary cirrhosis, sclerosing cholangitis, Budd-Chiari syndrome, hereditary diseases that cause damage to the liver (e.g., hemochromatosis and/or Wilson's disease), alpha l-antitrypsin deficiency, glycogen storage disease type II, transthyretin-related hereditary amyloidosis, Gilbert's syndrome, biliary atresia, alagille syndrome, progressive familial intrahepatic cholestasis, and any combinations thereof.

In accordance with some embodiments of the invention, the disease-specific state can be associated with a kidney or renal disease, including, e.g., but not limited to, chronic renal failure, acute renal failure, heterologous nephrotoxic nephritis, glomerulonephritis, sclerosis of the glomerulus, systemic lupus erythematosus (SLE), diabetic nephropathy, diabetic nephropathy, glomerulonephritis, various renal inflammation-associated diseases, immune-mediated diseases which affects the cells of the kidney and/or kidney function, including, but not limited to, immunoglobulin A nephropathy, membranoproliferative glomerulonephritis, mesangial proliferative glomerulonephritis, kidney ischemia, kidney vasculitis, Hepatitis C, and any combinations thereof.

In accordance with some embodiments of the invention, the disease-specific state can include a specific stage of a tumor. A tumor can be associated with any tissue and/or organ described herein. Example stages of a tumor can include, without limitations, a precancerous stage (e.g., dysplasia), a pre-malignant stage (e.g., carcinoma in situ) or a malignant stage (e.g., invasion or metastasis).

The cell in a disease-specific state can be obtained either from a biopsy of a patient carrying the disease, disorder or an injury, or by inducing a normal healthy cell with a condition-inducing agent that is known to induce the cell to acquire at least one characteristic associated with the disease, disorder, or injury. In accordance with some embodiments of the invention, a condition-inducing agent can include, but is not limited to, an environmental agent such as radiation; a chemical or biological agent, e.g., but not limited to, cytokines described herein and/or pathogens, and any combinations thereof.

As used herein, the term "growth state" refers to a state at which cells are growing in size and/or in numbers. In accordance with some embodiments of the invention, the cells at a growth state are undergoing an exponential growth.

As used herein, the term "migratory state" refers to cells having or adopting at least one or more migratory phenotypes, e.g., but not limited to, disruption of cadherens junctions (e.g., E-cadherin junctions); increased metalloproteinase expression; loss of an apico-basal polarity, a spindle-shaped morphology, cell-cell interaction through focal points, and any combinations thereof. In accordance with some embodiments of the invention, the migratory state can include an epithelial-mesenchymal transition or transformation (EMT), which is a process by which epithelial cells lose their cell polarity and cell-cell adhesion, and gain migratory properties to become mesenchymal cells. EMT occurs in various developmental processes including mesoderm formation and neural tube formation. EMT also occurs in wound healing, in organ fibrosis and in the initiation of metastasis for cancer progression. In accordance with some embodiments of the invention, the devices described herein can be used to model metastasis, wherein at least some cancer cells undergo EMT and become migratory and migrate from one surface of the membrane (where the tumor cells reside) to the other surface of the membrane.

As used herein, the term "metamorphosing state" refers to a tissue (e.g., a group of cells) being readily capable of or undergoing metamorphosis or a developmental transition. In accordance with some embodiments of the invention, a metamorphosing state refers to an embryonic tissue undergoing induction (e.g., epithelial—mesenchyme interface transforming into a fully or partially-developed specific tissue, e.g., tooth, bone or epithelial gland). In accordance with some embodiments of the invention, a metamorphosing state refers to an insect tissue undergoing metamorphosis or any whole tissue undergoing a whole developmental transition.

As used herein, the term "three-dimensional state" refers to arrangement of cells in a three-dimensional structure. By way of example only, intestinal epithelial cells grow into folds and form villi in form of tubular projections.

Example Validation/Quality Control Tests of the Physiological Endpoints: Cells with different physiological endpoints defined herein (e.g., precursor cells or non-differentiated cells vs. differentiated or mature cells; or normal healthy cells vs. disease-specific cells) can be identified by methods and assays known to one of skill in the art. For example, a physiological endpoint can be identified based on, but not limited to, cell function, molecule release from cells, cell morphology, cell metabolism, expression level or presence/absence of a molecule known to be associated with the pre-determined physiological endpoint. Cells can be analyzed "on-device" (e.g., cells remain inside the first central microchannel and/or second central microchannel during analysis) or some cells can be removed and analyzed "off-device" (e.g., cells are removed from the device for subsequent analysis that is not performed on the device).

In accordance with some embodiments of the invention, the membrane can be removed from the devices for analysis, e.g., immunohistochemical detection, immunofluorescence microscopy and/or scanning electron microscopy. In other embodiments, the membrane can be evaluated and analyzed using on-chip detection methods, e.g., immunohistochemical detection and/or microscopy. In accordance with some embodiments of the invention, the entire device including the membrane can be evaluated and analyzed, e.g., under a microscope.

For example, in contrast to non-differentiated epithelial cells, differentiated airway cells typically form ciliated cells, globet cells (mucus-secreting cells) and a tight epithelial barrier, the phenotypes of each of which can be detected, e.g., by staining the cells for cilia-associated markers (e.g., but not limited to β-tubulin IV), goblet cell-associated markers (e.g., but not limited to MU5AC) and/or tight junction-associated markers (e.g., TJP-1 and ZO-1), followed by microscopy imaging. Alternatively or additionally, cilia beating frequency can be determined by scanning electron microscopy. The barrier function of a differentiated epithelium can also be determined by a functional assay, e.g., adding fluorescently-labeled large molecules (e.g., inulin-FITC) into a fluid flowing through the first central microchannel and then detecting the presence of the fluorescently-labeled large molecules in the second central microchannel, wherein the no detectable fluorescent signal from the second central microchannel is indicative of a functional barrier formed by the differentiated epithelium.

To determine an inflamed state, cell response to inflammation can be quantified by a functional assay and/or cytokine and/or chemokine expression analysis. For example, attachment and recruitment of immune cells (e.g., but not limited to neutrophils, monocytes, lymphocytes, dendritic cells and immature macrophages) from a static or flowing fluid in the second central microchannel ("blood vessel" channel) to the membrane and/or epithelium on the side of the first central microchannel can be quantified by microscopy, histology, and/or by tracking movement of detectable markers (e.g., fluorescently-labeled immune cells) using, e.g., fluorescence activated cell sorter (FACS). Alternatively or additionally, cytokine and/or chemokine expression analysis (including secreted and/or intracellular molecules) can be performed by collecting effluents and/or cells from the first central microchannel and/or second central microchannel and detecting inflammation-associated cytokines and/or chemokines, e.g., by microarray, ELISA, immunofluorescence, microscopy, and/or quantitative real-time polymerase chain reaction (PCR). For example, an increase in secretion or cellular expression of pro-inflammatory factors can be an indicator of inflamed cells. In accordance with some embodiments of the invention, the inflamed stated can be detected by measuring the functional response of the cells. By way of example only, inflamed airway cells can display lower frequency of cilia beating, e.g., which can be detected by microscopy.

In order to distinguish normal healthy cells from disease-specific cells, one of skill in the art can compare and contrast phenotypes (e.g., gene expression, chemokine/cytokine profile) and/or morphology of the diseased cells with the normal healthy cells, thereby identifying distinct features between the normal healthy cells and the diseased cells. Any art recognized methods, e.g., ELISA, microscopy, immunofluorescence, and/or PCR, can be used to determine cell morphology and its behavior/response.

The device described herein can be utilized to grow and culture cells to reach a pre-determined physiological endpoint by optimizing cell culture conditions. Cell culture conditions that can be optimized include, but are not limited to, seeding density, cell source and/or type, supporting cells, composition of the media, flow rate of air and/or media, presence or absence of an air-liquid interface, requirement of mechanical stimulation (e.g., induced by the membrane movement), membrane surface properties, dimensions of the first central microchannel and/or second central microchannel, or any combinations thereof. The pre-determined physiological endpoint can be detected by cell morphology and/or the presence of at least one marker associated with the pre-determined physiological endpoint, which is further illustrated in the example below.

Optimization of cell culture conditions to reach a pre-determined physiological endpoint: As discussed above, a number of cell culture condition parameters can be optimized in a device described herein for different pre-determined physiological endpoints. Exemplary cell culture condition parameters include, but are not limited to, cell-related parameters (e.g., cell sources, cell types, supporting cells, seeding density, and degree of confluency); culture medium-related parameters (e.g., composition or formulation of culture media); microenvironment-related parameters (e.g., flow rates of air and/or media, presence or absence of an air-liquid interface, mechanical stimulation requirement, membrane surface properties, and dimensions of the first central microchannel and/or second central microchannel), and any combinations thereof.

Cell-related parameters: Cells used in the device can be primary cells (e.g., any cells obtained directly from a living tissue, e.g., a biopsy material, of a human or an animal, which include, but are not limited to normal healthy cells, and disease-specific cells), immortalized or established cell lines, stem cells (e.g., embryonic stem cells, fetal stem cells, adult stem cells, stem cells derived from bone marrow, cord blood, and/or an amniotic fluid, induced pluripotent stem cells, and patient-specific stem cells), and/or modified cells.

In accordance with some embodiments of the invention, the cells used in the device described herein can comprise primary cells. For example, normal healthy cells can be obtained from one or more healthy donors. Disease-specific cells can be obtained from one or more patients diagnosed with the specific disease.

In accordance with some embodiments of the invention, the phenotype and/or behavior of the cells can be modified with a condition-inducing agent described herein. For example, normal healthy cells can be transformed to behave like disease-specific cells phenotypically and/or morphologically by stimulating the normal healthy cells with an agent known to induce symptom(s) of a specific disease in the cells. In one embodiment, cigarette smoke can be used to stimulate normal healthy cells for inducing chronic obstructive pulmonary disease (COPD) phenotype. In another embodiment, asthmatic-like cells can be derived from normal healthy cells by inducing inflammation in the normal healthy cells, e.g., by exposure to a pro-inflammatory factor described herein, e.g., but not limited to, TNF-alpha; by stimulation of normal cells with an allergen (e.g., house dust mite); and/or by stimulation with TH2 cytokines such as IL-13.

In accordance with some embodiments of the invention, the cells used in the device described herein can be genetically modified, e.g., by silencing one or more genes, or over-expressing one or more genes. Exemplary methods of gene silencing include, but are not limited to, RNA interference (e.g., but not limited to small interfering RNA (siRNA), microRNA (miRNA), and/or short hairpin RNA (shRNA)), antisense oligonucleotides, ribozymes, triplex forming oligonucleotides, and the like. Alternatively or additionally, the cells can be labeled with a detectable reporter (e.g., an optical reporter such as a fluorescent molecule, and/or a protein tag).

Different cell types can be appropriately selected in accordance with a tissue and/or its function to be mimicked. By way of example only, lung alveolar cells can be selected for use in a device described herein to simulate a microenvironment in a portion of a lung air sac during breathing; while airway or bronchial epithelial cells can be used to simulate a microenvironment in an airway (e.g., a small airway) or bronchus during breathing. Heart cells (e.g., but not limited to, cardiac muscle cells, connective tissue cells, aorta cells, atrial cells, ventricular cells, and heart valve interstitial cells,) can be selected for use in a device described herein to simulate a microenvironment in a portion of a heart during beating. Gut or intestinal cells (e.g., but not limited to, esophagus cells, stomach cells, intestine cells, and colon cells) can be selected for use in a device described herein to simulate a microenvironment in a portion of an intestine during peristalsis. Other various tissue-specific cells such as liver cells (e.g., but not limited to, karat parenchymal cells, and non-parenchymal cells such as sinusoidal hepatic endothelial cells, Kupffer cells and hepatic stellate cells), and skin cells (e.g., but not limited to, keratinocytes, fibroblasts, adipocytes, connective tissue cells, dermal cells, epidermal cells, and/or gland cells) can be used in the devices described herein to simulate a portion of a corresponding tissue. Additional cell types of various tissues that can be used in the devices described herein are described in the section "Cells" below. In accordance with some embodiments of the invention, stem cells can be used to differentiate into different cell types. Examples of stem cells can include, but are not limited to, embryonic stem cells, fetal stem cells, adult stem cells, induced pluripotent stem cells, bone marrow-derived stem cells, cord blood-derived stem cells, amniotic fluid-derived stem cells, adipocyte-derived stem cells, and patient-specific stem cells.

In accordance with some embodiments of the invention, supporting cells can be cultured together with subject cells of interest. As used herein, the term "supporting cells" refers to cells that provide protection, support, chemical signals (e.g., factors secreted by the supporting cells) and/or physical signals (e.g., direct physical contact between the subject cells and the supporting cells) that can be essential for proper phenotypes and/or functions of the subject cells of interest. For example, interstitial cells (e.g., but not limited to fibroblasts and/or smooth muscle cells) can be used as supporting cells for epithelial cells and act as a "feeder" layer for the epithelium. In one embodiment, lung interstitial cells (e.g., fibroblasts and/or smooth muscle cells) can be used as supporting cells for airway epithelial cells.

Seeding density and/or degree of cell confluency can influence cell morphology and/or their behavior (e.g., but not limited to, proliferation, viability, migration, protein synthesis, and/or differentiation). The cell seeding density and/or degree of cell confluency can be optimized for individual cell types (e.g., cell size, and/or modes of cell signaling such as direct contact, paracrine signaling, and/or endocrine signaling. For example, cells that require at least a part of the cell body to be in direct contact with neighboring cells in order to proliferate and remain viable generally need to be seeded at a higher cell density, as compared to cells that can also rely on paracrine signaling. Accordingly, the seeding density of cells can range from about 0.01 cell/$\mu m^2$ to about 1 cell/$\mu m^2$, or from about 0.05 cell/$\mu m^2$ to about 0.5 cell/$\mu m^2$. Similarly, some cells can be grown a in a sparsely-populated environment, while other cell types can require a denser population. Thus, degree of cell confluency can range from about 30% to 100% or about 50% to 100%.

Culture medium-related parameters: The formulation of cell culture media can vary with individual cell types and/or their stages within a cell cycle as different cell types can require a unique combination and concentrations of nutrients and/or supplements (e.g., growth factors and/or small molecules such as amino acids and minerals) during different stages of a cell cycle (e.g., proliferation vs. differentiation). Accordingly, one or more cell culture media (or a mix of at least two cell culture media) can be used in the devices described herein to achieve any of the physiological endpoints described herein. In accordance with some embodiments of the invention, a mix of at least two cell culture media can be used in the devices described herein to accommodate at least two or more cell types in a co-culture condition. By way of example only, in a co-culture condition, epithelial cells (optionally with supporting cells such as fibroblasts and/or smooth muscle cells) can be cultured in the first central microchannel, while endothelial cells (optionally with supporting cells) can be cultured in the second central microchannel. Alternatively or additionally, immune cells can be introduced into the second central microchannel, either with a static fluid or a flowing fluid.

In accordance with some embodiments of the invention, the cell culture media for use in the device described herein can comprise one or more ingredients of cell culture media described in the International Application Publication Nos.: WO 2003/048313; WO 2006/004728; WO 2005/065341; WO 2002/077202; WO 2010/096588; WO 2005/095582; and WO 1998015614, the contents of which are incorporated herein by reference in their entireties.

In accordance with some embodiments of the invention, the cell culture medium can comprise blood (e.g., whole blood, plasma, serum, or any combinations thereof). In one embodiment, the cell culture medium can comprise blood or blood components derived from a patient for culturing patient-specific cells.

The media can comprise one or more differentiation agents. As used herein, the term "differentiation agent" refers to molecule(s) and/or composition(s) that can induce differentiation of a stem cell or an undifferentiated or partially differentiated cell to a desired state. This can be useful when stem cells or undifferentiated or partially differentiated cells are used.

Microenvironment-related parameters: In addition to the cell-related and culture medium-related parameters, one or more microenvironment-related parameters (e.g., flow rates of air and/or cell culture media, presence or absence of an air-liquid interface, mechanical cue, membrane surface properties, and dimensions of the first central microchannel and/or second central microchannel) can be regulated to achieve any of the physiological endpoints described herein.

In accordance with some embodiments of the invention, an air-liquid interface can be established in the devices described herein to mimic the native tissue microenvironment of tissue-specific cells and/or induce differentiation and/or maturation of the tissue-specific cells. As used herein, the term "air-liquid interface" refers to one of the first central microchannel and second central microchannel having air therein while the remaining channel has a liquid fluid, e.g., cell culture medium and/or blood. There can be substantially no liquid fluid present in the "air" channel. However, cells present on the membrane facing the "air" channel can secrete a liquid-like substance, such as mucus, and/or a small amount of a liquid fluid can permeate through the membrane from the "liquid" channel to the "air" channel. In accordance with some embodiments of the invention, the term "air-liquid interface" refers to substantially no liquid fluid being introduced into one of the first central microchannel and second central microchannel, while a liquid fluid is introduced into the remaining channel. In one embodiment, an air-liquid interface refers to the first central microchannel having air therein while the second central microchannel has a liquid fluid, e.g., cell culture medium and/or blood. Stated another way, substantially no liquid fluid is introduced into the first central microchannel, while a liquid fluid is introduced into the second central microchannel. For example, an air-liquid interface can be established in the devices described herein to induce differentiation or maturation of tissue-specific epithelial cells (e.g., but not limited to airway cells, intestinal cells, and/or skin cells). In other embodiments, the native microenvironment of some tissue-specific cells (e.g., heart cells, liver cells and/or gut cells) may not require an air-liquid interface. In these embodiments, a liquid fluid, e.g., cell culture medium, can be present in both the first central microchannel and the second central microchannel.

Air and/or culture media can be introduced into the appropriate channels in the devices (e.g., first central microchannel and second central microchannel) as a static fluid (which can be periodically replaced) or a continuous (dynamic) flow. Flow rates of air and/or culture media in the first central microchannel and/or second central microchannel can be adjusted independently to reflect the physiological values specific to a tissue-specific condition or state (e.g., a resting state vs. an active state, e.g., during exercise; or a normal healthy state vs. a disease-specific state). For example, air flow can be controlled at a volumetric rate to provide a fluid shear stress of about 0 dynes/cm$^2$ to about 2000 dynes/cm$^2$, or 0.1 dynes/cm$^2$ to about 2000 dynes/cm$^2$. In accordance with some embodiments of the invention where the device is used to mimic breathing through an airway and/or a lung, the air flow through the first central microchannel can be adjusted to have a rate of about 1 µL per breath to about 50 mL per breath, or about 5 µL per breath to about 25 mL per breath, or about 10 µL per breath to about 10 mL per breath, or about 25 µL per breath to about 1 mL per breath. As used herein in reference to the device, the term "breath" refers to air flow induced in the first central microchannel to mimic inspiration and expiration of air in a lung. The air flow volume and/or rhythm can vary depending on the state of a lung to be mimicked. For example, when stimulating air flow in a lung during exercise, e.g., running, the volume of air getting into and out of the lungs can increase per breath and unit time.

Culture medium flow rates can be controlled to simulate the flow rate of blood corresponding to a tissue-specific condition or state (e.g., a resting state vs. an active state, e.g., during exercise; or a normal healthy state vs. a disease-specific state, e.g., hypertension). In accordance with some embodiments of the invention, the culture medium flow rates can be provided in a range of about 0 µL/hr to about 50 mL/hr.

In accordance with some embodiments of the invention where the cells are exposed to a mechanical stress or strain in their native tissue microenvironment such as a strain produced by motion associated with breathing, peristalsis or heart beating, the cells present on the membrane can be subjected to a simulated mechanical strain for development of a pre-determined physiological endpoint. The simulated mechanical strain can be produced by modulating the movement of the membrane, which can be parallel to and/or perpendicular to a force/pressure applied to the membrane, including, but are not limited to, stretching, bending, compressing, vibrating, contracting, waving, or any combinations thereof. By way of example only, in a pulmonary alveolus, alveolar cells experience stretching when the alveolus is filled with air during inhalation but restore to an original state or relaxed state during exhalation in order to expel carbon-dioxide-rich air. Another example is that esophagus cells or intestinal cells are subjected to a mechanical stress or strain produced by peristaltic waves occurring in the esophagus, or intestines, respectively. In a heart, the atria and ventricles work together, alternately contracting and relaxing to pump blood through the heart. In order to simulate a physiological strain produced by motion associated with breathing, peristalsis, or heart beating, the membrane can be, in one embodiment, modulated to stretch and release along the plane, e.g., by a pneumatic mechanism based on application of a pressure differential between the central channel and the operating microchannel(s) as described herein, thereby providing the cells (e.g., alveolar cells, esophagus cells, intestinal cells, atrial myocardial cells, and ventricular myocardial cells) with a simulated mechanical cue as they reside in the native tissue microenvironment. In accordance with some embodiments of the invention, a constant mechanical stress/strain can be applied to the cells on the membrane for a desirable period of time. For example, a constant static mechanical stress/strain can be applied to skin cells on one side of the membrane, e.g., to mimic the skin cells naturally under tension in vivo. Some examples and aspects of systems and methods for mechanical stretch actuation and imparting strains to microfluidic devices, including microfluidic devices with microchannels and/or membranes with cells disposed thereon, are provided in the related discussions above in the context of FIGS. 16 through 29.

In accordance with some embodiments of the invention, the membrane can be treated or coated with cell adhesion molecules and/or extracellular matrix molecules to facilitate development of a pre-determined physiological endpoint. Examples of cell adhesion molecules, and/or extracellular matrix molecules include, without limitations, fibronectin, laminin, various collagen types, glycoproteins, vitronectin, elastins, fibrin, proteoglycans, heparin sulfate, chondroitin sulfate, keratin sulfate, hyaluronic acid, integrin-binding peptides such as Arg-Gly-Asp (RGD) peptides, or any combinations thereof.

Exemplary applications of the devices described herein: In accordance with some embodiments of the invention, the devices and/or in vitro microphysiological systems can be used as cell culture devices. Compared to 2-D tissue culture flasks, the devices and/or in vitro microphysiological systems described herein can provide organ-specific cells a more physiological condition for their growth, and/or maintenance of their differentiated states. For example, lung cells in vivo are generally exposed to a mechanical stimulation, e.g., during breathing. To mimic the breathing action in vitro, organ chips such as lung chips can be used to culture lungs cells as described above. In accordance with some embodiments of the invention, the cells can be cultured and remain viable (e.g., capable of proliferation) for at least about 2 weeks, at least about 3 weeks, at least about 4 weeks, at least about 5 weeks, at least about 6 weeks, at least about 9 weeks, at least about 12 weeks or longer inside the organ chips described herein.

In accordance with some embodiments of the invention, the cells can be cultured in the devices to reach a differentiated or mature state of tissue-specific epithelial cells, e.g., airway epithelial cells, skin keratinocytes, and/or intestinal epithelial cells. Thus, the devices described herein can also be used to produce a tissue-specific organoid. For example, in order to differentiate airway epithelial cells to ciliated cells, one can seed airway or bronchial epithelial cells on the membrane in the first central microchannel. The cells are cultured in a submerged condition by flowing a culture medium through both the first central microchannel and the second central microchannel. In accordance with some embodiments of the invention, the cells are cultured in a submerged condition until the cells reach a full confluence. Then, an air-liquid interface is optionally established by removing the culture medium from the first central microchannel through its outlet. As the air-liquid interface can induce differentiation of certain cell-types, e.g., airway epithelial cells and skin keratinocytes, the cells can differentiate after a period of culture (e.g., about 3-4 weeks or longer) in the device at the air-liquid interface. A static air flow can be sufficient to induce cell differentiation. While not necessary, in accordance with some embodiments of the invention, a dynamic air flow can be induced in the first central microchannel during cell differentiation to improve the cellular function(s) of the differentiated epithelial cells (e.g., differentiated airway epithelial cells and/or skin cells). For example, a dynamic air flow can improve cilia beating frequency, mucous secretion, monolayer barrier function (e.g., permeability of epithelial layer) and/or surface protein expression of differentiated airway epithelial cells.

However, it should be noted that depending on cell types, an air-liquid interface is not always necessary for cell differentiation. In these embodiments, a liquid flow can be maintained in the first central microchannel during cell differentiation.

In accordance with some embodiments of the invention, a liquid fluid, e.g., cell growth media, flowing through the second central microchannel can comprise at least one differentiation-inducing agent, including, e.g., at least two, at least three, at least four, at least five differentiation-inducing agents.

In accordance with some embodiments of the invention, the cells can require exposure to a mechanical strain in order to reach a differentiated or mature state. For example, the cells in the first central microchannel can be exposed to a mechanical cyclic strain (e.g., about 0.1% to about 50%, or about 1% to about 30%, or about 10% to about 25%) at a frequency of about 0 Hz to about 1 Hz, or about 0.01 Hz to about 1 Hz) by stretching and/or retracting the membrane. In one embodiment, intestinal epithelial cells in the first central microchannel can be exposed to a cyclic stain (e.g., about 10% at ~0.15 Hz). In accordance with some embodiments of the invention, the cells in the first central microchannel can be exposed to a constant mechanical strain (e.g., about 0.1% to about 50%, or about 1% to about 30%, or about 10% to about 25%), or a constant mechanical stress over a period of time. Some examples and aspects of systems and methods for mechanical stretch actuation and imparting strains to microfluidic devices, including microfluidic devices with microchannels and/or membranes with cells disposed thereon, are provided in the related discussions above in the context of FIGS. 16 through 29.

Co-culture: As used herein, the term "co-culture" refers to two or more different cell types being cultured in a device described herein. The different cell types can be cultured in the same channel (e.g., first central microchannel or second central microchannel) and/or in different channels (e.g., one cell type in a first central microchannel and another cell type in a second central microchannel). For example, in accordance with some embodiments of the invention, in order to recapitulate in vivo microenvironment, in accordance with some embodiments of the invention, one side of the membrane can be cultured with blood vessel-associated cells, e.g., but not limited to, endothelial cells, fibroblasts, smooth muscle cells, pericytes, or any combinations thereof. As endothelial cells generally play a significant role in immune cell recruitment and/or extravasation, co-culture of tissue-specific epithelial cells (e.g., airway epithelial cells) on one surface of the membrane with endothelial cells on another surface of the membrane can create a physiologically-relevant model to perform an immune cell recruitment assay, e.g., by introducing immune cells (e.g., but not limited to, CD8+ T cells, lymphocytes, monocytes, neutrophils) in one of the central microchannels comprising blood vessel-associated cells, followed by determination of the number of immune cells adhered onto the endothelial monolayer. In accordance with some embodiments of the invention, endothelial cells can also participate in cytokine/chemokine secretion during a virus infection.

As used herein throughout the specification, the term "immune cells" generally refer to resting and/or activated cells of the immune system involved in defending a subject against both infectious disease and foreign materials. Examples of immune cells include, without limitations, white blood cells including, e.g., neutrophils, eosinophils, basophils, lymphocytes (e.g., B-cells, T-cells, and natural killer cells), monocytes, macrophages (including, e.g., resident macrophages, resting macrophages, and activated macrophages); as well as Kupffer cells, histiocytes, dendritic cells, Langerhans cells, mast cells, microglia, and any combinations thereof. In some embodiment, immune cells include derived immune cells, for example, immune cells derived from lymphoid stem cells and/or myeloid stem cells.

When there is more than one cell type in a channel, a culture medium supplied to the channel can comprise a mixture of culture media typically used to culture individual cell types.

In accordance with some embodiments of the invention, tumor cells can be co-cultured with normal epithelial cells in one of the central microchannels.

In accordance with some embodiments of the invention, the cells on the membrane can be co-cultured with microbial cells and/or pathogens. In accordance with some embodiments of the invention, the microbial cells and/or pathogens can be present in the same microchannel as the cells and/or in a different microchannel from where the cells are present. In accordance with some embodiments of the invention, the microbial cells can be found on a skin surface.

In accordance with some embodiments of the invention, the microbial cells can be found in the intestine or gut of a healthy animal or human. In accordance with some embodiments of the invention, the microbial cells and/or pathogens can be organisms found in the intestine or gut of an unhealthy animal or human, e.g. one with an intestinal disease or disorder. In accordance with some embodiments of the invention, the microbial cells and/or pathogens can be organisms that cause or contribute to a disease or disorder of the intestine. In these embodiments, the devices and/or in vitro microphysiological systems described herein can be used for studying the role of gut flora (e.g., microorganisms that live in the digestive tracts of animals) and other bacteria within a body of an animal that can have a symbiotic relationship with the host. Various factors other than infections, such as aging, geographical transplant, changes in diet, and/or various therapeutic regimens such as antibiotics can alter the gut flora demographics and the physiology of the host. See, e.g., Maynard C L et al. "Reciprocal interactions of the intestinal microbiota and immune system." Nature. 2012 Sep. 13; 489(7415):231-41; Tremaroli V. and Bäckhed F. "Functional interactions between the gut microbiota and host metabolism." Nature. 2012 Sep. 13; 489 (7415):242-9; Lozupone C A et al. "Diversity, stability and resilience of the human gut microbiota" Nature. 2012 Sep. 13; 489(7415):220-30; and Ottman N et al. "The function of our microbiota: who is out there and what do they do?" Front Cell Infect Microbiol. 2012; 2:104. Epub 2012 Aug. 9, for information on gut microbiome and human health/disease. For example, *C. difficile* is a serious cause of antibiotic-associated diarrhea (AAD) and can lead to pseudomembranous colitis, a severe inflammation of the colon, often resulting from eradication of the normal gut flora by antibiotics. Accordingly, in accordance with some embodiments of the invention, "cassettes" of gut bacteria colonies can be co-cultured with gut cells and/or intestine cells in the devices described herein, for example, to model gut flora in a host, and/or to study the effects of different factors on the gut flora demographics and/or physiology of the host cells. In accordance with some embodiments of the invention, the devices described herein can be connected to other organ chips to form in vitro microphysiological systems that can be desirable when considering the mind body axis and the coupling of the enteric and central nervous system. These systems can be also used to study, e.g., but not limited to, digestion, and mental illness.

In accordance with some embodiments of the invention, methods to study microbial growth, adhesion to host-related surfaces and/or the host-microbiota interactions, e.g., as described in the U.S. Application Publication No. US 2012/0058551, the content of which is incorporated herein by reference in its entirety, can be integrated or utilized together with the organ chips and/or in vitro microphysiological system described herein to study the role of gut flora within a body of an animal.

In accordance with some embodiments of the invention, the device described herein can be used to create an in vitro model that mimics a tissue-specific condition. As used herein, the term "tissue-specific condition" refers to any condition that can be diagnosed in a tissue of an organ in vivo. The condition can occur naturally in the tissue in vivo (including, e.g., a normal healthy condition, or a condition induced or caused by a congenital defect), or induced or caused by a condition-inducing agent or stimulant (e.g., including, but not limited to an environmental agent). Examples of a tissue-specific condition include, without limitations, a normal state, a disease-specific state, a pre-disease state, a disease remission state, a distressed state, an inflamed state, an infected state, and a stimulated state. In these embodiments, the tissue-specific cells placed on one surface of the membrane can be adapted to display at least one characteristic associated with the tissue-specific condition. For example, in accordance with some embodiments of the invention, patient- and disease-specific epithelial cells and optional structural cells can be cultured and differentiated on the surface of the membrane, for example, to model acute and/or chronic disorders associated with a specific tissue and/or organ.

In accordance with some embodiments of the invention, disease-specific cells can be obtained from one or more patients diagnosed with the specific disease. In other embodiments, the tissue-specific cells (e.g., normal tissue-specific cells) can be contacted with a condition-inducing agent described herein that is capable of inducing the tissue-specific cells to acquire at least one characteristic associated with the tissue-specific condition. In accordance with some embodiments of the invention, it can be desirable to induce a disease-specific in normal cells (rather than using diseased cells collected from patients diagnosed with the specific disease), for example, to reduce or eliminate genetic variability/heterogeneity among different diseased donors. By way of example only, lung infections can be modeled by introducing a biological and/or chemical agent, e.g., pathogens such as influenza virus, and/or an immunostimulant (e.g., polyinosinic:polycytidylic acid (usually abbreviated as poly I:C) to model lung infections, including bacterial and/or viral infections. In one embodiment, cigarette smoke can be used to stimulate normal healthy cells for inducing chronic obstructive pulmonary disease (COPD) phenotype. In another embodiment, asthmatic-like cells can be derived from normal healthy cells by inducing inflammation in the normal healthy cells, e.g., by exposure to a pro-inflammatory agent described herein. Pro-inflammatory agents are described below in the section "Additional examples of cytokines".

The stimulants or condition-inducing agents as described herein (e.g., but not limited to, particles, pathogens, cytokines such as pro-inflammatory agents, and/or drugs) can be delivered to the cells via diffusion across the membrane from another central microchannel, and/or as an aerosol or liquid through the central microchannel where the cells are present. The aerosol of molecules or pathogens can be generated on-chip, e.g., modifying the device described herein to integrate with an in vitro aerosol delivery device described in the PCT Application Nos. PCT/US12/37096, now published as International Publication No. WO 2012/154834, and PCT/US13/36569, now published as International Publication No. WO 2013/155513, the contents of each of the forgoing applications and publications being incorporated herein by reference in their entireties. In one embodiment, an inertial impactor as described in the PCT Application No. PCT/US12/37096 can be placed in the bottom portion of the device body and fluidically connects to the first central microchannel in the top portion of the device body. An access port can be placed on the lateral surface of the bottom portion of the device body and fluidically connects to the inertial impactor. Thus, an aerosol produced from an aerosol-producing element can be introduced into the access port, flowing through the inertial impactor where larger droplets of the aerosol are captured on the wall surface of the inertial impactor (e.g., to prevent blocking of the first central microchannel), while smaller droplets of the aerosol continue to flow into the first central microchannel.

In accordance with some embodiments of the invention, a tissue-specific condition, e.g., a disease-specific condition can be created by genetically modifying normal healthy cells, e.g., by silencing one or more genes, or over-expressing one or more genes. Methods of gene silencing include, but are not limited to, RNA interference (e.g., but not limited to small interfering RNA (siRNA), microRNA (miRNA), and/or short hairpin RNA (shRNA)), antisense oligonucleotides, ribozymes, triplex forming oligonucleotides, and the like.

In accordance with some embodiments of the invention where the devices described herein are used to create a disease-specific model, the devices can further comprise normal healthy cells (e.g., obtained from one or more healthy donors) cultured in a separate central channel, e.g., to create a baseline for comparison.

In accordance with some embodiments of the invention, the device can comprise both healthy and disease-specific cells. In accordance with some embodiments of the invention, the device can include only disease-specific cells. Accordingly, in accordance with some embodiments of the invention, the device described herein can be used to model a tissue-specific condition.

The following is an example to illustrate the capability of using one embodiment of the device described herein to model a tissue-specific condition such as a bacterial/viral infection in an airway, and is not construed to be limiting. One of skill in the art can follow similar methods described herein and adapt one or more embodiments of the devices to mimic a different tissue-specific condition, e.g., but not limited to, using different tissue-specific cells and/or stimulants.

In some embodiments, a fluid comprising immune cells described herein (e.g., but not limited to, human monocytes) can be introduced into another central microchannel across the membrane, either as a static fluid or a flowing fluid, in order to determine effects of a pro-inflammatory agent-induced inflammation on cytokine/chemokine profiles of the differentiated cells and/or recruitment of immune cells described herein (e.g., but not limited to, monocytes and/or neutrophils). Cytokines or chemokines secreted into the fluid flowing in the first central microchannel and/or second central microchannel can be measured by collecting from the outlet an aliquot of the fluid exiting the first central microchannel and/or second central microchannel, which is then subjected to cytokine/chemokine expression analyses.

In accordance with some embodiments of the invention, the devices described herein can be used to determine an effect of a test agent on the cells on one or both surface of the membrane. Effects of a test agent can include, but are not limited to, ciliary clearance, villi absorption, cell membrane disruption, receptor binding, cell viability, permeability of a cell layer, cell morphology, protein expression, gene expression, cell adhesion, adhesiveness of immune cells, cell differentiation, cytokine or chemokine production, inflammation, or any combinations thereof.

In accordance with some embodiments of the invention, the devices described herein can be used to determine an efficacy of a test agent upon exposure of the cells on one or both surfaces of the membrane to the test agent. For example, the efficacy of a test agent can be determined by measuring response of the cells and/or at least one component present in a fluid (e.g., gaseous and/or liquid fluid) within the device or present in an output fluid (e.g., gaseous and/or liquid fluid) from the device after exposure to the test agent. As used herein, the term "efficacy" generally refers to ability of a test agent to produce a desired effect or outcome. Depending on the nature and/or type of the test agents, examples of desired effects or outcomes include, but are not limited to, therapeutic effect, cytotoxicity, cell growth, cell differentiation, improved or reduced cell function or phenotype (e.g., but not limited to, ciliary clearance, permeability of a cell layer, cell migration, expression and/or secretion of a protein or cytokine that can be affected by cell exposure to the test agent), and any combinations thereof. The term "therapeutic effect" as used herein refers to a consequence of treatment, the results of which are judged to be desirable and beneficial.

In accordance with some embodiments of the invention, the devices described herein can be used to determine toxicity of a test agent upon exposure of the cells on one or both surfaces of the membrane to the test agent. For example, the toxicity of a test agent can be determined by measuring response of the cells and/or at least one component present in a fluid (e.g., gaseous and/or liquid fluid) within the device or present in an output fluid (e.g., gaseous and/or liquid fluid) from the device after exposure to the test agent. As used herein, the term "toxicity" refers to ability of a test agent to induce or cause any adverse and/or side effect on a cell and/or even cell death. For example, the toxicity of a test agent can be characterized by its ability to induce or cause an adverse effect on cell function and/or phenotype, including, but not limited to, alteration in cell metabolism, mutagenicity, carcinogenicity, teratogenicity, DNA damage, protein or membrane damage, cell energy depletion, mitochondrial damage, genotoxicity, apoptosis, cell death, cell rupture, and any combinations thereof.

In accordance with some embodiments of the invention, the devices described herein can be used to determine a mechanism of action upon exposure of the cells on one or both surfaces of the membrane to the test agent. For example, the mechanism of action can be determined by measuring response of the cells and/or at least one or more components present in a fluid (e.g., gaseous and/or liquid fluid) within the device or present in an output fluid (e.g., gaseous and/or liquid fluid) from the device after exposure to the test agent. As used herein, the term "mechanism of action" refers generally to a cellular pathway or biological interaction through which an agent exerts its biological effect on a cell. For example, when an agent is a drug substance, mechanism of action can refer to the biochemical interaction through which a drug substance produces its pharmacological effect. Depending on the nature and/or type of test agents, the mechanism of action can be associated with any art-recognized cellular pathways or biological interaction, e.g., including, but not limited to, protein synthesis, cell migration, chromatin regulation/epigenetics or acetylation, MAPK signaling, apoptosis, autophagy, PI3K/Akt signaling, translation control, cell cycle/checkpoint, Jak/Stat Pathway, NF-κB signaling, TGF-β/Smad signaling, lymphocyte signaling, angiogenesis, cytoskeletal signaling, cell adhesion, cell metabolism, cell development and/or differentiation, tyrosine kinase/adaptors, protein stability, protein folding, nuclear receptor signaling, and any combinations thereof. Accordingly, in some embodiments, a mechanism of action can encompass a mechanism of efficacy and/or toxicity of a test agent.

In those embodiments of some aspects described herein, the tissue-specific epithelial cells on one surface of the membrane, e.g., of the first central microchannel, can be contacted with a test agent. The test agent can be delivered to the cells as an aerosol and/or liquid through the first central microchannel or "tissue-specific" channel and/or via diffusion from the second central microchannel or "blood vessel" channel. As described earlier, an aerosol (e.g., of the test agent) can be generated on-chip, e.g., modifying the device described herein to integrate with an in vitro aerosol delivery device described in the PCT Application Nos. PCT/US12/37096, now published as International Publication No. WO 2012/154834, and PCT/US13/36569, now published as International Publication No. WO2013/155513, the contents of each of the forgoing applications and publications being incorporated herein by reference in their entireties.

Any test agent can be introduced into the device described herein to determine its effect on the cells. Examples of the test agent can include, but are not limited to, proteins, peptides, antigens, nanoparticles, environmental toxins or pollutant, cigarette smoke, chemicals or particles used in cosmetic products, small molecules, drugs or drug candidates, vaccine or vaccine candidates, aerosols, inflammatory molecules, naturally occurring particles including pollen, chemical weapons, single or double-stranded nucleic acids, viruses, bacteria and unicellular organisms.

Effects of the test agent on the cells can be determined by measuring response of the cells on at least one side of the membrane to the test agent, the gaseous and/or liquid fluid exiting the first central microchannel, the gaseous and/or liquid fluid exiting the second central microchannel, or any combinations thereof; and comparing the measured response with the cells not contacted with the test agent. Various methods to measure cell response are known in the art, including, but not limited to, cell labeling, immunostaining, optical or microscopic imaging (e.g., immunofluorescence microscopy and/or scanning electron microscopy), spectroscopy, gene expression analysis, cytokine/chemokine secretion analysis, metabolite analysis, polymerase chain reaction (PCR), immunoassays, ELISA, gene arrays, spectroscopy, immunostaining, electrochemical detection, polynucleotide detection, fluorescence anisotropy, fluorescence resonance energy transfer, electron transfer, enzyme assay, magnetism, electrical conductivity (e.g., trans-epithelial electrical resistance (TEER)), isoelectric focusing, chromatography, immunoprecipitation, immunoseparation, aptamer binding, filtration, electrophoresis, use of a CCD camera, mass spectroscopy, or any combination thereof. Detection, such as cell detection, can be carried out using light microscopy with phase contrast imaging and/or fluorescence microscopy based on the characteristic size, shape and refractile characteristics of specific cell types. Greater specificity can be obtained using optical imaging with fluorescent or cytochemical stains that are specific for individual cell types or microbes.

In accordance with some embodiments of the invention, adhesion of immune cells that are introduced through the "blood vessel" channel to the endothelium or membrane can be measured to determine effects of a test agent on immune response.

In accordance with some embodiments of the invention where the tissue-specific cells to be assayed are adapted to be condition-specific (e.g., disease-specific), exposure of the tissue-specific cells to a test agent followed by determination of the effect of the test agent on the cells can facilitate identification of a therapeutic agent for treatment of the condition. In accordance with some embodiments of the invention where the tissue-specific cells are patient-specific, exposure of the patient-specific cells to a test agent, followed by determination of the effect of the test agent on the cells can facilitate identification of a personalized treatment for a subject.

In accordance with some embodiments of the invention where the tissue-specific cells are patient population-specific, exposure of the patient population-specific cells to a test agent, followed by determination of the effect of the test agent on the cells can facilitate identification of a treatment specified for that particular patient population. As used herein, the term "patient population-specific" refers to cells collected from a population of patients sharing at least one or more phenotypes and/or characteristics (e.g., but not limited to, specific gene mutation, ethnicity, gender, life styles, BMI, resistance to treatment, and any combinations thereof) other than the disease or disorder.

Drugs intended for oral administration generally require good bioavailability in order to achieve therapeutic concentrations at the targeted site of action. Good bioavailability implies that an effective amount of drug is able to reach the systemic circulation. However, drug absorption via oral route can be affected by drug properties and/or the physiology of the gastrointestinal tract, including drug dissolution from the dosage form, the manner in which drug interacts with the aqueous environment and membrane, permeation across membrane, and irreversible removal by first-pass organs such as the intestine, liver, and lung (Martinez and Amidon, 2002 J Clin Pharmacol 42: 620-643). In particular, the majority of drug absorption generally occurs at the small intestine where the presence of villi and microvilli markedly increases the absorptive area. Thus, in accordance with some embodiments of the invention, the devices modeling the function of an intestinal villus structure as described above can be used to assess intestinal absorption, metabolism, and/or excretion of a test agent for the prediction of its bioavailability. In accordance with some embodiments of the invention, the devices modeling the function of the intestinal villus structure can be fluidically connected to another device mimicking a target tissue to be treated by the test agent.

In accordance with some embodiments of the invention, one or more devices described herein can be used in combination with a pharmacokinetic (PK) model, a pharmacodynamics (PD) model, or a PK-PD model to quantitatively analyze the effect of an agent to be tested. For example, a series of devices, each modeling a tissue, e.g., one for gut, one for liver, and another one for heart, can be connected to provide a microphysiological system that can be used to determine the fate of an agent administered into the system. The term "pharmacokinetics" is used herein in accordance with the art, and refers to the study of the action of agents, e.g., drugs, in the body, for example, the effect and duration of drug action, the rate at which they are absorbed, distributed, metabolized, and eliminated by the body etc. (e.g. the study of a concentration of an agent, e.g., a drug, in the serum of a patient following its administration via a specific dose or therapeutic regimen). The term "pharmacodynamics" is used in accordance with the art, and refers to the study of the biochemical and physiological effects of an agent, e.g., a drug, on a subject's body or on microorganisms such as viruses within or on the body, and the mechanisms of drug action and the relationship between drug concentration and effect (e.g. the study of a pathogen, e.g., a virus, present in a patient's plasma following one or more therapeutic regimens). Methods for PK-PD modeling and analysis are known in the art. See, e.g., Bonate, P. L. (2006). Pharmacokinetic-Pharmacodynamic Modeling and Simulation. New York, Springer Science & Business Media; Gabrielsson, J. and D. Weiner (2000); and Pharmacokinetic and Pharmacodynamic Data Analysis: Concepts and Applications. Stockholm, Swedish Pharmaceutical Press. For example, a PK model can be developed to model a microphysiological system comprising a plurality of the devices described herein, wherein each device can model a different tissue that can produce an effect (e.g., absorption, metabolism, distribution and/or excretion) on an agent to be administered. To construct a PK model for a device described herein, mass balance equations describing the flow in, flow out, and metabolism of an agent can be set up for each first central microchannel and second central microchannel. A PD model can be integrated into each device described herein, describing the kinetics of potential cell response (e.g., inflammation, cytokine release, ligand binding, cell membrane disruption, cell mutation and/or cell death) in each device that mimics a tissue or an organ. This in vitro/in silico system, combining one or more devices described herein with an integrated PK-PD modeling approach, can be used to predict drug toxicity in a more realistic manner than conventional in vitro systems. In some embodiments, one or more of the devices described herein can be used to quantify, estimate or gauge one or more physical-chemical, pharmacokinetic and/or pharmacodynamic parameters. Various physical-chemical, pharmacokinetic and pharmacodynamic parameters are known in the art, including, for example, the ones discussed in the aforementioned references. Exemplary physical-chemical, pharmacokinetic and pharmacodynamic parameters include, but are not limited to, permeability, log P, log D, volume of distribution, clearances (including intrinsic clearances), absorption rates, rates of metabolism, exchange rates, distribution rates and properties, excretion rates, IC50, binding coefficients, etc.

In accordance with some embodiments of the invention, the devices described herein can be used for target identification/validation. For example, the devices described herein can be used to mimic a tissue-specific condition as described herein (e.g., a disease or disorder) in order to elucidate the molecular mechanism underlying a disease or a condition, the identification of candidate target molecules and the evaluation of said target molecules. In accordance with some embodiments of the invention, use of genetically modified cells, e.g., by silencing or over-expressing a specific gene, in the devices described herein can be used to identify target molecules for a specific disease. Once such a validated target molecule, e.g., ligand, receptor, transcription factor, and/or enzyme, which is herein referred to also as target, is identified, drug candidates directed to the target (e.g., suppression or activation) can be tested. The drug candidate can be introduced to the disease-specific cells in the devices described herein and cell response to the drug candidate can be measured to validate the identified target. This can also promote drug discovery for a specific disease or condition. In many cases such drug candidates can be members of a compound library which can comprise synthetic and/or natural compounds. Combinatorial libraries can also be used.

In another example, the device can have tissue-specific cells grown on one side of a porous membrane and blood vessel-associated cells (e.g., endothelial cells, fibroblasts, smooth muscle cells, and/or pericytes) maintained on the other side of the membrane. During the operation of the device, these two cells layers can communicate with each other through passage of chemical and/or molecular cues through the pores on the membrane. This communication can be monitored and analyzed to understand how the cells function differently as a tissue-tissue interface, with or without physiological mechanical simulation, and compared to when grown as single tissue types in isolation as in standard tissue culture systems. By monitoring changes in cell and tissue physiology, as well as passage of chemicals, molecules, particulates and cells across this tissue-tissue interface, information can be obtained which can be used to produce more effective drugs or therapies, to identify previously unknown toxicities, and to significantly shorten the timescale of these development processes. In particular, the behavior of cells in such a controlled environment can allow one to study a variety of physiological phenomena taking place in the systems mentioned above that cannot be recreated using conventional in vitro culture techniques. In other words, the device can function to create a monitorable artificial blood or liquid-air barrier or liquid-liquid barrier outside a patient's body and in a controllable environment that still retains key physiological functions and structures of at least a portion of a tissue or organ to be mimicked. In accordance with some embodiments of the invention, the devices described herein can be used to mimic airway or bronchus function. In accordance with some embodiments of the invention, the devices described herein can be used to mimic peristalsis and/or absorption in the gastrointestinal tract containing living microbial populations. In accordance with some embodiments of the invention, the devices described herein can be used to mimic perfusion and urine production in the kidney. In accordance with some embodiments of the invention, the devices described herein can be used to mimic function of the blood-brain barrier. In accordance with some embodiments of the invention, the devices described herein can be used to study effects of mechanical deformation on skin aging. In accordance with some embodiments of the invention, the devices described herein can be used to model bone marrow-microvessel interface with hematopoietic stem cell niche.

Similarly, the devices described herein can be used to mimic a physiological environment under which a drug fails during a clinical trial. Thus, mechanism of action of the drug can be studied to facilitate identification of a new drug target.

In accordance with some embodiments of the invention, the devices described herein can be cultured with animal cells (e.g., but not limited to, pig cells, rabbit cells, dog cells, mouse cells, and/or rat cells) to determine response of the animal cells to an agent introduced into the devices described herein. The measured response of the animal cells in the devices can then be correlated with the actual response occurred in vivo when the agent is administered to a living animal (e.g., a pig, a rabbit, a dog, a mouse, and/or a rat). By identifying the correlation between the in vitro and in vivo responses in one or more animal models, one can extrapolate or predict effect of the agent on a human subject in vivo, based on the measured responses of the human cells to the agent in the devices. Additionally or alternatively, a therapeutic dose of an agent for a human subject can be determined accordingly.

In accordance with some embodiments of the invention, at least two or more devices described herein can be connected in series and/or in parallel to determine the infectivity and/or virulence of an air-borne or body fluid-borne pathogen. In accordance with some embodiments of the invention, the combination of simulated breathing through the "air" central microchannel and ability to connect to two or more devices described herein (e.g., in series and/or in parallel) can allow studying how airborne pathogens, e.g., but not limited to virus, bacteria, respiratory syncytial virus, influenza virus, or *Mycobacterium Tuberculosis* (MTB), from a "pathogen-infected" device can infect one or more "non-infected" devices. In these embodiments, a first device comprising pathogen-infected epithelial cells can be adapted to connect, e.g., in series and/or in parallel, to at least one a second device comprising non-infected cells. The distance between two devices can be adjusted to simulate closeness of contact between two subjects and/or control the rate of airborne pathogen transmission between two subjects.

In accordance with some embodiments of the invention, the pathogen-infected epithelial cells can be obtained from one or more infected subjects. In accordance with some embodiments of the invention, the non-infected cells can be obtained from one or more normal healthy subjects and/or subjects with a disease or disorder such as a respiratory disease. An air flow can then be directed from the "air" central microchannel of the first device to the "air" central microchannel of the second device. Response of the non-infected cells (including immune cells) upon exposure to the air flow from the first device as well as response of the infected cells (including immune cells) can be measured to determine transmissibility of airborne pathogens.

In some embodiments, by measuring the response of immune cells from different subject populations in the individual connected devices, one can also identify risk populations for a pathogenic strain.

In accordance with some embodiments of the invention, the "airborne pathogen transmission" model as described herein can be used to assess risk of a novel (i.e., new in humans) virus strain acquiring the ability to spread easily and efficiently in humans. Ten evaluation criteria that Centers for Disease Control and Prevention (CDC) currently use to measure the potential pandemic risk posed by influenza A viruses (Influenza Risk Assessment Tool accessible at www.cdc.gov/flu/pandemic-resources/tools/risk-assessment.htm) can be used as guidelines to determine the potential pandemic risk associated with emergence of a novel virus strain using the devices described herein. In accordance with some embodiments of the invention, the "airborne pathogen transmission" model as described above can also be used to determine prophylactic or therapeutic efficacy of an anti-pathogen agent (e.g., anti-viral agent) or a vaccine against an airborne pathogen. Similarly, for therapeutic agents or vaccines (e.g., anti-viral vaccines), the pathogen-infected cells in the first device can be treated with an agent or vaccine of interest before directing an air flow from the first device to the second device comprising non-infected cells. A reduction or an inhibition of the transmissibility of the airborne pathogens is indicative of the efficacy of a therapeutic agent or vaccine.

In accordance with some embodiments of the invention, the exclusion of fluorescently labeled large molecules (e.g. dextrans of different weight or FITCs) can be quantitated to determine the permeability of the membrane and thus assess the barrier function of the epithelium, e.g., in a tissue-specific condition. For example, flowing a fluid containing fluorescently labeled large molecules (e.g., but not limited to, inulin-FITC) into one of the central microchannels cultured with differentiated epithelium can provide a non-invasive barrier measurement. As a functional tight junction barrier will prevent large molecules from passing through the epithelium from the first central microchannel to the second central microchannel, the absence of the detection of the fluorescently labeled large molecules in the second central microchannel is indicative of a functional barrier function of the epithelium.

Additionally, histological, biochemical, microfluorimetric and/or functional techniques can be employed to demonstrate formation of a functional airway-endothelial that reproduces the key structural organization of its in vivo counterpart on the membrane.

In an example, the gas exchange between the cells on apposing surfaces of the membrane can be determined by injecting different fluids, each having their own oxygen partial pressures and blood, into the respective first central microchannel and second central microchannel, whereby the first central microchannel acts as the "air" compartment and the second central microchannel acts as the "liquid" or "blood vessel" compartment. A blood-gas measurement device preferably within the device can be used to measure the level of oxygen in the blood in the respective sections before and after the passing of the blood through the device. For example, blood can flow through the channel while air is being injected into the first central microchannel, whereby the exiting air is collected and measured to determine the oxygen level using an oximeter. Oximeters can be integrated with the existing system or as a separate unit connected to the outlet port of one or more central sub-channels. In an embodiment, air or another medium with aerosols containing drugs or particulates can flow through the device, whereby the transport of these drugs or particulates to the fluid flowing in the "liquid" second central microchannel (e.g., blood, culture medium) via the membrane is then measured. In accordance with some embodiments of the invention, pathogens or cytokines can be added to the air or gaseous medium side and then the adhesion of immune cells introduced in the microvascular second central microchannel to nearby capillary endothelium and their passage along with edema fluid from the blood side to the airway side, as well as pathogen entry into blood, can be measured.

Since the functionality of an epithelium requires polarization of constituent cells, the structure of the membrane can be visualized using transmission electron microscopy, immunohistocytochemistry, confocal microscopy, or other appropriate means to monitor the polarization of the airway epithelial cell side of the membrane. In an airway mimic embodiment, a florescent dye can be applied to the first central microchannel and second central microchannel to determine pulmonary surfactant production by the airway epithelium at the membrane. In particular, airway epithelial cells on the membrane can be monitored by measuring the fluorescence resulting from cellular uptake of the fluorescence dye that specifically labels intracellular storage of pulmonary surfactant (e.g. quinacrine) or using specific antibodies.

In accordance with some embodiments of the invention, the device described herein can be used to develop a mucosal immunity platform, e.g., to study immune cell recruitment, maturation, and activation, cell killing, and drainage. In some embodiments, the platform can be used for vaccine development.

As discussed above, in accordance with some embodiments of the invention, the devices described herein can be used to model an infectious disease, to determine transmissibility of an infectious pathogen, and/or to identify effective agents (e.g., drugs molecules, and/or vaccine) for therapeutic and/or prophylactic treatments. Various methods can be used to detect the presence or absence of infection in the devices described herein. For example, where fluorescently-labeled (e.g., GFP-expressing) pathogens (e.g., virus or bacteria) are used, normal healthy cells that are infected with the fluorescently-labeled pathogens can be directly followed over time or real-time by fluorescent microscopy. Alternatively or additionally, the infection-suspected cells can be immuno-stained for viral/bacterial proteins and detected by immunofluorescence. In accordance with some embodiments of the invention where virus or bacteria can produce a cytopathic effect on infected cells, e.g., causing damages to the infected cells' epithelium, the integrity of the infection-suspected cells' epithelium can be examined over time under light or fluorescent microscopy.

Additional methods that can be used to detect the presence or absence of infection in the device described herein can include, e.g., but are not limited to, quantification of pathogen (e.g., virus) replication, which, for example, can be measured by collecting effluent of infection-suspected cells from the top central microchannel (termed "apical wash", e.g., using cell culture medium) and/or effluent from the bottom central microchannel (termed "basal medium") and then titrating pathogen growth over time in the apical wash and/or basal medium using a plaque assay. Alternatively or additionally, cytokines/chemokines secreted by the infection-suspected cells can be determined by analysis of effluents collected from the top central microchannel and/or the bottom central microchannel. Some cytokines/chemokines such as CXCL10 or IL-8 can be significantly elevated in the device with the infected cells as compared to non-infected cells. In accordance with some embodiments of the invention where cellular antiviral proteins such as MX proteins can be up-regulated following infection of the cultures, the cellular antiviral proteins such as MX proteins can be stained in the infection-suspected cells for immunofluorescence detection. In accordance with some embodiments of the invention, expression analysis of at least one or more genes that are known to be upregulated following pathogen (e.g., viral/bacterial) infection (as compared to non-infected cells) can be performed on the infection-suspected cells, e.g., by microarray and/or quantitative real-time polymerase chain reaction (qRT-PCR).

Without wishing to be limiting, in other embodiments, the device can also be used to examine how nanomaterials or particulates behave with respect to the air-tissue interface. In particular, nanomaterials (e.g. silica nanoparticles, superparamagnetic nanoparticles, gold nanoparticles, single-walled carbon nanotubes) can be applied to the "airway" surface or "skin" surface of the membrane to investigate any potential toxic effects of nanomaterials on "airway" or "skin" epithelial cells grown on the membrane, as well as their passage from the "airway" microchannel or "skin" microchannel into the other microchannel. For instance, sensors can be used to monitor transmigration of nanomaterials through a tissue barrier or an epithelium formed on the membrane and nanomaterial-induced changes in barrier functions such as gas exchange and fluid/ion transport.

As stated above, more than one devices can be multiplexed and automated to provide high-throughput analysis of cell and tissue responses to drugs, chemicals, particulates, toxins, pathogens or other environmental stimuli for drug, toxin and vaccine screening, as well as toxicology and biodetection applications. The device can be used for studying complex tissue and organ physiology in vitro, as well as tissue and organ engineering in vivo with biocompatible or biodegradable devices.

In accordance with some embodiments of the invention, provided herein is an organomimic device in accordance with an embodiment that contains three or more parallel channels separated by at least two membranes. The organomimic device can include at least one first central microchannel and at least one second central microchannel. For example, in one embodiment, one first central microchannel can be positioned between two second central microchannels. In accordance with some embodiments of the invention, the device can further comprise operating microchannels or mechanical means as described herein for mechanical modulation of the membrane. The overall central microchannel can include multiple membranes positioned along respective parallel x-y planes which separate the central channel into at least three distinct central sub-microchannels. The membranes can be permeable and rigid or flexible.

The advantages of the organomimic device, as opposed to conventional cell cultures or tissue cultures are numerous. For instance, when cells are placed in the organ mimic device, fibroblast, SMC (smooth muscle cell), endothelial cells, and/or epithelial cell differentiation can occur that reestablishes a defined three-dimensional architectural tissue-tissue relationships that are close to the in vivo situation, and cell functions and responses to pharmacological agents or active substances or products can be investigated at the tissue and organ levels.

In addition, many cellular or tissue activities are amenable to detection in the organ mimic device, including, but not limited to, diffusion rate of the drugs into and through the layered tissues in transported flow channel; cell morphology, differentiation and secretion changes at different layers; cell locomotion, growth, apoptosis, and the like. Further, the effect of various drugs on different types of cells located at different layers of the system can be assessed easily.

For drug discovery, for example, there can be two advantages for using the organ mimic device described herein: (1) the organ mimic device is better able to mimic in vivo layered architecture of tissues and therefore allow one to study drug effect at the organ level in addition to at the cellular and tissue levels; and (2) the organ mimic device decreases the use of in vivo tissue models and the use of animals for drug selection and toxicology studies.

In addition to drug discovery and development, the organ mimic device described herein can be also useful in basic and clinical research. For example, the organ mimic device can be used to research the mechanism of tumorigenesis. It is well established that in vivo cancer progression is modulated by the host and the tumor micro-environment, including the stromal cells and extracellular matrix (ECM). For example, stromal cells were found being able to convert benign epithelial cells to malignant cells, thereby ECM was found to affect the tumor formation. There is growing evidence that cells growing in defined architecture are more resistant to cytotoxic agents than cells in mono layers. Therefore, an organ mimic device is a better means for simulating the original growth characteristics of cancer cells and thereby better reflects the real drug's sensitivity of in vivo tumors.

The organ mimic device can be employed in engineering a variety of tissues including, but not limited to, the cardiovascular system, lung, intestine, kidney, brain, bone marrow, bones, teeth, and skin. If the device is fabricated with a suitable biocompatible and/or biodegradable material, such as poly-lactide-co-glycolide acid (PLGA), the organ mimic device can be used for transplantation or implantation in vivo. Moreover, the ability to spatially localize and control interactions of several cell types presents an opportunity to engineer hierarchically, and to create more physiologically correct tissue and organ analogs. The arrangement of multiple cell types in defined arrangement has beneficial effects on cell differentiation, maintenance, and functional longevity.

The organ mimic device can also allow different growth factors, chemicals, gases and nutrients to be added to different cell types according to the needs of cells and their existence in vivo. Controlling the location of those factors or proteins can direct the process of specific cell remodeling and functioning, and also can provide the molecular cues to the whole system, resulting in such beneficial developments as neotissue, cell remodeling, enhanced secretion, and the like.

In yet another aspect, the organ mimic device can be utilized as multi cell type cellular microarrays, such as microfluidic devices. Using the organ mimic device, pattern integrity of cellular arrays can be maintained. These cellular microarrays can constitute the future "lab-on-a-chip", particularly when multiplexed and automated. These miniaturized multi cell type cultures will facilitate the observation of cell dynamics with faster, less noisy assays, having built-in complexity that will allow cells to exhibit in vivo-like responses to the array.

In yet another aspect, the organ mimic device can be utilized as biological sensors. Cell-based biosensors can provide more information than other biosensors because cells often have multifaceted physiological responses to stimuli, as well as novel mechanisms to amplify these responses. All cell types in the organ mimic device can be used to monitor different aspects of an analyte at the same time; different cell type in the organ mimic device can be used to monitor different analytes at the same time; or a mixture of both types of monitoring. Cells ranging from *E. coli* to cells of mammalian lines have been used as sensors for applications in environmental monitoring, toxin detection, and physiological monitoring.

In yet another aspect, the organ mimic device can be used in understanding fundamental processes in cell biology and cell-ECM interactions. The in vivo remodeling process is a complicated, dynamic, reciprocal process between cells and ECMs. The organ mimic device would be able to capture the complexity of these biological systems, rendering these systems amenable to investigation and beneficial manipulation. Furthermore, coupled with imaging tools, such as fluorescence microscopy, microfluorimetry or optical coherence tomography (OCT), real-time analysis of cellular behavior in the multilayered tissues is expected using the device. Examples of cell and tissue studies amenable to real-time analysis include cell secretion and signaling, cell-cell interactions, tissue-tissue interactions, dynamic engineered tissue construction and monitoring, structure-function investigations in tissue engineering, and the process of cell remodeling matrices in vitro.

Another example of the use of this device is to induce tissue-tissue interfaces and complex organ structures to form within the device by implanting it in vivo within the body of a living animal, and allowing cells and tissues to impregnate the device and establish normal tissue-tissue interfaces. Then the whole device and contained cells and tissues is surgically removed while perfusing it through one or more of the fluid channels with medium and gases necessary for cell survival. This complex organ mimic can then be maintained viable in vitro through continuous perfusion and used to study highly complex cell and tissue functions in their normal 3D context with a level of complexity not possible using any existing in vitro model system.

Membrane surface treatment: Details of membrane surface treatment which can be optionally applied to the membrane are discussed below. The membrane can be coated with substances such as various cell adhesion promoting substances or ECM proteins, such as fibronectin, laminin, various collagen types, glycoproteins, vitronectin, elastins, fibrin, proteoglycans, heparin sulfate, chondroitin sulfate, keratin sulfate, hyaluronic acid, fibroin, chitosan, or any combinations thereof. In general, one or more cell adhesion molecules is coated on one surface of the membrane whereas another cell adhesion molecule is applied to the opposing surface of the membrane, or both surfaces can be coated with the same cell adhesion molecules. In accordance with some embodiments of the invention, the ECMs, which can be ECMs produced by cells, such as primary cells or embryonic stem cells, and other compositions of matter are produced in a serum-free environment.

In an embodiment, one coats the membrane with a cell adhesion factor and/or a positively-charged molecule that are bound to the membrane to improve cell attachment and/or stabilize cell growth. The positively charged molecule can be selected from the group consisting of polylysine, chitosan, poly(ethyleneimine) or acrylics polymerized from acrylamide or methacrylamide and incorporating positively-charged groups in the form of primary, secondary or tertiary amines, or quaternary salts. The cell adhesion factor can be added to the membrane and is fibronectin, laminin, various collagen types, glycoproteins, vitronectin, elastins, proteoglycans, heparin sulfate, chondroitin sulfate, keratin sulfate, hyaluronic acid, tenascin, antibodies, aptamers, or fragments or analogs having a cell binding domain thereof. The positively-charged molecule and/or the cell adhesion factor can be covalently bound to the membrane. In another embodiment, the positively-charged molecule and/or the cell adhesion factor are covalently bound to one another and either the positively-charged molecule or the cell adhesion factor is covalently bound to the membrane. Also, the positively-charged molecule or the cell adhesion factor or both cam be provided in the form of a stable coating non-covalently bound to the membrane.

In an embodiment, the cell attachment-promoting substances, matrix-forming formulations, and other compositions of matter are sterilized to prevent unwanted contamination. Sterilization can be accomplished, for example, by ultraviolet light, filtration, gas plasma, ozone, ethylene oxide, and/or heat. Antibiotics can also be added, particularly during incubation, to prevent the growth of bacteria, fungi and other undesired micro-organisms. Such antibiotics include, by way of non-limiting example, gentamicin, streptomycin, penicillin, amphotericin and ciprofloxacin.

In some embodiments, the membrane and/or other components of the devices described herein can be treated using gas plasma, charged particles, ultraviolet light, ozone, or any combinations thereof.

Cells: The devices described herein can be provided with pre-seeded cells or a pre-formed tissue structure, or without pre-seeded cells. In another embodiment, the membrane is coated with cell cultures, including without limitation, primary cell cultures, established cell lines, or stem cell cultures (such as embryonic stem cells, fetal stem cells, adult stem cells, induced pluripotent stem cells, bone marrow-derived stem cells, cord blood-derived stem cells, amniotic fluid-derived stem cells, adipocyte-derived stem cells, and patient-specific stem cells). In some embodiments, the membrane can be coated with ECM substances and/or cell adhesion molecules, which can facilitate cell attachment and/or adhesion. Any prokaryotic and eukaryotic cells, including, e.g., but not limited to, human cells, animal cells, insect cells, plant cells, bacteria, fungus, and/or parasites, can be used in the devices described herein. In accordance with some embodiments of the invention, mammalian cells (e.g., a human or an animal) are used in the device described herein. Usually an animal is a vertebrate such as a primate, rodent, domestic animal or game animal. Primates include chimpanzees, cynomolgous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, and avian species, e.g., chicken, emu, ostrich, and birds. In accordance with some embodiments of the invention, the animal cells include cells from fish, reptiles and amphibians. The cells can be derived from a normal healthy subject (e.g., a human or an animal) or a subject (e.g., a human or an animal) determined to have a specific type or stage of a disease or disorder.

In accordance with some embodiments of the invention, cells can be derived from an invertebrate. For example, invertebrates can include, but are not limited to, protozoa, annelids, mollusks, crustaceans, arachnids, echinoderms, and insects.

In accordance with some embodiments of the invention, insects cells can be used in the devices described herein. In accordance with some embodiments of the invention, plant cells can be used in the devices described herein. In accordance with some embodiments of the invention, cells derived from fungi can be used in the devices described herein. Examples of fungi can include, but are not limited to mushrooms, mold, and yeast. In accordance with some embodiments of the invention, cells derived from microorganisms can be used in the devices described herein. Examples of microorganisms can include, but are not limited to, bacteria and viruses.

In an embodiment, the cells attached to either side of the membrane can include epithelial cells, endothelial cells, fibroblasts, smooth muscle cells, basal cells, ciliated cells, columnar cells, goblet cells, muscle cells, immune cells, neural cells, hematopoietic cells, lung cells (e.g., alveolar epithelial cells, airway cells (e.g., small airway cells, and large airway cells), bronchial cells, tracheal cells, and nasal epithelial cells), gut cells, brain cells, stem cells, skin cells, liver cells, heart cells, spleen cells, kidney cells, pancreatic cells, intestinal cells, keratinocytes, dermal keratinocytes, reproductive cells, blood cells (including, e.g., white blood cells, red blood cells, platelets and hematopoietic stem and progenitor cells) and any combinations thereof. In other embodiments, the primary cells or cell lines can be fibroblast cells, which include without limitation, human fetal fibroblast cells. In accordance with some embodiments of the invention, the stem cells of the stem cell cultures are embryonic stem cells. The source of embryonic stem cells can include without limitation mammals, including non-human primates and humans. Non-limiting examples of human embryonic stem cells include lines BG01, BG02, BG03, BG01v, CHA-hES-1, CHA-hES-2, FCNCBS1, FCNCBS2, FCNCBS3, H1, H7, H9, H13, H14, HSF-1, H9.1, H9.2, HES-1, HES-2, HES-3, HES-4, HES-5, HES-6, hES-1-2, hES-3-0, hES-4-0, hES-5-1, hES-8-1, hES-8-2, hES-9-1, hES-9-2, hES-101, hICM8, hICM9, hICM40, hICM41, hICM42, hICM43, HSF-6, HUES-1, HUES-2, HUES-3, HUES-4 HUES-5, HUES-6, HUES-7 HUES-8, HUES-9, HUES-10, HUES-11, HUES-12, HUES-13, HUES-14, HUESS-15, HUES-16, HUES-17, 13, 14, 16, 13.2, 13.3, 16.2, J3, J3.2, MB01, MB02, MB03, Miz-hES1, RCM-1, RLS ES 05, RLS ES 07, RLS ES 10, RLS ES 13, RLS ES 15, RLS ES 20, RLS ES 21, SA01, SA02, and SA03. In an embodiment, the stem cells of the stem cell cultures are induced pluripotent stem cells. Other stem cells such as fetal stem cells, adult stem cells, bone marrow-derived stem cells, cord blood-derived stem cells, amniotic fluid-derived stem cells, adipocyte-derived stem cells, and/or patient-specific stem cells can also be used.

To study the effects of a test agent, e.g., pharmaceuticals, environmental stressors, pathogens, toxins and such, one can add these into the desired cell culture medium suitable for growing the cells attached to the membrane in the channel. Thus, one can introduce pathogens, such as bacteria, viruses, aerosols, various types of nanoparticles, toxins, gaseous substances, and such into the culture medium which flows in the chambers to feed the cells.

A skilled artisan will also be able to control the pH balance of the medium according to the metabolic activity of the cells to maintain the pH in a suitable level for any cell or tissue type in question. Monitors and adjustment systems to monitor and adjust pH can be inserted into the device.

The membrane is preferably coated on one or both sides with cells, molecules or other matter, whereby the device provides a controlled environment to monitor cell behavior along and/or between the first central microchannel and the second central microchannel via the membrane. One can use any cells from a multicellular organism in the device. For example, the human body comprises at least 210 known types of cells. A skilled artisan can easily construct useful combinations of the cells in the device.

Additional Examples of Cytokines

As used herein, the term "cytokine" refers to an agent that can stimulate, inhibit, and/or mediate a cellular process, including, e.g., but not limited to, proliferation, differentiation, inflammation, apoptosis, cellular metabolism, cytoskeletal regulation, cell adhesion, cell migration, angiogenesis, DNA repair, protein synthesis, and any combinations thereof. A "cytokine" can be or include a small molecule, a biological molecule (e.g., but not limited to, a protein, peptide, nucleic acid, lipid, carbohydrate, glycoprotein, glycolipid, proteoglycan, lipoprotein), an antibody, oligonucleotide, a metal, a vitamin, or any combinations thereof. For example, a cytokine can include, but are not limited to, a growth-promoting agent, a cell differentiation agent, an anti-inflammatory agent, a pro-inflammatory agent, an apoptosis-inducing agent, an anti-apoptotic agent, a pro-angiogenic agent, an anti-angiogenic agent, or any combinations thereof.

In accordance with some embodiments of the invention, the cytokine can include a pro-inflammatory agent. As used herein, the term "pro-inflammatory agent" refers to an agent that can directly or indirectly induce or mediate an inflammatory response in cells, or is directly or indirectly involved in production of a mediator of inflammation. A variety of proinflammatory agents are known to those skilled in the art. Illustratively, pro-inflammatory agents include, without limitation, eicosanoids such as, for example, prostaglandins (e.g., PGE2) and leukotrienes (e.g., LTB4); gases (e.g., nitric oxide (NO)); enzymes (e.g., phospholipases, inducible nitric oxide synthase (iNOS), COX-1 and COX-2); and cytokines such as, for example, interleukins (e.g., IL-1α, IL-1β, IL-2, IL-3, IL-4, IL-5, IL-6, IL-8, IL-10, IL-12 and IL-18), members of the tumor necrosis factor family (e.g., TNF-α, TNF-β and lymphotoxin β), interferons (e.g., IFN-β and IFN-γ), granulocyte/macrophage colony-stimulating factor (GM-CSF), transforming growth factors (e.g., TGF-β1, TGF-β2 and TGF-β3, leukemia inhibitory factor (LTF), ciliary neurotrophic factor (CNTF), migration inhibitory factor (MTF), monocyte chemoattractant protein (MCP-I), macrophage inflammatory proteins (e.g., MIP-1α, MIP-1β and MIP-2), and RANTES, as well as environmental or physical agents such as silica micro- and nano-particles and pathogens. In accordance with some embodiments of the invention, at least one or more of these pro-inflammatory agents can be added to a cell culture medium, e.g., to stimulate or challenge tissue-specific cells and/or immune cells within the device to simulate an inflammatory response or an inflammation-associated disease, disorder, or injury in vivo.

In accordance with some embodiments of the invention, the cytokine can include an anti-inflammatory agent. The term "anti-inflammatory agent," as used herein, refers to an agent capable of counteracting the effects of pro-inflammatory and/or inflammatory agents and other agents that mediate an inflammatory condition or reaction. Examples of an anti-inflammatory agent can include, but are not limited to, inhibitors of any pro-inflammatory agents as described above, e.g., in a form of soluble receptors, receptor antagonists, aptamers, antibodies, or any combinations thereof; and/or an agent that can mediate an inflammatory pathway in a cell, e.g., in a form of soluble proteins, antisense oligonucleotides, siRNA, shRNA, vectors, or any combinations thereof. For example, an anti-inflammatory agent can include an agent that can inhibit a particular protein function and/or silence a specific gene that induces inflammation; or an agent that can promote a particular protein function and/or express a specific gene that inhibits inflammation. In accordance with some embodiments of the invention, an anti-inflammatory agent can be or include a steroid, a nonsteroidal anti-inflammatory drug, an analgesic, an inhibitor of at least one or more chemokines (e.g., but not limited to, CXCL-8, CCL2, CCL3, CCL4, CCL5, CCL11, and CXCL10) and/or a COX-2 inhibitor. A variety of anti-inflammatory agents are known to those skilled in the art, e.g., as described in International Publication No. WO 2004/082588, the contents of which is incorporated herein by reference in its entirety, and can be added to a cell culture medium and/or used to stimulate or challenge tissue-specific cells and/or immune cells within the device to provoke an anti-inflammatory response.

In accordance with some embodiments of the invention, the cytokine can include a growth-promoting agent. As used herein, the term "growth-promoting agent" refers to an agent that stimulates cell proliferation. Examples of a growth-promoting agent can include but are not limited to any art-recognized growth factors such as Bone morphogenetic proteins (BMPs); Brain-derived neurotrophic factor (BDNF); Epidermal growth factor (EGF); Erythropoietin (EPO); Fibroblast growth factor (FGF); Glial cell line-derived neurotrophic factor (GDNF); Granulocyte colony-stimulating factor (G-CSF); Granulocyte macrophage colony-stimulating factor (GM-CSF); Hepatocyte growth factor (HGF); Hepatoma-derived growth factor (HDGF); Insulin-like growth factor (IGF); Myostatin (GDF-8); Nerve growth factor (NGF) and other neurotrophins; Platelet-derived growth factor (PDGF); Thrombopoietin (TPO); Transforming growth factor alpha (TGF-α); Transforming growth factor beta (TGF-β); Vascular endothelial growth factor (VEGF); Placental growth factor (P1GF); hormones, steroid hormones, and any combinations thereof.

In accordance with some embodiments of the invention, the cytokine can include a differentiation agent as described earlier. Appropriate differentiation agent(s) can be selected based on different cell types, including, e.g., stem cells, and undifferentiated or partially differentiated cells.

In accordance with some embodiments of the invention, the cytokine can include an apoptosis modulating agent. The term "apoptosis modulating agents," as used herein, refers to agents which are involved in modulating (e.g., inhibiting, decreasing, increasing, promoting) apoptosis. Apoptosis is generally known as a process of programmed cell death. Examples of apoptosis modulating agents include, but are not limited to, Fas/CD95, TRAMP, TNF RI, DR1, DR2, DR3, DR4, DR5, DR6, FADD, RIP, TNFα, Fas ligand, antibodies to Fas/CD95 and other TNF family receptors, TRAIL, antibodies to TRAIL-R1 or TRAIL-R2, Bcl-2, p53, BAX, BID, BAD, BAK, Akt, CAD, PI3 kinase, PP1, and caspase proteins. Modulating agents broadly include agonists and antagonists of TNF family receptors and TNF family ligands. Apoptosis modulating agents can be soluble or membrane bound (e.g. ligand or receptor).

In accordance with some embodiments of the invention, the cytokine can include a pro-angiogenic agent. As used herein, the term "pro-angiogenic agent" is intended to mean an agent that directly or indirectly stimulates, enhances and/or stabilizes angiogenesis. Exemplary pro-angiogenic agents include, but are not limited to, VEGF, FGF, Ang1, Ang2, PDGF-BB, and any combinations thereof.

In accordance with some embodiments of the invention, the cytokine can include an anti-angiogenic agent. As used herein, the term "anti-angiogenic agent" refers to an agent that directly or indirectly reduces or inhibits formation of new blood vessels, and/or destabilizes the formed blood vessels. Examples of anti-angiogenic agents include, but are not limited to, inhibitors and/or antagonists of the pro-angiogenic agents as described above, soluble VEGF receptors, angiopoietin 2, TSP-1, TSP-2, angiostatin, endostatin, vasostatin, platelet factor-4, and any combinations thereof.

According to an alternative embodiment BA, a device for simulating a function of a tissue comprises a first microchannel, a second microchannel, and a membrane. The membrane is located at an interface region between the first microchannel and the second microchannel. The membrane includes a first side facing toward the first microchannel and a second side facing toward the second microchannel. The first side has cells of a first type thereon. The membrane separates the first microchannel from the second microchannel and permits the migration of at least one of cells, particulates, chemicals, molecules, fluids and gases between the first side to the second side. A first wall portion is coupled to the membrane. A second wall portion includes the membrane being fastened to the second wall portion such that the membrane is modulated by motion of at least one of the first wall portion and the second wall portion.

According to an alternative embodiment BB, a device for simulating a function of a tissue comprises a first microchannel, a second microchannel, and a membrane. The membrane is located at an interface region between the first microchannel and the second microchannel. The membrane includes a first side facing toward the first microchannel and a second side facing toward the second microchannel. The first side has cells of a first type thereon. The second side has cells of a second type thereon. The membrane separates the first microchannel from the second microchannel and permits the migration of at least one of cells, particulates, chemicals, molecules, fluids and gases from the first type of cells to the second type of cells. A first wall portion is coupled to the membrane.

According to an alternative embodiment BC, an organomimetic device comprises a first microchannel, a second microchannel, and a membrane. The membrane is located at an interface region between the first microchannel and the second microchannel. The membrane includes a first side facing toward the first microchannel and a second side facing toward the second microchannel. The first side has cells of a first type thereon. The membrane separates the first microchannel from the second microchannel. A first engagement element is coupled to the membrane whereby the membrane is modulated in at least a first direction along a plane by motion of the first engagement element.

According to an alternative embodiment BD, an organomimetic device comprises a first microchannel, a second microchannel, and a membrane located at an interface region between the first microchannel and the second microchannel. The membrane includes a first side facing toward the first microchannel and a second side facing toward the second microchannel. The first side has cells of a first type thereon. The second side has cells of a second type thereon. The membrane separates the first microchannel from the second microchannel. A first engagement element is coupled to the membrane whereby the membrane is modulated in at least a first direction along a plane by motion of the first engagement element.

According to an alternative embodiment BE, the devices of any one of alternatives BA to BD further comprise that the cells of the first type are adhered to the first side of the membrane.

According to an alternative embodiment BF, the devices of any one of alternatives BA to BE further comprise that the cells of the second type are adhered to the second side of the membrane.

According to an alternative embodiment BG, the devices of any one of alternatives BA to BF further comprise that the second side has cells of a second type thereon, and the device includes a central microchannel. The membrane divides the central microchannel into the first microchannel and the second microchannel.

According to an alternative embodiment BH, the devices of any one of alternatives BA to BG further comprise that the device includes a central microchannel. The membrane divides the central microchannel into the first microchannel and the second microchannel. The central channel further includes a second wall portion and the membrane is fastened to the second wall portion whereby the membrane is modulated by motion of at least one of the first wall portion and the second wall portion.

According to an alternative embodiment BI, the devices of any one of alternatives BA to BH further comprise that the first wall portion includes an elastomeric material that is adapted to move relative to the body by application of a force.

According to an alternative embodiment BJ, the devices of any one of alternatives BA to BI further comprise that the force is applied to the first wall portion in a direction parallel to the plane of the membrane.

According to an alternative embodiment BK, the devices of any one of alternatives BA to BJ further comprise that the force is induced by a pressure differential.

According to an alternative embodiment BL, the devices of any one of alternatives BA to BK further comprise that the force is applied to at least a portion of the body in a direction transverse to the membrane such that the first wall portion flexes in a direction along a plane.

According to an alternative embodiment BM, the devices of any one of alternatives BA to BL further comprise that the force is a compressive force.

According to an alternative embodiment BN, the devices of any one of alternatives BA to BM further comprise that at least one of a top wall portion and a bottom wall portion can be releasably in contact with a load element.

According to an alternative embodiment BO, the devices of any one of alternatives BA to BN further comprise that the load element can deform the at least one of the top wall portion and the bottom wall portion, thereby causing the first wall portion and/or the second wall portion to stretch or retract along the plane.

According to an alternative embodiment BP, the devices of any one of alternatives BA to BO further comprise a pneumatic chamber separated from the first microchannel by the top wall portion or the bottom wall portion.

According to an alternative embodiment BQ, the devices of any one of alternatives BA to BP further comprise that the load element is disposed in the pneumatic chamber.

According to an alternative embodiment BR, the devices of any one of alternatives BA to BQ further comprise a first operating channel separated from the first and second microchannels by the first wall portion such that a first pressure differential applied by the first operating channel causes the membrane to stretch or retract in a first direction along a plane.

According to an alternative embodiment BS, the devices of any one of alternatives BA to BR further comprise a second operating channel separated from the first and second central microchannels by the second wall portion such that a second pressure differential applied by the second operating channel causes the membrane to stretch or retract in a second direction along the plane.

According to an alternative embodiment BT, the devices of any one of alternatives BA to BS further comprise at least one of the first and the second operating channels connected to a pressure generation device is adapted to generate the pressure differential between at least one of the first and the second operating channels and the first and second central microchannels.

According to an alternative embodiment BU, the devices of any one of alternatives BA to BT further comprise at least one rigid element configured to cause the first wall portion to move toward the first operating channel when a positive pressure is applied into the first operating channel, thereby stretching the membrane in the first direction along the plane.

According to an alternative embodiment BV, the devices of any one of alternatives BA to BU further comprise that the aspect ratio of at least one of the first and second operating channels is configured to cause the first wall portion to move toward the first operating channel when a positive pressure is applied into the first operating channel, thereby stretching the membrane in the first direction along the plane.

According to an alternative embodiment BW, the devices of any one of alternatives BA to BV further comprise that the first wall portion includes a hard stop that prevents the membrane from over-stretching.

According to an alternative embodiment BX, the devices of any one of alternatives BA to BW further comprise that the first wall portion includes a pivoted lever, whereby a force applied to the lever causes the membrane to stretch or retract in a first direction along the plane.

According to an alternative embodiment BY, the devices of any one of alternatives BA to BX further comprise that a top closure of the first microchannel includes an elastomeric layer.

According to an alternative embodiment BZ, the devices of any one of alternatives BA to BY further comprise that the force applied to the lever causes the elastomeric layer to stretch or retract in a direction parallel to the first direction.

According to an alternative embodiment CA, the devices of any one of alternatives BA to BZ further comprise that the elastomeric layer is transparent.

According to an alternative embodiment CB, the devices of any one of alternatives BA to CA further comprise that the elastomeric layer is sufficiently thin to maintain structural integrity and to permit optical examination of cells present on the membrane.

According to an alternative embodiment CC, the devices of any one of alternatives BA to CB further comprise that the second side has cells thereon of a second type.

According to an alternative embodiment CD, the devices of any one of alternatives BC to CC further comprise that the first engagement element can be releasably engaged by an engagement element modulation device. The engagement element modulation device adapted to modulate the motion of the engagement element.

According to an alternative embodiment CE, the devices of any one of alternatives BC to CD further comprise that the first engagement element includes at least one of a bead, a pin, a block, a clamp, a knob, a hole, or any combination thereof.

According to an alternative embodiment CF, the devices of any one of alternatives BC to CE further comprise that the first direction is perpendicular to a fluid flow through the central channel.

According to an alternative embodiment CG, the devices of any one of alternatives BC to CF further comprise that the first direction is parallel to a fluid flow through one of the microchannels.

According to an alternative embodiment CH, the devices of any one of alternatives BA to CG further comprise that at least one of a top closure and a bottom closure of one of the microchannels comprises an elastomeric layer.

According to an alternative embodiment CI, the devices of any one of alternatives BA to CH further comprise that the elastomeric layer is transparent.

According to an alternative embodiment CJ, the devices of any one of alternatives BA to CI further comprise that the elastomeric layer is sufficiently thin to maintain structural integrity and to permit optical examination of cells present on the membrane.

According to an alternative embodiment CK, the devices of any one of alternatives BC to CJ further comprise that the membrane is coupled to a second engagement element, whereby the membrane is modulated in at least a second direction along the plane by motion of the second engagement element.

According to an alternative embodiment CL, the devices of any one of alternatives BA to CK further comprise that the central channel includes a curved wall.

According to an alternative embodiment CM, the devices of any one of alternatives BA to CL further comprise that the central channel includes at least one straight wall.

According to an alternative embodiment CN, the devices of any one of alternatives BC to CM further comprise that the engagement element modulation device is adapted to modulate the movement of first engagement member by modulating a magnetic field.

According to an alternative embodiment CO, the devices of any one of alternatives BC to CN further comprise that the engagement element modulation device includes a solenoid.

According to an alternative embodiment CP, the devices of any one of alternatives BC to CO further comprise that the engagement element modulation device includes a motor.

According to an alternative embodiment CQ, the devices of any one of alternatives BC to CP further comprise that the engagement element modulation device includes a pneumatic cylinder.

According to an alternative embodiment CR, the devices of any one of alternatives BC to CQ further comprise that the engagement element modulation device includes a shape memory alloy based actuator, a piezo-based actuator, or a combination thereof.

According to an alternative embodiment CS, the devices of any one of alternatives BA to CR further comprise that the membrane is substantially rigid.

According to an alternative embodiment CT, the devices of any one of alternatives BA to CS further comprise that the membrane is at least partially flexible.

According to an alternative embodiment CU, the devices of any one of alternatives BA to CT further comprise that the membrane has a thickness of about 10 µm to about 100 µm.

According to an alternative embodiment CV, the devices of any one of alternatives BA to CT further comprise that the membrane has a thickness of about 100 nm to about 10 µm.

According to an alternative embodiment CW, the devices of any one of alternatives BA to CV further comprise that the membrane is non-porous.

According to an alternative embodiment CX, the devices of any one of alternatives BA to CV further comprise that the membrane is at least partially porous.

According to an alternative embodiment CY, the devices of any one of alternatives BA to CX further comprise that the membrane includes pores having a diameter in the range of about 0.1 µm to about 15 µm.

According to an alternative embodiment CZ, the devices of any one of alternatives BA to CY further comprise that the membrane has an average center-to-center pore spacing in a range from about 1 µm to about 100 µm.

According to an alternative embodiment DA, the devices of any one of alternatives BA to CZ further comprise that at least a portion of the membrane is treated to enhance adhesion of the cells to the membrane.

According to an alternative embodiment DB, the devices of any one of alternatives BA to DA further comprise that at least a portion of the membrane is treated by coating at least one surface of the membrane with at least one cell adhesion agent.

According to an alternative embodiment DC, the devices of any one of alternatives BA to DB further comprise that the at least one cell adhesion agent comprises an extracellular matrix molecule.

According to an alternative embodiment DD, the devices of any one of alternatives BA to DC further comprise that the extracellular matrix molecule comprises glycoproteins, collagen, fibronectin, laminin, vitronectin, elastins, fibrin, proteoglycans, heparin sulfate, chondroitin sulfate, keratan sulfate, hyaluronic acid, fibroin, chitosan or any combinations thereof.

According to an alternative embodiment DE, the devices of any one of alternatives BA to DD further comprise that the at least a portion of the membrane is treated by modifying a surface property of the membrane.

According to an alternative embodiment DF, the devices of any one of alternatives BA to DE further comprise that at least one surface of the membrane comprises cells of at least two cell types.

According to an alternative embodiment DG, the devices of any one of alternatives BA to DF further comprise that the cells form one or more cell layers.

According to an alternative embodiment DH, the devices of any one of alternatives BA to DG further comprise the cells comprise plant cells.

According to an alternative embodiment DI, the devices of any one of alternatives BA to DH further comprise the cells comprise insect cells.

According to an alternative embodiment DJ, the devices of any one of alternatives BA to DI further comprise that the cells are mammalian cells.

According to an alternative embodiment DK, the devices of any one of alternatives BA to DJ further comprise that the mammalian cells comprise human cells and/or animal cells.

According to an alternative embodiment DL, the devices of any one of alternatives BA to DK further comprise that at least a portion of the cells are selected from the group consisting of epithelial cells, endothelial cells, fibroblasts, smooth muscle cells, basal cells, ciliated cells, mucus-secreting cells, columnar cells, goblet cells, muscle cells, immune cells, neural cells, hematopoietic cells, lung cells (e.g., alveolar epithelial cells, small airway cells, bronchial cells, tracheal cells, and nasal epithelial cells), gut cells, brain cells, stem cells, skin cells, liver cells, heart cells, spleen cells, kidney cells, pancreatic cells, reproductive cells, blood cells (including, e.g., white blood cells, red blood cells, platelets, and hematopoietic stem and progenitor cells), and any combinations thereof.

According to an alternative embodiment DM, the devices of any one of alternatives BA to DL further comprise that the cells are selected to create an in vitro model that mimics cell behavior of at least a portion of a tissue.

According to an alternative embodiment DN, the devices of any one of alternatives BA to DM further comprise that the tissue is selected from the group consisting of lung, airway, heart, liver, gut, intestine, spleen, pancreas, ovary, testis, prostate, blood-brain-barrier, brain, muscle, skeletal, vascular network, skin, bone marrow, and eye.

According to an alternative embodiment DO, the devices of any one of alternatives BA to DN further comprise that the cells display at least one characteristic corresponding to a pre-determined physiological endpoint.

According to an alternative embodiment DP, the devices of any one of alternatives BA to DO further comprise that the pre-determined physiological endpoint is selected from the group consisting of a mature state, a differentiated state, a precursor state, a stratified state, a pseudo-stratified state, a confluency state, an inflamed state, an infected state, a stimulated state, an activated state, an inhibitory state, a normal healthy state, a pre-disease state, a disease-specific state, a growth state, a migratory state, a metamorphosing state, or any combinations thereof.

According to an alternative embodiment DQ, the devices of any one of alternatives BA to DP further comprise that the disease-specific state is a specific stage of a disease, disorder or injury.

According to an alternative embodiment DR, the devices of any one of alternatives BA to DQ further comprise that the disease-specific state comprises a cancerous state.

According to an alternative embodiment DS, the devices of any one of alternatives BA to DR further comprise that a first surface of the membrane includes tissue-specific cells, precursor cells, stem cells, or any combinations thereof.

According to an alternative embodiment DT, the devices of any one of alternatives BA to DS further comprise that a second surface of the membrane includes blood vessel-associated cells.

According to an alternative embodiment DU, the devices of any one of alternatives BA to DT further comprise that the blood vessel-associated cells comprise endothelial cells, fibroblasts, smooth muscle cells, pericytes, or any combinations thereof.

According to an alternative embodiment DV, the devices of any one of alternatives BA to DU further comprise that at least one of the body and the membrane includes a biocompatible polymer.

According to an alternative embodiment DW, the devices of any one of alternatives BA to DV further comprise that the biocompatible polymer includes polydimethylsiloxane (PDMS), polymethylmethacrylate (PMMA), polyurethane, styrene-ethylene-butylene-styrene (SEBS), polypropylene, polycarbonate, polyester, cyclic polyolefins, cyclic polyolefin copolymers, or any combinations thereof.

According to an alternative embodiment DX, the devices of any one of alternatives BA to DW further comprise that at least one of the body and the membrane includes an extracellular matrix polymer, gel, and/or scaffold.

According to an alternative embodiment DY, the devices of any one of alternatives BA to DX further comprise that the body further includes a second central channel therein; and a second membrane positioned within the second central channel and extending along a second plane, wherein the second membrane is configured to separate the second central channel to form a third central microchannel and a fourth central microchannel.

According to an alternative embodiment DZ, the devices of any one of alternatives BA to DY further comprise that the first plane and second plane are co-planar.

According to an alternative embodiment EA, the devices of any one of alternatives BA to DZ further comprise that at least one of the first and second microchannels is adapted to fluidically connect to at least one fluid flow-modulation device. The at least one fluid flow modulation device is adapted to modulate flow of a liquid or a gas through the first or second microchannel.

According to an alternative embodiment EB, the devices of any one of alternatives BA to EA further comprise that the at least one fluid flow-modulation device is incorporated into the body of the organomimetic device.

According to an alternative embodiment EC, the devices of any one of alternatives BA to EB further comprise that the at least one fluid flow-modulation device is separately connected to the organomimetic device.

According to an alternative embodiment ED, the devices of any one of alternatives BA to EC further comprise that the at least one fluid flow-modulation device includes a pump.

According to an alternative embodiment EE, the devices of any one of alternatives BA to ED further comprise that at least one of the first and second microchannels is adapted to fluidically connect to at least one bubble trap for removing gas bubbles from a liquid flowing through the first or second microchannel.

According to an alternative embodiment EF, the devices of any one of alternatives BA to EE further comprise a cartridge configured to incorporate the device therein.

According to an alternative embodiment EG, the devices of any one of alternatives BA to EF further comprise that the cartridge is configured to establish at least one fluidic connection during operation and optionally provide a sealing of the fluidic connection when not in use.

According to an alternative embodiment EH, the devices of any one of alternatives BA to EG further comprise that the first microchannel and the second microchannel have substantially the same height.

According to an alternative embodiment EI, the devices of any one of alternatives BA to EH further comprise that the first microchannel has a height substantially greater than the height of the second microchannel.

According to an alternative embodiment EJ, the devices of any one of alternatives BA to EI further comprise that the height of the first or second microchannel ranges from about 20 μm to about 5 mm.

According to an alternative embodiment EK, the devices of any one of alternatives BA to EJ further comprise that the height of the first or second microchannel is sufficient to form a stratified or a three-dimensional tissue therein.

According to an alternative embodiment EL, an organomimetic device comprises a first microchannel height-defining layer having a bottom surface and a first microchannel disposed in the bottom surface; a second microchannel height-defining layer having a top surface and a second microchannel disposed in the top surface; and a membrane layer having a membrane portion. The membrane layer is laminated between the bottom surface of the first microchannel height-defining layer and the top surface of the second microchannel height-defining layer. A first surface portion of the membrane portion provides a lower boundary of the first microchannel and a second surface portion of the membrane portion provides an upper boundary of the second microchannel. At least a portion of the first microchannel is aligned with at least a portion of the second microchannel on an opposite side of the membrane portion.

According to an alternative embodiment EM, the device of alternative EL further comprises that at least one of the first microchannel height-defining layer and the second microchannel height-defining layer is produced by a process comprising molding.

According to an alternative embodiment EN, the device of one of alternatives EL or EM further comprise that the first microchannel height-defining layer includes a first lamination layer having a first microchannel aperture therein, wherein thickness of the first lamination layer defines the height of the first microchannel; and a first sealing layer disposed on top of the first lamination layer, wherein the first sealing layer is in contact with the first lamination layer and provides a top closure of the first microchannel aperture, thereby forming the first microchannel.

According to an alternative embodiment EO, the device of any one of alternatives EL to EN further comprise that the second microchannel height-defining layer includes a second lamination layer having a second microchannel aperture therein, wherein thickness of the second lamination layer defines the height of the second microchannel; and a second sealing layer disposed below the second lamination layer, wherein the second sealing layer is in contact with the second lamination layer and provides a bottom closure of the second microchannel aperture, thereby forming the second microchannel.

According to an alternative embodiment EP, the device of any one of alternatives EL to EO further comprise that at least one of the first sealing layer and the second sealing layer is transparent.

According to an alternative embodiment EQ, the device of any one of alternatives EL to EP further comprise that at least one of the first sealing layer and the second sealing layer is sufficiently thin for optical examination of cells present on the membrane.

According to an alternative embodiment ER, the device of any one of alternatives EL to EQ further comprise that at least one of the first lamination layer, first sealing layer, second sealing layer and the second lamination layer includes an optically clear adhesive layer According to an alternative embodiment ES, the device of any one of alternatives EL to ER further comprise that the optically clear adhesive layer is at least one of pressure-sensitive adhesive (e.g., acrylic), thermal adhesive and light-sensitive adhesive.

According to an alternative embodiment ET, the device of any one of alternatives EL to ES further comprise that a top surface of the first microchannel height-defining layer further includes a substantially rigid layer.

According to an alternative embodiment EU, the device of any one of alternatives EL to ET further comprise that a bottom surface of the second microchannel height-defining layer further includes a substantially rigid layer.

According to an alternative embodiment EV, the device of any one of alternatives EL to EU further comprise that the rigid layer comprises at least one of polyethylene terephthalate, polycarbonate, PMMA, cyclic polyolefins, cyclic polyolefin copolymers, polypropylene and polystyrene.

According to an alternative embodiment EW, the device of any one of alternatives EL to EV further comprise that the membrane layer further includes a carrier layer adapted to provide structural support for the membrane.

According to an alternative embodiment EX, the device of any one of alternatives EL to EW further comprise a port-defining layer disposed on top of the first microchannel height-defining layer. The port-defining layer defines (a) an aperture for visualization of at least a portion of the membrane separating the first microchannel from the second microchannel, and (b) least one port adapted to provide with the organomimetic device at least one of a fluidic connection, a mechanical connection, and an electrical connection.

According to an alternative embodiment EY, the device of any one of alternatives EL to EX further comprise that the membrane layer includes at least one engagement element.

According to an alternative embodiment EZ, the device of any one of alternatives EL to EY further comprise that the engagement element includes at least one hole in the membrane layer.

According to an alternative embodiment FA, the device of any one of alternatives EL to EZ further comprise that the engagement element includes a plurality of holes in the membrane layer.

According to an alternative embodiment FB, the device of any one of alternatives EL to FA further comprise that the engagement element includes at least one bead extending along a portion of the membrane layer.

According to an alternative embodiment FC, the device of any one of alternatives EL to FB further comprise that the engagement element includes at least one block fastened along a portion of the membrane layer.

According to an alternative embodiment FD, the device of any one of alternatives EL to FC further comprise that the engagement element includes at least one pin extending through the membrane layer.

According to an alternative embodiment FE, the device of any one of alternatives EL to FD further comprise that the engagement element includes at least one clamp coupled to a portion of the membrane layer.

According to an alternative embodiment FF, the device of any one of alternatives EL to FE further comprise that at least the membrane layer is constructed to include a central region and two side regions on either side of the central region, wherein the central region includes the portion of the membrane separating the first microchannel from the second microchannel.

According to an alternative embodiment FG, the device of any one of alternatives EL to FF further comprise that a portion of the central region is separated from the two end regions.

According to an alternative embodiment FH, an organomimetic device is produced by a process comprising (i) providing at least one first body having a central channel therein along a first axis; and wherein the central channel has a first wall portion; and a membrane is positioned within the central channel and extends along a plane, wherein the membrane is configured to separate the central channel to form a first central microchannel and a second central microchannel; wherein the membrane is fastened to the first wall portion whereby the membrane is modulated by motion of the first wall portion; and wherein the first wall portion comprises an elastomeric material; (ii) providing a second body having a housing channel therein along a second axis; wherein the housing channel has a height that is substantially the same as (and/or greater than) the height of the first body; and a width that is greater than the width of the first body; and wherein the second body comprises a rigid material; (iii) placing the at least one first body within the housing channel of the second body such that the at least one operating chamber forms adjacent to the first wall portion of the first body along the first axis (and/or the second axis), thereby forming at least one organomimetic device.

According to an alternative embodiment FI, the device of alternative FH further comprises that the central channel further includes a second wall portion and the membrane is fastened to the second wall portion whereby the membrane is modulated by motion of at least one of the first wall portion and the second wall portion, and wherein the second wall portion comprises an elastomeric material.

According to an alternative embodiment FJ, the device of one of alternatives FH or FI further comprise that the at least one first body is placed within the housing channel of the second body such that a first operating chamber and a second operating chamber form along the first axis and the second axis. The first operating chamber is formed adjacent to the first wall portion of the first body, and the second operating chamber is formed adjacent to the second wall portion of the second body.

According to an alternative embodiment FK, the device of any one of alternatives FH to FJ further comprise that a bottom surface of the housing channel includes a notch along the second axis, and wherein the notch is configured to fit the first body therein.

According to an alternative embodiment FL, the device of any one of alternatives FH to FK further comprise that the process further includes cutting traverse to the first axis and the second axis of the at least one organomimetic device to produce a first smaller organomimetic device and a second smaller organomimetic device.

According to an alternative embodiment FM, the device of any one of alternatives EL to FL further comprise that the membrane portion or the membrane is substantially rigid.

According to an alternative embodiment FN, the device of any one of alternatives EL to FM further comprise that the membrane portion or the membrane is at least partially flexible.

According to an alternative embodiment FO, the device of any one of alternatives EL to FN further comprise that the membrane portion or the membrane has a thickness of about 10 µm to about 100 µm.

According to an alternative embodiment FP, the device of any one of alternatives EL to FO further comprise that the membrane portion or the membrane is non-porous.

According to an alternative embodiment FQ, the device of any one of alternatives EL to FO further comprise that the membrane portion or the membrane is at least partially porous.

According to an alternative embodiment FR, the device of any one of alternatives EL to FQ further comprise that the membrane portion or the membrane includes pores having a diameter in the range of about 0.1 µm to about 15 µm.

According to an alternative embodiment FS, the device of any one of alternatives EL to FR further comprise that the membrane portion or the membrane has an average center-to-center pore spacing in a range from about 1 µm to about 100 µm.

According to an alternative embodiment FT, the device of any one of alternatives EL to FN and FP to FS further comprise that the membrane portion or the membrane has a thickness of about 100 nm to about 10 µm.

According to an alternative embodiment FU, the device of any one of alternatives EL to FT further comprise that at least a portion of the membrane layer or the membrane is treated to enhance adhesion of the cells to the membrane portion.

According to an alternative embodiment FV, the device of any one of alternatives EL to FU further comprise that the at least a portion of the membrane layer or the membrane is treated by coating at least one surface of the membrane portion with at least one cell adhesion agent.

According to an alternative embodiment FW, the device of any one of alternatives EL to FV further comprise that the at least one cell adhesion agent comprises an extracellular matrix molecule.

According to an alternative embodiment FX, the device of any one of alternatives EL to FW further comprise that the extracellular matrix molecule comprises glycoproteins, collagen, fibronectin, laminin, vitronectin, elastins, fibrin, proteoglycans, heparin sulfate, chondroitin sulfate, keratan sulfate, hyaluronic acid, silk, chitosan, or any combinations thereof.

According to an alternative embodiment FY, the device of any one of alternatives EL to FX further comprise that the at least a portion of the membrane layer or the membrane is treated by modifying a surface property of the membrane portion.

According to an alternative embodiment FZ, the device of any one of alternatives EL to FY further comprise that at least one surface of the membrane portion comprises cells of at least two cell types.

According to an alternative embodiment GA, the device of any one of alternatives EL to FZ further comprise that the cells form one or more cell layers.

According to an alternative embodiment GB, the device of any one of alternatives EL to GA further comprise that the cells include insect cells and/or plant cells.

According to an alternative embodiment GC, the device of any one of alternatives EL to GB further comprise that the cells are mammalian cells, human cells, and/or animal cells.

According to an alternative embodiment GD, the device of any one of alternatives EL to GC further comprise that at least a portion of the cells are selected from the group consisting of epithelial cells, endothelial cells, fibroblasts, smooth muscle cells, basal cells, ciliated cells, mucus-secreting cells, columnar cells, goblet cells, muscle cells, immune cells, neural cells, hematopoietic cells, lung cells (e.g., alveolar epithelial cells, small airway cells, bronchial cells, tracheal cells, and nasal epithelial cells), gut cells, brain cells, stem cells, skin cells, liver cells, heart cells, spleen cells, kidney cells, pancreatic cells, reproductive cells, blood cells (including, e.g., white blood cells, red blood cells, platelets and hematopoietic stem and progenitor cells) and any combinations thereof.

According to an alternative embodiment GE, the device of any one of alternatives EL to GD further comprise that the cells are selected to create an in vitro model that mimics cell behavior of at least a portion of a tissue.

According to an alternative embodiment GF, the device of any one of alternatives EL to GE further comprise that the tissue is selected from the group consisting of lung, airway, heart, liver, gut, intestine, spleen, pancreas, ovary, testis, prostate, blood-brain-barrier, brain, muscle, skeletal, vascular network, skin, bone marrow, and eye.

According to an alternative embodiment GG, the device of any one of alternatives EL to GF further comprise that the cells display at least one characteristic corresponding to a pre-determined physiological endpoint.

According to an alternative embodiment GH, the device of any one of alternatives EL to GG further comprise that the pre-determined physiological endpoint is selected from the group consisting of a mature state, a differentiated state, a precursor state, a stratified state, a pseudo-stratified state, a confluency state, an inflamed state, an infected state, a stimulated state, an activated state, an inhibitory state, a normal healthy state, a pre-disease state, a disease-specific state, a growth state, a migratory state, a metamorphosing state, or any combinations thereof.

According to an alternative embodiment GI, the device of any one of alternatives EL to GH further comprise that the disease-specific state is a specific stage of a disease, disorder or injury.

According to an alternative embodiment GJ, the device of any one of alternatives EL to GI further comprise that the disease-specific state comprises a cancerous state.

According to an alternative embodiment GK, the device of any one of alternatives EL to GJ further comprise that a first surface of the membrane or the membrane portion includes tissue-specific cells, precursor cells and/or stem cells.

According to an alternative embodiment GL, the device of any one of alternatives EL to GK further comprise that a second surface of the membrane includes blood vessel-associated cells.

According to an alternative embodiment GM, the device of any one of alternatives EL to GL further comprise that the blood vessel-associated cells comprise endothelial cells, fibroblasts, smooth muscle cells, pericytes, or any combinations thereof.

According to an alternative embodiment GN, the device of any one of alternatives EL to GM further comprise that at least one of the first microchannel height-defining layer, the second microchannel height-defining layer, and the membrane layer comprises a biocompatible polymer.

According to an alternative embodiment GO, the device of any one of alternatives EL to GN further comprise that the biocompatible polymer comprises polydimethylsiloxane (PDMS), polymethylmethacrylate (PMMA), polyurethane, styrene-ethylene-butylene-styrene (SEBS), polypropylene, polycarbonate, polyester, cyclic polyolefins, cyclic polyolefin copolymers, or any combinations thereof.

According to an alternative embodiment GP, the device of any one of alternatives EL to GO further comprise that at least one of the first microchannel height-defining layer, the second microchannel height-defining layer, and the membrane layer comprises an extracellular matrix polymer, gel and/or scaffold.

According to an alternative embodiment GQ, a method of using an organomimetic device comprises providing at least one device of any one of alternatives BA to GP; introducing a first fluid into the first microchannel of the at least one device; and introducing a second fluid into the second microchannel of the at least one device.

According to an alternative embodiment GR, the method of alternative GQ further comprises mechanically modulating the membrane.

According to an alternative embodiment GS, the method of one of alternatives GQ or GR further comprise that the mechanical modulation of the membrane causes the membrane to move in at least a first direction along a plane within the channel of the at least one device.

According to an alternative embodiment GT, the method of any one of alternatives GQ to GS further comprise the mechanical modulation of the membrane being performed by a pneumatic means, a mechanical means, an electrical means, a magnetic means, or a combination thereof.

According to an alternative embodiment GU, the method of any one of alternatives GQ to GT further comprise the first fluid being a gaseous fluid or a liquid fluid.

According to an alternative embodiment GV, the method of any one of alternatives GQ to GU further comprise the second fluid being a gaseous fluid or a liquid fluid.

According to an alternative embodiment GW, the method of any one of alternatives GQ to GV further comprise the first fluid and/or the second fluid being maintained in the device as a static flow.

According to an alternative embodiment GX, the method of any one of alternatives GQ to GW further comprise the first fluid and/or the second fluid being continuously flowed through the first central microchannel and/or the second central microchannel.

According to an alternative embodiment GY, the method of any one of alternatives GQ to GX further comprise the first fluid and/or the second fluid being intermittently or cyclically flowed through the first central microchannel and/or the second central microchannel.

According to an alternative embodiment GZ, the method of any one of alternatives GQ to GY further comprise the at least one provided device including cells on at least one surface of the membrane.

According to an alternative embodiment HA, the method of any one of alternatives GQ to GZ further comprise the at least one provided device includes no cells.

According to an alternative embodiment HB, the method of any one of alternatives GQ to HA further comprise introducing cells into the first microchannel, wherein at least a portion of the cells adhere to a first surface of the membrane.

According to an alternative embodiment HC, the method of any one of alternatives GQ to HB further comprise the cells forming a cell monolayer, a stratified structure, a pseudostratified structure, or a three-dimensional tissue structure on the membrane.

According to an alternative embodiment HD, the method of any one of alternatives GQ to HC further comprise the cells being selected from the group consisting of human cells, animal cells, insect cells, plants cells, and any combinations thereof.

According to an alternative embodiment HE, the method of any one of alternatives GQ to HD further comprise at least a portion of the human cells or animal cells being selected from the group consisting of epithelial cells, endothelial cells, fibroblasts, smooth muscle cells, basal cells, ciliated cells, mucus-secreting cells, columnar cells, goblet cells, muscle cells, immune cells, neural cells, hematopoietic cells, lung cells (e.g., alveolar epithelial cells, small airway cells, bronchial cells, tracheal cells, and nasal epithelial cells), gut cells, brain cells, stem cells, skin cells, liver cells, heart cells, spleen cells, kidney cells, pancreatic cells, reproductive cells, blood cells (including, e.g., white blood cells, red blood cells, platelets, and hematopoietic stem and progenitor cells) and any combinations thereof.

According to an alternative embodiment HF, the method of any one of alternatives GQ to HE further comprise the organomimetic device being used to display at least one characteristic corresponding to a pre-determined physiological endpoint.

According to an alternative embodiment HG, the method of any one of alternatives GQ to HF further comprise the pre-determined physiological endpoint being selected from the group consisting of a mature state, a differentiated state, a precursor state, a stratified state, a pseudo-stratified state, a confluency state, an inflamed state, an infected state, a stimulated state, an activated state, an inhibitory state, a normal healthy state, a pre-disease state, a disease-specific state, a growth state, a migratory state, a metamorphosing state, or any combinations thereof.

According to an alternative embodiment HH, the method of any one of alternatives GQ to HG further comprise exposing the cells on the first surface of the membrane to a gas flow.

According to an alternative embodiment HI, the method of any one of alternatives GQ to HH further comprise one end of the first central microchannel being adapted to engage to a gas-flow modulation device.

According to an alternative embodiment HJ, the method of any one of alternatives GQ to HI further comprise the gas-flow modulation device being adapted to provide a unidirectional and/or a bidirectional flow of the gaseous fluid.

According to an alternative embodiment HK, the method of any one of alternatives GQ to HJ further comprise the bidirectional flow of the gaseous fluid simulating air flow during respiration.

According to an alternative embodiment HL, the method of any one of alternatives GQ to HK further comprise forming a second cell layer on a second surface of the membrane.

According to an alternative embodiment HM, the method of any one of alternatives GQ to HL further comprise the second cell layer including blood vessel-associated cells.

According to an alternative embodiment HN, the method of any one of alternatives GQ to HM further comprise the blood vessel-associated cells including endothelial cells, fibroblasts, smooth muscle cells, pericytes, or any combinations thereof.

According to an alternative embodiment HO, the method of any one of alternatives GQ to HN further comprise creating within the central channel an in vitro model that mimics a tissue-specific condition (e.g., in a normal healthy state or in a disease-specific state).

According to an alternative embodiment HP, the method of any one of alternatives GQ to HO further comprise the cells on the first surface of the membrane being selected to create an in vitro model that mimics cell behavior of at least a portion of a tissue.

According to an alternative embodiment HQ, the method of any one of alternatives GQ to HP further comprise the tissue being selected from the group consisting of lung, airway, heart, liver, gut, intestine, spleen, pancreas, ovary, testis, prostate, blood-brain-barrier, brain, muscle, skeletal, vascular network, skin, bone marrow, and eye.

According to an alternative embodiment HR, the method of any one of alternatives GQ to HQ further comprise the cells being adapted to display at least one characteristic associated with the tissue-specific condition in a disease-specific state.

According to an alternative embodiment HS, the method of any one of alternatives GQ to HR further comprise the disease-specific state is a specific stage of a disease, disorder or injury.

According to an alternative embodiment HT, the method of any one of alternatives GQ to HS further comprise the disease-specific state including a cancerous state.

According to an alternative embodiment HU, the method of any one of alternatives GQ to HT further comprise the cells on the first surface of the membrane being selected to create an in vitro model that mimics cell behavior of at least a portion of a tissue, the cells being disease-specific cells isolated from at least one subject or at least one subject population.

According to an alternative embodiment HV, the method of any one of alternatives GQ to HU further comprise the cells on the first surface of the membrane being selected to create an in vitro model that mimics cell behavior of at least a portion of a tissue, the cells being contacted with a condition-inducing agent that is capable of inducing the cells to acquire at least one characteristic associated with the disease-specific state.

According to an alternative embodiment HW, the method of any one of alternatives GQ to HV further comprise the condition-inducing agent including a physical agent or an environmental stimulus (e.g., radiation or air flow rhythm).

According to an alternative embodiment HX, the method of any one of alternatives GQ to HW further comprise the condition-inducing agent comprises a chemical and/or biological agent (e.g., pathogens, and/or pro-inflammatory agents).

According to an alternative embodiment HY, the method of any one of alternatives GQ to HX further comprise contacting the cells on the first surface of the membrane with a test agent.

According to an alternative embodiment HZ, the method of any one of alternatives GQ to HY further comprise the cells on the first surface of the membrane being contacted with the test agent by delivery as an aerosol or liquid through the first central microchannel and/or via diffusion from the second central microchannel.

According to an alternative embodiment IA, the method of any one of alternatives GQ to HZ further comprise the test agent being selected from the group consisting of proteins, peptides, nucleic acids, antigens, nanoparticles, environmental toxins or pollutant, cigarette smoke, chemicals or particles used in cosmetic products, small molecules, drugs or drug candidates, vaccine or vaccine candidates, aerosols, pro-inflammatory agents, naturally occurring particles including pollen, chemical weapons, viruses, bacteria, unicellular organisms, cytokines, and any combinations thereof.

According to an alternative embodiment IB, the method of any one of alternatives GQ to IA further comprise measuring response of the device and/or the cells on at least one side of the membrane to the test agent, with the first fluid exiting the first central microchannel, the second fluid exiting the second central microchannel, or any combinations thereof.

According to an alternative embodiment IC, the method of any one of alternatives GQ to IB further comprise the measuring the response of the cells includes measuring adhesion of immune cells that are flowing through the second central microchannel, cell labeling, immunostaining, optical or microscopic imaging (e.g., immunofluorescence microscopy and/or scanning electron microscopy), gene expression analysis, cytokine/chemokine secretion analysis, metabolite analysis, polymerase chain reaction, immunoassays, ELISA, gene arrays, or any combinations thereof.

According to an alternative embodiment ID, the method of any one of alternatives GQ to IC further comprise measuring the response of the cells or at least one component present in a fluid within the device or present in an output fluid from the device after exposure to the test agent determines an effect of the test agent on the cells.

According to an alternative embodiment IE, the method of any one of alternatives GQ to ID further comprise the effect including cell viability, permeability of a cell layer, cell morphology, protein expression, gene expression, cell adhesion, adhesiveness of immune cells, cell differentiation, cytokine or chemokine production, inflammation, or any combinations thereof.

According to an alternative embodiment IF, the method of any one of alternatives GQ to IE further comprise measurement of the response of the cells or at least one component present in a fluid within the device or present in an output fluid from the device after exposure to the test agent determines an efficacy of the test agent.

According to an alternative embodiment IG, the method of any one of alternatives GQ to IF further comprise measurement of the response of the cells or at least one component present in a fluid within the device or present in an output fluid from the device after exposure to the test agent determines toxicity of the test agent.

According to an alternative embodiment IH, the method of any one of alternatives GQ to IG further comprise measurement of the response of the cells or at least one component present in a fluid within the device or present in an output fluid from the device after exposure to the test agent determines a mechanism of efficacy or toxicity of the test agent.

According to an alternative embodiment II, the method of any one of alternatives GQ to IH further comprise measurement of the response of the cells or at least one component present in a fluid within the device or present in an output fluid from the device after exposure to the test agent determines physical-chemical, pharmacokinetic or pharmacodynamic parameters.

According to an alternative embodiment IJ, the method of any one of alternatives GQ to II further comprise that when the cells are disease-specific, the determination of the effect of the test agent identifies a therapeutic agent for treatment of the disease.

According to an alternative embodiment IK, the method of any one of alternatives GQ to IJ further comprise that when the cells are patient-specific, the determination of the effect of the test agent identifies a personalized treatment for a subject.

According to an alternative embodiment IL, the method of any one of alternatives GQ to IK further comprise that when the cells are patient population-specific, the determination of the effect of the test agent identifies a treatment specified for that particular patient subpopulation.

According to an alternative embodiment IM, the method of any one of alternatives GQ to IL further comprise introducing immune cells into the second central microchannel.

According to an alternative embodiment IN, the method of any one of alternatives GQ to IM further comprise that the cells in the first central microchannel and the immune cells flowing in the second central microchannel form an in vitro mucosal immunity model.

According to an alternative embodiment IO, the method of any one of alternatives GQ to IN further comprise that the mucosal immunity model is adapted to determine efficacy or immunogenicity of a vaccine, and/or to be used for vaccine development.

According to an alternative embodiment IP, the method of any one of alternatives GQ to IO further comprise measuring response of the immune cells.

According to an alternative embodiment IQ, the method of any one of alternatives GQ to IP further comprise that the response of the immune cells includes trans-epithelial migration, maturation, activation, cell killing, and/or drainage.

According to an alternative embodiment IR, the method of any one of alternatives GQ to IQ further comprise performing a pharmacokinetic, a pharmacodynamics, or a pharmacokinetic-pharmacodynamic (PK-PD) assay and/or analysis of an effect of the test agent on the cells, thereby determining an in vitro pharmacokinetic and/or pharmacodynamics effect of the test agent on the cells.

According to an alternative embodiment IS, the method of any one of alternatives GQ to IR further comprise performing a target identification analysis to identify a drug target.

According to an alternative embodiment IT, the method of any one of alternatives GQ to IS further comprise validating the drug target.

According to an alternative embodiment IU, the method of any one of alternatives GQ to IT further comprise that the drug target is validated by exposing the cells to an agent known to target the drug target.

According to an alternative embodiment IV, the method of any one of alternatives GQ to IU further comprise connecting the at least one device to a second device of any one of alternatives BA to HE.

According to an alternative embodiment IW, the method of any one of alternatives GQ to IV further comprise directing the first fluid from the first microchannel of the at least one device to flow to the first microchannel of the second device.

According to an alternative embodiment IX, the method of any one of alternatives GQ to IW further comprise directing the second fluid from the second central microchannel of the at least one device to flow to the second central microchannel of the second device.

According to an alternative embodiment IY, the method of any one of alternatives GQ to IX further comprise that the cells in the at least one device include pathogen-infected cells and the cells in the second device are normal healthy cells.

According to an alternative embodiment IZ, the method of any one of alternatives GQ to IY further comprise measuring response of the pathogen-infected cells upon exposure of the fluid flow.

According to an alternative embodiment JA, the method of any one of alternatives GQ to IZ further comprise measuring response of the normal healthy cells upon exposure to the fluid flow from the at least one device.

According to an alternative embodiment JB, the method of any one of alternatives GQ to JA further comprise that the measured response of the normal healthy cells determines transmissibility of airborne or body fluid-borne pathogens.

According to an alternative embodiment JC, a composition comprises at least 50 wt % of a styrenic block copolymer; wherein the styrenic block copolymer includes a polymer block of predominantly styrene monomers and a random polymer block of alkene monomers, provided that the predominant alkene monomers exclude isoprene or butadiene; and from about 0.5 wt % to about 30 wt % of a polyolefin.

According to an alternative embodiment JD, the composition of alternative JC is used in cell-culture devices or organomimetic devices.

According to an alternative embodiment JE, the composition of one of alternatives JC or JD further comprises that the alkene monomers are selected from the group consisting of ethylene, propylene, butylene, and any combinations thereof.

According to an alternative embodiment JF, the composition of any one of alternatives JC to JE further comprise that the alkene monomers are ethylene and butylene.

According to an alternative embodiment JG, the composition of any one of alternatives JC to JF further comprise that the polyolefin includes polypropylene.

According to an alternative embodiment JH, the composition of any one of alternatives JC to JG further comprise that the styrenic block copolymer includes a styrene content of about 10 wt % to about 60 wt %.

According to an alternative embodiment JI, the composition of any one of alternatives JC to JH further comprise that the styrenic block copolymer includes styrene-ethylene-butylene-styrene (SEBS), styrene-ethylene-propylene-styrene (SEPS), or a combination thereof.

According to an alternative embodiment JJ, the composition of any one of alternatives JC to JI further comprise that the styrenic block copolymer is SEBS and the polyolefin is polypropylene.

According to an alternative embodiment JK, the composition of any one of alternatives JC to JJ further comprise that the composition comprises 90-95 wt % of SEBS and about 5-10 wt % of polypropylene.

According to an alternative embodiment JL, the composition of any one of alternatives JC to JK further comprise that the composition is optically clear.

According to an alternative embodiment JM, the composition of any one of alternatives JC to JL further comprise that the composition has a Shore A hardness of at least about 30, or about 30 to about 60.

According to an alternative embodiment JN, the composition of any one of alternatives JC to JM further comprise that the composition is adapted for injection molding, extrusion or a combination thereof.

According to an alternative embodiment JO, the composition of any one of alternatives JC to JN further comprise that the composition is in a form of a solid article.

According to an alternative embodiment JP, the composition of any one of alternatives JC to JO further comprise that the solid article shows a decreased absorption of molecules.

According to an alternative embodiment JQ, the composition of any one of alternatives JC to JP further comprise that the molecules are selected from the group consisting of drugs, biologics, contrast agents, fluorescent dyes, proteins, peptides, antibodies, and any combinations thereof.

According to an alternative embodiment JR, the composition of any one of alternatives JC to JQ further comprise that the molecules are hydrophobic molecules.

According to an alternative embodiment JS, the composition of any one of alternatives JC to JR further comprise that the solid article is a membrane or a film.

According to an alternative embodiment JT, the composition of any one of alternatives JC to JS further comprise that the membrane or the film has a thickness of no more than 500 μm.

According to an alternative embodiment JU, the composition of any one of alternatives JC to JT further comprise that the membrane or the film is porous.

According to an alternative embodiment JV, the composition of any one of alternatives JC to JU further comprise that the membrane or the film further comprises one or more cells thereon.

According to an alternative embodiment JW, the composition of any one of alternatives JC to JV further comprise that the solid article includes a body and at least one fluidic element disposed therein.

According to an alternative embodiment JX, the composition of any one of alternatives JC to JW further comprise that the solid article is a microfluidic device.

According to an alternative embodiment JY, the composition of any one of alternatives JC to JX further comprise that the solid article is an organomimetic device of any one of alternatives BA to GP.

According to an alternative embodiment JZ, the composition of any one of alternatives JC to JY further comprise that the solid article is produced by a process comprising injection molding, extrusion, or a combination thereof.

According to an alternative embodiment KA, a solid article comprises a body and at least one fluidic element disposed therein. At least one fluid-contact surface of the at least one fluid element includes a composition according to any one of alternatives JC to JZ.

According to an alternative embodiment KB, the solid article of alternative KA further comprises that the composition displays a decreased absorption of molecules onto the at least one fluid-contact surface.

According to an alternative embodiment KC, the solid article of one of alternatives KA or KB further comprise that the molecules are selected from the group consisting of drugs, biologics, contrast agents, fluorescent dyes, proteins, peptides, antibodies, and any combinations thereof.

According to an alternative embodiment KD, the solid article of any one of alternatives KA to KC further comprise that the molecules are hydrophobic molecules.

According to an alternative embodiment KE, the solid article of any one of alternatives KA to KD further comprise that the solid article or the composition is optically clear.

According to an alternative embodiment KF, the solid article of any one of alternatives KA to KE further comprise that the at least one fluidic element is a microwell.

According to an alternative embodiment KG, the solid article of any one of alternatives KA to KF further comprise that the at least one fluidic element is a microchannel.

According to an alternative embodiment KH, the solid article of any one of alternatives KA to KG further comprise that the width and height of the cross-section of the fluidic element are at least about 100 μm.

According to an alternative embodiment KI, the solid article of any one of alternatives KA to KH further comprise that the at least one fluidic element includes one or more cells therein.

According to an alternative embodiment KJ, the solid article of any one of alternatives KA to KI further comprise that the solid article is a microfluidic device.

According to an alternative embodiment KK, the solid article of any one of alternatives KA to KJ further comprise that the solid article is an organomimetic device of any one of alternative BA to GP.

According to an alternative embodiment KL, the solid article of any one of alternatives KA to KK further comprise that the pores are laser cut or etched.

According to an alternative embodiment KM, the solid article of any one of alternatives KA to KL further comprise that the membrane is defined by photolithography.

According to an alternative embodiment KN, the devices, methods, compositions, and solid articles of any one of alternatives BA to KM further comprise that the membrane is track-etched.

According to an alternative embodiment KO, a mechanical modulation system for stretch actuation of a microfluidic device includes a mechanical actuation arrangement configured to impart an undulating motion along a single plane defined by a microfluidic device mounted within the mechanical modulation system. A plurality of opposing connection elements are physically connected to the mechanical actuation system. The plurality of opposing connection elements are configured to fasten a first location and a second location of a microfluidic device to the opposing connection elements such that the first location and the second location of the microfluidic device are each fixed to one of the connection elements and such that straining of the microfluidic device during cyclical linear motions of a stretch actuation process is transferred to the portion of the microfluidic device between the first location and the opposing second location.

According to an alternative embodiment KP, the system of alternative KO further comprises a sensor arrangement for identifying strain in the microfluidic device.

According to an alternative embodiment KQ, the system of one of alternatives KO or KP further comprise that the undulating motion is a cyclical linear motion.

According to an alternative embodiment KR, the system of any one of alternatives KO to KQ further comprise that the first location is a first end of a microfluidic device and the second location is an opposing second end of the microfluidic device.

According to an alternative embodiment KS, the system of any one of alternatives KO to KR further comprise that the microfluidic device includes a membrane with cells adhered thereto.

According to an alternative embodiment KT, the system of any one of alternatives KO to KS further comprise that the straining causes a deformation to both the membrane and the microfluidic device.

According to an alternative embodiment KU, the system of any one of alternatives KO to KT further comprise that the fastening of the first location and second location of the microfluidic device to the opposing connection elements includes a plurality of male pin and female slot mating elements.

According to an alternative embodiment KV, the system of any one of alternatives KO to KU further comprise that the undulating motion during stretch actuation is generally parallel to a long dimension of the microfluidic device. The undulating motion is controlled by at least one of one or more guide rails operatively connected to one of more of the plurality of opposing connection elements.

According to an alternative embodiment KW, the system of any one of alternatives KO to KV further comprise that one of the plurality of opposing connection elements is a fixed connection that is non-movable and another of the opposing connection elements is a non-fixed connection that is movable.

According to an alternative embodiment KX, the system of any one of alternatives KO to KW further comprise that at least two of the plurality of opposing connection elements are movable.

According to an alternative embodiment KY, the system of any one of alternatives KO to KX further comprise that the mechanical actuation system includes at least one arm integral with at least one of the plurality of opposing connection elements.

According to an alternative embodiment KZ, the system of any one of alternatives KO to KY further comprise that the mechanical actuation arrangement includes a motor coupled to a rotating cam configured to impart movement to at least one drive arm that is operatively connected to at least one of the plurality of connection elements.

According to an alternative embodiment LA, the system of any one of alternatives KO to KZ further comprise that the mechanical actuation arrangement is a fluid-based system including one or more piston shafts connected to at least one of the plurality of opposing connection elements.

According to an alternative embodiment LB, the system of any one of alternatives KO to LA further comprise that the sensor arrangement is a pressure control system including one or more pressure sensors such that straining of the microfluidic device is controlled based on applied pressures to a piston connected to at least one of the plurality of opposing connection elements. The applied pressures correlate to predetermined strain values.

According to an alternative embodiment LC, the system of any one of alternatives KO to LB further comprise that the sensor arrangement includes one or more strain gauges and/or linear encoders mounted between the plurality of opposing connection elements.

According to an alternative embodiment LD, the system of any one of alternatives KO to LC further comprise that the sensor arrangement includes one or more strain gauges and/or linear encoders mounted along a piston shaft and/or linear rail.

According to an alternative embodiment LE, the system of any one of alternatives KO to LD further comprise that at least one of the strain gauges includes a marking element to allow for visual observation of straining due to stretch actuation of the microfluidic device.

According to an alternative embodiment LF, the system of any one of alternatives KO to LE further comprise that the sensor arrangement includes a linear encoder, a rotary encoder, an optical positioning detector, and/or any combinations thereof.

According to an alternative embodiment LG, the system of any one of alternatives KO to LF further comprise that the sensor arrangement includes imaging for calibrating the strain associated with the linear motions imparted to the microfluidic device by the mechanical actuation arrangement.

According to an alternative embodiment LH, the system of any one of alternatives KO to LG further comprise that the sensor arrangement indirectly identifies strain in the microfluidic device through monitoring of a moving portion of the mechanical actuation arrangement. Movement of the moving portion is directly correlated to the stretch of the microfluidic device.

According to an alternative embodiment LI, the system of any one of alternatives KO to LH further comprise that the first location and the second location of the microfluidic device are each fixed to one of the opposing connection elements such that entry and exit ports positioned at the first location and second location are not exposed to additional strains caused by stretch actuation of the microfluidic device.

According to an alternative embodiment LJ, the system of any one of alternatives KO to LI further comprise that the sensor arrangement includes an imaging device, a limit switch, a proximity switch, and/or any combinations thereof.

According to an alternative embodiment LK, the system of any one of alternatives KO to LJ further comprise that the mechanical actuation arrangement includes an electric motor, a voice coil, a solenoid, a piczo driver, and/or any combinations thereof.

According to an alternative embodiment LL, the system of any one of alternatives KO to LK further comprise that the sensor arrangement includes one or more sensors for determining a current, a voltage, an applied force, and/or any combinations, in the electric motor, voice coil, solenoid, and/or piezo driver.

According to an alternative embodiment LM, the system of any one of alternatives KO to LL further comprise that the microfluidic device includes a plurality of microfluidic devices each having a first location and a second location. Each of the first locations of the microfluidic devices are fastened to the respective ones of the plurality of opposing connection elements and each of the second locations of the microfluidic devices are fastened to the respective another ones of the plurality of opposing connection elements.

According to an alternative embodiment LN, a microfluidic system for monitoring a behavior of cells includes a microfluidic device having at least one microchannel in which the cells are disposed. A mechanical actuation device for stretching the microfluidic device includes a plurality of opposing connection elements configured to be fastened to a first location and a second location of a microfluidic device.

According to an alternative embodiment LO, the system of alternative LN further comprises a strain monitoring system that identifies a strain in the microfluidic device in response to the stretching.

According to an alternative embodiment LP, the system of one of alternatives LN or LO further comprise that the mechanical actuation device for stretching the microfluidic device is along a single plane defined by the microfluidic device.

According to an alternative embodiment LQ, the system of any one of alternatives LN to LP further comprise that the microfluidic device includes a membrane on which the cells are attached.

According to an alternative embodiment LR, the system of any one of alternatives LN to LQ further comprise that the mechanical actuation device imparts an undulating motion. The fastening of the first location and the opposing second location of the microfluidic device provides a fixed connection such that the strain of the microfluidic device during the undulating motions of the stretching is transferred to the portion of the microfluidic device between the first location and the opposing second location.

According to an alternative embodiment LS, the system of any one of alternatives LN to LR further comprise that the undulating motion is a cyclical linear motion.

According to an alternative embodiment LT, the system of any one of alternatives LN to LS further comprise entry and exit ports to the at least one microchannel, wherein the microfluidic device is adapted to substantially isolate the entry and exit ports from strains created during the stretching of the microfluidic device.

According to an alternative embodiment LU, the system of any one of alternatives LN to LT further comprise that one of the plurality of opposing connection elements is a fixed connection that is non-movable and another of the opposing connection elements is a non-fixed connection that is movable.

According to an alternative embodiment LV, the system of any one of alternatives LN to LU further comprise that at least two of the plurality of opposing connection elements are movable.

According to an alternative embodiment LW, the system of any one of alternatives LN to LV further comprise that the microfluidic device includes a plurality of microfluidic devices each having a first location and an opposing second location. Each of the first locations of the microfluidic devices is fastened to a respective one of the plurality of opposing connection elements and each of the opposing second locations of the microfluidic devices is fastened to a respective another one of the plurality of opposing connection elements.

According to an alternative embodiment LX, a method of stretch actuation using a mechanical modulation system for a microfluidic device including at least one microchannel in which cells are disposed includes mounting a first location and a second location of the microfluidic device to a first connection element and a second connection element of the mechanical modulation system. Stretching of the microfluidic device occurs in response to generally undulating motions imparted to the microfluidic device.

According to an alternative embodiment LY, the method of alternative LX further comprises identifying strains in the microfluidic device in response to the stretching. The strains are identified by one or more sensor arrangements.

According to an alternative embodiment LZ, the method of one of alternatives LX or LY further comprise that stretching of the microfluidic device occurs along a single plane defined by the microfluidic device.

According to an alternative embodiment MA, the method of any one of alternatives LX to LZ further comprises that the microfluidic device includes a membrane on which the cells are disposed.

According to an alternative embodiment MB, the method of any one of alternatives LX to MA further comprises that the mounting of the first location and the second location of the microfluidic device provides a fixed connection such that strains in the microfluidic device in response to the stretching are transferred to the portion of the microfluidic device between the first location and the second location.

Unless defined otherwise, all technical and scientific terms used herein have the same meaning as commonly understood by one of ordinary skill in the art to which this invention belongs.

It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used to described the present invention, in connection with percentages means±5%.

In one aspect, the present invention relates to the herein described compositions, methods, and respective component(s) thereof, as essential to the invention, yet open to the inclusion of unspecified elements, essential or not ("comprising"). In accordance with some embodiments of the invention, other elements to be included in the description of the composition, method or respective component thereof are limited to those that do not materially affect the basic and novel characteristic(s) of the invention ("consisting essentially of"). This applies equally to steps within a described method as well as compositions and components therein. In other embodiments, the inventions, compositions, methods, and respective components thereof, described herein are intended to be exclusive of any element not deemed an essential element to the component, composition or method ("consisting of").

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:
1. A microfluidic device comprising:
   a) a central microchannel having a longitudinal axis, an inlet port, an outlet port, and a plurality of cut-outs that extend transverse to said longitudinal axis of said central microchannel, said plurality of cut-outs are not fluidically connected to said central microchannel, and are positioned between said inlet and said outlet ports; and b) a plurality of opposing connection elements fastened to a first and opposing second location of said microfluidic device, said opposing connection elements physically connected to a mechanical stretch actuator configured to impart motion that is transferred to a portion of the microfluidic device between said first location and the opposing second location.

2. The device of claim 1, wherein said central microchannel of said device is disposed in a first microchannel layer comprising a substantially rigid layer.

3. The device of claim 1, wherein said device comprises a polymer selected from the group consisting of styrene-ethylene-butylene-styrene (SEES), a SEBS/polypropylene combination, and a cyclic polyolefin.

4. The device of claim 1, wherein said central microchannel of said device is disposed in a first microchannel layer comprising a material selected from the group consisting of an extracellular matrix polymer, gel, biopolymer and a scaffold.

5. The device of claim 1, further comprising a membrane which divides said central microchannel into first and second microchannels.

6. The device of claim 5, further comprising a second microchannel layer.

7. The device of claim 5, wherein at least a portion of said central microchannel is aligned with at least a portion of said second microchannel.

8. The device of claim 1, wherein said device is comprised of one or a mixture of biocompatible materials each having a thickness, and wherein said plurality of cut-outs define a void extending through each thickness of each of said one or a mixture of biocompatible materials.

* * * * *